US012397047B2

(12) United States Patent
Park et al.

(10) Patent No.: US 12,397,047 B2
(45) Date of Patent: Aug. 26, 2025

(54) BACTERIA-DERIVED VESICLES AND USES THEREOF

(71) Applicant: Exocure Sweden AB, Gothenburg (SE)

(72) Inventors: Kyong-su Park, Gothenburg (SE); Rossella Crescitelli, Gothenburg (SE); Jan Lötvall, San Diego, CA (US)

(73) Assignee: Exocure Sweden AB, Goeteborg (SE)

( * ) Notice: Subject to any disclaimer, the term of this patent is extended or adjusted under 35 U.S.C. 154(b) by 1017 days.

(21) Appl. No.: 17/420,348

(22) PCT Filed: Jan. 7, 2020

(86) PCT No.: PCT/US2020/012586
§ 371 (c)(1),
(2) Date: Jul. 1, 2021

(87) PCT Pub. No.: WO2020/146390
PCT Pub. Date: Jul. 16, 2020

(65) Prior Publication Data
US 2022/0080035 A1 Mar. 17, 2022

Related U.S. Application Data

(60) Provisional application No. 62/790,366, filed on Jan. 9, 2019.

(51) Int. Cl.
| A61K 39/108 | (2006.01) |
| A61K 39/00 | (2006.01) |
| A61K 39/104 | (2006.01) |
| A61K 39/39 | (2006.01) |
| A61P 11/00 | (2006.01) |
| A61P 31/04 | (2006.01) |
| A61P 35/00 | (2006.01) |
| C12N 1/20 | (2006.01) |
| C12N 5/0784 | (2010.01) |
| C12R 1/19 | (2006.01) |
| C12R 1/385 | (2006.01) |

(52) U.S. Cl.
CPC ...... *A61K 39/0258* (2013.01); *A61K 39/0011* (2013.01); *A61K 39/104* (2013.01); *A61P 11/00* (2018.01); *A61P 31/04* (2018.01); *A61P 35/00* (2018.01); *C12N 1/20* (2013.01); *C12N 5/0639* (2013.01); *A61K 39/39* (2013.01); *A61K 2039/55555* (2013.01); *A61K 2039/55594* (2013.01); *A61K 2039/57* (2013.01); *C12N 2501/22* (2013.01); *C12N 2506/1353* (2013.01); *C12R 2001/19* (2021.05); *C12R 2001/385* (2021.05)

(58) Field of Classification Search
None
See application file for complete search history.

(56) References Cited

U.S. PATENT DOCUMENTS

| 9,149,542 | B2 | 10/2015 | Gho et al. | |
| 9,220,763 | B2 | 12/2015 | Gho et al. | |
| 11,333,665 | B2 | 5/2022 | Lotvall et al. | |
| 2008/0207723 | A1 | 8/2008 | Kopreski | |
| 2015/0086639 | A1 | 3/2015 | Huang | |
| 2015/0218254 | A1* | 8/2015 | Sabbadini | C12P 21/02 435/252.3 |
| 2016/0061842 | A1 | 3/2016 | Di Vizio | |
| 2016/0120818 | A1* | 5/2016 | Grandi | A61P 21/00 424/450 |
| 2017/0246288 | A1* | 8/2017 | Li | A61K 39/00115 |
| 2018/0036240 | A1 | 2/2018 | Gho et al. | |
| 2018/0296483 | A1 | 10/2018 | Gho et al. | |
| 2018/0318409 | A1 | 11/2018 | Valiante et al. | |
| 2020/0249234 | A1 | 8/2020 | Lotvall et al. | |

FOREIGN PATENT DOCUMENTS

| EP | 2617413 A2 | 7/2013 | |
| EP | 3251659 A1 | 12/2017 | |
| EP | 2450032 B1 | 9/2018 | |
| WO | WO2009051427 | 4/2009 | |
| WO | WO2009130649 | 10/2009 | |
| WO | 2010010983 | 1/2010 | |
| WO | WO-2010010983 A1 * | 1/2010 | ............. C12N 15/00 |
| WO | WO2010056337 | 5/2010 | |
| WO | WO2010070124 | 6/2010 | |
| WO | WO2013063439 | 5/2013 | |
| WO | WO2015085096 | 6/2015 | |
| WO | WO2016136372 | 9/2016 | |

(Continued)

OTHER PUBLICATIONS

Corrales et al., Direct Activation of Sting in the Tumor Microenvironment Leads to Potent and Systemic Tumor Regression and Immunity. 2015. Cell Reports. 11:1018-1030. (Year: 2015).*

(Continued)

*Primary Examiner* — Daniel E Kolker
*Assistant Examiner* — Maureen Varina Driscoll
(74) *Attorney, Agent, or Firm* — Shweta Chandra; Bozicevic, Field & Francis LLP

(57) ABSTRACT

Non-naturally occurring vesicles derived from bacteria, e.g., pathogenic bacteria, methods for making the vesicles, and methods for using compositions of these vesicles are disclosed. Methods of using the vesicles include prevention and/or treatment of bacterial infections. Also provided herein are compositions that include vesicles derived front bacteria and tumor vesicles, methods for making the tumor vesicles, and methods for using the compositions of bacterial vesicles and tumor vesicles. Methods of using the compositions of bacterial vesicles and tumor vesicles include treatment of cancer in a subject. Tumor vesicles may be derived from cancer cells present in the subject to be treated or from a cancer cell line expressing at least one neoantigen. The neoantigen may be specific to the subject and may have been identified by sequencing of the cancer cells from the subject. The neoantigen may be a neoantigen known to be commonly expressed in a particular type of cancer.

20 Claims, 61 Drawing Sheets

(56) References Cited

FOREIGN PATENT DOCUMENTS

| WO | 2017161010 | | 9/2017 | |
| --- | --- | --- | --- | --- |
| WO | WO-2017161010 A1 | * | 9/2017 | ......... A61K 38/1841 |
| WO | 2017205810 | | 11/2017 | |
| WO | WO2018171947 | | 9/2018 | |

OTHER PUBLICATIONS

Filip et al., Solubilization of the Cytoplasmic Membrane of *Escherichia coli* by the Ionic Detergent Sodium-Lauryl Sarcosinate. 1973. J Bacteriol. 115(3):717-722. (Year: 1973).*
Zariri et al. Meningococcal Outer Membrane Vesicle Composition-Dependent Activation of the Innate Immune Response. 2016; 84(10): 3024-3033. (Year: 2016).*
D'Atri et al., (2019) "Nano-Ghosts: mesenchymal stem cells derived nanoparticles as a novel approach for cartilage regeneration." Journal of Extracellular Vesicles, vol. 8, 1 page.
Furman et al., (2013) "Reconstructed Stem Cell Nano ghosts: A Natural Tumor Targeting Platform." Nano Letters, vol. 13, No. 7, pp. 3248-3255.
Go et al., (2018) "Extracellular Vesicle-Mimetic Ghost Nanovesicles for Delivering Anti-Inflammatory Drugs to Mitigate Gram-Negative Bacterial Outer Membrane Vesicle-Induced Systemic Inflammatory Response Syndrome." Advance Healthcare Materials, vol. 8, No. 4.
Corrales et al., (2015) "Direct Activation of Sting in the Tumor Microenvironment Leads to Potent and Systemic Tumor Regression and Immunity", Cell Reports, 11(7):1018-1030, XP055771217.
Van Der Pol et al. (2015) "Outer membrane vesicles as platform vaccine technology", Biotechnology Journal, 10(11):1689-1706, XP055465407.
Morein et al. (1994) "Separation of inner and outer membrane vesicles from *Escherichia coli* in self-generating Percoll gradients", Analytical Biochemistry, 216(1):47-51, XP055982965.
Coumans et al., (2017) "Methodological guidelines to study extracellular Vesicles", Circ. Res., 120(10):1632-1648.
Jeppesen et al., (2014) "Quantitative proteomics of fractionated membrane and lumen exosome proteins from isogenic metastatic and nonmetastatic bladder cancer cells reveal differential expression of EMT factors", Proteomics (14)6:699-712.
Karimi et al., (2018) "Detailed analysis of the plasma extracellular vesicle proteome after separation from lipoproteins", Cell. Mol. Life Sci., 75(15):2873-2886.
Mariantonia et al., (2009) "High levels of exosomes expressing CD63 and caveolin-1 in plasma of melanoma patients. e5219", PLoS One, 4(4):1-10.
Shin et al., (2015) "High-yield isolation of extracellular vesicles using aqueous two-phase system", Scientific Reports, (5)1:1-11.
Tauro et al., (2012) "Two Distinct Populations of Exosomes Are Released from LIM1863 Colon Carcinoma Cell-derived Organoids", Molecular & Cellular Proteomics, 12(3):587-598.
Yoshioka et al., (2014) "Ultra-sensitive liquid biopsy of circulating extracellular vesicles using ExoScreen". Nature Communications, (5)3591:1-8.
U.S. Appl. No. 17/642,140, filed Mar. 10, 2022.
U.S. Appl. No. 17/731,833, filed Apr. 28, 2022.
Matsushita et al., (1989) "Effect of Extracellular pH on the Respiratory Chain and Energetics of Gluconobacter suboxydans", Agricultural and Biological Chemistry, 53(11):2895-2902.

* cited by examiner

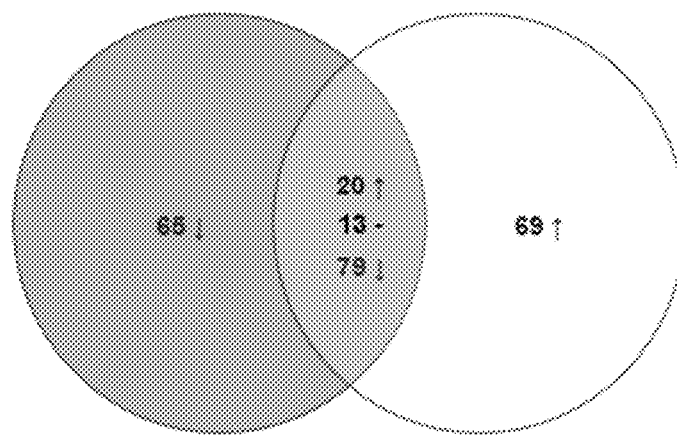
FIG. 8
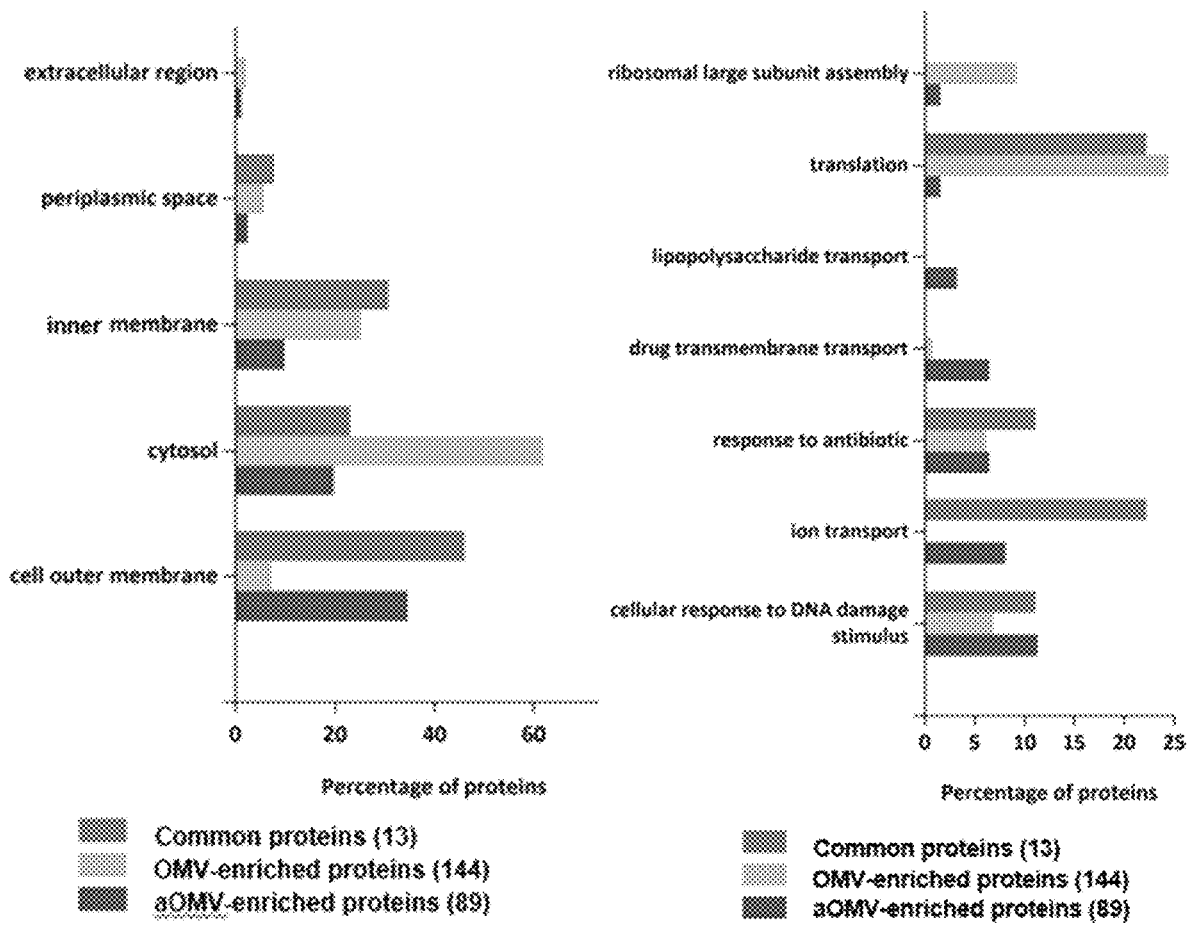
FIG. 9
FIG. 10

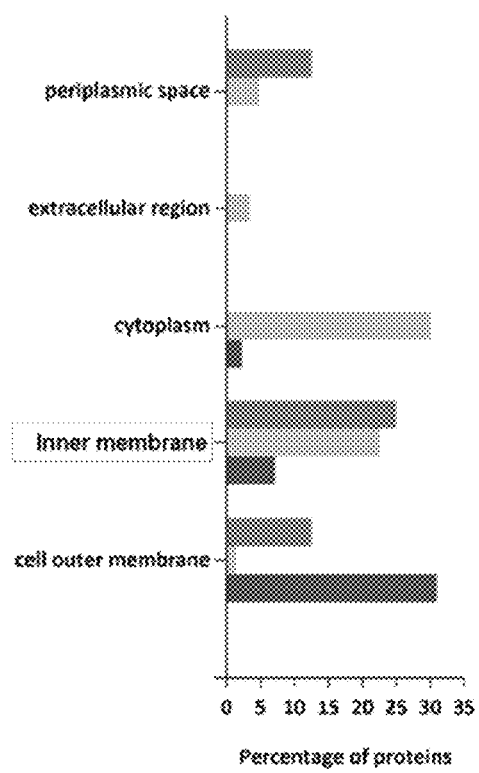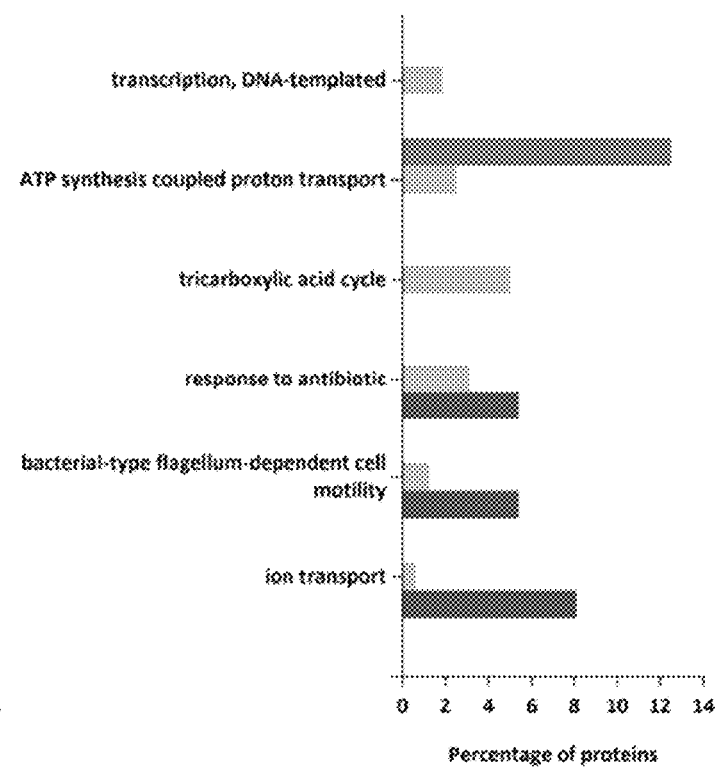
FIG. 30
FIG. 31

BACTERIA-DERIVED VESICLES AND USES THEREOF

CROSS-REFERENCE TO RELATED APPLICATION

This application claims the benefit of priority to U.S. Provisional Patent Application No. 62/790,366, filed Jan. 9, 2019, which application is incorporated herein by reference in its entirety.

INTRODUCTION

Naturally released bacterial vesicles, including outer membrane vesicles (OMVs), have been developed as vaccines. One example is the meningococcus vaccine, which is available clinically. However, such vaccines are known to activate innate immunity resulting in severe side effects at the time of immunization, including fever and flu-like symptoms. Therefore, there is a need to produce bacterial vesicles that do not evoke serious side effects caused by activation of innate immunity but can still induce protective immunity. The present disclosure addresses the above issues as well as other issues and provides related advantages.

SUMMARY

Non-naturally occurring vesicles derived from bacteria, e.g., pathogenic bacteria, methods for making the vesicles, and methods for using compositions of these vesicles are disclosed. Methods of using the vesicles include prevention and/or treatment of bacterial infections. Also provided herein are compositions that include vesicles derived from bacteria and tumor vesicles, methods for making the tumor vesicles, and methods for using the compositions of bacterial vesicles and tumor vesicles. Methods of using the compositions of bacterial vesicles and tumor vesicles include treatment of cancer in a subject. Tumor vesicles may be derived from cancer cells present in the subject to be treated or from a cancer cell line expressing at least one neoantigen. The neoantigen may be specific to the subject and may have been identified by sequencing of cancer cells from the subject. Alternatively, the neoantigen may be a neoantigen known to be commonly expressed in a particular type of cancer.

The artificial outer membrane vesicles (aOMVs) generated from a gram-negative bacterium, wherein the aOMVs are deficient in one or more of the following components present in the gram-negative bacterium: inner membrane proteins, nucleic acids, cytoplasmic proteins, and ribosomes, and/or wherein the aOMVs are enriched in outer membrane proteins; and tumor vesicles, wherein the tumor vesicles comprise at least one tumor antigen disclosed herein find use in methods for treating cancer in a subject, e.g., a mammalian, such as, a human subject. The method may include administering the aOMVs and the tumor vesicles to the subject. The aOMVs and the tumor vesicles also find use for treating cancer in a subject, wherein the treating includes administering an immune checkpoint inhibitor (e.g., anti-PD1 antibody) to the subject prior to, concurrently with, or subsequent to the administration of the aOMVs and the tumor vesicles to the subject. The aOMVs used in the methods disclosed herein may be loaded with a therapeutic agent, such as, a STING agonist. Advantages associated with the use of the aOMVs and the tumor vesicles for treating cancer in a subject as well as co-treatment with an immune checkpoint inhibitor and use of aOMVs loaded with a therapeutic agent are described in the detailed description below.

BRIEF DESCRIPTION OF THE DRAWINGS

FIG. 2, Panel B depicts transmission electron microscopy images of E. coli OMVs (upper panel) and aOMVs (lower panel).

FIG. 3, Panel B depicts Western blot analysis of E. coli lysates (10 μg total protein), OMVs (1 μg total protein), and aOMVs (0.20 μg total protein), with anti-OmpA antibody.

FIG. 4, Panel B depicts the concentration of LPS per particle number from E. coli OMVs and aOMVs analyzed by Limulus amoebocyte lysate assay. ns, not significant; two-tailed unpaired T test. Error bars indicate SEM. N=3.

FIG. 8 depicts Venn diagram comparing proteomes of E. coli aOMVs to that of OMVs. ↑ indicates the number of aOMV proteins that were present at a level more than 1.5 times the level of the same protein present in OMVs. ↓ indicates the number of aOMV proteins that were expressed at a level less than 0.67 times the level of the same protein present in OMVs.

FIG. 9 depicts comparison of percentage of the indicated E. coli proteins present in (i) both OMVs and aOMVs "common proteins", (ii) OMVs, and (iii) aOMVs, as analyzed by GO subcellular localization annotations.

FIG. 10 depicts proteomes of percentage of the indicated E. coli proteins present in (i) both OMVs and aOMVs "common proteins", (ii) OMVs, and (iii) aOMVs, as analyzed by GO biological process annotations.

FIG. 15, Panel B depicts the percentage of bone marrow-derived dendritic cells taking up DiO-labeled *E. coli* aOMVs at 0, 3, 6, and 12 h. ***, P<0.001; versus 0 h group; one-way ANOVA with Tukey's multiple comparison test. Error bars indicate SEM. N=3.

FIG. 16, Panel B is a graph of IL-6 level (pg/ml) in the supernatants of bone marrow-derived dendritic cells treated with *E. coli* OMVs or aOMVs for 24 h. ***, P<0.001; versus control; one-way ANOVA with Tukey's multiple comparison test. Error bars indicate SEM. N=3. FIG. 16, Panel C is a graph of IL-12p70 level (pg/ml) in the supernatants of bone marrow-derived dendritic cells treated with *E. coli* OMVs or aOMVs for 24 h. , P<0.01; *, P<0.001; versus control; one-way ANOVA with Tukey's multiple comparison test. Error bars indicate SEM. N=3. FIG. 16, Panel D is a graph of IL-4 level (pg/ml) in the supernatants of bone marrow-derived dendritic cells treated with *E. coli* OMVs or aOMVs for 24 h. Versus control; one-way ANOVA with Tukey's multiple comparison test. Error bars indicate SEM. N=3.

FIG. 17, Panel B is a graph showing the levels of OMV protein-specific antibodies measured in the course of three intraperitoneal injection of $5\times10^9$ of *E. coli* OMVs or aOMVs at regular intervals of one week. ***, P<0.001; versus sham group; one-way ANOVA with Tukey's multiple comparison test. Error bars indicate SEM. N=4.

FIG. 18, Panel B depicts the level of IFN-γ secreted from mouse splenic CD4+ T cells upon ex vivo treatment with *E. coli* OMVs after the mice were immunized with $5\times10^9$ of *E. coli* OMVs or aOMVs. , P<0.01; *, P<0.001; versus sham group; one-way ANOVA with Tukey's multiple comparison test. Error bars indicate SEM. N=3. FIG. 18, Panel C depicts the level of IL-4 secreted from mouse splenic CD4+ T cells upon ex vivo treatment with *E. coli* OMVs after the mice were immunized with $5\times10^9$ of *E. coli* OMVs or aOMVs. Versus sham group; one-way ANOVA with Tukey's multiple comparison test Error bars indicate SEM. N=3.

FIG. 21, Panel B depicts the number of total leukocytes in the bronchoalveolar lavage (BAL) fluid at 6 h after intraperitoneal challenge with nonlethal dose of *E. coli* OMVs (15 μg) in mice immunized with $5\times10^9$ of *E. coli* OMVs or aOMVs at weekly intervals for three weeks. *, P<0.05; one-way ANOVA with Tukey's multiple comparison test. Error bars indicate SEM. N=4.

FIG. 22, Panel B depicts the number of platelets in the blood at 6 h after intraperitoneal challenge with nonlethal dose of *E. coli* OMVs (15 μg) in mice immunized with $5\times10^9$ of *E. coli* OMVs or aOMVs at weekly intervals for three weeks. ***, P<0.001; one-way ANOVA with Tukey's multiple comparison test. Error bars indicate SEM. N=4. FIG. 22, Panel C depicts the levels of cardiac troponin T in the serum at 6 h after intraperitoneal challenge with nonlethal dose of *E. coli* OMVs (15 μg) in mice immunized with $5\times10^9$ of *E. coli* OMVs or aOMVs at weekly intervals for three weeks. ***, P<0.001; one-way ANOVA with Tukey's multiple comparison test. Error bars indicate SEM. N=4.

Error bars indicate SEM. N=4.

FIG. 26, Panel B depicts transmission electron microscopy images of *P. aeruginosa* OMVs (upper) and aOMVs (lower).

FIG. 30 depicts comparison of percentage of the indicated *P. aeruginosa* proteins present in (i) both OMVs and aOMVs "common proteins", (ii) OMVs, and (iii) aOMVs, as analyzed by GO subcellular localization annotations.

FIG. 31 depicts proteomes of percentage of the indicated *P. aeruginosa* proteins present in (i) both OMVs and aOMVs "common proteins", (ii) OMVs, and (iii) aOMVs, as analyzed by GO biological process annotations.

FIG. 34, Panel B depicts the level of IFN-γ secreted from mouse splenic CD4+ T cells upon ex vivo treatment with *P. aeruginosa* proteins (1 μg/mL) after the mice were immunized with $5 \times 10^9$ of *P. aeruginosa* OMVs or aOMVs. ***, P<0.001; versus sham group; one-way ANOVA with Tukey's multiple comparison test. Error bars indicate SEM. N=3. FIG. 34, Panel C depicts the level of IL-4 secreted from mouse splenic CD4+ T cells upon ex vivo treatment with *P. aeruginosa* proteins (1 μg/mL) after the mice were immunized with $5 \times 10^9$ of *P. aeruginosa* OMVs or aOMVs. Versus sham group; one-way ANOVA with Tukey's multiple comparison test. Error bars indicate SEM. N=3. FIG. 34, Panel D depicts the level of IL-17 secreted from mouse splenic CD4+θT cells upon ex vivo treatment with *P. aeruginosa* proteins (1 μg/mL) after the mice were immunized with $5 \times 10^9$ of *P. aeruginosa* OMVs or aOMVs. ***, P<0.001; versus sham group; one-way ANOVA with Tukey's multiple comparison test. Error bars indicate SEM. N=3.

FIG. 35, Panel B depicts the differential counting of leukocytes in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. *, P<0.05; n.s., not significant; versus sham group; one-way ANOVA with Tukey's multiple comparison test. Error bars indicate SEM. N=4.

FIG. 36, Panel B depicts the levels of IL-6 in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. *, P<0.05; n.s., not significant; versus sham group; one-way ANOVA with Tukey's multiple comparison test. Error bars indicate SEM. N=4. FIG. 36, Panel C depicts the levels of keratinocyte chemoattractant (KC) in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. *, P<0.05; n.s., not significant; versus sham group; one-way ANOVA with Tukey's multiple comparison test. Error bars indicate SEM. N=4. FIG. 36, Panel D depicts the levels of RANTES in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. *, P<0.05; n.s., not significant; versus sham group; one-way ANOVA with Tukey's multiple comparison test. Error bars indicate SEM. N=4.

FIG. 39, Panel B depicts transmission electron microscopy images of *E. coli* PDNVs (upper) and rePDNVs (lower).

FIG. 40, Panel B depicts Western blot analysis of *E. coli* lysates, PDNVs and rePDNVs with anti-FtsZ, anti-OmpA, and anti-Lipid A antibody.

FIG. 41, Panel B depicts an electropherogram of DNA molecules isolated from *E. coli* rePDNVs in comparison to DNA molecules isolated from PDNVs.

FIG. 45**, Panel B is a graph showing IL-6 level in the supernatants of bone marrow-derived dendritic cells treated with *E. coli* PDNVs or rePDNVs for 24 h. *, $P<0.001$; versus control; one-way ANOVA with Tukey's multiple comparison test. Error bars indicate SEM. N=3. FIG. 45**, Panel C is a graph of showing IL-12p70 level in the supernatants of bone marrow-derived dendritic cells treated with *E. coli* PDNVs or rePDNVs for 24 h. *, $P<0.001$; versus control; one-way ANOVA with Tukey's multiple comparison test. Error bars indicate SEM. N=3. FIG. 45**, Panel D is a graph showing IL-4 level in the supernatants of bone marrow-derived dendritic cells treated with *E. coli* PDNVs or rePDNVs for 24 h. Versus control; one-way ANOVA with Tukey's multiple comparison test. Error bars indicate SEM. N=3.

FIG. 51, Panel B is a graph showing the levels of melanoma lysate-specific antibodies measured in the course of three intraperitoneal injection of mouse melanoma EVs (10 μg) with *E. coli* aOMVs or rePDNVs ($5 \times 10^9$) at regular intervals of 5 days. *, $P<0.05$; , $P<0.01$; *, $P<0.001$; versus sham group; one-way ANOVA with Tukey's multiple comparison test. Error bars indicate SEM. N=6.

FIG. 52, Panel B depicts the level of IFN-γ secreted from mouse splenic CD4+ T cells upon ex vivo treatment with melanoma EV proteins (1 μg/mL) after the mice were immunized with mouse melanoma EVs (10 μg) with *E. coli* aOMVs or rePDNVs ($5 \times 10^9$). , $P<0.01$; versus sham group; one-way ANOVA with Tukey's multiple comparison test. Error bars indicate SEM. N=3. FIG. 52**, Panel C depicts the level of IL-4 secreted from mouse splenic CD4+ T cells upon ex vivo treatment with melanoma EV proteins (1 μg/mL) after the mice were immunized with mouse melanoma EVs (10 μg) with *E. coli* aOMVs or rePDNVs ($5 \times 10^9$). Versus sham group; one-way ANOVA with Tukey's multiple comparison test. Error bars indicate SEM. N=3. FIG. 52, Panel D depicts the level of IL-17 secreted from mouse splenic CD4+ T cells upon ex vivo treatment with melanoma EV proteins (1 μg/mL) after the mice were immunized with mouse melanoma EVs (10 μg) with *E. coli* aOMVs or rePDNVs ($5 \times 10^9$). Versus sham group; one-way ANOVA with Tukey's multiple comparison test. Error bars indicate SEM. N=3.

FIG. 54, Panel B depicts colon cancer volume in mice immunized with/without 10 μg of mouse colon cancer EVs with *E. coli* aOMVs or rePDNVs ($5 \times 10^9$) at 5-day intervals three times. , $P<0.01$; *, $P<0.001$; versus sham group; one-way ANOVA with Tukey's multiple comparison test. Error bars indicate SEM. N=5. FIG. 54, Panel C depicts dissected colon cancer weight from mice immunized with/without 10 μg of mouse colon cancer EVs with *E. coli* aOMVs or rePDNVs ($5 \times 10^9$) at 5-day intervals three times. , $P<0.01$; *, $P<0.001$; versus sham group; one-way ANOVA with Tukey's multiple comparison test. Error bars indicate SEM. N=5.

FIG. 55, Panel B is a graph showing the levels of colon cancer lysate-specific antibodies measured in the course of three intraperitoneal injection of mouse colon cancer EVs (10 μg) with *E. coli* aOMVs or rePDNVs ($5\times10^9$) at regular intervals of 5 days. ***, P<0.001; versus sham group; one-way ANOVA with Tukey's multiple comparison test. Error bars indicate SEM. N=5.

FIG. 56, Panel B depicts the level of IFN-γ secreted from mouse splenic CD4+ T cells upon ex vivo treatment with colon cancer EV proteins (1 μg/mL) after the mice were immunized with mouse colon cancer EVs (10 μg) with *E. coli* aOMVs or rePDNVs ($5\times10^9$). ***, P<0.001; versus sham group; one-way ANOVA with Tukey's multiple comparison test. Error bars indicate SEM. N=3. FIG. 56, Panel C depicts the level of IL-4 secreted from mouse splenic CD4+ T cells upon ex vivo treatment with colon cancer EV proteins (1 μg/mL) after the mice were immunized with mouse colon cancer EVs (10 μg) with *E. coli* aOMVs or rePDNVs ($5\times10^9$). Versus sham group; one-way ANOVA with Tukey's multiple comparison test. Error bars indicate SEM. N=3. FIG. 56, Panel D depicts the level of IL-17 secreted from mouse splenic CD4+ T cells upon ex vivo treatment with colon cancer EV proteins (1 μg/mL) after the mice were immunized with mouse colon cancer EVs (10 μg) with *E. coli* aOMVs or rePDNVs ($5\times10^9$). ***, P<0.001; versus sham group; one-way ANOVA with Tukey's multiple comparison test. Error bars indicate SEM. N=3.

FIG. 58, Panel B depicts the number of platelets in the blood of mice immunized intraperitoneally with human melanoma EVs (10 μg) with/without *E. coli* aOMVs ($5\times10^9$) 1 week after the last immunization. Versus sham group; one-way ANOVA with Tukey's multiple comparison test. Error bars indicate SEM. N=4. FIG. 58, Panel C depicts the levels of TNF-α in the serum of mice immunized intraperitoneally with human melanoma EVs (10 μg) with/without *E. coli* aOMVs ($5\times10^9$) 1 week after the last immunization. Versus sham group; one-way ANOVA with Tukey's multiple comparison test. Error bars indicate SEM. N=4. FIG. 58, Panel D depicts the levels of IL-6 in the serum of mice immunized intraperitoneally with human melanoma EVs (10 μg) with/without *E. coli* aOMVs ($5\times10^9$) 1 week after the last immunization. Versus sham group; one-way ANOVA with Tukey's multiple comparison test. Error bars indicate SEM. N=4.

FIG. 60, Panel B depicts the level of IFN-γ secreted from mouse splenic CD4+ T cells upon ex vivo treatment with human melanoma EVs after the mice were immunized with 10 μg of human melanoma EVs with/without *E. coli* aOMVs ($5\times10^9$). ***, P<0.001; versus sham group; one-way ANOVA with Tukey's multiple comparison test. Error bars indicate SEM. N=3. FIG. 60, Panel C depicts the level of IL-4 secreted from mouse splenic CD4+ T cells upon ex vivo treatment with human melanoma EVs after the mice were immunized with 10 μg of human melanoma EVs with/without *E. coli* aOMVs ($5\times10^9$). Versus sham group; one-way ANOVA with Tukey's multiple comparison test. Error bars indicate SEM. N=3. FIG. 60, Panel D depicts the level of IL-17 secreted from mouse splenic CD4+ T cells upon ex vivo treatment with human melanoma EVs after the mice were immunized with 10 μg of human melanoma EVs with/without *E. coli* aOMVs ($5\times10^9$). ***, P<0.001; versus sham group; one-way ANOVA with Tukey's multiple comparison test. Error bars indicate SEM. N=3.

DEFINITIONS

Figure 1A:
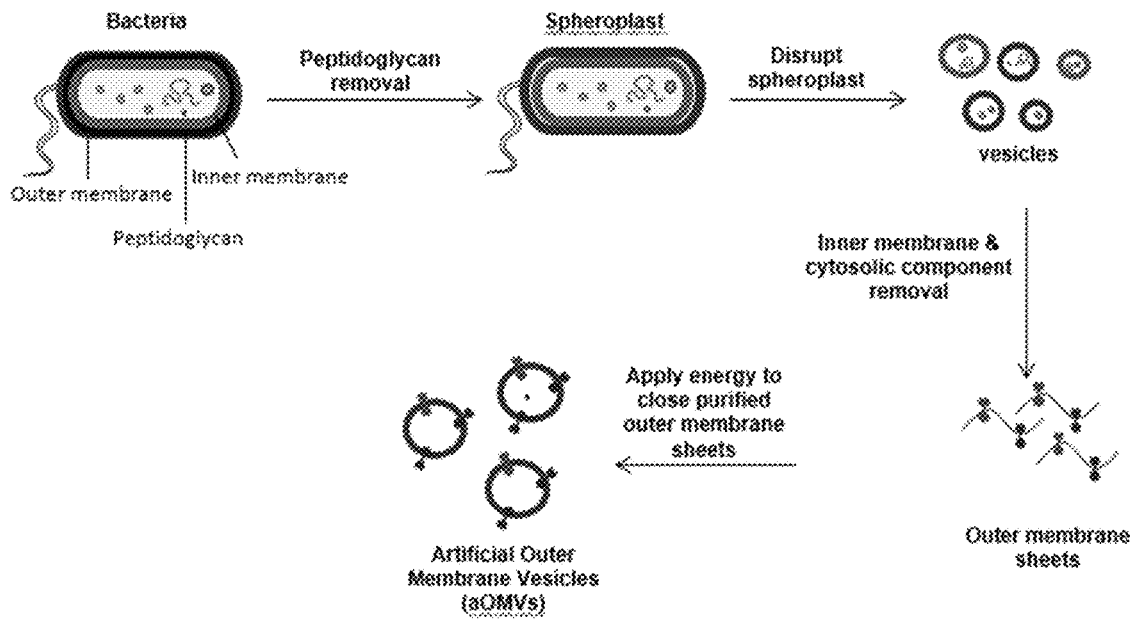
FIG. 1A depicts steps for generating artificial outer membrane vesicles (aOMVs) from a gram-negative bacterium.

The term "pathogenic" as used herein refers to organisms that cause disease, particularly in animals and especially in humans.

The term "non-pathogenic" refers to organisms that do not cause disease in animals, in particular in humans. The term includes commensal organisms. Commensal organisms are those that can colonize a host organism without signs of disease.

A "gram-negative bacterium" refers to bacterium that has been classified as such based on Gram stain test. A gram-negative bacterium includes a cell wall composed of an outer membrane, periplasmic space that includes proteins such as lipoproteins and a peptidoglycan layer. The outer membrane (OM) is made of an asymmetric lipid bilayer, the inner leaflet of the lipid layer is composed of phospholipids and the outer leaflet of the lipid layer is composed of lipopolysaccharides (LPS). The OM houses outer membranes proteins, such as, outer membrane protein A (OmpA), OmpE, OmpC, LptD, BamA, etc.

A "gram-positive bacterium" refers to bacterium that has been classified as such based on Gram stain test. A gram-positive bacterium includes a cell wall composed of peptidoglycan, teichoic acid, and lipoteichoic acid. A gram-positive bacterium lacks an outer membrane. The cell wall in both gram-positive bacterium and gram-negative bacterium enclose an inner membrane made of a phospholipid bilayer, which includes several proteins. The inner membrane is also referred to as a cell membrane, plasma membrane, or a cytoplasmic membrane. The plasma membrane in prokaryotic cells surrounds a cytoplasm that includes nucleic acids, cytoplasmic proteins, and ribosomes.

The term "outer membrane vesicle(s)" or "OMV(s)" as used herein refers to vesicles that include an outer membrane enclosing periplasmic contents, cytoplasmic contents and inner membrane components. The term OMVs includes blebs produced by budding of the outer membrane of organisms, such as, gram-negative bacteria. Such OMVs can also be referred to as native OMVs. OMVs can also be produced by disrupting (e.g., by extrusion, sonication, detergents, or osmotic shock) a gram-negative bacterium in a hydrophilic solution thereby forcing the cell to form vesicles.

The term "spheroplast," as used herein, refers a spherical structure produced from a cell by removing the peptidoglycan layer of the cell. A spheroplast includes an outer membrane and an inner membrane. A spheroplast may be generated from a bacterial, archaeal, fungal, or plant cell. A spheroplast may be generated from a gram-negative bacterium.

The term "protoplast," as used herein, refers to a bacterial, archaeal, fungal, or plant cell in which the cell wall is partially or completely removed, exposing the cytoplasmic membrane. A protoplast may be produced from a gram-negative or a gram-positive bacterium.

The term "protoplast-derived vesicle," as used herein, is intended to refer to a sub-protoplast sized vesicle the interior of which contains cytoplasmic component which is separated from the outside environment only by a lipid bilayer membrane composed of cell membrane lipids and membrane proteins. Protoplast derived vesicles (PDVs) may be protoplast derived nanovesicles which differ from each other in size. Nanovesicles may have a diameter in the range of 1 nm to less than 1 µm, e.g., 1 nm-999 nm. Examples of the protoplast-derived vesicles include, but are not limited to, those that are spontaneously secreted from protoplasts, those that are artificially synthesized from protoplasts using a physical, mechanical, electrical or chemical method, and those that are prepared by treatment with a specific substance or by a genetic modification which induces the secretion of vesicles from protoplasts.

The term "vesicle" as used herein refers to a spherical structure which contains an interior volume that is separated from the outside environment by a lipid bilayer membrane. A vesicle can be secreted from cells or can be artificially synthesized from a cell, a spheroplast, or a protoplast. A vesicle is generally smaller than the cell, a spheroplast, or a protoplast from which it is derived. A vesicle may be an outer membrane vesicle or a cell membrane vesicle (e.g. a protoplast derived vesicle).

The term "revesiculation" and grammatical equivalents thereof, as used herein refers to a process of opening a vesicle, e.g., an outer membrane vesicle, a protoplast-derived vesicle, or a tumor vesicle, such that the interior contents of the vesicle are released, followed by isolation of the open lipid bilayer membrane, and closing of the open lipid bilayer membrane to reform vesicles. Such vesicles are referred to as revesiculated vesicles.

The term "non-revesiculated" and grammatical equivalents thereof, as used herein refers to a vesicle, e.g., an outer membrane vesicle, a protoplast-derived vesicle, or a tumor vesicle that has not been revesiculated, i.e., has not been subjected to the process of opening the vesicle such that the interior contents of the vesicle are released, followed by isolation of the open lipid bilayer membrane, and closing of the open lipid bilayer membrane to reform vesicles. Thus, a non-revesiculated vesicle encloses more of the interior contents of the cell from which it is derived as compared to a revesiculated vesicle prepared from the same type of cell.

The term "deficient" as used in the context of a component present in the non-naturally occurring outer membrane vesicles (artificial OMVs, aOMVs) derived from a bacterium as disclosed herein means having at least 50% less of the component, for example, 60%, 70%, 80%, 90%, or 99%, as compared to amount of the component present in naturally occurring OMVs or non-revesiculated OMVs produced from the bacterium. The term "deficient" as used in the context of a component present in the revesiculated protoplast derived vesicles (rePDVs) derived from a bacterium as disclosed herein means having at least 50% less of the component, for example, 60%, 70%, 80%, 90%, or 99%, as compared to amount of the component present in non-revesiculated protoplast derived vesicles produced from the same bacterium.

The term "enriched" as used in the context of a protein (e.g., an outer membrane protein, OMP) present in the aOMVs derived from a bacterium as disclosed herein means that the component makes up a bigger fraction of the total amount of protein in the aOMVs as compared to the fraction of the same protein in naturally occurring OMVs produced by the bacterium or in non-revesiculated OMVs produced from the bacterium. For example, the enriched protein may represent at least 25% or more of the total proteins in the aOMVs while the same protein may represent at most 20% of the total proteins in the naturally occurring OMVs. An enriched component may be present in the aOMVs at a higher concentration by total weight, e.g., at least a three-fold greater concentration by total weight, e.g., at least 5-fold greater concentration, at least 10-fold greater concentration, at least 30-fold greater concentration, at least 50-fold greater concentration, or at least 100-fold greater concentration than the concentration of that component by total weight in OMVs or non-revesiculated OMVs isolated from the same bacterium from which the aOMVs were derived.

The term "enriched" as used in the context of a protein (e.g., a plasma membrane protein) present in the rePDVs derived from a bacterium as disclosed herein means that the component makes up a bigger fraction of the total amount of protein in the rePDVs as compared to the fraction of the same protein in non-revesiculated PDVs produced from the bacterium. For example, the enriched protein may represent at least 25% or more of the total proteins in the rePDVs while the same protein may represent at most 20% of the total proteins in the non-revesiculated PDVs. An enriched component may be present in the rePDNVs at a higher concentration by total weight, e.g., at least a three-fold greater concentration by total weight, e.g., at least 5-fold greater concentration, at least 10-fold greater concentration, at least 30-fold greater concentration, at least 50-fold greater concentration, or at least 100-fold greater concentration than the concentration of that component by total weight in PDVs (i.e., non-rePDVs) derived from the same bacterium from which the rePDVs were derived.

As used herein, the term "extracellular vesicle" means a vesicle released by a eukaryotic, e.g., a mammalian cell. Examples of "extracellular vesicles" include exosomes, ectosomes, microvesicles, prostasomes, oncosomes, and apoptotic bodies. As used herein, the term "tumor vesicle" refers to an extracellular vesicle released by a tumor cell. A tumor vesicle may be revesiculated to produce a reTV such as revesiculated tumor micro or nanovesicles (reTMVs or reTNVs). "Enriched" in the context of a component enriched in the reTVs disclosed herein means that the enriched component is present in the reTVs at a higher concentration by total weight, e.g., at least a three-fold greater concentration by total weight, e.g., at least 5-fold greater concentration, at least 10-fold greater concentration, at least 30-fold greater concentration, at least 50-fold greater concentration, or at least 100-fold greater concentration than the concentration of that component by total weight in naturally occurring tumor vesicles and TVs that are not re-vesiculated.

Thus, if the concentration of a particular component is 1 microgram per gram of total cell preparation (or of total cell protein), an enriched preparation would contain greater, e.g., at least 3 micrograms of the component per gram of total cell preparation (or of total cell protein).

The term "protective immunity" means that a vaccine or immunization schedule that is administered to a mammal induces an immune response that prevents, retards the development of, or reduces the severity of a disease that is caused by a pathogen, or diminishes or altogether eliminates the symptoms of the disease.

The term "inflammatory response" as used herein refers to secretion of proinflammatory cytokines, activation of toll-like receptors (TLR) and/or systemic inflammation. Examples of proinflammatory cytokines include IL-1, TNF-$\alpha$ and IL-6.

The term "reduced" in the context of inflammatory response means production of a lower level of a proinflammatory cytokine upon administration of aOMVs as compared to that produced by administering naturally occurring OMVs produced by the bacterium. In some embodiments, production of cytokines is lowered by at least 5%, for example, at least 10%, at least 20%, at least 30%, at least 40%, at least 50%, at least 60% or more as compared to that produced by administering naturally occurring OMVs. Examples of proinflammatory cytokines include IL-2, IL-4, IL-6, IL-12, IL-12p70, IL-17, tumor necrosis factor alpha (TNF-$\alpha$) and interferon gamma (IFN-$\gamma$).

The term "toxic response" as used herein refers to any harmful reaction that occurs in the affected cells and adjacent tissues in a subject in response to administration of a composition to the subject. Examples of toxic responses include, but are not limited to, reduction in the number of leukocytes, reduction in the number of platelets, and/or body weight.

The phrase "specifically binds to an antibody" or "specifically immunoreactive with", when referring to an antigen such as a polysaccharide, phospholipid, protein or peptide, refers to a binding reaction which is based on and/or is probative of the presence of the antigen in a sample which may also include a heterogeneous population of other molecules. Thus, under designated immunoassay conditions, the specified antibody or antibodies bind(s) to a particular antigen or antigens in a sample and do not bind in a significant amount to other molecules present in the sample. Specific binding to an antibody under such conditions may require an antibody or antiserum that is selected for its specificity for a particular antigen or antigens.

The phrase "in a sufficient amount to elicit an immune response to epitopes present in said preparation" means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay, flow cytometry, immunoprecipitation, Ouchter-Lowny immunodiffusion, spot blot, Western blot, antigen arrays, etc.

A "surface antigen" is an antigen that is present in a surface structure of a cell.

The term "endogenous" refers to a naturally-occurring biological component of a cell, i.e., as found in nature.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to a coding sequence. "Heterologous" as used herein in the context of genes or proteins includes bacterial genes or proteins that are naturally expressed in two different bacterial strains. Genes and proteins are also said to be "heterologous" where they expressed in the same strain, but originate from different strains. For example, a strain that expresses an endogenous outer membrane polypeptide and also expresses a recombinant outer membrane polypeptide that differs in amino acid sequence from the endogenous outer membrane polypeptide (e.g., is of a different variant group or variant subtype) is said to contain a heterologous outer membrane polypeptide.

"Recombinant" as used herein refers to nucleic acid encoding a gene product, or a gene product (e.g., polypeptide) encoded by such a nucleic acid, that has been manipulated by the hand of man, and thus is provided in a context or form in which it is not found in nature. "Recombinant" thus encompasses, for example, a nucleic acid encoding a gene product operably linked to a heterologous promoter (such that the construct that provides for expression of the gene product from an operably linked promoter with which the nucleic acid is not found in nature). For example, a "recombinant outer membrane polypeptide" encompasses an outer membrane polypeptide encoded by a construct that provides for expression from a promoter heterologous to the outer membrane polypeptide coding sequence, outer membrane polypeptides that are modified relative to a naturally-occurring outer membrane (e.g., as in a fusion protein), and the like. It should be noted that a recombinant outer membrane polypeptide can be endogenous to or heterologous to a cell in which such a recombinant nucleic acid is present.

The term "neoantigen" or "neoantigenic" means a class of tumor antigens that arises from a tumor-specific mutation(s) which alters the amino acid sequence of genome encoded proteins.

A "knock-out" or "knockout" of a target gene refers to an alteration in the sequence of the gene that results in a decrease of function of the target gene, e.g., such that target gene expression is undetectable or insignificant, and/or the gene product is not functional or not significantly functional. For example, a "knockout" of a gene involved in LPS synthesis indicates means that function of the gene has been substantially decreased so that the expression of the gene is not detectable or only present at insignificant levels and/or a biological activity of the gene product (e.g., an enzymatic activity) is significantly reduced relative to prior to the modification or is not detectable. "Knock-outs" encompass conditional knock-outs, where alteration of the target gene can occur upon, for example, exposure to a predefined set of conditions (e.g., temperature, osmolarity, exposure to substance that promotes target gene alteration, and the like.

"Isolated" refers to an entity of interest that is in an environment different from that in which it may naturally occur. "Isolated" is meant to include entities that are within samples that are substantially enriched for the entity of interest and/or in which the entity of interest is partially or substantially purified.

The terms "subject" and "patient" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The terms "treatment," "treat," or "treating," as used herein cover any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

The term "therapeutic effect" refers to some extent of relief of one or more of the symptoms of a disorder (e.g., infection, a neoplasia or tumor) or its associated pathology. "Therapeutically effective amount" as used herein refers to an amount of an agent which is effective, upon single or multiple dose administration to the cell or subject, in prolonging the survivability of the patient with such a disorder, reducing one or more signs or symptoms of the disorder, preventing or delaying, and the like beyond that expected in the absence of such treatment. "Therapeutically effective amount" is intended to qualify the amount required to achieve a therapeutic effect. A physician or veterinarian having ordinary skill in the art can readily determine and prescribe the "therapeutically effective amount" (e.g., ED50) of the pharmaceutical composition required. For example, the physician or veterinarian could start doses of the vesicles of the present disclosure employed in a pharmaceutical composition at levels lower than that required in order to achieve the desired therapeutic effect and gradually increase the dosage until the desired effect is achieved.

Any cells, agents, vesicles, compositions or methods provided herein can be combined with one or more of any of the other cells, agents, vesicles, compositions and methods provided herein, regardless of whether they are disclosed in separate sections of the application or within the same section of the application.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a vesicle" includes a plurality of such vesicles and reference to "the vesicle" includes reference to one or more vesicles and equivalents thereof known to those skilled in the art, reference to "a bacterium" includes a plurality of bacteria of the same type, reference to "a protoplast" includes reference to a plurality of such protoplasts, reference to "a spheroplast" includes reference to a plurality of such spheroplasts, reference to "a neoantigen" includes reference to one or more neoantigens that may be different, reference to "a heterologous protein" includes reference to one or more heterologous protein that may be different, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

DETAILED DESCRIPTION

Non-naturally occurring vesicles derived from bacteria, e.g., pathogenic bacteria, methods for making the vesicles, and methods for using compositions of these vesicles are disclosed. Methods of using the vesicles include prevention and/or treatment of bacterial infections. Also provided herein are compositions that include vesicles derived from bacteria and tumor vesicles, methods for making the tumor vesicles, and methods for using the compositions of bacterial vesicles and tumor vesicles. Methods of using the compositions of bacterial vesicles and tumor vesicles include treatment of cancer in a subject. Tumor vesicles may be derived from cancer cells present in the subject to be treated or from a cancer cell line expressing at least one neoantigen. The neoantigen may be specific to the subject and may have been identified by sequencing of cancer cells from the subject. The neoantigen may be a neoantigen known to be commonly expressed in a particular type of cancer. These aspects of the present disclosure are described in further detail in the following sections.

Bacterial Vesicles

Artificial Outer Membrane Vesicles and Compositions Thereof

The present disclosure provides non-naturally occurring artificial outer membrane vesicles (aOMVs) derived from a gram-negative bacterium. The aOMVs derived from a gram-negative bacterium are distinguishable from the naturally occurring outer membrane vesicles (OMVs) produced by the gram-negative bacterium on the basis of one or more of the following features: the aOMVs are enriched in outer membrane proteins and are deficient in one or more of the following components present in the gram-negative bacterium: inner membrane proteins, nucleic acids, cytoplasmic proteins, and ribosomes.

In certain aspects, in the aOMVs enriched in outer membrane proteins, the outer membrane proteins represent a higher fraction of the total protein content of the aOMVs as compared to naturally occurring OMVs. In certain aspects, the aOMVs have a higher amount of an outer membrane protein (OMP) per total amount of proteins, e.g., at least a three-fold greater concentration by total concentration, e.g., at least 5-fold greater concentration, at least 10-fold greater concentration, at least 30-fold greater concentration, at least 50-fold greater concentration, or at least 100-fold greater concentration than the concentration of that OMP by total protein concentration in OMVs produced from the same bacterium from which the aOMVs are derived.

In certain aspects, in the aOMVs enriched in outer membrane proteins, the outer membrane protein representing a higher fraction of the total protein content of the aOMVs as compared to naturally occurring OMVs secreted by the same bacterium from which the aOMVs are derived, may be a porin or BamA. In certain aspects, the aOMVs described herein may have a higher amount of a porin and/or BamA per total amount of proteins in the aOMVs as compared to OMVs and to OMVs prepared by a process different from the process of making the aOMVs as disclosed herein.

In certain aspects, the aOMVs provided herein may be derived from a gram-negative bacterium by disrupting a spheroplast prepared from the gram-negative bacterium to generate vesicles comprising outer membrane and vesicles comprising inner membrane; exposing the vesicles to an ionic surfactant to disrupt the vesicles comprising inner membrane and to an alkaline pH to open the vesicles comprising outer membrane thereby generating outer membrane sheets; purifying the outer membrane sheets; and applying energy or force to the purified outer membrane sheets sufficient to convert the outer membrane sheets into OMVs, thereby generating the non-naturally occurring OMVs. The step of removing vesicles that include inner membrane by treatment with an ionic surfactant reduces contamination from inner membrane components. The step of opening the vesicles releases any inner membrane, periplasmic, cytoplasmic components present within the vesicles and revesiculation of the open outer membrane sheets provides OMVs that are enriched in OMPs and are deficient in one or more of inner membrane, periplasmic, and cytoplasmic components. The aOMVs may have the same topology of the lipid bilayer as the cell from which they are derived. In certain aspects, the aOMVs of the present disclosure are prepared by removing inner membrane contamination by exposing vesicles generated from spheroplasts to an ionic surfactant and to an alkaline pH to open the vesicles to release any inner membrane, periplasmic, or cytoplasmic components present within the vesicles prior to reforming the vesicles.

In certain aspects, the aOMVs provided herein are enriched in outer membrane proteins such that the outer membrane proteins are at least 25% of the total protein content of the aOMVs. In contrast, outer membrane proteins generally form at most only 15% of the total protein content of OMVs produced by the same gram-negative bacterium from which the aOMVs are derived. In certain aspects, the aOMVs provided herein are enriched in outer membrane proteins such that the outer membrane proteins form at least 30%, at least 35%, at least 40%, at least 50%, or more (e.g., 25%-80%, 25%-75%, 25%-70%, 25%-50%, 25%-40%, 30%-80%, 30%-75%, 30%-70%, 30%-50%, 30%-40%) of the total protein content of the aOMVs.

In certain aspects, the aOMVs provided herein are deficient in one, two, or more of the following non-outer membrane components present in the bacterium from which the aOMVs are derived: peptidoglycans, periplasmic proteins, inner membrane proteins, nucleic acids, cytoplasmic proteins, and ribosomes. In certain aspects, the aOMVs are deficient in one, two, or more of the non-outer membrane components such that the amount of a non-outer membrane component present in the aOMVs is reduced by at least 50% (e.g., at least 55%, 60%, 65%, 70%, or more, e.g., up to 90%, 95%, 99%, or 100%) as compared to the amount of the same non-outer membrane component present in OMVs produced by the gram-negative bacterium.

In certain aspects, the aOMVs provided herein are deficient in cytosolic proteins such that the amount of cytosolic proteins present in the aOMVs is less than 25%, e.g., less than 20%, 15%, or 10% of the total protein content of the aOMVs. In contrast, the OMVs produced by the same gram-negative bacterium may include an amount of cytoplasmic proteins that is at least 50% (e.g., at least 60%, 65%, 70%, or more) of the total protein content of the OMVs.

In certain aspects, the aOMVs provided herein are deficient in inner membrane proteins such that the amount of inner membrane proteins present in the aOMVs is less than 20%, e.g., less than 15%, or 10% of the total protein content of the aOMVs. In contrast, the OMVs produced by the same gram-negative bacterium may include an amount of inner membrane proteins that is at least 25% (e.g., at least 30%, 40%, or up to 50%) of the total protein content of the OMVs.

In certain aspects, the aOMVs provided herein are enriched in outer membrane proteins such that at least 25% (e.g., at least 30%-40%) of the total protein content of the aOMVs are outer membrane proteins and these aOMVs are deficient in cytosolic proteins such that less than 25% (e.g. 1%-20% or less) of the total protein content of the aOMVs are cytosolic proteins.

The aOMVs of the present disclosure may be roughly spherical in shape. The aOMVs may range in diameter or greatest dimension from 20 nm-200 nm, e.g., 40 nm-200 nm, 50 nm-200 nm, 30 nm-175 nm, 30 nm-150 nm, 40 nm-175 nm, or 50 nm-150 nm. The aOMVs of the present disclosure may also be referred to as aOMV particles, reOMVs, or revesiculated aOMVs.

In certain aspects, the aOMVs may be derived from a gram-negative bacterium that is genetically modified for decreased production of lipopolysaccharides (LPS). The genetic modification may include a mutation resulting in decreased activity in one or more proteins required for LPS synthesis. The genetic modification may include a mutation resulting in reduced Lipid A.

In certain aspects, the gram-negative bacterium is genetically modified for increased expression of an endogenous outer membrane protein, such as, an OMP that is a virulence factor and increases immunogenicity of the aOMVs as compared to immunogenicity of aOMVs derived from a gram-negative bacterium not genetically modified for decreased production of the OMP.

In certain aspects, the gram-negative bacterium is genetically modified for expression of a heterologous protein in the outer membrane. The heterologous protein may be a cancer antigen. Any cancer antigen may be expressed in the gram-negative bacterium. In certain aspects, the cancer antigen may be an antigen that is localized to the outer membrane. In certain aspects, the heterologous protein is an outer membrane protein from a different gram-negative bacterium. The heterologous protein may be an OMP from a gram-negative bacterium that is a different strain, a different species, or different genus as compared to the genetically modified gram-negative bacterium.

In certain aspects, compositions that include the aOMVs are provided. The compositions may include the aOMVs and a carrier, diluent, vehicle, excipient, and the like. In certain aspects, the compositions of the present disclosure may include the aOMVs and a pharmaceutically acceptable carrier, diluent, vehicle, excipient, and the like. In certain aspects, the compositions may further include an additional prophylactic or therapeutic agent. As used herein, a carrier, diluent, vehicle, excipient, and the like includes salt, buffer, antioxidant (e.g., ascorbic acid and sodium bisulfate), preservative (e.g., benzyl alcohol, methyl parabens, ethyl or n-propyl, p-hydroxybenzoate), emulsifying agent, suspending agent, dispersing agent, solvent, filler, bulking agent, detergent, and/or adjuvant. For example, a suitable vehicle may be physiological saline solution or buffered saline, possibly supplemented with other materials common in pharmaceutical compositions for, e.g., parenteral administration. Neutral buffered saline or saline mixed with serum albumin are further exemplary vehicles. Those skilled in the art will readily recognize a variety of buffers that could be used in the compositions. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS). In certain aspects, an adjuvant included in the disclosed compositions may be poly-ICLC, 1018 ISS, aluminum salts, Amplivax, AS15, BCG, CP-870, 893, CpG7909, CyaA, dSLIM, GM-CSF, IC30, IC31, Imiquimod, ImuFact IMP321, IS Patch, ISS, ISCOMATRIX, JuvImmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, acrylic or methacrylic polymers, or copolymers of maleic anhydride and Aquila's QS21 stimulon.

In certain aspects, a composition may include a first population of aOMVs generated from a first gram-negative bacterium and a second population of aOMVs generated from a second gram-negative bacterium, where the first and second gram-negative bacterium are different from each other, e.g., are different strains, different species, or different genus. In certain aspects, a composition may include a first, a second, a third, a fourth, or more populations of aOMVs derived from different types of gram-negative bacteria.

The aOMVs described herein may be synthesized from any gram-negative bacterium, e.g., pathogenic gram-negative bacterium, such as, any human and/or animal pathogen. In certain aspects, the bacterium may be from genus *Escherichia, Pseudomonas, Moraxella, Shigella, Treponema, Porphyromonas, Helicobacter, Neisseria, Kingella, Acinetobacter, Brucella, Bordetella, Haemophilus, Chlamydia, Legionella, Proteus,* or *Yersinia*. In certain aspects, the gram-negative bacterium may be from the genus *Escherichia*. In certain aspects, the gram-negative bacterium may be from the genus *Pseudomonas*. In certain aspects, the gram-negative bacterium may be *E. coli, N. meningitidis, N gonorrhoeae, N. lactamica, Moraxella catarrhalis, Shigella flexneri, Pseudomonas aeruginosa, Porphyromonas gingivalis, Treponema pallidum, Haemophilus influenzae, H. influenzae, Y. pestis, Helicobacter pylori, Chlamydia, Listeria, Francisella, Brucella, Shigella, Salmonella, Streptococcus, Neisseria* or *Mycobacterium*. In certain aspects, the gram-negative bacterium may be *P. aeruginosa*. In certain aspects, the gram-negative bacterium may be *E. coli*, e.g., an extraintestinal pathogenic *E. coli* (ExPEC), enterotoxigenic *E. coli* (ETEC), enteropathogenic *E. coli* (EPEC), enterohemorrhagic *E. coli* (EHEC), Shiga toxin-producing *E. coli* (STEC), enteroaggregative *E. coli* (EAEC), enteroinvasive *E. coli* (EIEC) or diffuse adhering *E. coli* (DAEC). In certain aspects, the *E. coli* may be ETEC, EPEC, EHEC, STEC, EAEC, EIEC or DAEC strains of *E. coli*.

Revesiculated Protoplast Derived Vesicles and Compositions Thereof

The present disclosure also provides vesicles that are derived from a protoplast generated from a bacterium, such as, a gram-negative bacterium or a gram-positive bacterium. These inner membrane vesicles are referred to as revesiculated protoplast-derived vesicles (rePDVs) as they are generated by a process that involves opening the vesicles generated from protoplast to release their cytoplasmic content and re-forming the vesicles. rePDVs are roughly spherical and can range in size, e.g., diameter or largest dimension, from 10 nm-200 nm, e.g., 20 nm-200 nm, 30 nm-200 nm, 40 nm-200 nm, 50 nm-200 nm, 30 nm-175 nm, 30 nm-150 nm, 40 nm-175 nm, or 50 nm-150 nm. rePDVs may also be referred to as revesiculated protoplast-derived nanovesicles (rePDNVs). PDVs may also be referred to as protoplast-derived nanovesicles (PDNVs).

In certain aspects, the rePDVs are generated from a gram-negative bacterium and are deficient in one or more of the following components present in the gram-negative bacterium: outer membrane proteins, nucleic acids, cytoplasmic proteins, and ribosomes.

In certain aspects, the rePDVs are generated from a gram-positive bacterium and are deficient in one or more of the following components present in the gram-positive bacteria: cell wall components, such as, peptidoglycan, teichoic acid, and lipoteichoic acid; nucleic acids; cytoplasmic proteins; and ribosomes.

In certain aspects, the rePDVs are enriched for inner membrane proteins (i.e. plasma membrane proteins) and are deficient in cytosolic proteins as compared to protoplast-derived nanovesicles (PDVs) that have not been subjected to revesiculation. For example, PDVs are generated from a protoplast generated from a bacterium by disrupting the protoplast to generate vesicles in which the inner membrane is enclosing the cytoplasmic contents of the bacterium. These vesicles are purified to obtain a population of PDVs. In embodiments of the revesiculation method disclosed herein for generating rePDVs, the purified PDVs are exposed to an alkaline pH sufficient to open the PDVs. The inner membrane sheets are isolated and reclosed to generate rePDVs. The rePDVs may have the same topology of the lipid bilayer as the cell from which they are derived.

In certain aspects, at least 60% (e.g., at least 65%, at least 70%, at least 75%, or at least 80%, or 60%-85%, 65%-80%, or 65%-75%) of the total protein present in the rePDVs may be inner membrane proteins. Enriched inner membrane proteins include, for example, Inner membrane protein YjiY, Succinate dehydrogenase hydrophobic membrane anchor subunit, Probable phospholipid ABC transporter-binding protein MlaD, Multidrug efflux pump subunit AcrA, ATP synthase subunit b, PTS system glucose-specific EIICB component, Protein translocase subunit SecF, Protein translocase subunit SecD, and Multidrug efflux pump subunit AcrB. In certain aspects, less than 20% (e.g., less than 15%, less than 10%, less than 5%, less than 2%, e.g. 1%-10%) of the total protein present in the rePDVs may be cytoplasmic proteins. In contrast, less than 20% (e.g., only 10%-20%) of the total protein present in the PDVs may be inner membrane proteins and more than 70% (e.g., 70-80%) of the total protein present in the PDVs may be cytoplasmic proteins, where the rePDVs and the PDVs are derived from the same bacterium.

In certain aspects, the rePDVs may be derived from a gram-negative bacterium that is genetically modified for decreased production of lipopolysaccharides (LPS). The genetic modification may include a mutation resulting in decreased activity in one or more proteins required for LPS synthesis. The genetic modification may include a mutation resulting in reduced Lipid A. In certain aspects, the rePDVs may be derived from a gram-positive bacterium that is genetically modified for decreased production of peptidoglycan, teichoic acid, and/or lipoteichoic acid.

In certain aspects, the gram-negative or gram-positive bacterium is genetically modified for increased expression of an endogenous inner membrane protein, such as, a protein that is a virulence factor and increases immunogenicity of the rePDVs as compared to immunogenicity of rePDVs derived from a bacterium not genetically modified for increased expression of the endogenous inner membrane protein.

In certain aspects, the bacterium is genetically modified for expression of a heterologous protein in the inner membrane. The heterologous protein may be a cancer antigen. Any cancer antigen may be expressed in the bacterium. In certain aspects, the cancer antigen may be an antigen that is localized to the inner membrane. In certain aspects, the heterologous protein is an inner membrane protein from a different bacterium. The heterologous protein may be an inner membrane protein from a gram-negative bacterium that is a different strain, a different species, or different genus as compared to the genetically modified gram-negative bacterium. The heterologous protein may be an inner membrane protein from a gram-positive bacterium that is a different strain, a different species, or different genus as compared to the genetically modified gram-positive bacterium.

In certain aspects, compositions that include the rePDVs are provided. The compositions may include the rePDVs and a carrier, diluent, vehicle, excipient, and the like. In certain aspects, the compositions of the present disclosure may include the rePDVs and a pharmaceutically acceptable carrier, diluent, vehicle, excipient, and the like. In certain aspects, the compositions may further include an additional prophylactic or therapeutic agent. A carrier, diluent, vehicle, excipient, and the like for making compositions comprising the rePDVs may be as provided herein, e.g., in the preceding section.

In certain aspects, a composition may include a first population of rePDVs generated from a first gram-negative bacterium and a second population of rePDVs generated from a second gram-negative bacterium, where the first and second gram-negative bacterium are different from each other, e.g., are different strains, different species, or different genus. In certain aspects, a composition may include a first, a second, a third, a fourth, or more populations of rePDVs derived from different types of gram-negative bacteria.

In certain aspects, a composition may include a first population of rePDVs generated from a first gram-positive bacterium and a second population of rePDVs generated from a second gram-positive bacterium, where the first and second gram-positive bacterium are different from each other, e.g., are different strains, different species, or different genus. In certain aspects, a composition may include a first, a second, a third, a fourth, or more populations of rePDVs derived from different types of gram-positive bacteria.

In certain aspects, a composition may include a first population of rePDVs generated from a first gram-positive bacterium and a second population of rePDVs generated from a second gram-negative bacterium.

The rePDVs described herein may be synthesized from any gram-negative bacterium, e.g., one or more of the gram-negative bacterium provided herein in the preceding section.

In certain aspects, the rePDVs described herein may be synthesized from any gram-positive bacteria, such as, pathogenic gram-positive bacteria, e.g., gram-positive bacteria pathogenic in humans and/or animals. In certain aspects, the gram-positive bacteria may be bacteria of the genus *Mycobacterium, Corynebacterium, Nocardia, Rhodococcus, Streptomyces, Enterococcus, Staphylococcus, Streptococcus* or *Bacillus, Chlamydia, Listeria, Francisella, Brucella, Shigella, Salmonella, Neisseria* or *Mycobacterium*. In certain aspects, the gram-positive bacteria may be *Enterococcus faecalis, Enterococcus faecium, Streptococcus pneumoniae, Streptococcus mutans, Staphylococcus aureus, Streptococcus pyogenes, Staphylococcus epidermidis*, or *Bacillus anthracis*.

In certain aspects, the gram-positive and gram-negative bacterium used for generating the vesicles provided herein may be wild-type bacteria as found in nature, which have not been genetically modified, e.g., have not been genetically modified to provide for low toxicity (e.g., by a mutation resulting in decreased or no expression of LPS, peptidoglycan, teichoic acid, and/or lipoteichoic acid). In certain aspects, the gram-positive and gram-negative bacterium used for generating the vesicles provided herein may be not be genetically modified to express a heterologous protein, e.g., a tumor antigen or an antibody that specifically binds to a tumor antigen.

In certain aspects, the bacterial vesicles disclosed herein, e.g., the aOMV and rePDVs, may be loaded with therapeutic agents, e.g., chemotherapeutic agents, anti-cancer antibodies, and the like. In certain aspects, the bacterial vesicles disclosed herein, e.g., the aOMV and rePDVs, may not be loaded with therapeutic agents. In certain aspects, the therapeutic agent may be an agonist of STimulator of Interferon Genes, STING. In certain aspects, the STING agonist may be a ligand of STING. In certain aspects, the ligand of STING may be 5,6-dimethylxanthenone-4-acetic acid (DMXAA) or MK-1454, a synthetic cyclic dinucleotide (CDN).

In certain aspects, the compositions comprising the bacterial vesicles as disclosed herein may not include an effective amount of an adjuvant, such as, those used to enhance immunogenicity of a composition.

Tumor Vesicles and Compositions Thereof

A "tumor vesicle" means a vesicle formed from a cell expressing a tumor antigen, e.g., a cancer cell line or cancer cells present in a tumor, where the tumor vesicle includes at least one tumor antigen. In certain aspects, the tumor antigen may be expressed on cell surface of the cell and may be exposed on the surface of the tumor vesicle. A tumor vesicle (TV) may be an extracellular vesicle (EV) secreted by a cell expressing a tumor antigen. An EV is also referred to herein as an exosome (EXO). A TV may be a revesiculated TV (reTV) formed by opening an EV, e.g., by exposing the EV to high pH, isolating the open sheets of cell membrane, and closing the open sheets of cell membrane to generate the reTVs. A reTV is also referred to herein as tumor nanovesicle "tNV". A TV that has not been revesiculated, e.g., isolated EVs secreted by a cell expressing a tumor antigen may include cytoplasmic components, such as, organelles, cytoplasmic proteins, nucleus, nucleic acids (e.g., RNA, such as, mRNA, miRNA, and the like). A reTV is deficient in such components, i.e., has at least 50% less of the component, for example, 60%, 70%, 80%, 90%, or 99% less, as compared to amount of the component present in a TV that has not been revesiculated. TVs may be roughly spherical in shape and may have a diameter smaller than the cell(s) that produced the TVs. In certain aspects, TVs may be relatively large TVs that may range in diameter from 100 nm-900 nm, e.g., 100 nm-800 nm, 100 nm-700 nm, 100 nm-600 nm, 100 nm-500 nm, 100 nm-400 nm, 100 nm-300 nm, or 100 nm-200 nm. In certain aspects, TVs may be relatively small TVs that may range in diameter from 10 nm-100 nm, e.g., 20 nm-100 nm, 30 nm-100 nm, or 40 nm-100 nm. In certain aspects, a preparation of TVs, such as a composition of TVs may include large and small TVs. The TVs in a composition of TVs may be EVs, reTVs, or a combination thereof and may include small and large TVs. In certain aspects, preparation of TVs, such as a composition of TVs may include small TVs which are also referred to herein as tEXO.

In certain aspects, the tumor vesicles may be vesicles generated from tumors using polyethylene glycol (PEG). In certain aspects, the method may involve isolating tumor vesicles secreted by cancer cells by, e.g., generating small pieces of tumor tissue; dissociating the tissue by dissolving fibrotic structures; removing cells, tissue debris, and large vesicles (by e.g., filtration and centrifugation); mixing a supernatant comprising small vesicles with PEG (e.g., 20%-80%, 30%-80%, 40%-80%, 20%-70%, 20%-60%, 40%-

60%, 45%-55%, or 50% PEG); after incubation, isolating the small vesicles; and optionally repeating mixing the small vesicles with PEG and after incubation, isolating the small vesicles, to generate tumor vesicles that include PEG. Such tumor vesicles that include PEG are referred to as tPEG.

TVs may be isolated from tumor tissue, such as, a tumor located in skin, brain, breast, lung, pancreas, stomach, esophagus, mouth, ovary, colon, bladder, testis, prostate, perineum, uterus, lymph node, bone, cartilage, and other tissues in a subject, such as, a mammalian subject, e.g., a human subject. In certain aspects, the TVs may be isolated from cancer cells, such as, solid tumors: carcinoma (e.g., adenocarcinomas, squamous cell carcinomas, or basal cell carcinoma) or sarcomas. In certain aspects, the TVs may be isolated from osteosarcomas or osteogenic sarcomas, chondrosarcomas, leiomyosarcomas, rhabdomyosarcomas, mesothelial sarcomas or mesotheliomas, fibrosarcomas, angiosarcomas or hemangioendotheliomas, liposarcomas, gliomas or astrocytomas, myxosarcomas, or mesenchymous or mixed mesodermal, tumorsosteogenic sarcoma, chordoma, lymphangiosarcoma, synovioma, Ewing's tumor, colon carcinoma, pancreatic cancer, breast cancer, ovarian cancer, prostate cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, Wilm's tumor, cervical cancer, uterine cancer, testicular cancer, lung carcinoma, small cell lung carcinoma, bladder carcinoma, epithelial carcinoma, glioma, astrocytoma, meduloblastoma, craniopharyngioma, pinealoma, hemangioblastoma, schwannoma, meningioma, melanoma, neuroblastoma, or retinoblastoma.

In certain aspects, the tumor vesicles of the present disclosure may be isolated from a cell culture of cells expressing a tumor antigen. In certain aspects, the tumor vesicles of the present disclosure are isolated from a cell culture of a cancer cell line, such as, a lung cancer cell line, ovarian cancer cell line, breast cancer cell line, brain cancer cell line, skin cancer cell line, pancreatic cancer cell line, lymph node cancer cell line, esophagus cancer cell line, oral cancer cell line, colon cancer cell line, gastric cancer cell line, bladder cancer cell line, testicular cancer cell line, prostate cancer cell line, uterine cancer cell line, lymphatic cancer cell line, bone cancer cell line, cartilage cancer cell line, etc.

A tumor antigen refers to a protein or peptide that a tumor cell possesses, which may be recognized by a tumor-specific cytotoxic T-lymphocyte (hereinafter may be abbreviated as CTL) and/or may induce a cytotoxic T-lymphocyte. A tumor antigen may be a peptide generated when a tumor antigen is degraded inside a tumor cell. This peptide may be recognized by tumor-specific cytotoxic T-lymphocytes and/or induce cytotoxic T-lymphocytes by binding to an HLA molecule and being presented on the surface of the cell. In certain aspects, a tumor antigen may be a tumor associated antigen or a tumor specific antigen. In certain aspects, a tumor antigen may be an oncogene. Examples of tumor antigen include Ras p21 protooncogenes, HER-2/neu, BCR-abl oncogenes, ErbB-2, KSA, oncofetal antigens such as alpha fetoprotein (AFP), human chorionic gonadotropin (hCG); carcinoembryonic antigen (CEA), and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn.

In certain aspects, the cell expressing a cancer antigen may be a cell expressing at least one neoantigen. For example, the cell may be a cell line genetically modified to express one or more neoantigens. In certain aspects, the cell line may be a cancer cell line. In certain aspects, the neoantigen may be a cancer antigen that is expressed in specific types of cancers, i.e., a tumor specific neoantigen. In certain aspects, the neoantigen may be a cancer antigen that is expressed by a subject, e.g., a human patient having a particular type of cancer, i.e., a patient specific neoantigen. In certain aspects, patient specific neoantigen(s) may be identified by sequencing cancer cells from the patient.

In certain aspects, a cell may be genetically modified to express a plurality of neoantigens, such as, two, three, four, or more neoantigens. Neoantigens may be proteins or peptides. In certain aspects, the neoantigens may be identified using methods known in the art, e.g., methods described in US20160339090, which is herein incorporated by reference. In certain aspects, a neoantigen may be an oncogene. In certain aspects, a neoantigen may be a neoantigen disclosed in US20180153975. In certain aspects, a neoantigen may be a mutated form of a protein selected from the group consisting of Programmed Death-Ligand 1 (PD-L1), androgen receptor (AR), Bruton's Tyrosine Kinase (BTK), Epidermal Growth Factor Receptor (EGFR), BCR-Abl, c-kit, PIK3CA, HER2, EML4-ALK, KRAS, ALK, ROS1, AKT1, BRAF, MEKJ, MEK2, NRAS, RAC1, and ESR1. In certain aspects, the neoantigen is a splice variant PD-L1, AR-V1 or AR-V7. In certain aspects, the neoantigen includes a drug resistance mutation selected from the group consisting of BTK/C481S, EGFR/T790M, BCR-Abl/T315I, BCR-Abl/Y253H, BCR-Abl/E255K, BCR-Abl/E255V, c-kit/T670L PIK3CA/E545K, PIK3CA/E542K, HER2/G776(YVMA), HER2/E545K, EML4-ALK/G1269A, KRAS/G12V/D, ALK/L196M, ALK/G1202R, ALK/S1206Y, ALK/1151T(ins), ALK/F1174C, ROS1/G2032R, AKT1/E17K, BRAF/V600E, MEK1/Q56P, MEK1/E203K, MEK1/C121S, MEK1N60E, MEK1/G128V, MEK1N/V541, MEK1/P124S, MEK1/P124L, NRAS/Q61K/L/R, NRAS/T581, MEK2/C125S, RAC1/P29S, ESR1/S463P, AR/V534E, AR/P535H, AR/L536Q, AR/L536R, AR/Y537C, AR/Y537S, AR/Y537N, AR/D538G and AR/F876L.

Also provided herein are compositions comprising the tumor vesicles and bacterial vesicles, such as, the aOMVs and/or the rePDVs described in the preceding sections. These compositions may further include a carrier, diluent, vehicle, excipient, and the like. In certain aspects, the compositions of the present disclosure may include a pharmaceutically acceptable carrier, diluent, vehicle, excipient, such as, those described herein.

In certain aspects, the compositions comprising the tumor vesicles and bacterial vesicles as disclosed herein may not include a significant amount of an adjuvant to enhance immunogenicity of a composition, where a significant amount is an amount of adjuvant effective to enhance immunogenicity of composition comprising the tumor vesicles and bacterial vesicles.

In certain aspects, the compositions provided herein, such as, compositions comprising aOMVs, rePDVs, aOMVs and tumor vesicles, and rePDVs and tumor vesicles may be freeze-dried to produce a lyophilized composition. In certain aspects, the compositions of the present disclosure may be provided in a kit that further includes a solution for dilution and/or reconstitution of the lyophilized composition.

Method of Making Bacterial Vesicles

The bacterial vesicles described in the foregoing sections may be produced using methods disclosed herein.

In certain aspects, the present disclosure provides a method for generating non-naturally occurring artificial outer membrane vesicles (aOMVs) from a gram-negative bacterium. The method may include: a) disrupting a spheroplast generated from the gram-negative bacterium to generate vesicles comprising outer membrane and vesicles comprising inner membrane; b) exposing the vesicles to an ionic surfactant to disrupt vesicles comprising inner membrane and to an alkaline pH to open the vesicles comprising outer membrane thereby generating outer membrane sheets; c) purifying the outer membrane sheets; and d) applying energy or force to the purified outer membrane sheets sufficient to convert the outer membrane sheets into OMVs, thereby generating the non-naturally occurring OMVs. In certain aspects, aOMVs may be generated by a method depicted in FIG. 1A.

In certain aspects, generating the spheroplast from the gram-negative bacterium may involve incubating the gram-negative bacterium with an enzyme having muramidase activity under conditions sufficient for removal of peptidoglycan layer in cell wall of the gram-negative bacterium, thereby converting the gram-negative bacterium into the spheroplast. In certain aspects, the enzyme having muramidase activity may be a murein hydrolase. In certain aspects, the murein hydrolase may be a glycosidase (e.g., N-acetylmuramide glycanhydrolase (also known as lysozyme)) or a glucosaminidases. In certain aspects, the murein hydrolase may be an endopeptidase or an amidase. Lysozymes are commercially available and conditions for removal of the peptidoglycan may be manufacturer's protocol which may optionally be modified to optimize results. In certain aspects, the lysozyme may be hen egg white lysozyme (HEWL).

In certain aspects, disrupting the spheroplast to generate the vesicles may involve mechanical, electrical or chemical methods. Examples of the methods include cytolysis using osmosis, electroporation, sonication, homogenization, detergent treatment, freeze-thawing, extrusion, mechanical degradation, and chemical treatment, but are not limited thereto. In a mechanical degradation method, a solution of spheroplasts is shaken together with metal, ceramic or sufficiently hard plastic balls. In certain aspects, disrupting the spheroplasts may include applying a shear force to the spheroplasts. Shear force may be applied by extruding the spheroplasts. Extrusion may include forcing the spheroplasts through pores smaller than the size of the spheroplasts. In the context of extrusion, spheroplast may be forced to sequentially pass through a series of filters having decreasing pore sizes. For example, spheroplasts are sequentially passed through three filters with respective pore sizes of 10 μm→5 μm→1 μm to form vesicles.

In certain aspects, disrupting the spheroplasts may include applying acoustic energy to the spheroplasts. Acoustic energy may be applied via a sonication device. Sonication conditions may be adjusted for the desired disruptive energy. For example, low temperature, low energy, and/or short duration for sonication may be used when disrupting spheroplasts to generate vesicles. Sonication can be performed with different degree of intensity, including low energy sonication over periods of 1 minute to 3 hours. In certain aspects, sonication may be performed using an ultrasonic probe-type device. In certain aspects, an ultrasonic bath may be used for sonication. The duration of sonication may be adjusted based on the type of device being used to perform the sonication. For example, an ultrasonic probe-type device may provide about 1000 times higher energy than an ultrasonic bath. In certain aspects, ultrasonic probe-type device may be used for disrupting the spheroplasts.

Following disruption of the spheroplasts to generate vesicles, such as, vesicles that have the outer membrane enclosing cytosolic contents and vesicles that have the inner membrane enclosing cytosolic contents (or both), these vesicles may be isolated from any remaining spheroplasts. Separation of these vesicles from spheroplasts may be performed using differences in size, density, buoyancy, etc. In certain aspects, centrifugation or filtration may be performed to isolate the vesicles.

The isolated vesicles may then be exposed to an ionic surfactant to disrupt vesicles comprising inner membrane and to an alkaline pH to open up the vesicles comprising the outer membrane. In certain aspects, the steps of exposing the vesicles to an ionic surfactant and to alkaline pH may be performed as a single step by using an alkaline solution comprising the ionic surfactant. In other aspects, exposing the vesicles to the ionic surfactant to disrupt vesicles comprising inner membrane may be performed first followed by exposing the vesicles comprising the outer membrane to the alkaline pH. In such aspects, the vesicles comprising the outer membrane may be separated from the disrupted inner membrane vesicles prior to exposing the vesicles comprising the outer membrane to the alkaline pH.

Any suitable ionic surfactant may be used for disrupting vesicles comprising inner membrane. In certain aspects, the ionic surfactant may be a detergent. In certain aspects, the detergent may be sodium lauroyl sarcosinate, also known as sarkosyl, deoxycholate, sodium dodecyl sulfate (SDS), cetyl trimethylammonium bromide (CTAB), or a combination thereof. In certain aspects, the conditions used for disruption of vesicles comprising inner membrane may involve use of 0.25%-2% sarkosyl for about 20 min, which can solubilize the inner membrane without substantially affecting the outer membrane.

In certain aspects, the alkaline pH used for opening vesicles comprising outer membrane may be a pH of 9-14, e.g., pH 9-13, pH 11-14, pH 9-12, or pH 10-12. An alkaline solution for opening vesicles comprising outer membrane may be prepared using sodium carbonate ($Na_2CO_3$), sodium hydroxide (NaOH), ammonia ($NH_3$), calcium hydroxide ($Ca(OH)_2$), potassium hydroxide (KOH), sodium hydrogen carbonate ($NaHCO_3$), or magnesium hydroxide ($Mg(OH)_2$). The duration of incubation of the vesicles comprising outer membrane in an alkaline solution may be adjusted based on the number of vesicles, total volume of the solution, and the like. In certain aspects, the duration of incubation may be 10 min-3 hrs. The incubation may be performed at room temperature (about 25° C.), 4° C., or 37° C. The incubation time may be decreased when performing incubation at a higher temperature and/or higher alkaline pH. The incubation time may be increased when performing incubation at a lower temperature and/or lower pH.

Outer membrane sheets generated from opening of vesicles comprising outer membrane may be separated from whole vesicles (i.e., unopened) vesicles by utilizing any suitable separation method. In certain aspects, purifying the outer membrane sheets may involve centrifugation, e.g., centrifugation (such as, density gradient centrifugation or density gradient ultracentrifugation), filtration, or another suitable method, such as size exclusion, dialysis, tangential flow filtration and the like. In certain aspects, purifying the outer sheet membranes may include performing centrifugation by collecting the outer membrane sheets (e.g., by centrifugation to obtain a pellet comprising the sheets) and fractionating the outer membrane sheets using density gradient centrifugation. In certain aspects, the density gradient may be formed by layering iodixanol or sucrose. For example, membrane sheets may be separated using an iodixanol gradient, such as, a density gradient formed by 10%, 30%, and 50% iodixanol. Outer membrane sheets present in a layer formed between 10% and 30% iodixanol after ultracentrifugation may be collected to provide purified outer membrane sheets.

In certain aspects, the method of generating the non-naturally occurring aOMVs may be involve applying energy or force to the purified outer membrane sheets sufficient to convert the outer membrane sheets into aOMVs. Suitable sources of energy include mild sonication, shear force, acoustic force, freeze-thaw, and the like. In certain aspects, the purified outer membrane sheets may be sonicated for a duration of time sufficient to convert the outer membrane sheets into aOMVs. In certain aspects, the purified outer membrane sheets may be sonicated by applying energy 100-1000 times less than that applied for disrupting spheroplasts. In certain aspects, mild sonication may include using an ultrasonic bath for converting the outer membrane sheets into aOMVs.

The methods of the present disclosure provide for increased yield of aOMVs as compared to prior art methods for isolating the naturally secreted OMVs. Per ml of bacterial culture, the methods of the present disclosure provide a yield of aOMVs that is at least about 2×, 3×, 4×, or even 5× higher than the number of OMVs isolated per ml of the same bacterial culture. In addition, the aOMVs compositions produced by the methods of the present disclosure have fewer contaminants as compared to those found in OMV preparations. For example, the number of aOMVs present per total amount of proteins is at least 2×, 3×, 4×, or even 5× higher than the number of OMVs per total amount of proteins. Furthermore, the aOMVs have less contamination from non-outer membrane components, such as, periplasm, inner membrane, and cytosol. Additional features of the aOMVs produced by the disclosed methods are provided in the preceding sections.

In a particular aspect, the aOMVs of the present disclosure may be prepared from an *E. coli* or *P. aeruginosa*. In a particular aspect, the aOMVs may be prepared by incubating a gram-negative bacterium (e.g., *E. coli* or *P. aeruginosa*) as a suspension in sucrose (e.g., 5%-30%), lysozyme, and EDTA (at e.g., pH 8.0) which results in removal of peptidoglycan layer. The resulting spheroplasts may be sonicated and subjected to centrifugation at different speeds to separate whole cells from membranes. The separated membranes may be freeze-thawed and incubated in a detergent (e.g., Sarkosyl). The outer membranes may be separated by centrifugation (e.g., at 40,000×g) and incubated in high pH solution and fractionated to isolate membrane layers formed between 10% and 30% iodixanol. The isolated membrane may be sonicated to produce aOMVs.

Figure 38A:
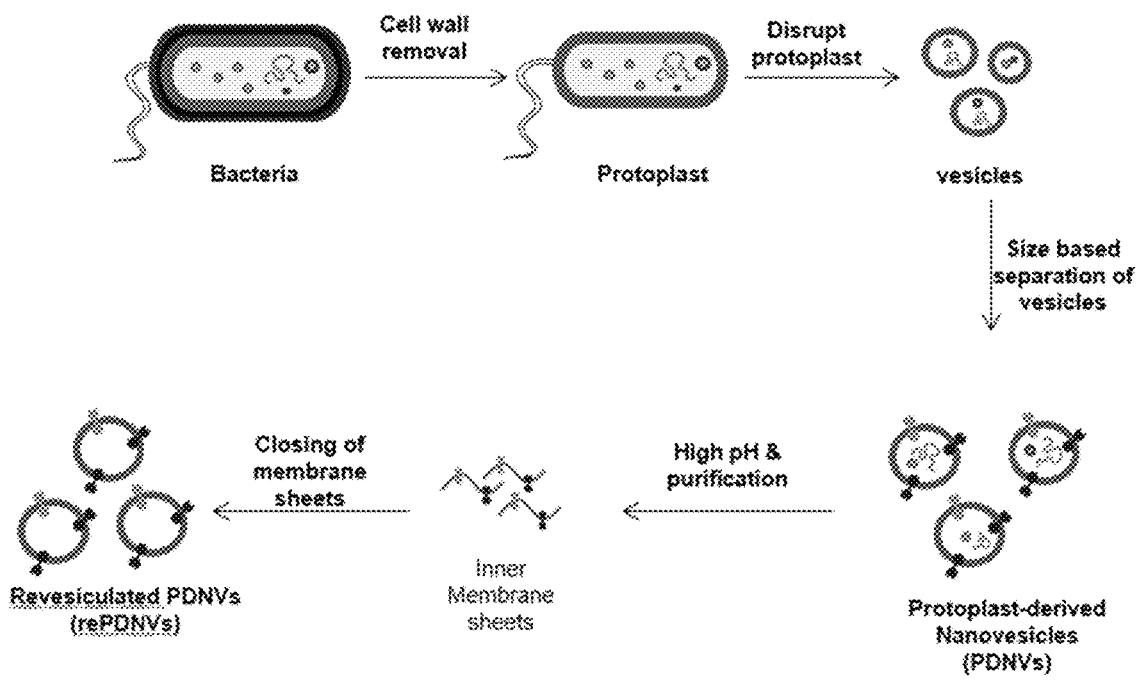
FIG. 38A depicts steps for generating revesiculated protoplast-derived nanovesicles (rePDNVs).

In certain aspects, a method for generating revesiculated protoplast derived vesicles (rePDVs) from a gram-negative bacterium is provided. The method may include: a) incubating the gram-negative bacterium with a divalent ion chelator or a surfactant under conditions sufficient to render the outer membrane sensitive to chemical or enzymatic disruption; b) chemically or enzymatically removing the outer membrane and the peptidoglycan layer in the cell wall of the gram-negative bacterium from step a), thereby converting the gram-negative bacterium into a protoplast comprising an inner membrane and lacking the outer membrane and the peptidoglycan layer; c) disrupting the protoplast to generate vesicles; d) purifying the vesicles; e) exposing the isolated vesicles to an alkaline pH to open the vesicles thereby generating inner membrane sheets; f) purifying the inner membrane sheets; and g) applying energy or force to the purified inner membrane sheets sufficient to convert the inner membrane sheets into rePDVs. In certain aspects, rePDVs may be generated by a method depicted in FIG. 38A.

In certain aspects, the step of incubating the gram-negative bacterium with a divalent ion chelator under conditions sufficient to render the outer membrane sensitive to chemical or enzymatic disruption may include incubating the bacterium with a divalent cation chelating agent, such as, an agent containing ethylenediamine (e.g., ethylenediaminetetraacetic acid (EDTA) or ethylene glycol-bis(β-aminoethyl ether)-N,N,N',N'-tetraacetic acid (EGTA)) or Porphine (e.g., porphyrins). In certain aspects, the step of incubating the gram-negative bacterium with a surfactant under conditions sufficient to render the outer membrane sensitive to chemical or enzymatic disruption may include incubating the bacterium with an ionic or a non-ionic detergent. In certain aspects, a non-ionic detergent, such as, Tween or Triton, e.g., Tween-20 or Triton X-100 may be used.

Chemically or enzymatically removing the outer membrane and peptidoglycan layer may involve using one or more of a divalent ion chelating agent and an enzyme having muramidase activity, as described herein, to produce a protoplast.

In certain aspects, disrupting the protoplast to generate vesicles may involve mechanical, electrical or chemical methods. Examples of the methods include cytolysis using osmosis, electroporation, sonication, homogenization, detergent treatment, freeze-thawing, extrusion, mechanical degradation, and chemical treatment, but are not limited thereto. In a mechanical degradation method, a solution of protoplasts is shaken together with metal, ceramic or sufficiently hard plastic balls. In certain aspects, disrupting the protoplast may include applying a shear force to the protoplast. Shear force may be applied by extruding the protoplasts. Extrusion may include forcing the protoplasts through pores smaller than the size of the protoplasts. In the context of extrusion, protoplasts may be forced to sequentially pass through a series of filters having decreasing pore sizes. For example, protoplasts are sequentially passed through three filters with respective pore sizes of 10 μm→5 μm→1 μm to form vesicles.

In certain aspects, disrupting the protoplasts may include applying acoustic energy or force to the spheroplast. Acoustic energy may be applied via a sonication device. Sonication conditions may be adjusted for the desired disruptive energy. For example, low temperature, low energy, and/or short duration for sonication may be used when disrupting protoplasts to generate vesicles. Vesicles comprising inner membrane generated from disrupting the protoplast may be purified using any appropriate method, such as, centrifugation (such as, density gradient centrifugation or density gradient ultracentrifugation), filtration, PEG-based precipitation or another suitable method.

In certain aspects, vesicles comprising inner membrane may be separated based on density to isolate vesicles that have a diameter in the range of 10 nm-700 nm. Such vesicles are referred to herein as protoplast derived nanovesicles (PDNVs) or simply as protoplast derived vesicles (PDVs). The PDVs may then be subjected to an alkaline pH sufficient to cause the vesicles to open up releasing any cytosolic or periplasmic contents, as described in the methods for generation of aOMVs herein.

The open sheets of inner membrane generated by opening of the PDVs may be purified using any suitable means (e.g., centrifugation (such as, density gradient centrifugation or density gradient ultracentrifugation), filtration, or another suitable method, such as size exclusion, dialysis, tangential flow filtration and the like).

In certain aspects, the method of generating the rePDVs may be involve applying energy to the purified inner membrane sheets sufficient to convert the inner membrane sheets into rePDVs. Suitable sources of energy include mild sonication, shear force, acoustic force, freeze-thaw, and the like. In certain aspects, the purified inner membrane sheets may be sonicated for a duration of time sufficient to convert the inner membrane sheets into rePDVs. In certain aspects, an ultrasonic bath may be used for generating the rePDVs.

The steps of opening vesicles, purifying membrane, and closing the purified membrane improves the purity of the rePDVs as compared to the PDVs. For example, these steps provide a composition of rePDVs where the number of rePDVs per total amount of protein in the composition is at least 2×, 3×, 4×, or even 5× higher than the number of PDVs per total amount of protein. Additional features of the rePDVs produced by the disclosed methods are provided in the preceding sections.

A method for generating revesiculated protoplast-derived vesicles (rePDVs) from a gram-positive bacterium is provided. The method may include: a) enzymatically or chemically removing the peptidoglycan layer in the cell wall of the gram-positive bacterium, thereby converting the gram-positive bacterium into a protoplast comprising an inner membrane and lacking the cell wall; b) disrupting the protoplast to generate vesicles; c) purifying the vesicles; d) exposing the isolated vesicles to an alkaline pH to open the vesicles thereby generating inner membrane sheets; e) purifying the inner membrane sheets; and f) applying energy or force to the purified inner membrane sheets sufficient to convert the inner membrane sheets into rePDVs.

The method of generating rePDVs from a gram-positive bacterium is similar to that for generating rePDVs from a gram-negative bacterium other than a step of removing the outer membrane is not needed.

As used herein the step of incubating or exposing vesicles to an alkaline pH may include using an alkaline solution having a pH of 9-14, e.g., pH of 10-14, pH of 11-14, pH of 12-14, or pH of 13-14.

Any gram-negative or gram-positive bacteria may be used for generating the vesicles using the methods described herein. In certain aspects, the gram-negative or gram-positive bacteria may be those listed in the preceding sections.

Method of Making aOMVs and rePDVs Comprising a Therapeutic Agent

The aOMVs and rePDVs described herein may be loaded with a therapeutic agent. In certain aspects, the therapeutic agent may be an agent that enhances the immune activation effect and/or neoplastic effect of the aOMV and the rePDV. In certain aspects, the therapeutic agent may be an agonist of STimulator of Interferon Genes, STING. In certain aspects, the STING agonist may be a ligand of STING. In certain aspects, the ligand of STING may be 5,6-dimethylxanthenone-4-acetic acid (DMXAA) or MK-1454, a synthetic cyclic dinucleotide (CDN).

In certain aspects, a therapeutic agent such as a STING agonist may be loaded into the aOMVs and the rePDVs by applying energy (e.g., by sonication) to a mixture of purified outer membrane sheets (obtained as described in the preceding sections) and the therapeutic agent to form aOMVs and rePDVs loaded with the therapeutic agent. A separation or a fractionation step may be used to separate unloaded aOMVs or rePDVs and free therapeutic agent from aOMVs or rePDVs loaded with the therapeutic agent. The fractionation step may involve separating the mixture using a density gradient formed by using 10%, 30%, and 50% iodixanol and collecting the layer formed between 30% and 50% or 10% and 30% iodixanol to obtain aOMVs or rePDVs loaded with the therapeutic agent.

Method of Making Tumor Vesicles

Tumor vesicles for the compositions and methods of the present disclosure may be generated using any suitable method, such as, the methods disclosed in U.S. Pat. No. 9,220,763 or WO2018171947, which are herein incorporated by reference. Briefly, tumor tissue or cell culture media from a culture of cells expressing a tumor antigen, e.g., a neoantigen may be obtained and tumor vesicles present in the tissue or media isolated by differential centrifugation. In some aspects, tumor cells may be disrupted to form tumor vesicles. In some aspects, cells from a tumor sample of a patient can be cultured and tumor vesicles secreted by the cells can be isolated. In some embodiments, the tumor sample is a biological fluid from a patient, e.g., lymph fluid, ascites fluid, blood, or spinal fluid from a subject.

Where the cancer cells are present in a solid tumor, the tumor vesicles released in the solid tumor may be isolated by digesting the tissue and/or chopping the tissue to generate a plurality of pieces of the tissue; and isolating the extracellular vesicles from the digested and/or chopped pieces of tissue.

In certain aspects, the EVs may be further processed by exposing the extracellular vesicles to an alkaline pH in a range of 9 to 14 to obtain membranes; isolating the membranes; and reclosing the membranes to generate revesiculated tumor vesicles.

In certain aspects, the method of generating tumor vesicles may include separating cells from a tumor tissue; constructing vesicles from a suspension of the cells by extrusion, sonication, cell lysis, homogenization, freeze-thawing, electroporation, mechanical degradation, and/or chemical treatment; and isolating the constructed vesicles from the suspension. The constructed vesicles may be further processed by exposing the extracellular vesicles to an alkaline pH in a range of 9 to 14 to obtain membranes; isolating the membranes; and reclosing the membranes to generate revesiculated tumor vesicles (reTVs).

Method of Using Vesicles

Bacterial Vesicles

Compositions comprising the bacterial vesicles provided herein may be used to induce an immune response to the bacterium from which the vesicles are derived. The immune response may be sufficient to prevent an infection from the bacterium or to treat a disorder caused by the bacterium.

In certain aspects, a method of producing an immune response to a gram-negative bacterium in a mammalian subject is provided. The method may include administering a composition comprising non-naturally occurring artificial outer membrane vesicles (aOMVs) generated from a gram-negative bacterium, wherein the aOMVs are deficient in one or more of the following components present in the gram-negative bacterium: inner membrane proteins, nucleic acids, cytoplasmic proteins, and ribosomes; and/or wherein the aOMVs are enriched in outer membrane proteins. In certain aspects, the aOMVs are as described in the preceding sections of the application. For example, the aOMVs have a diameter of 50 nm-150 nm. The OMVs may be derived from a gram-negative bacterium genetically modified for decreased production of lipopolysaccharides (LPS). The gram-negative bacterium may be genetically modified for increased expression of an endogenous outer membrane protein. The gram-negative bacterium may be genetically modified for expression of a heterologous protein in the outer membrane. The heterologous protein may be a cancer antigen. The heterologous protein may be an outer membrane protein from a different gram-negative bacterium. The composition may include OMVs generated from a first gram-negative bacterium and OMVs generated from a second gram-negative bacterium wherein the first and second gram-negative bacterium are different strains, different species, or different genus.

The composition may be administered to the subject in an amount effective to induce an immune response to the gram-negative bacterium in the mammalian subject. The immune response induced by the administering may be generation of antibodies against the gram-negative bacterium and/or activation of T cells, e.g., Th1.

In certain aspects, the administering produces reduced inflammatory response as compared to that produced by administering naturally occurring OMVs released by the gram-negative bacterium. The reduced inflammatory response may include production of a lower level of pro-inflammatory cytokines as compared to that produced by administering naturally occurring OMVs released by the gram-negative bacterium. The reduced inflammatory response may include production of a lower level of tumor necrosis factor alpha (TNF-α) and/or interleukin-6 (IL-6) as compared to that produced by administering naturally occurring OMVs released by the gram-negative bacterium.

In certain aspects, the administering produces reduced toxic response as compared to that produced by administering naturally occurring OMVs released by the gram-negative bacterium. The toxic response may include reduction in number of leukocytes, reduction in number of platelets, and/or reduction in body weight.

In certain aspects, a method of producing an immune response to a gram-negative bacterium in a mammalian subject may include administering the composition of the rePDVs produced from gram-negative bacterium as disclosed herein to the subject in an amount effective to induce an immune response to the gram-negative bacterium in the mammalian subject. As described in the preceding sections, the rePDVs may be deficient in one or more of the following components present in the gram-negative bacteria from which the rePDVs are derived: outer membrane proteins, nucleic acids, cytoplasmic proteins, and ribosomes. In certain aspects, the gram-negative bacterium from which the rePDVs may be genetically modified for decreased production of lipopolysaccharides (LPS). In certain aspects, the composition may include rePDNVs generated from a first gram-negative bacterium and rePDNVs generated from a second gram-negative bacterium wherein the first and second gram-negative bacterium are different strains, different species, or different genus. In certain aspects, the rePDNVs have a diameter of 50 nm-150 nm.

In certain aspects, the administering produces reduced inflammatory response as compared to that produced by administering PDVs derived from the gram-negative bacterium. The reduced inflammatory response may include production of a lower level of pro-inflammatory cytokines as compared to that produced by administering PDVs derived from the gram-negative bacterium. The reduced inflammatory response may include production of a lower level of tumor necrosis factor alpha (TNF-α) and/or interleukin-6 (IL-6) as compared to that produced by administering PDVs derived from the gram-negative bacterium.

In certain aspects, the administering produces reduced toxic response as compared to that produced by administering PDVs derived from the gram-negative bacterium. The toxic response may include reduction in number of leukocytes, reduction in number of platelets, and/or reduction in body weight.

In certain aspects, a method of producing an immune response to a gram-positive bacterium in a mammalian subject is provided. The method may include administering the composition comprising the rePDVs produced from gram-positive bacterium as disclosed herein to the subject in an amount effective to induce an immune response to the gram-positive bacterium in the mammalian subject. As described in the preceding sections, the rePDVs may be deficient in one or more of the following components present in the gram-positive bacteria from which the rePDVs are derived: nucleic acids, cytoplasmic proteins, and ribosomes.

In certain aspects, the compositions of bacterial vesicles, such as, the aOMVs and the rePDVs may be used to prevent or treat a bacterial infection, e.g., infection by the same bacteria as used to produce the aOMVs or rePDVs.

Treatment or prevention of any disease caused by a pathogenic bacterium is contemplated. In certain, aspects the mammalian subject has or is at risk of developing a disease or disorder caused by a pathogenic bacterium. For example, the mammalian subject has or is at risk of developing tuberculosis, pneumonia, sepsis, diarrhea, tetanus, typhoid fever, diphtheria, syphilis, meningitis, urinary tract infection, or leprosy.

In certain aspects, the mammalian subject has or is at risk of developing sepsis and wherein the OMVs or the rePDVs are generated from a strain of *Escherichia coli* (*E. coli*) that causes sepsis. In certain aspects, the mammalian subject has or is at risk of developing pneumonia and wherein the OMVs or the rePDVs are generated from *Pseudomonas aeruginosa* (*P. aeruginosa*).

In certain aspects, a subject having a disease or infection caused by bacteria may be assessed to identify the causative agent, e.g., to type the strain of the bacteria and aOMVs or rePDVs may be derived using the same strain of bacteria.

Tumor Vesicles and Bacterial Vesicles

Compositions of the tumor vesicles (e.g., the EVs or the reTVs) and the bacterial vesicles (the aOMVs and/or the rePDVs), described in the preceding sections may be used to induce an immune response against a tumor in a mammalian subject. The immune response may be effective to treat the tumor in the mammalian subject. In certain aspects, administering the compositions of the present disclosure may reduce growth of cancer cells in the subject and/or reduce the volume of tumor in the subject.

In certain aspects, a method of treating cancer in a mammalian subject may include administering a composition comprising artificial outer membrane vesicles (aOMVs) generated from a gram-negative bacterium, where the aOMVs are deficient in one or more of the following components present in the gram-negative bacterium: inner membrane proteins, nucleic acids, cytoplasmic proteins, and ribosomes, and/or wherein the OMVs are enriched in outer membrane proteins; and tumor vesicles, wherein the tumor vesicles comprise at least one tumor antigen.

In certain aspects, a method of treating cancer in a mammalian subject may include administering artificial outer membrane vesicles (aOMVs) generated from a gram-negative bacterium, where the aOMVs are deficient in one or more of the following components present in the gram-negative bacterium: inner membrane proteins, nucleic acids, cytoplasmic proteins, and ribosomes, and/or wherein the OMVs are enriched in outer membrane proteins; and administering tumor vesicles, wherein the tumor vesicles comprise at least one tumor antigen. The administering of aOMVs and tumor vesicles may be carried out simultaneously or sequentially. For example, aOMVs and tumor vesicles may be administered simultaneously (e.g., within 12 hr, 6 hr, 3 hr, 1 hr, 30 min, 10 min, or 5 min period). In certain aspects, the method of treating cancer may include sequential administration comprising first administering aOMVs followed by administration of tumor vesicles or vice versa. For example, during a sequential administration, administration of aOMVs and tumor vesicles may be separated by a time period of more than 12 hrs, e.g., more than 24 hrs, such as, 12 hrs-5 days. In certain aspects, the routes of administration of aOMVs and tumor vesicles may be the same. In certain aspects, the sites of administration of aOMVs and tumor vesicles may be the same, e.g., separated by up to 10 cm, such as, 0.1 cm-5 cm.

In certain aspects, the tumor vesicles are isolated from a tumor present in the mammalian subject. The tumor may be any tumor such as those listed herein, e.g., colon tumor, lung tumor, melanoma, ovarian tumor, gastric tumor, or pancreatic tumor.

In certain aspects, the tumor vesicles are isolated from a culture medium comprising tumor vesicles produced by a cancer cell line, as described in the preceding sections.

In certain aspects, the administering of compositions comprising the bacterial vesicles and tumor vesicles provided herein produces reduced inflammatory response as compared to that produced by administering naturally occurring OMVs released by the same bacterium or the PDVs from the same bacterium.

In certain aspects, the administering produces antibodies against the tumor and/or activates a T cell response (e.g., a Th1 cell response) against the tumor.

Any type of cancer listed herein may be treated using the compositions of the present disclosure. In certain aspects, the tumor vesicles present in the compositions may be matched to the type of cancer in a subject to be treated.

In certain aspects, the tumor in the mammalian subject is a colon tumor and the tumor vesicles are isolated from the colon tumor, the tumor in the mammalian subject is a colon tumor and the tumor vesicles are isolated from a colon cancer cell line, the tumor in the mammalian subject is a lung tumor and the tumor vesicles are isolated from the lung tumor, the tumor in the mammalian subject is a lung tumor and the tumor vesicles are isolated from a lung cancer cell line, the tumor in the mammalian subject is a melanoma, and the tumor vesicles are isolated from the melanoma, the tumor in the mammalian subject is a melanoma, and the tumor vesicles are isolated from a melanoma cell line, the tumor in the mammalian subject is a breast tumor, and the tumor vesicles are isolated from the breast tumor, the tumor in the mammalian subject is a breast tumor, and the tumor vesicles are isolated from a breast cancer cell line, the tumor in the mammalian subject is an ovarian tumor, and the tumor vesicles are isolated from the ovarian tumor; or the tumor in the mammalian subject is an ovarian tumor, or the tumor vesicles are isolated from an ovarian cancer cell line.

As demonstrated by the data provided herein, the bacterial vesicles (e.g., the aOMVs) provide an immune response superior to that provided by traditional adjuvants, such as, an adjuvant comprising aluminum, e.g., aluminum hydroxyphosphate sulfate (AAHS), aluminum hydroxide, aluminum phosphate, or potassium aluminum sulfate (Alum); Incomplete Freund's adjuvant (IFA); and/or cytosine phosphoguanine (CpG).

In certain aspects, the method for treating cancer may include administering a composition comprising a bacterial vesicle (e.g., aOMV) as disclosed herein and a tumor vesicle (e.g., a EV) as disclosed herein where the composition does not include an adjuvant, such as, an adjuvant comprising aluminum, e.g., aluminum hydroxyphosphate sulfate (AAHS), aluminum hydroxide, aluminum phosphate, or potassium aluminum sulfate (Alum); Incomplete Freund's adjuvant (IFA); and/or cytosine phosphoguanine (CpG).

In certain aspects, the treatment results in induction of antibodies against the tumor vesicles at a titer more than twice (e.g., more than 3×, 4×, or 5×) the titer of antibodies against the tumor vesicles induced using an adjuvant instead of the aOMVs.

In certain aspects, a method of treating cancer in a mammalian subject may include administering to the subject a composition comprising a bacterial vesicle (e.g., aOMV) as disclosed herein and a tumor vesicle (e.g., an EV) as disclosed herein and administering an anti-PD1 antibody. The composition and the anti-PD1 antibody may be administered simultaneously (e.g., in a single composition or as separate administrations given within a single day). The composition and the anti-PD1 antibody may be administered on different days, for example, the anti-PD1 antibody may be administered prior to the composition or vice versa. In some aspects, the treatment regimen may include multiple administrations of the composition and the anti-PD1 antibody.

In certain aspects, the bacterial vesicles (e.g., aOMVs as disclosed herein) used for treatment of cancer in a mammalian subject may be loaded with a therapeutic agent. The therapeutic agent may be a STING agonist, such as a STING ligand. In certain aspects, the STING ligand may be DMXAA. As shown in the Examples, aOMVs loaded with the STING ligand DMXAA induce an IFN-β response that is significantly higher (more than 5 times) than that produced by aOMVs alone or DMXAA alone indicating a strong synergy between aOMV and DMXAA in induction of the IFN-β response.

Immunization

Immunogenic compositions used as vaccines or for treatment may include an immunologically effective amount of the active component, e.g., bacterial vesicles (aOMVs or rePDVs) for treatment or prevention of bacterial infections, and a combination of components (e.g., tumor vesicles and aOMVs or rePDVs) for treatment of cancer, as well as any other compatible components, as needed. By "immunologically effective amount" is meant that the administration of that amount to an individual, either in a single dose or as part of a series, is effective to elicit treatment or prevention. This amount varies depending upon the health and physical condition of the individual to be treated, age, the taxonomic group of the individual to be treated (e.g., non-human primate, primate, human, etc.), the capacity of the individual's immune system to synthesize antibodies, the degree of protection desired, the formulation of the vaccine, the treating clinician's assessment of the medical situation, and other relevant factors. It is expected that the amount will fall in a relatively broad range that can be determined through routine trials.

Dosage regimen may be a single dose schedule or a multiple dose schedule (e.g., including booster doses) with a unit dosage form of the composition administered at different times. The term "unit dosage form," as used herein, refers to physically discrete units suitable as unitary dosages for human and animal subjects, each unit containing a predetermined quantity of the compositions of the present invention in an amount sufficient to produce the desired effect, which compositions are provided in association with a pharmaceutically acceptable excipient (e.g., pharmaceutically acceptable diluent, carrier or vehicle). The vaccine may be administered in conjunction with other immunoregulatory agents.

The compositions are administered in an amount effective to elicit an immune response, particularly a humoral immune response, in the subject. Amounts for the immunization of the mixture generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the composition is administered to a secluded site and not into the blood stream, such as into a body cavity or into a lumen of an organ. Substantially higher dosages (e.g. 10 to 100 mg or more) are possible in oral, nasal, or topical administration. The initial administration of the mixture can be followed by booster immunization of the same of different mixture, with at least one booster, more usually two boosters.

Routes of Administration

The present disclosure contemplates the administration of the disclosed compositions in any appropriate manner. Suitable routes of administration include parenteral (e.g., intramuscular, intravenous, subcutaneous (e.g., injection), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. In certain aspects, the compositions of bacterial vesicles and tumor vesicles may be injected into or adjacent a tumor. In certain aspects, a composition of bacterial vesicles and a composition of tumor vesicles may be administered simultaneously to a subject.

The present disclosure contemplates methods wherein the compositions of the present disclosure is administered to a subject at least twice daily, at least once daily, at least once every 48 hours, at least once every 72 hours, at least once weekly, at least once every 2 weeks, or once monthly.

Combination Therapy

The present disclosure contemplates the use of the compositions provided herein in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, compositions of the present disclosure are administered or applied sequentially, e.g., where one agent is administered prior to one or more other agents. In other embodiments, the compositions are administered simultaneously, e.g., where two or more compositions are administered at or about the same time; the two or more compositions may be present in two or more separate formulations or combined into a single formulation (i.e., a co-formulation). Regardless of whether the two or more compositions are administered sequentially or simultaneously, they are considered to be administered in combination for purposes of the present disclosure.

The compositions of the present disclosure can be used in combination with other agents useful in the treatment, prevention, suppression or amelioration of the diseases, disorders or conditions set forth herein, including those that are normally administered to subjects suffering from bacterial infections or cancer.

In certain aspects, a method of treating cancer in a subject may involve administering to the subject aOMVs, tumor vesicles, and an anti-neoplastic agent (e.g., an immunotherapeutic agent or a chemotherapeutic agent).

Useful immunotherapeutic agents include: anti-PD-1 antibody, anti-PD-L1 antibody, inhibitors of other immune check point markers, such as CTLA-4, LAG-3 and TIM-3, for example, an anti-CTLA antibody, an anti-LAG-3 antibody, and/or an anti-TIM-3 antibody. Anti-PD-1/PD-L1 immunotherapies may include but are not limited to e.g., administering to the subject an effective amount of one or more of OPDIVO® (nivolumab), KEYTRUDA® (pembrolizumab), Tecentriq™ (atezolizumab), durvalumab (MEDI4736), avelumab (MSB0010718C), BMS-936559 (MDX-1105), CA-170, BMS-202, BMS-8, BMS-37, BMS-242 and the like.

Non-limiting examples of chemotherapeutic agents include alkylating agents (e.g., nitrosoureas), antimetabolites (e.g., methotrexate), antitumor antibiotics (e.g., anthracyclins), plant alkaloids (e.g., *vinca* alkaloids, taxanes, etc.), toposiomerase inhibitors, and steroid hormones.

EXAMPLES OF NON-LIMITING ASPECTS OF THE DISCLOSURE

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

1. A composition comprising non-naturally occurring artificial outer membrane vesicles (aOMVs) generated from a gram-negative bacterium, wherein the OMVs are deficient in one or more of the following components present in the gram-negative bacterium: periplasmic proteins, inner membrane proteins, nucleic acids, cytoplasmic proteins, and ribosomes; and/or wherein the OMVs are enriched in outer membrane proteins.

2. The composition of aspect 1, wherein the aOMVs have a diameter of 50 nm-150 nm.

3. The composition of aspect 1 or 2, wherein the gram-negative bacterium is genetically modified for decreased production of lipopolysaccharides (LPS).

4. The composition of any one of aspects 1-3, wherein the gram-negative bacterium is genetically modified for increased expression of at least one endogenous outer membrane protein.

5. The composition of any one of aspects 1-4, wherein the gram-negative bacterium is genetically modified for expression of at least one heterologous protein in the outer membrane.

6. The composition of aspect 5, wherein the at least one heterologous protein comprises a cancer antigen.

7. The composition of aspect 5, wherein the at least one heterologous protein comprises an outer membrane protein from a different gram-negative bacterium.

8. The composition of any one of aspects 1-7, wherein the aOMVs are generated from a first gram-negative bacterium and the composition further comprises aOMVs generated from a second gram-negative bacterium wherein the first and second gram-negative bacterium are different strains, different species, or different genus.

9. A method of producing an immune response to a gram-negative bacterium in a mammalian subject, the method comprising administering the composition of any one of aspects 1-8 to the subject in an amount effective to induce an immune response to the gram-negative bacterium in the mammalian subject.

10. The method of aspect 9, wherein the administering produces reduced inflammatory response as compared to that produced by administering naturally occurring OMVs released by the gram-negative bacterium.

11. The method of aspect 10, wherein the reduced inflammatory response comprises production of a lower level of pro-inflammatory cytokines as compared to that produced by administering naturally occurring OMVs released by the gram-negative bacterium.

12. The method of aspect 10, wherein the reduced inflammatory response comprises production of a lower level of tumor necrosis factor alpha (TNF-α) and/or interleukin-6 (IL-6) as compared to that produced by administering naturally occurring OMVs released by the gram-negative bacterium.

13. The method of aspect 9, wherein the administering produces a reduced toxic response as compared to that produced by administering naturally occurring OMVs released by the gram-negative bacterium.

14. The method of aspect 13, wherein the reduced toxic response comprises reduction in number of leukocytes.

15. The method of aspect 13, wherein the reduced toxic response comprises reduction in number of platelets.

16. The method of aspect 13, wherein the reduced toxic response comprises reduction in body weight.

17. The method of any one of aspects 9-16, wherein the immune response comprises generation of antibodies against the gram-negative bacterium.

18. The method of any one of aspects 9-17, wherein the immune response comprises activation of T cells. 19. The method of any one of aspects 9-18, wherein the mammalian subject has or is at risk of developing sepsis and wherein the aOMVs are generated from a strain of *Escherichia coli* (*E. coli*) that causes sepsis.

20. The method of any one of aspects 9-18, wherein the mammalian subject has or is at risk of developing pneumonia and wherein the aOMVs are generated from *Pseudomonas aeruginosa* (*P. aeruginosa*).

21. A composition comprising:
artificial outer membrane vesicles (aOMVs) generated from a gram-negative bacterium, wherein the aOMVs are deficient in one or more of the following components present in the gram-negative bacterium: inner membrane proteins, nucleic acids, cytoplasmic proteins, and ribosomes, and/or wherein the aOMVs are enriched in outer membrane proteins; and tumor vesicles, wherein the tumor vesicles comprise at least one tumor antigen.

22. The composition of aspect 21, wherein the tumor vesicles are large tumor vesicles having a diameter of 100 nm-200 nm.

23. The composition of aspect 21, wherein the tumor vesicles are small tumor vesicles having a diameter of 40 nm-100 nm.

24. The composition of aspect 21, wherein the tumor vesicles comprise large tumor vesicles having a diameter of 100 nm-200 nm and small tumor vesicles having a diameter of 40 nm-100 nm.

25. The composition of any one of aspects 21-24, wherein the tumor vesicles are isolated from a tumor present in a mammalian subject.

26. The composition of aspect 25, wherein the tumor is a colon tumor, lung tumor, melanoma, ovarian tumor, gastric tumor, or pancreatic tumor.

27. The composition of any one of aspects 21-24, wherein the tumor vesicles are isolated from a culture medium comprising tumor vesicles produced by a cancer cell line.

28. The composition of aspect 27, wherein the cancer cell line expresses at least one cancer neoantigen.

29. The composition of aspect 28, wherein the cancer neoantigen is expressed by cancer cells present in a subject.

30. The composition of aspect 28, wherein the cancer neoantigen is a conserved cancer neoantigen expressed by cancer cells present in a plurality of subjects.

31. The composition of any one of aspects 28-30, wherein the cancer neoantigen is encoded by a mutant oncogene.

32. The composition of any one of aspects 21-31, wherein the aOMVs have a diameter of 50 nm-150 nm.

33. The composition of any one of aspects 21-32, wherein the gram-negative bacterium is genetically modified for decreased production of lipopolysaccharides (LPS) as compared to LPS produced in the unmodified parental bacterium.

34. The composition of any one of aspects 21-33, wherein the gram-negative bacterium is genetically modified for increased expression of at least one endogenous outer membrane protein.

35. The composition of any one of aspects 21-34, wherein the gram-negative bacterium is genetically modified for expression of at least one heterologous protein in the outer membrane.

36. The composition of aspect 35, wherein the at least one heterologous protein comprises a cancer antigen.

37. The composition of aspect 35, wherein the at least one heterologous protein comprises an outer membrane protein from a different gram-negative bacterium.

38. The composition of any one of aspects 21-37, wherein the aOMVs are generated from a first gram-negative bacterium and the composition further comprises aOMVs generated from a second gram-negative bacterium wherein the first and second gram-negative bacterium are different strains, different species, or different genus.

39. A method for inducing an immune response against a tumor in a mammalian subject, the method comprising administering the composition of any one of aspects 21-38 to the mammalian subject in an amount effective to induce an immune response to the tumor in the mammalian subject.

40. The method of aspect 39, wherein the administering produces reduced inflammatory response as compared to that produced by administering naturally occurring OMVs released by the gram-negative bacterium.

41. The method of aspect 39 or 40, wherein the administering produces antibodies against the tumor.

42. The method of any one of aspects 39-41, wherein the administering activates a T cell response against the tumor.

43. The method of any one of aspects 39-42, wherein the tumor vesicles are isolated from the tumor.

44. The method of any one of aspects 39-42, wherein the tumor in the mammalian subject is a colon tumor and the tumor vesicles are isolated from the colon tumor; wherein the tumor in the mammalian subject is a colon tumor and the tumor vesicles are isolated from a colon cancer cell line; wherein the tumor in the mammalian subject is a lung tumor and the tumor vesicles are isolated from the lung tumor; wherein the tumor in the mammalian subject is a lung tumor and the tumor vesicles are isolated from a lung cancer cell line; wherein the tumor in the mammalian subject is a melanoma, and the tumor vesicles are isolated from the melanoma; wherein the tumor in the mammalian subject is a melanoma, and the tumor vesicles are isolated from a melanoma cell line; wherein the tumor in the mammalian subject is a breast tumor, and the tumor vesicles are isolated from the breast tumor; wherein the tumor in the mammalian subject is a breast tumor, and the tumor vesicles are isolated from a breast cancer cell line; wherein the tumor in the mammalian subject is an ovarian tumor, and the tumor vesicles are isolated from the ovarian tumor; or wherein the tumor in the mammalian subject is an ovarian tumor, and the tumor vesicles are isolated from an ovarian cancer cell line.

45. A method for treating cancer in a mammalian subject, the method comprising administering the composition of any one of aspects 21-38 to the mammalian subject in an amount effective to treat the cancer in the mammalian subject.

46. The method of aspect 45, wherein the treatment reduces growth of cancer cells in the subject.

47. The method of aspect 45 or 46, wherein the treatment reduces volume of tumor present in the mammalian subject.

48. The method of any one of aspects 45-47, wherein the administering produces reduced inflammatory response as compared to that produced by administering naturally occurring OMVs released by the gram-negative bacterium.

49. The method of aspect 48, wherein the inflammatory response comprises production of proinflammatory cytokines.

50. A method for generating non-naturally occurring artificial outer membrane vesicles (aOMVs) from a gram-negative bacterium, the method comprising:
   a) disrupting a spheroplast generated from the gram-negative bacterium to generate vesicles comprising outer membrane and vesicles comprising inner membrane;
   b) exposing the vesicles to an ionic surfactant to disrupt vesicles comprising inner membrane and to an alkaline pH to open the vesicles comprising outer membrane thereby generating outer membrane sheets;
   c) purifying the outer membrane sheets; and
   d) applying energy to the purified outer membrane sheets sufficient to convert the outer membrane sheets into aOMVs, thereby generating the non-naturally occurring aOMVs.

51. The method of aspect 50, comprising generating the spheroplast from the gram-negative bacterium by incubating the gram-negative bacterium with lysozyme under conditions sufficient for removal of peptidoglycan layer in cell wall of the gram-negative bacterium, thereby converting the gram-negative bacterium into the spheroplast.

52. The method of aspect 50 or 51, wherein disrupting the spheroplast to generate the vesicles comprises applying shear force to the spheroplast.

53. The method of aspect 50 or 51, wherein disrupting the spheroplast to generate the vesicles comprises applying acoustic energy to the spheroplast.

54. The method of any one of aspects 50-53, wherein step b) comprises exposing the vesicles to the ionic surfactant to disrupt vesicles comprising inner membrane, isolating the vesicles comprising the outer membrane, and exposing the vesicles comprising the outer membrane to the alkaline pH.

55. The method of any one of aspects 50-54, wherein the alkaline pH comprises a pH of 11-14.

56. The method of any one of aspects 50-55, wherein step c) comprises density centrifugation.

57. The method of any one of aspects 50-55, wherein step d) comprises applying shear force to the purified outer membrane sheets.

58. The method of any one of aspects 50-55, wherein step d) comprises applying acoustic energy to the purified outer membrane sheets.

59. A composition comprising revesiculated protoplast-derived vesicles (rePDVs) generated from a gram-negative bacterium, wherein the rePDVs are deficient in one or more of the following components present in the gram-negative bacteria: outer membrane proteins, nucleic acids, cytoplasmic proteins, and ribosomes.

60. The composition of aspect 59, wherein the gram-negative bacterium is genetically modified for decreased production of lipopolysaccharides (LPS).

61. The composition of aspect 59 or 60, wherein the rePDVs are generated from a first gram-negative bacterium and the composition further comprises rePDVs generated from a second gram-negative bacterium wherein the first and second gram-negative bacterium are different strains, different species, or different genus.

62. The composition of aspect 60 or 61, wherein the rePDVs have a diameter of 50 nm-150 nm.

63. A composition comprising revesiculated protoplast-derived vesicles (rePDVs) generated from a gram-positive bacterium, wherein the rePDVs are deficient in one or more of the following components present in the gram-positive bacteria: nucleic acids, cytoplasmic proteins, and ribosomes.

64. The composition of aspect 63, wherein the rePDVs are generated from a first gram-positive bacterium and the composition further comprises rePDVs generated from a second gram-positive bacterium wherein the first and second gram-positive bacterium are different strains, different species, or different genus.

65. The composition of aspect 63 or 64, wherein the rePDVs have a diameter of 50 nm-150 nm.

66. A method of producing an immune response to a gram-negative bacterium in a mammalian subject, the method comprising administering the composition of any one of aspects 59-62 to the subject in an amount effective to induce an immune response to the gram-negative bacterium in the mammalian subject.

67. The method of aspect 66, wherein the immune response comprises generation of antibodies against the gram-negative bacterium.

68. The method of aspect 66, wherein the immune response comprises activation of T cells.

69. The method of any one of aspects 66-68, wherein the mammalian subject has or is at risk of developing sepsis and wherein the rePDVs are generated from a strain of *Escherichia coli* (*E. coli*) that causes sepsis and wherein the administering produces reduced inflammatory response as compared to that produced by administering PDVs generated from the strain of *E. coli.*

70. The method of any one of aspects 66-68, wherein the mammalian subject has or is at risk of developing pneumonia and wherein the rePDVs are generated from *Pseudomonas aeruginosa* (*P. aeruginosa*) and wherein the administering produces reduced inflammatory response as compared to that produced by administering PDVs generated by *P. aeruginosa.*

71. A method of producing an immune response to a gram-positive bacterium in a mammalian subject, the method comprising administering the composition of any one of aspects 63-65 to the subject in an amount effective to induce an immune response to the gram-positive bacterium in the mammalian subject.

72. The method of aspect 71, wherein the immune response comprises generation of antibodies against the gram-positive bacterium.

73. The method of aspect 71, wherein the immune response comprises activation of T cells.

74. A composition comprising:
revesiculated protoplast-derived vesicles (rePDVs) generated from a gram-negative bacterium, wherein the rePDVs are deficient in one or more of the following components present in the gram-negative bacteria: outer membrane proteins, nucleic acids, cytoplasmic proteins, and ribosomes, or
revesiculated protoplast-derived vesicles (rePDVs) generated from a gram-positive bacterium, wherein the rePDVs are deficient in one or more of the following components present in the gram-positive bacteria: nucleic acids, cytoplasmic proteins, and ribosomes; and
tumor vesicles, wherein the tumor vesicles comprise at least one tumor antigen.

75. The composition of aspect 74, wherein the tumor vesicles are large tumor vesicles having a diameter of 100 nm-200 nm.

76. The composition of aspect 74, wherein the tumor vesicles are small tumor vesicles having a diameter of 40 nm-100 nm.

77. The composition of aspect 74, wherein the tumor vesicles comprise large tumor vesicles having a diameter of 100 nm-200 nm and small tumor vesicles having a diameter of 40 nm-100 nm.

78. The composition of any one of aspects 74-77, wherein the tumor vesicles are isolated from a tumor present in a mammalian subject.

79. The composition of aspect 78, wherein the tumor is a colon tumor, lung tumor, melanoma, breast tumor, or ovarian tumor.

80. The composition of any one of aspects 74-78, wherein the tumor vesicles are isolated from a culture medium comprising tumor vesicles produced by a cancer cell line.

81. The composition of aspect 80, wherein the cancer cell line expresses a cancer neoantigen.

82. The composition of aspect 81, wherein the cancer neoantigen is expressed by cancer cells present in a subject.

83. The composition of aspect 81, wherein the cancer neoantigen is a conserved cancer neoantigen expressed by cancer cells present in a plurality of subjects.

84. The composition of any one of aspects 81-83, wherein the cancer neoantigen is encoded by a mutant oncogene.

85. A method for inducing an immune response against a tumor in a mammalian subject, the method comprising administering the composition of any one of aspects 74-84 to the mammalian subject in an amount effective to induce an immune response to tumor in the mammalian subject.

86. The method of aspect 85, wherein the rePDVs are generated from a gram-negative bacterium and wherein the administering produces reduced inflammatory response as compared to that produced by administering PDVs generated from the gram-negative bacterium.

87. The method of aspect 85, wherein the rePDVs are generated from a gram-positive bacterium and wherein the administering produces reduced inflammatory response as compared to that produced by administering PDVs generated from the gram-positive bacterium.

88. The method of any one of aspects 85-87, wherein the administering produces antibodies against the tumor.

89. The method of any one of aspects 85-87, wherein the administering activates a T cell response against the tumor.

90. The method of any one of aspects 85-89, wherein the tumor vesicles are isolated from the tumor.

91. The method of any one of aspects 85-89, wherein the tumor in the mammalian subject is a colon tumor and the tumor vesicles are isolated from the colon tumor; wherein the tumor in the mammalian subject is a colon tumor and the tumor vesicles are isolated from a colon cancer cell line; wherein the tumor in the mammalian subject is a lung tumor and the tumor vesicles are isolated from the lung tumor; wherein the tumor in the mammalian subject is a lung tumor and the tumor vesicles are isolated from a lung cancer cell line; wherein the tumor in the mammalian subject is a melanoma, and the tumor vesicles are isolated from the melanoma; wherein the tumor in the mammalian subject is a melanoma, and the tumor vesicles are isolated from a melanoma cell line; wherein the tumor in the mammalian subject is a breast tumor, and the tumor vesicles are isolated from the breast tumor; wherein the tumor in the mammalian subject is a breast tumor, and the tumor vesicles are isolated from a breast cancer cell line; wherein the tumor in the mammalian subject is an ovarian tumor, and the tumor vesicles are isolated from the ovarian tumor; or wherein the tumor in the mammalian subject is an ovarian tumor, and the tumor vesicles are isolated from an ovarian cancer cell line.

92. A method for treating cancer in a mammalian subject, the method comprising administering the composition of any one of aspects 74-84 and 139-143 to the mammalian subject in an amount effective to treat the cancer in the mammalian subject.

93. The method of aspect 92, wherein the treatment reduces growth of cancer cells in the subject.

94. The method of aspect 92 or 93, wherein the treatment reduces volume of tumor present in the mammalian subject.

95. A method for generating revesiculated protoplast derived vesicles from a gram-negative bacterium, the method comprising:
a) incubating the gram-negative bacterium with a divalent ion chelator under conditions sufficient to render the outer membrane sensitive to chemical or enzymatic disruption;
b) chemically or enzymatically removing the outer membrane and the peptidoglycan layer in the cell wall of the gram-negative bacterium from step a), thereby converting the gram-negative bacterium into a protoplast comprising an inner membrane and lacking the outer membrane and the peptidoglycan layer;
c) disrupting the protoplast to generate vesicles;
d) purifying the vesicles;
e) exposing the isolated vesicles to an alkaline pH to open the vesicles thereby generating inner membrane sheets;
f) purifying the inner membrane sheets; and
g) applying energy or force to the purified inner membrane sheets sufficient to convert the inner membrane sheets into rePDVs.

96. The method of aspect 95, wherein disrupting the protoplast to generate vesicles comprises extruding the protoplast.

97. The method of aspect 95 or 96, wherein the alkaline pH comprises a pH of 11-14.

98. The method of any one of aspects 64-66, wherein the divalent ion chelator comprises ethylenediaminetetraacetic acid (EDTA).

99. The method of any one of aspects 95-98, wherein step a) comprises incubating the gram-negative bacterium with lysozyme.

100. A method for generating revesiculated protoplast-derived vesicles (rePDVs) from a gram-positive bacterium, the method comprising:
   a) enzymatically or chemically removing the peptidoglycan layer in the cell wall of the gram-positive bacterium, thereby converting the gram-positive bacterium into a protoplast comprising an inner membrane and lacking the cell wall;
   b) disrupting the protoplast to generate vesicles;
   c) purifying the vesicles;
   d) exposing the isolated vesicles to an alkaline pH to open the vesicles thereby generating inner membrane sheets;
   e) purifying the inner membrane sheets; and
   f) applying energy or force to the purified inner membrane sheets sufficient to convert the inner membrane sheets into rePDVs.

101. The method of aspect 100, wherein disrupting the protoplast to generate vesicles comprises extruding the protoplast.

102. The method of aspect 100 or 101, wherein the alkaline pH comprises a pH of 11-14.

103. The composition of any one of aspects 21-38, wherein the tumor vesicles comprise revesiculated tumor vesicles.

104. The composition of any one of aspects 21-38 and 103, wherein the composition does not include an adjuvant.

105. The composition of any one of aspects 21-38 and 103-104, wherein the aOMVs are loaded with a therapeutic agent.

106. The composition of aspect 105, wherein the therapeutic agent comprises an agonist of STING.

107. The composition of aspect 106, wherein the STING agonist comprises a cyclic dinucleotide (CDN) or a xanthenone derivative DMXAA. 108. The method of any one of aspects 39-49 and 105, wherein the method does not include administering an adjuvant to the subject.

109. The composition of any one of aspects 45-49 and 74-84, wherein the tumor vesicles comprise revesiculated tumor vesicles.

110. The composition of any one of aspects 74-84 and 109, wherein the composition does not include an adjuvant.

111. The method of any one of aspects 85-94, wherein the tumor vesicles comprise revesiculated tumor vesicles.

112. A method for treating cancer in a subject, the method comprising administering to the subject:
   artificial outer membrane vesicles (aOMVs) generated from a gram-negative bacterium, wherein the aOMVs are deficient in one or more of the following components present in the gram-negative bacterium: inner membrane proteins, nucleic acids, cytoplasmic proteins, and ribosomes, and/or wherein the aOMVs are enriched in outer membrane proteins; and
   tumor vesicles, wherein the tumor vesicles comprise at least one tumor antigen,
   wherein the aOMVs and the tumor vesicles are administered in a therapeutically effective amount.

113. The method of aspect 112, wherein the treatment results in induction of antibodies against the tumor vesicles at a titer more than twice the titer of antibodies against the tumor vesicles induced using an adjuvant instead of the aOMVs.

114. The method of aspect 113, wherein the adjuvant comprises aluminum.

115. The method of aspect 113, wherein the adjuvant comprises aluminum hydroxyphosphate sulfate (AAHS), aluminum hydroxide, aluminum phosphate, or potassium aluminum sulfate (Alum).

116. The method of aspect 113, wherein the adjuvant comprises Incomplete Freund's adjuvant (IFA).

117. The method of aspect 113, wherein the adjuvant comprises cytosine phosphoguanine (CpG).

118. The method of any one of aspects 112-117, wherein the method comprises administering an immune checkpoint inhibitor to the subject.

119. The method of aspect 118, wherein the immune checkpoint inhibitor comprises an anti-PD-1 antibody or an anti-PDL1 antibody.

120. The method of aspect 119, wherein the immune checkpoint inhibitor comprises an anti-PD-1 antibody and wherein the administration of aOMVs, TVs, and the anti-PD-1 antibody results in reduction of tumor volume in the subject which reduction is at least two time higher than achieved by administration of aOMVs and the anti-PD-1 antibody or TVs and the anti-PD-1 antibody.

121. The method of any one of aspects 112-120, wherein the aOMVs are prepared by revesiculation of vesicles composed of outer membrane.

122. The method of aspect 118, wherein revesiculation comprises exposing the vesicles to an alkaline pH.

123. The method of aspect 122, wherein the alkaline pH comprises pH 9-pH 12.

124. The method of any one of aspects 112-123, wherein the gram negative bacterium is *Escherichia coli*.

125. The method of any one of aspects 112-123, wherein the gram negative bacterium is *Pseudomonas aeruginosa*.

126. The method of any one of aspects 112-125, wherein the tumor vesicles (TVs) small TVs that range in diameter from 10 nm-100 nm.

127. The method of any one of aspects 112-125, wherein the tumor vesicles (TVs) large TVs that range in diameter from 100 nm-500 nm.

128. The method of any one of aspects 112-127, wherein the tumor vesicles comprise large and small TVs.

129. The method of any one of aspects 112-128, wherein the tumor vesicles comprise polyethylene glycol.

130. The method of any one of aspects 112-129, wherein the administering comprises intratumoral injection.

131. The method of any one of aspects 112-130, wherein the cancer is a melanoma.

132. The method of any one of aspects 112-130, wherein the cancer is colon cancer.

133. The method of any one of aspects 112-130, wherein the tumor vesicles are derived from the cancer cells of the subject.

134. The method of any one of aspects 112-130, wherein the OMVs are loaded with a therapeutic agent.

135. The method of aspect 134, wherein the therapeutic agent is a STING agonist.

136. The method of aspect 135, wherein the STING agonist comprises a STING ligand.

137. The method of aspect 135, wherein the STING agonist a cyclic dinucleotide (CDNs) or the xanthenone derivative DMXAA.

138. The method of aspect 137, wherein the STING agonist comprises DMXAA.

139. The composition of any one of aspects 74-84 and 109-110, wherein the re PDV comprise a therapeutic agent.

140. The composition of aspect 139, wherein the therapeutic agent is a STING agonist.

141. The composition of aspect 140, wherein the STING agonist comprises a STING ligand.

142. The composition of aspect 140, wherein the STING agonist a cyclic dinucleotide (CDNs) or the xanthenone derivative DMXAA.

143. The composition of aspect 142, wherein the STING agonist comprises DMXAA.

144. Artificial outer membrane vesicles (aOMVs) and tumor vesicles (TVs) for use in a method for treating cancer in a subject, the method comprising administering the aOMVs and tumor vesicles to the subject, wherein the aOMVs are generated from a gram-negative bacterium, wherein the aOMVs are deficient in one or more of the following components present in the gram-negative bacterium: inner membrane proteins, nucleic acids, cytoplasmic proteins, and ribosomes, and/or wherein the aOMVs are enriched in outer membrane proteins and wherein the tumor vesicles comprise at least one tumor antigen, wherein the aOMVs and the tumor vesicles are administered in a therapeutically effective amount.

145. The aOMVs and TVs for use according to aspect 144, wherein the use results in induction of antibodies against the tumor vesicles at a titer more than twice the titer of antibodies against the tumor vesicles induced using an adjuvant instead of the aOMVs.

146. The aOMVs and TVs for use according to aspect 145, wherein the adjuvant comprises aluminum.

147. The aOMVs and TVs for use according to aspect 145, wherein the adjuvant comprises aluminum hydroxyphosphate sulfate (AAHS), aluminum hydroxide, aluminum phosphate, or potassium aluminum sulfate (Alum).

148. The aOMVs and TVs for use according to aspect 145, wherein the adjuvant comprises Incomplete Freund's adjuvant (IFA).

149. The aOMVs and TVs for use according to aspect 145, wherein the adjuvant comprises cytosine phosphoguanine (CpG).

150. The aOMVs and TVs for use according to aspect 145, wherein the method comprises administering an immune checkpoint inhibitor to the subject.

151. The aOMVs and TVs for use according to aspect 150, wherein the immune checkpoint inhibitor comprises an anti-PD-1 antibody or an anti-PDL1 antibody.

152. The aOMVs and TVs for use according to aspect 150, wherein the immune checkpoint inhibitor comprises an anti-PD-1 antibody and wherein the administration of aOMVs, TVs, and the anti-PD-1 antibody results in reduction of tumor volume in the subject which reduction is at least two time higher than achieved by administration of aOMVs and the anti-PD-1 antibody or TVs and the anti-PD-1 antibody.

153. The aOMVs and TVs for use according to any one of aspects 144-152, wherein the aOMVs are prepared by revesiculation of vesicles composed of outer membrane.

154. The aOMVs and TVs for use according to aspect 153, wherein revesiculation comprises exposing the vesicles to an alkaline pH.

155. The aOMVs and TVs for use according to aspect 154, wherein the alkaline pH comprises pH 9-pH 12.

156. The aOMVs and TVs for use according to one of aspects 144-155, wherein the gram negative bacterium is *Escherichia coli*.

157. The aOMVs and TVs for use according to one of aspects 144-155, wherein the gram negative bacterium is *Pseudomonas aeruginosa*.

158. The aOMVs and TVs for use according to one of aspects 144-155, wherein the tumor vesicles (TVs) small TVs that range in diameter from 10 nm-100 nm.

159. The aOMVs and TVs for use according to one of aspects 144-155, wherein the tumor vesicles (TVs) large TVs that range in diameter from 100 nm-500 nm.

160. The aOMVs and TVs for use according to one of aspects 144-159, wherein the tumor vesicles comprise large and small TVs.

161. The aOMVs and TVs for use according to one of aspects 144-160, wherein the tumor vesicles comprise polyethylene glycol.

162. The aOMVs and TVs for use according to one of aspects 144-155, wherein the administering comprises intratumoral injection.

163. The aOMVs and TVs for use according to one of aspects 144-162, wherein the cancer is a melanoma.

164. The aOMVs and TVs for use according to one of aspects 144-162, wherein the cancer is colon cancer.

165. The aOMVs and TVs for use according to one of aspects 144-162, wherein the tumor vesicles are derived from the cancer cells of the subject.

166. The aOMVs and TVs for use according to one of aspects 144-166, wherein the aOMVs are loaded with a therapeutic agent. 167. The aOMVs and TVs for use according to aspect 166, wherein the therapeutic agent is a STING agonist.

168. The aOMVs and TVs for use according to aspect 167, wherein the STING agonist comprises a STING ligand.

169. The aOMVs and TVs for use according to aspect 167, wherein the STING agonist a cyclic dinucleotide (CDNs) or the xanthenone derivative DMXAA.

170. The aOMVs and TVs for use according to aspect 169, wherein the STING agonist comprises DMXAA.

171. The aOMVs and TVs for use according to any one of aspects 144-171, wherein the aOMVs and TVs are formulated in a composition.

172. The aOMVs and TVs for use according to aspect 171, wherein the composition further comprises a pharmaceutically acceptable excipient.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s);

nt, nucleotide(s); i.m., intramuscular(ly); i.p., intraperitoneal (ly); s.c., subcutaneous(ly); and the like.

Example 1: Isolation and Characterization of *E. coli* aOMVs

Methods
Preparation of aOMVs

Figure 1B:
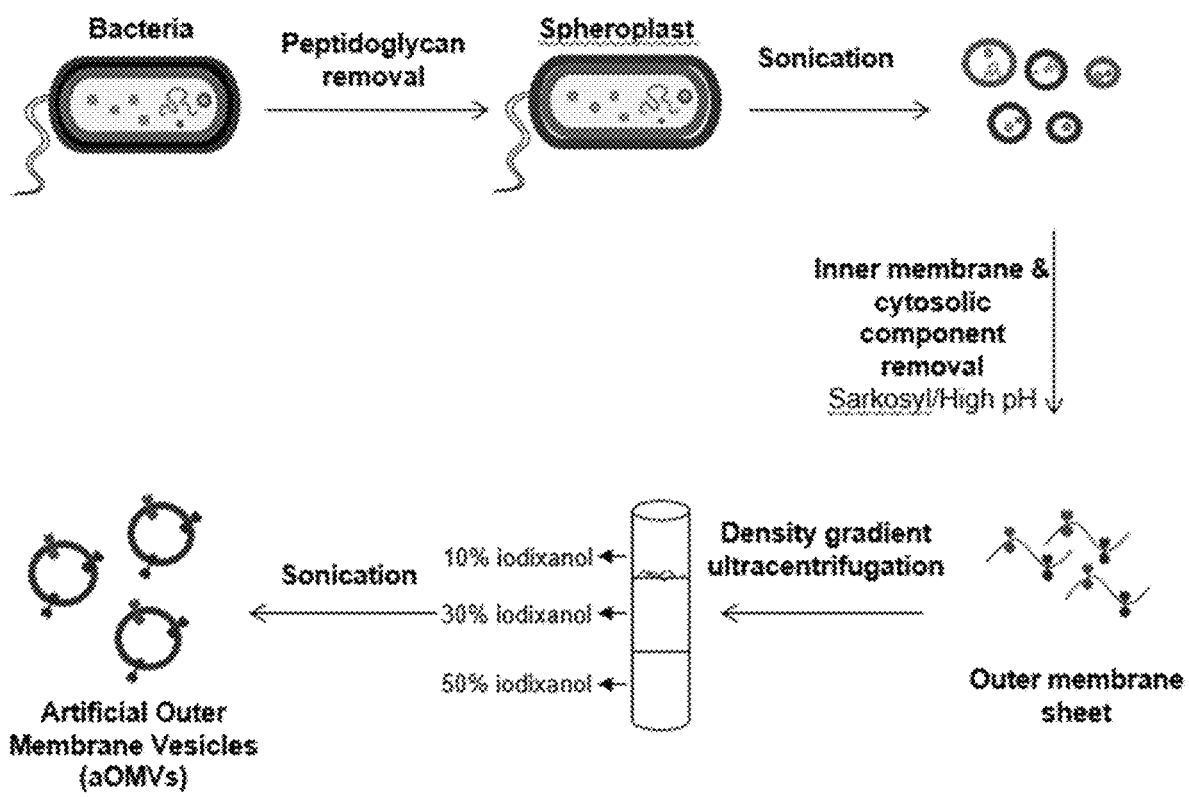
FIG. 1B depicts steps for generation of artificial outer membrane vesicles (aOMVs) from a gram-negative bacterium according to an embodiment of the present disclosure.

A uropathogenic *Escherichia coli* strain was acquired to produce aOMVs. The bacterial culture was pelleted, resuspended in 20% sucrose in 20 mM Tris, pH 8.0 (4 mL per g cells), lysozyme (600 µg per g cells), and 0.1 M EDTA (0.2 mL per g cells) were added. The resulting spheroplasts were pelleted, and then sonicated in ice-cold 10 mM Tris, pH 8.0. The cells were pelleted at 8,000×g for 5 min, and then whole membranes were pelleted from the supernatants at 40,000×g for 60 min. The membranes were resuspended in distilled water, freeze-thawed, and incubated in 0.5% Sarkosyl (sodium N-lauroylsarcinosinate; 20 min, 25° C.). The outer membrane was pelleted (40,000×g for 90 min), and incubated with high pH solution (200 mM Na2CO3, pH 14.0) for 1 hour at 25° C. The pellets were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min, and considered aOMVs (FIG. 1).

Quantification of aOMVs

Protein concentration of aOMVs was determined with a Bradford dye assay (Bio-Rad Laboratories). aOMV particle concentration were assessed by ZetaView analyzer (Particle Metrix GmbH). Measurements were assessed in triplicates and each individual data was obtained from two stationary layers with five times measurements in each layer. Sensitivity of camera was configured at 70 in all measurements. Data were analyzed using ZetaView analysis software version 8.2.30.1.

Preparation of OMVs

*E. coli* cultures were pelleted at 6,000×g, 4° C. for 20 min, twice, and then the supernatant fraction was filtered through a 0.45-µm vacuum filter and was concentrated by ultrafiltration Vivaflow 200 module (Sartorius) with a 100 kDa cut-off membrane. The retentate was again filtered through a 0.22-µm vacuum filter to remove any remaining cells. The resulting filtrate was subjected to ultracentrifugation at 150,000×g, 4° C. for 3 h and resuspended in PBS.

Transmission Electron Microscopy

Formvar/carbon Cu copper grids (Electron Microscopy Sciences) were glow discharge-treated before aOMVs were loaded. Then aOMVs were washed two times in distilled water and then fixed using 2.5% glutaraldehyde dissolved PBS. After two further washes in filtered water, the samples were stained using 2% uranyl acetate for 1.5 min. Negative-stained samples were examined on a digitized LEO 912AB Omega electron microscope (Carl Zeiss SMT) at 120 kV with a Veleta CCD camera (Olympus-SiS).

SDS-PAGE

*E. coli* lysates, OMVs, and aOMVs were separated by 10% SDS-PAGE and whole protein bands were stained by Coomassie brilliant blue G-250 dye (Thermo Fisher Scientific). For Western blot analysis, separated gel by 10% SDS-PAGE was transferred to a polyvinylidene difluoride membrane. The blocked membrane was then incubated with anti-OmpA antibody (lab-made), anti-lipid A antibody (Abcam), or anti-FtsZ antibody (Antibodies-online, Inc.). After incubation with horseradish peroxidase-conjugated secondary antibody, the immunoreactive bands were visualized with a chemiluminescent substrate.

RNA and DNA Analysis

RNA from aOMVs or OMVs was isolated using miR-CURY™ RNA isolation kit for biofluids (Exiqon) according to manufacturer's protocol. DNA was isolated using Qiamp DNA Blood Mini kit (Qiagen) according to manufacturer's protocol. One microliter of isolated RNA or DNA were analyzed for its quality, yield, and nucleotide length with capillary electrophoresis using Agilent RNA 6000 Nanochip and Agilent High sensitivity DNA chip, respectively, on an Agilent 2100 Bioanalyzer® (Agilent Technologies).

Figure 2:
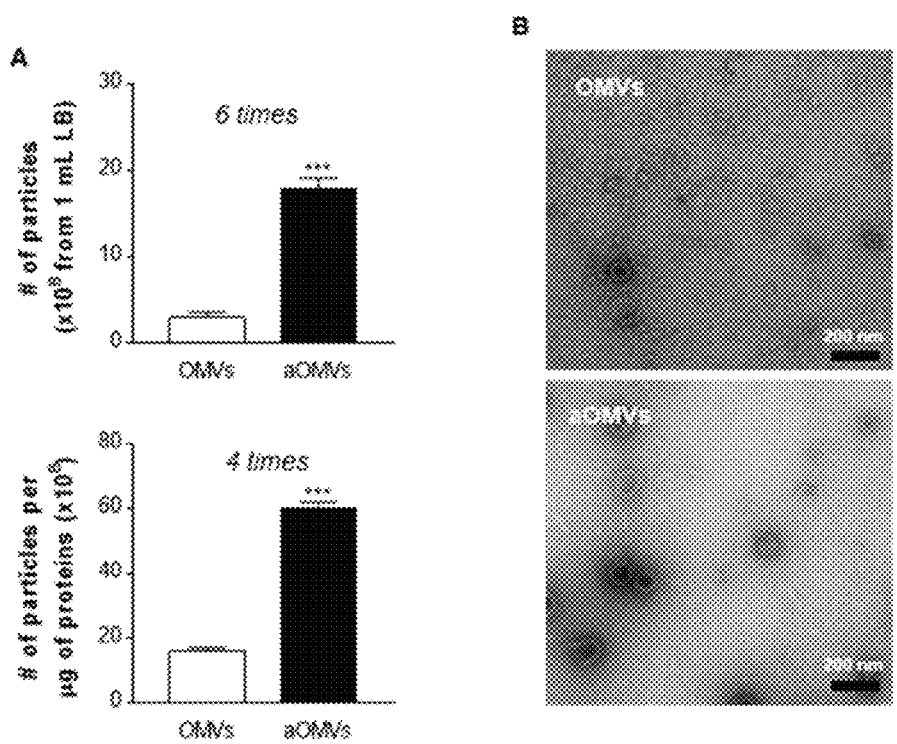
FIG. 2, Panel A depicts the particle numbers of naturally occurring Escherichia coli (E. coli) outer membrane vesicles (OMVs) and E. coli aOMVs per 1 mL LB media (upper graph) and the particle numbers of E. coli OMVs and E. coli aOMVs per one microgram of proteins (lower graph). ***, $P<0.001$; two-tailed unpaired T test. Error bars indicate SEM. N=3.
Figure 3:
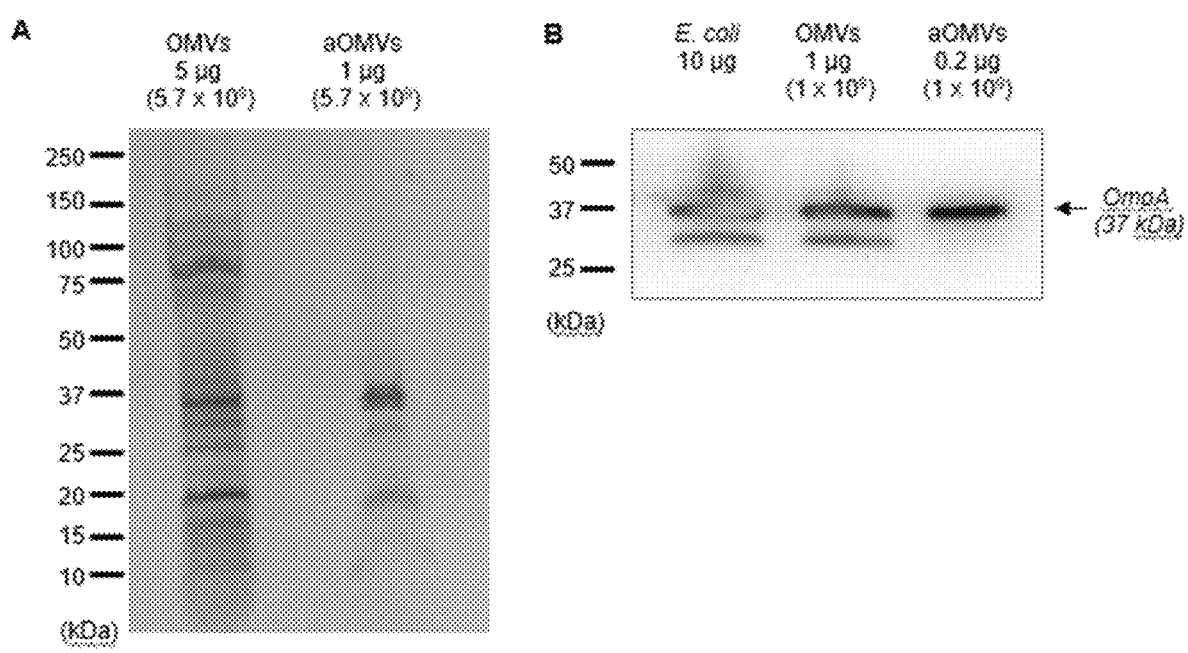
FIG. 3, Panel A depicts SDS-PAGE analysis of E. coli OMVs and aOMVs visualized by Coomassie Brilliant Blue staining.
Figure 4:
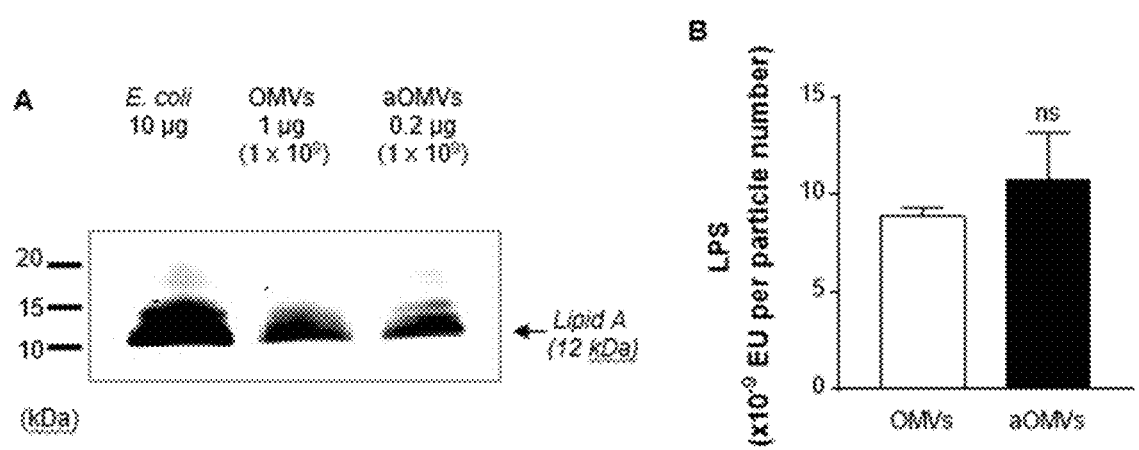
FIG. 4, Panel A depicts Western blot analysis of E. coli lysates (10 μg total protein), OMVs (1 μg total protein), and aOMVs (0.20 μg total protein), with anti-Lipid A antibody.
Figure 5:
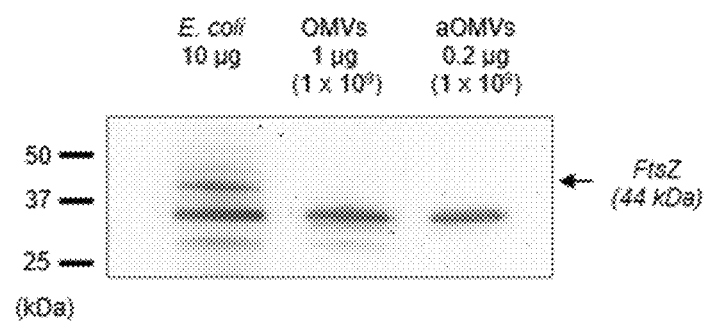
FIG. 5 depicts Western blot analysis of E. coli lysates (10 μg total protein), OMVs (1 μg total protein), and aOMVs (0.20 μg total protein), with anti-FtsZ antibody.
Figure 6:
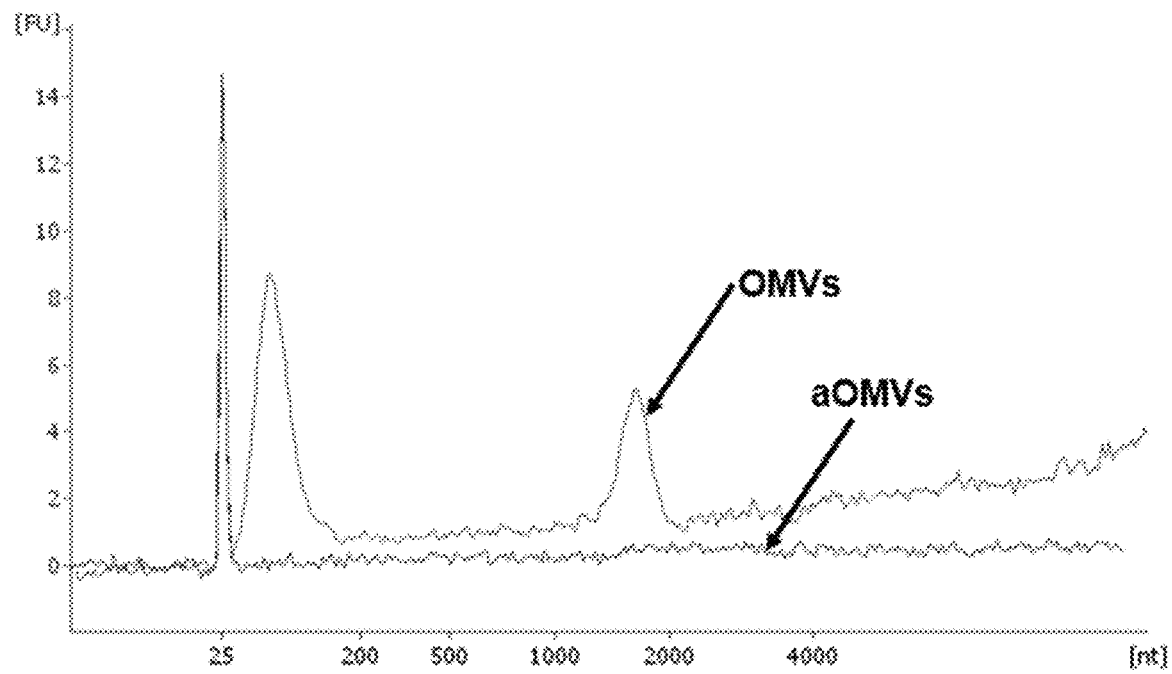
FIG. 6 depicts an electropherogram of RNA molecules isolated from E. coli aOMVs and RNA molecules isolated from E. coli OMVs.
Figure 7:
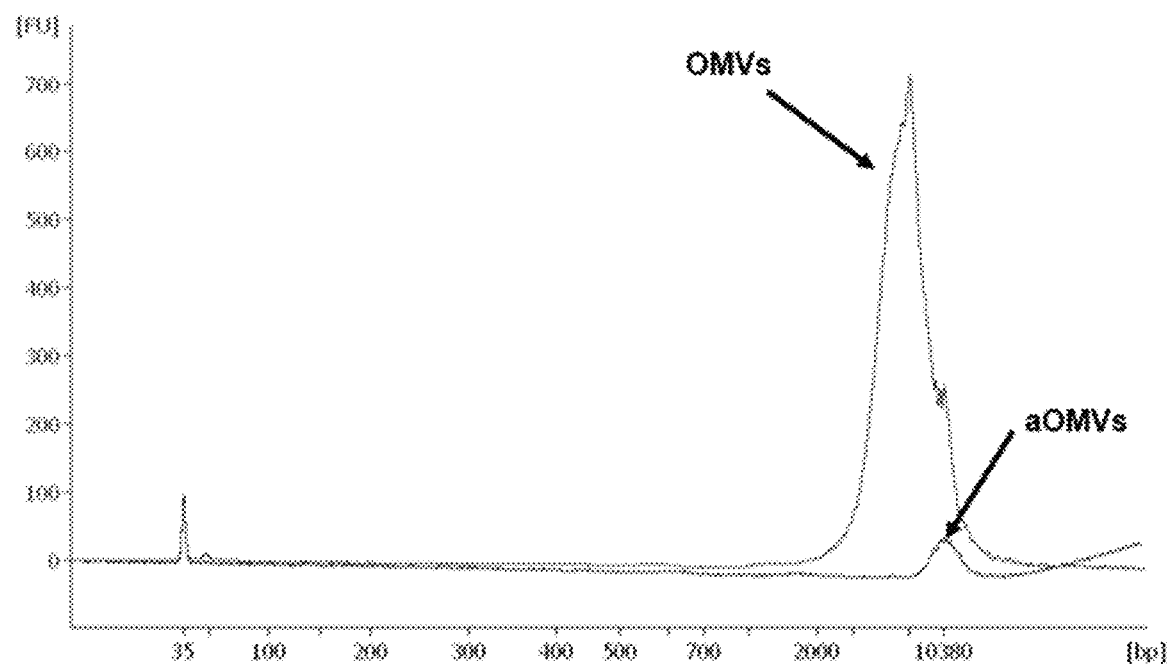
FIG. 7 depicts an electropherogram of DNA molecules isolated from E. coli aOMVs and DNA molecules isolated from E. coli OMVs.

Results aOMVs were prepared in higher yield than naturally produced OMVs (FIG. 2, Panel A). aOMVs presented similar shape and size as OMVs, as shown by a transmission electron microscopy image (FIG. 2, Panel B). aOMV proteins had mostly similar size with outer membrane proteins (FIG. 3, Panel A), especially OmpA (FIG. 3, Panel B) and LPS (FIG. 4, Panels A-B), which are major components on outer membrane. In addition, cytosolic proteins such as FtsZ were completely removed in aOMVs (FIG. 5). RNA peaks were not detected in aOMVs in contrast to OMVs (FIG. 6). And DNA contents in aOMVs were mostly removed (FIG. 7).

Example 2: Proteomic Analysis of *E. coli* aOMV Proteins

Methods
LC-MS/MS Analysis

Two biological replicate aOMVs or OMVs (30 µg) were digested with trypsin using the filter-aided sample preparation (FASP) method and C18 spin columns desalting according to manufacturer's instructions. All fractions were dried on Speedvac and reconstituted in 3% acetonitrile and 0.2% formic acid and analyzed on Orbitrap Fusion Tribrid mass spectrometer interfaced with Easy-nLC 1200 (Thermo Fisher Scientific, Waltham, Mass.). Peptides were trapped on the Acclaim Pepmap 100 C18 trap column (100 µm×2 cm, particle size 5 µm; Thermo Fischer Scientific) and separated on the in-house packed C18 analytical column (75 µm×30 cm, particle size 3 µm) using the gradient from 5% to 33% B in 160 min, from 33% to 100% B in 5 min, solvent A was 0.2% formic acid and solvent B was 80% acetonitrile and 0.2% formic acid. Precursor ion mass spectra were recorded at 120 000 resolution, the most intense precursor ions were selected, fragmented using HCD at collision energy setting of 30 and the MS/MS spectra were recorded at 30 000 resolution with the maximum injection time of 125 ms and the isolation window of 1.0 Da. Charge states 2 to 7 were selected for fragmentation, dynamic exclusion was set to 45 s with 10 ppm tolerance.

Results 177 and 181 proteins were identified from OMVs and aOMVs, respectively (FIG. 8). 112 proteins were identified in both vesicle preparations, whereas 65 and 69 proteins were uniquely identified in OMVs and aOMVs, respectively. Based on the relative protein abundance, 13 proteins did not change markedly in abundance among 112 proteins. However, 20 and 79 proteins were relatively increased and decreased in aOMVs as compared to OMVs, respectively. In the GO term subcellular localization analysis, aOMV proteome showed features distinct from OMV proteome (FIG. 9). aOMV proteome was enriched with cell outer membrane proteins, whereas OMV proteome was enriched with cytosol and inner membrane proteins. In the GO term biological process analysis, aOMV proteome was enriched for proteins involved in ion transport (FIG. 10). By contrast, OMV proteome was enriched for proteins involved translation and ribosomal subunit assembly.

Example 3: Less Toxicity of E. coli aOMVs In Vitro and In Vivo

Figure 11:
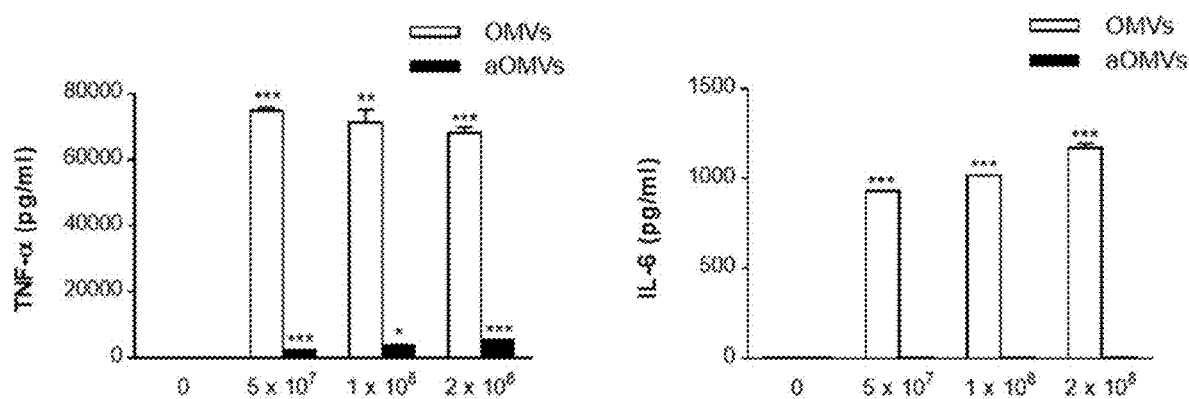
FIG. 11 depicts E. coli OMV- or aOMV-induced pro-inflammatory cytokines in the supernatants of RAW 264.7 cells. Indicated numbers of OMVs or aOMVs were added to the cells for 15 h, and then TNF-α (left) and IL-6 (right) were measured by ELISA. *, $P<0.05$; , $P<0.01$; *, $P<0.001$; one-way ANOVA with Tukey's multiple comparison test. Error bars indicate SEM. N=3.
Figure 12:
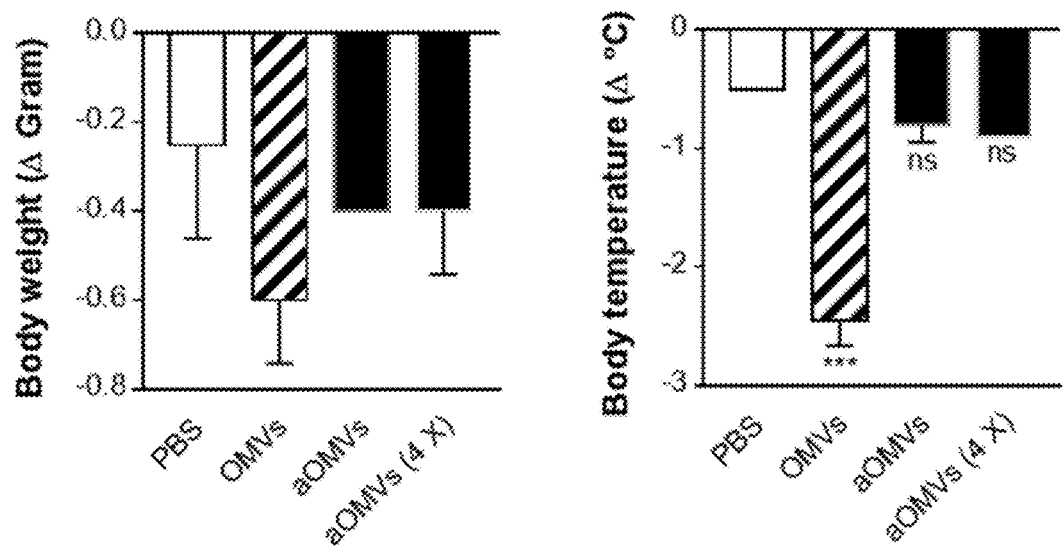
FIG. 12 depicts the body weight (left) and body temperature (right) at 6 h of mice injected intraperitoneally with E. coli OMVs ($5\times10^9$), aOMVs ($5\times10^9$), or 4-fold excess amount of aOMVs ($2\times10^{10}$). ***, P<0.001; ns, not significant; versus PBS group; one-way ANOVA with Tukey's multiple comparison test. Error bars indicate SEM. N=3.
Figure 13:
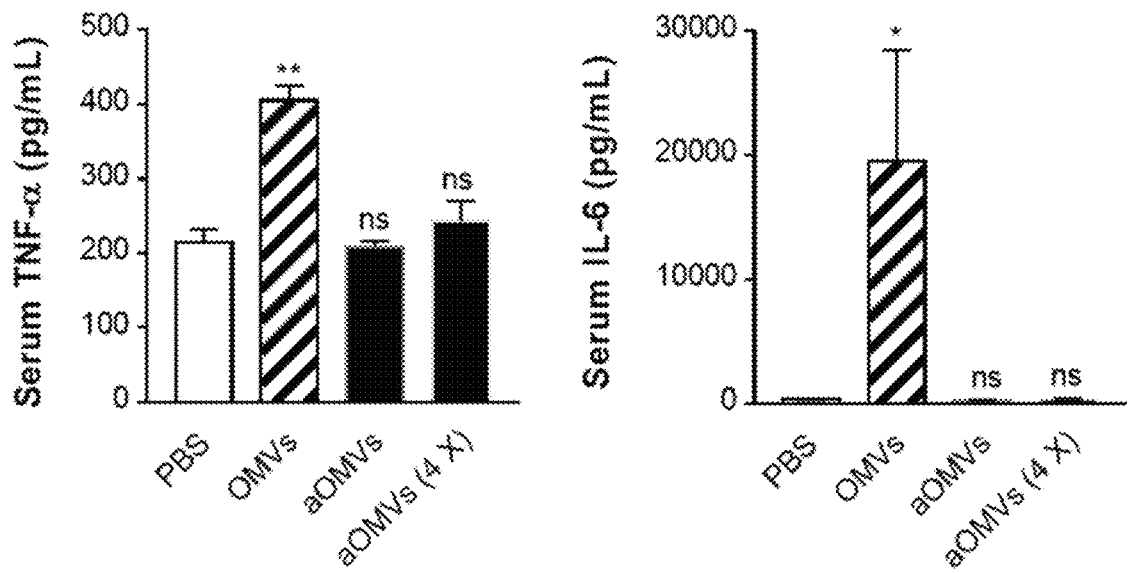
FIG. 13 depicts inflammatory cytokines TNF-α (left) and IL-6 (right) in the peritoneum at 6 h of mice injected intraperitoneally with *E. coli* OMVs ($5\times10^9$), aOMVs ($5\times10^9$), or 4-fold excess amount of aOMVs ($2\times10^{10}$). *, P<0.05; ns, not significant; versus PBS group; one-way ANOVA with Tukey's multiple comparison test. Error bars indicate SEM. N=3.
Figure 14:
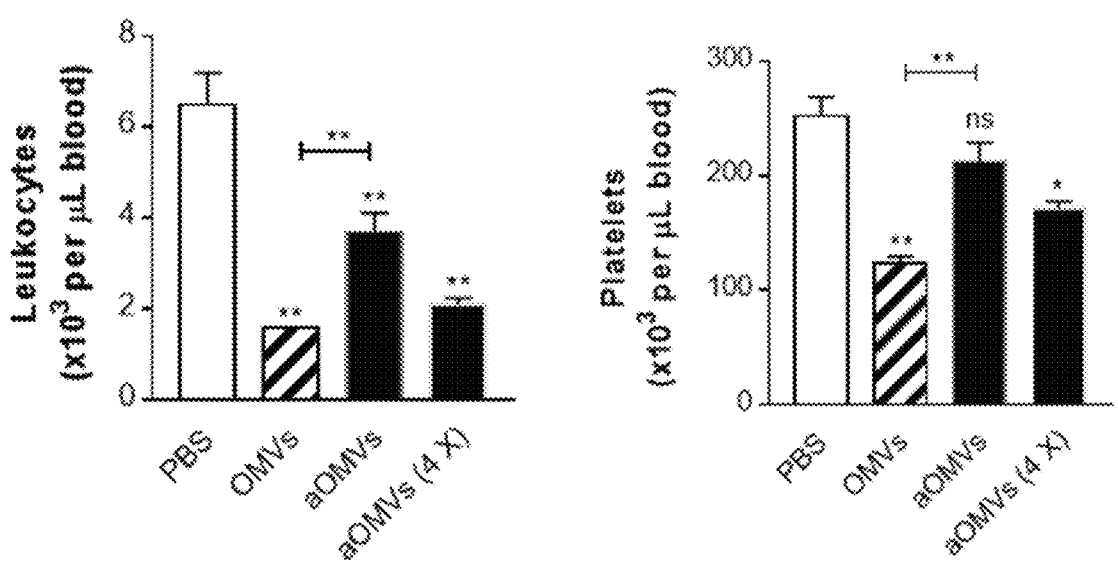
FIG. 14 depicts the number of total leukocytes (left) and platelets (right) in the blood at 6 h of mice injected intraperitoneally with *E. coli* OMVs ($5\times10^9$), aOMVs ($5\times10^9$), or 4-fold excess amount of aOMVs ($2\times10^{10}$). *, P<0.05; **, P<0.01; ns, not significant; versus PBS group; one-way ANOVA with Tukey's multiple comparison test. Error bars indicate SEM. N=3.

Methods
RAW 264.7 Cytokines
RAW 264.7 ($1\times10^5$), a mouse macrophage cell line, were seeded into 24-well plates. Various dose of aOMVs and OMVs were applied to the cells to induce pro-inflammatory cytokines (TNF-α and IL-6) for 15 h. Supernatant concentrations of cytokines were measured by ELISA kit (R&D systems).
Mice Experiments
Mice (wild type mice of the C57BL/6 genetic background, 6 weeks old) were intraperitoneally (i.p.) injected with OMVs ($5\times10^9$) or aOMVs ($5\times10^9$, $2\times10^{10}$). Mice were sacrificed at 6 h following anesthetization with i.p. injection of xylazine chloride (Bayer) and ketamine hydrochloride (Pfizer). Rectal temperature was measured by thermometer (Bioseb). Peritoneal fluid (PF) and blood were collected from mice, and then cytokines in the supernatant were analyzed by DuoSet ELISA Development kit (R&D Systems). Leukocytes and platelets in blood were counted using the light microscopy following incubation with 1% hydrochloride and Rees-Ecker diluting fluid (Thermo Fisher Scientific), respectively.
Results
aOMVs did not induce IL-6 from macrophages, as compared to OMVs (FIG. 11). TNF-α secretion from cells incubated with aOMVs was significantly lower than from cells incubated OMVs. There were no significant changes in body weight and temperature in aOMV-injected mice (FIG. 12). Also, aOMVs did not cause increase in pro-inflammatory cytokines (FIG. 13) and induced decrease in leukocyte and platelet number to a lesser extent than OMVs (FIG. 14).

Example 4: Immunological Properties of E. coli aOMVs In Vitro and In Vivo

Figure 15:
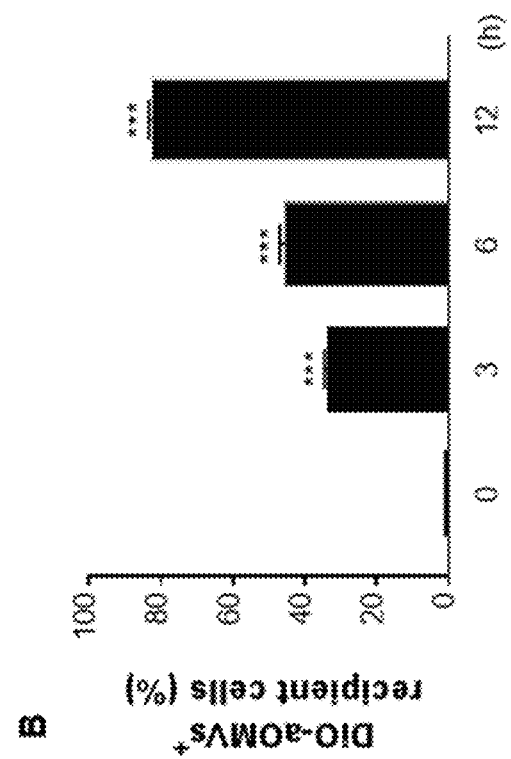
FIG. 15, Panel A is a flow cytogram showing uptake of DiO-labeled *E. coli* aOMVs by bone marrow-derived dendritic cells at 0, 3, 6, and 12 h.
Figure 15:
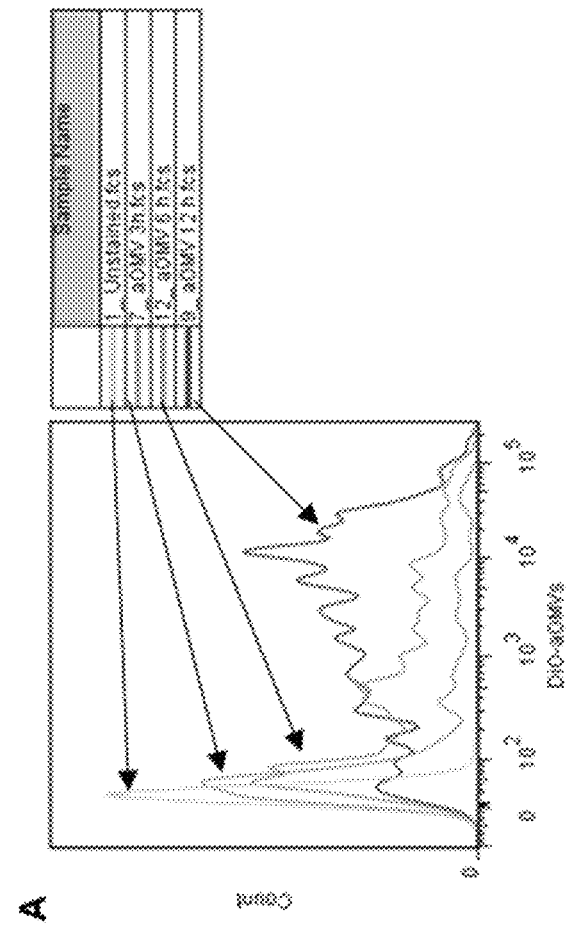
Figure 16:
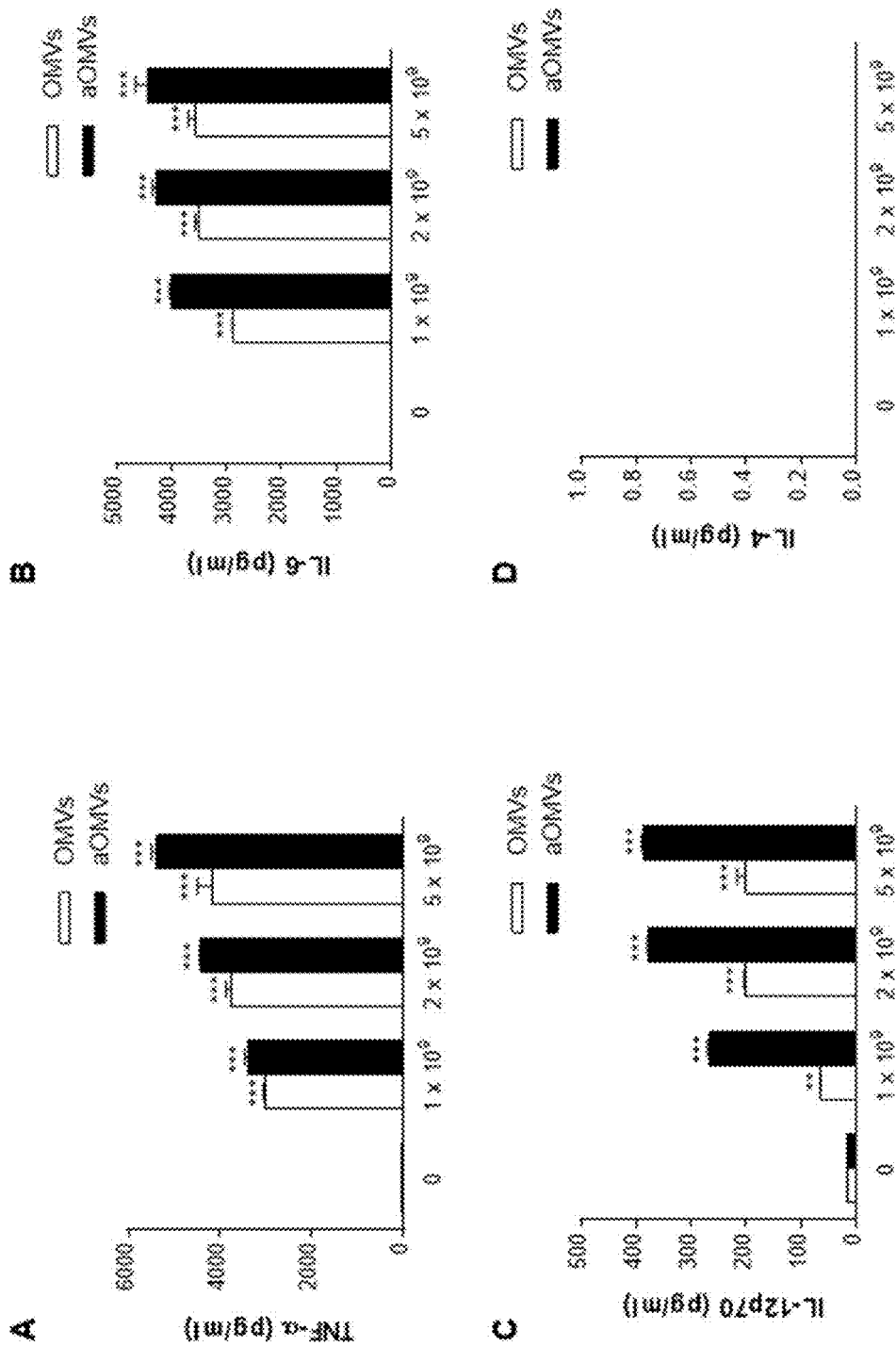
FIG. 16, Panel A is a graph of TNF-α level (pg/ml) in the supernatants of bone marrow-derived dendritic cells treated with *E. coli* OMVs or aOMVs for 24 h. ***, P<0.001; versus control; one-way ANOVA with Tukey's multiple comparison test. Error bars indicate SEM. N=3.
Figure 17:
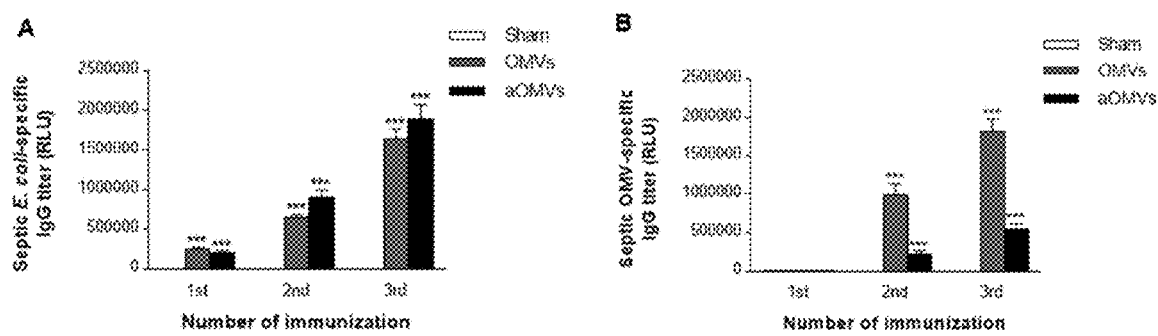
FIG. 17, Panel A is a graph showing the levels of *E. coli* protein-specific antibodies measured in the course of three intraperitoneal injection of $5\times10^9$ of *E. coli* OMVs or aOMVs at regular intervals of one week. ***, P<0.001; versus sham group; one-way ANOVA with Tukey's multiple comparison test. Error bars indicate SEM. N=4.
Figure 18:
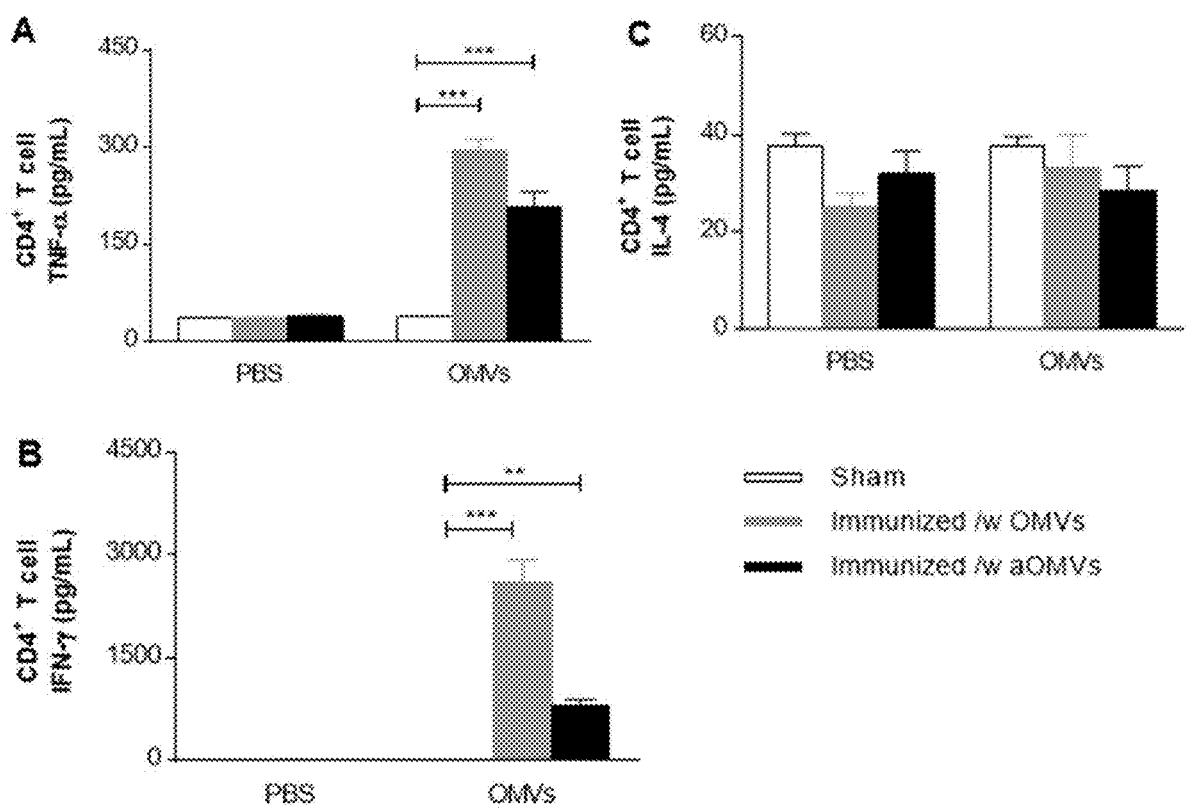
FIG. 18, Panel A depicts the level of TNF-α secreted from mouse splenic CD4+ T cells upon ex vivo treatment with *E. coli* OMVs after the mice were immunized with $5\times10^9$ of *E. coli* OMVs or aOMVs. ***, P<0.001; versus sham group; one-way ANOVA with Tukey's multiple comparison test. Error bars indicate SEM. N=3.

Methods
Dendritic Cell Uptake and Cytokines
Bone marrow cells were harvested from the femur and the tibia of mice (C57BL/6). The cells were differentiated into dendritic cells in 10% FBS/RPMI supplemented with nutrients and 20 ng/mL GM-CSF for one week. Separately, isolated aOMVs were labeled with DiO, followed by incubation with dendritic cells, and examined for uptake by dendritic cells using FACS. For the uptake inhibitor treatment, dendritic cells pretreated with dynasore (Sigma Aldrich) for 1 h were sequentially incubated with DiO-labeled aOMVs for 6 h. For cytokine analysis, differentiated dendritic cells ($1\times10^5$) were seeded into 24-well plates. Various doses of aOMVs and OMVs were applied to the cells to induce TNFα, IL-6, IL-12p70, and IL-4 for 24 h. Supernatant concentrations of cytokines were measured by ELISA kit (R&D systems).
Antibody Titer Against E. coli Lysates or OMV Proteins
$5\times10^9$ of OMVs or aOMVs were intraperitoneally injected to mice (wild-type C57BL/6 genetic background, 6 weeks old) once a week for three weeks. Blood samples were taken from mice 3 days after each injection and assayed for their antibodies specific for E. coli lysates or OMV proteins. The mouse serum was 1:500 diluted in 1% BSA/PBS and placed in 96-well plates coated with 200 ng of E. coli lysates or OMV proteins. After incubation for 2 h, immunological changes were measured with a peroxidase-conjugated anti-mouse antibody.
Splenocyte Cytokines
Seven days after the three injections of OMVs or aOMVs ($5\times10^9$), CD4+ T cells from spleen were isolated from the mice. The cells ($5\times10^5$) were incubated for 72 h with 100 ng/mL of OMVs, followed by ELISA to quantitatively analyze TNF-α, IFN-γ, and IL-4.
Results
aOMVs were increasingly taken up by dendritic cells with prolonged incubation time, shown by FACS analysis (FIG. 15, Panels A-B). Secretion of TNF-α, IL-6, and IL-12p70, cytokines that induce T helper type 1 response, increased with an increase in the dose of aOMVs (FIG. 16, Panels A-D). However, there was no change in the level of IL-4, a cytokine inducing T helper type 2 response. E. coli lysates or OMV-specific antibodies in the mouse blood were detectable 7 days after the first injection of aOMVs, and were increased by the second and the third injections, with a peak at 7 days after the third injection (FIG. 17, Panels A-B). Higher levels of TNF-α and IFN-γ were secreted from splenic CD4+ T cells of aOMV-immunized group, compared to the sham group (FIG. 18, Panels A-C). However, there was no change in the level of IL-4 between aOMV-immunized and sham group.

Figure 19:
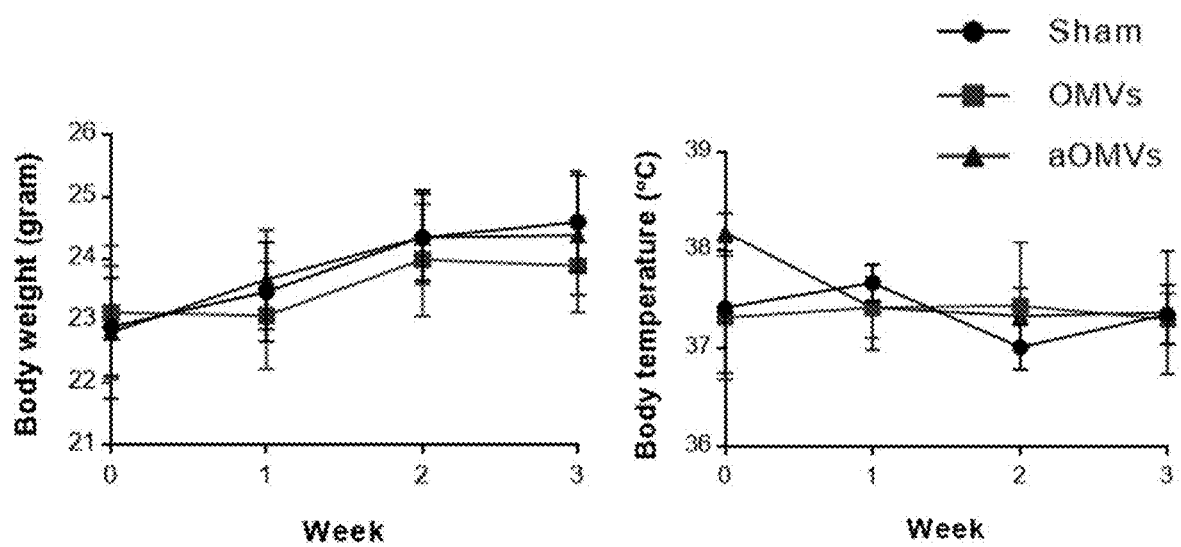
FIG. 19 depicts change in body weight (left) and body temperature (right) of mice immunized intraperitoneally with $5\times10^9$ of *E. coli* OMVs or aOMVs at weekly intervals for three weeks. Error bars indicate SEM. N=4.
Figure 20:
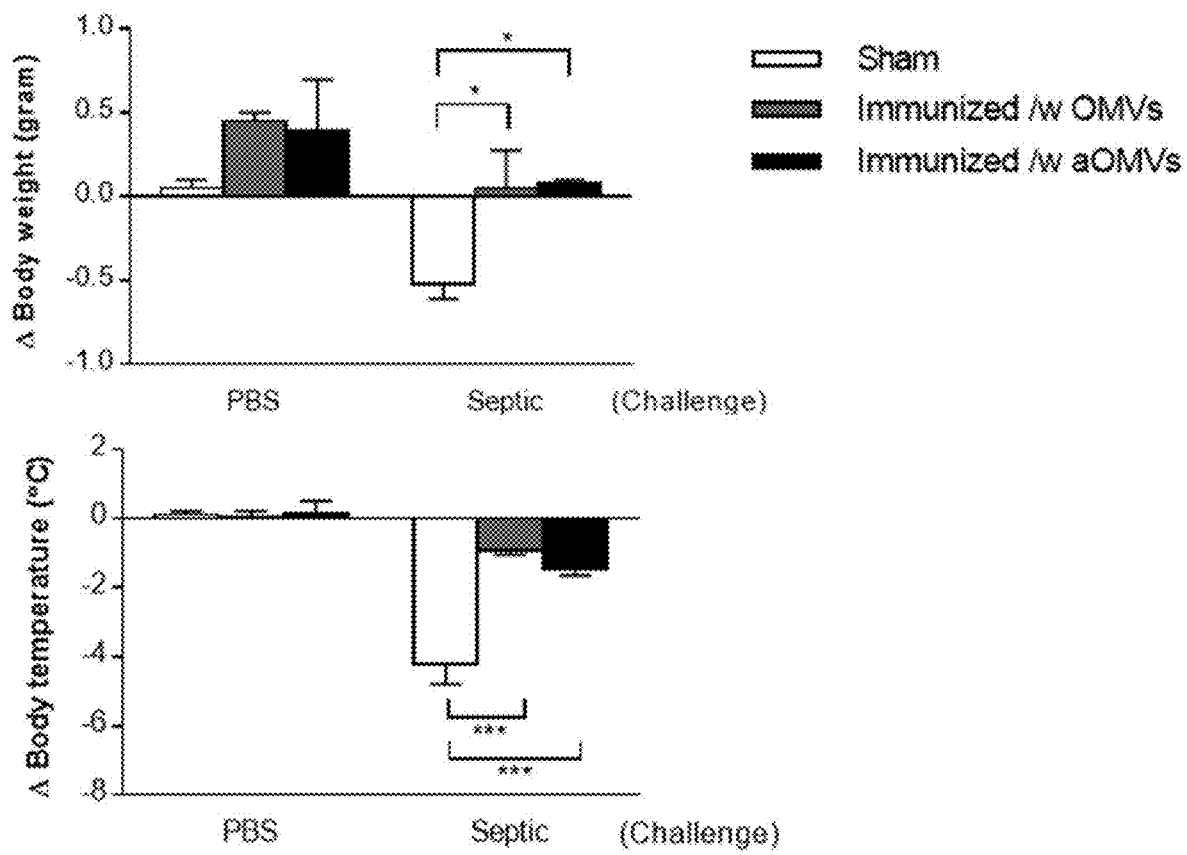
FIG. 20 depicts the body weight (left) and body temperature (right) measured at 6 h after intraperitoneal challenge with nonlethal dose of *E. coli* OMVs (15 μg) in mice immunized with $5\times10^9$ of *E. coli* OMVs or aOMVs at weekly intervals for three weeks. *, P<0.05; ***, P<0.001; versus sham group; one-way ANOVA with Tukey's multiple comparison test. Error bars indicate SEM. N=4.
Figure 21:
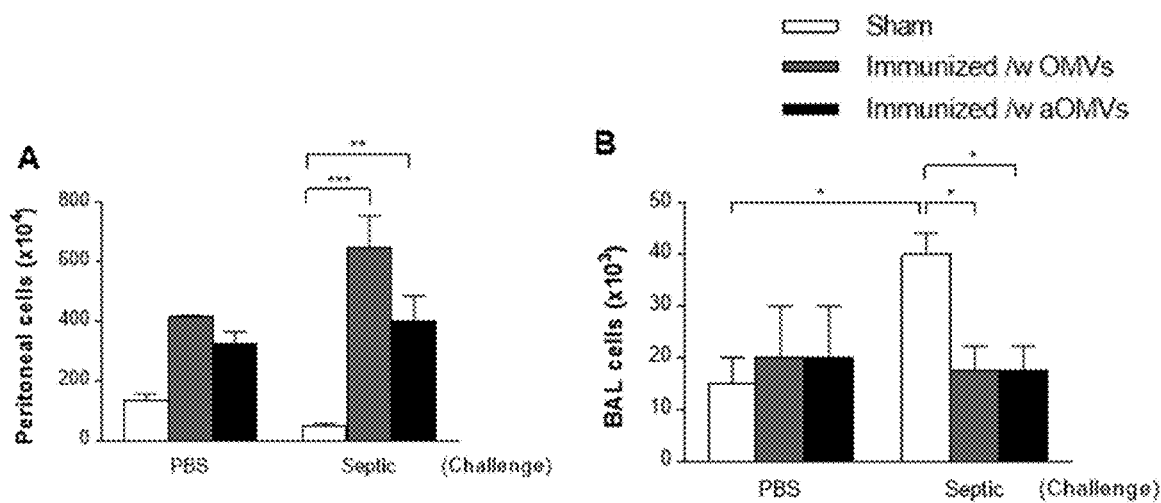
FIG. 21, Panel A depicts the number of total leukocytes in the peritoneum at 6 h after intraperitoneal challenge with nonlethal dose of *E. coli* OMVs (15 μg) in mice immunized with $5\times10^9$ of *E. coli* OMVs or aOMVs at weekly intervals for three weeks. , P<0.01; *, P<0.001; one-way ANOVA with Tukey's multiple comparison test. Error bars indicate SEM. N=4.
Figure 22:
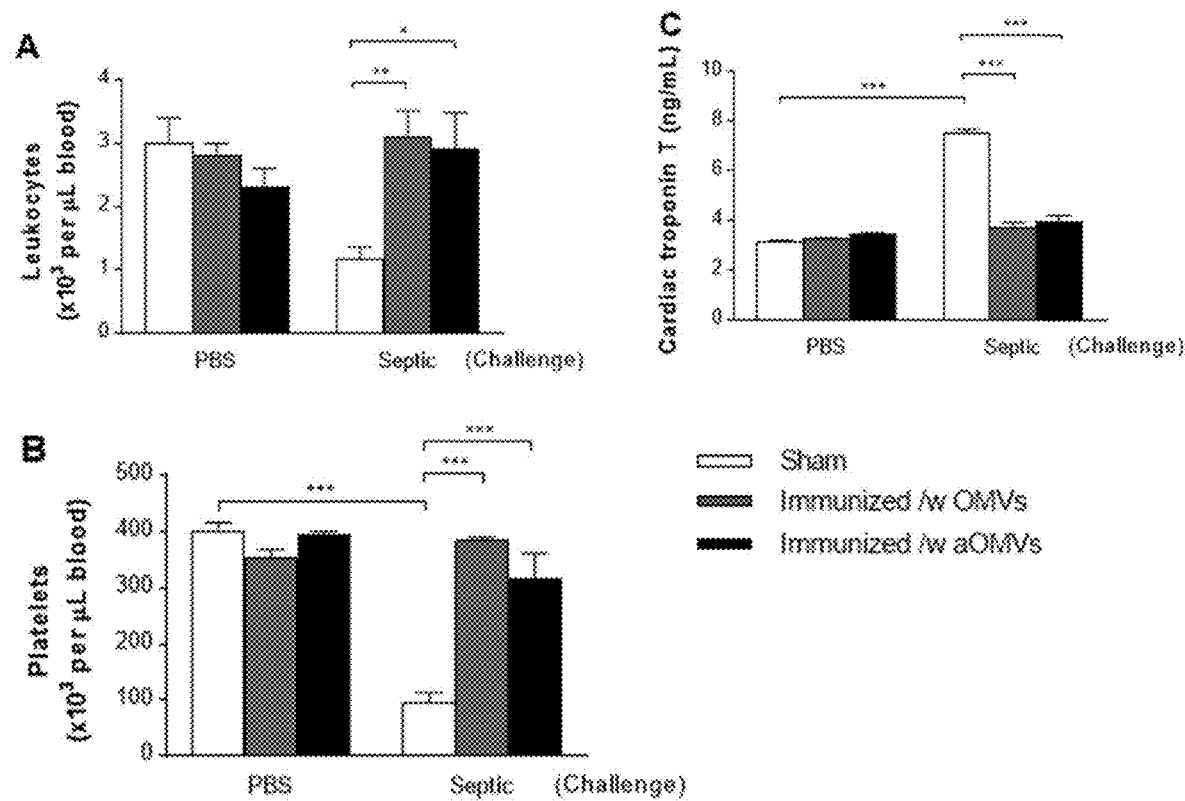
FIG. 22, Panel A depicts the number of total leukocytes in the blood at 6 h after intraperitoneal challenge with nonlethal dose of *E. coli* OMVs (15 μg) in mice immunized with $5\times10^9$ of *E. coli* OMVs or aOMVs at weekly intervals for three weeks. *, P<0.05; **, P<0.01; one-way ANOVA with Tukey's multiple comparison test. Error bars indicate SEM. N=4.
Figure 23:
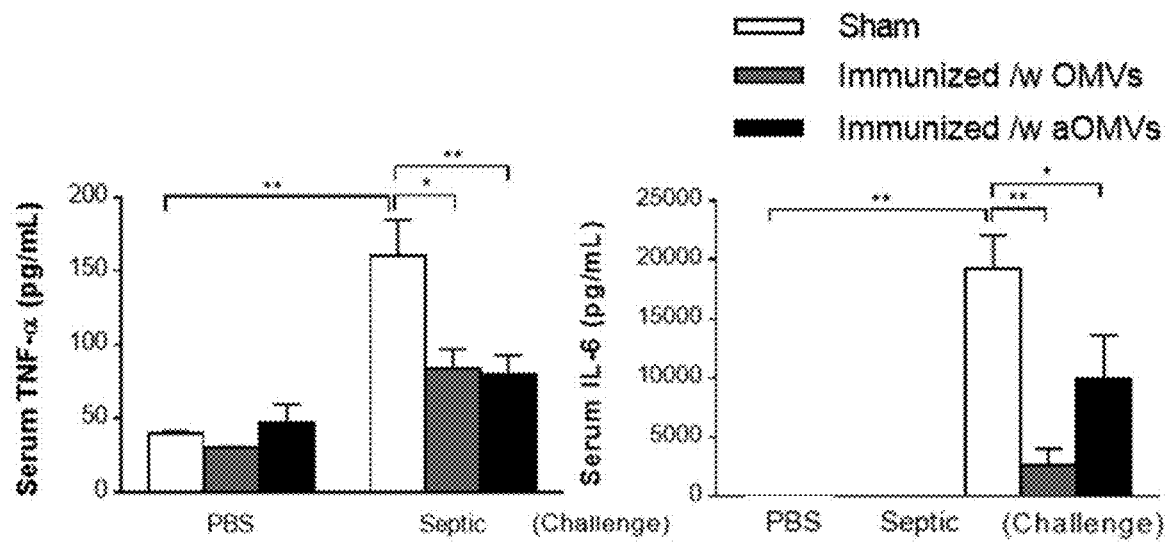
FIG. 23 depicts the levels of TNF-α (left) and IL-6 (right) in the serum at 6 h after intraperitoneal challenge with nonlethal dose of *E. coli* OMVs (15 μg) in mice immunized with $5\times10^9$ of *E. coli* OMVs or aOMVs at weekly intervals for three weeks. *, P<0.05; **, P<0.01; one-way ANOVA with Tukey's multiple comparison test. Error bars indicate SEM. N=4.
Figure 24:
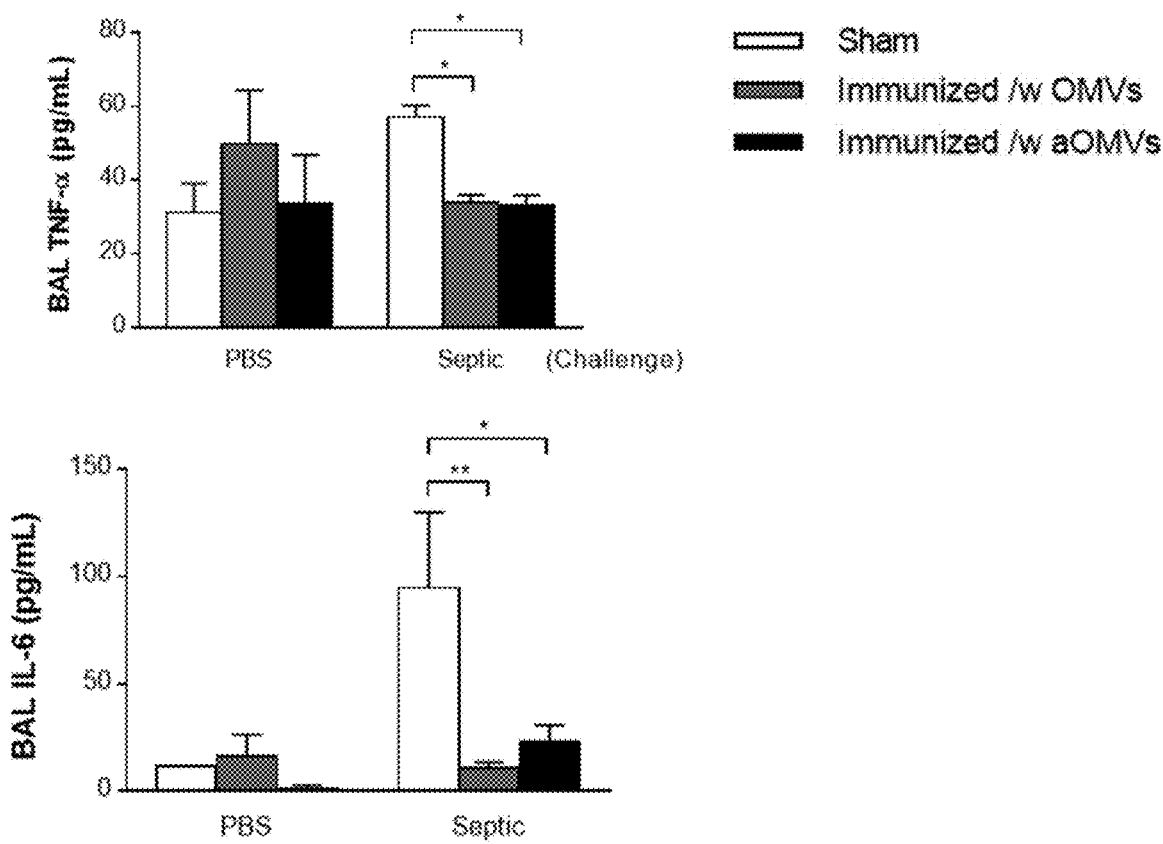
FIG. 24 depicts the levels of TNF-α (left) and IL-6 (right) in the bronchoalveolar lavage (BAL) fluid at 6 h after intraperitoneal challenge with nonlethal dose of *E. coli* OMVs (15 μg) in mice immunized with $5\times10^9$ of *E. coli* OMVs or aOMVs at weekly intervals for three weeks. *, P<0.05; **, P<0.01; one-way ANOVA with Tukey's multiple comparison test. Error bars indicate SEM. N=4.

Example 5: Efficacy of E. coli aOMVs Vaccine Against E. coli or OMV-Induced Sepsis Methods
Mice Experiments
$5\times10^9$ of OMVs or aOMVs were intraperitoneally injected to mice (wild-type C57BL/6 genetic background, 6 weeks old) once a week for three weeks. One week after the last immunization, sub-lethal dose (15 µg) of E. coli OMVs was intraperitoneally injected once. Mice were sacrificed at 6 h following anesthetization with i.p. injection of xylazine chloride (Bayer) and ketamine hydrochloride (Pfizer). Rectal temperature was measured by thermometer (Bioseb). Peritoneal fluid (PF), blood, and bronchoalveolar lavage (BAL) fluid were collected from mice, and then cytokines in the supernatant were analyzed by DuoSet ELISA Development kit (R&D Systems). Leukocytes and platelets in blood were counted using the light microscopy following incubation with 1% hydrochloride and Rees-Ecker diluting fluid (Thermo Fisher Scientific), respectively. For survival study, lethal dose of bacteria ($1\times10^{10}$ c.f.u.) were intraperitoneally challenged one week after the last immunization. And then, mice lethality, temperature, and weight were monitored for 5 days.
Results
There were no changes of body weight and temperature in aOMV-immunized mice before challenge with OMVs (FIG. 19).
Six hours after the challenge with OMVs, a decrease in body temperature and body weight was observed in negative control mice (sham), whereas the decrease in body temperature and body weight in aOMV-immunized mice was significantly less as compared to sham mice (FIG. 20). The number of immune cells in peritoneal fluid of aOMV-immunized mice were increased by challenge with OMVs (FIG. 21, Panel A). The number of immune cells in Bronchoalveolar lavage (BAL) fluid was significantly increased in sham mice by OMV challenge, whereas a greatly decreased number was detected if the mice had been immunized with aOMVs (FIG. 21, Panel B). Sham mice were observed to have decreased leukocyte and platelet numbers in the blood, and increased cardiac troponin T levels, a marker of cardiac injury after septic challenge. However, mice vaccinated with aOMVs recovered to normal levels (FIG. 22, Panels A-C). Moreover, blood and BAL fluid TNF-α and IL-6 levels were significantly decreased in mice immunized with aOMVs, as compared to sham mice (FIGS. 23 and 24). Taken together, the data obtained above indicate that E. coli aOMVs can be used as an effective vaccine comparable to OMVs for septic diseases.

Example 6: Immunological Properties Response to Various Doses of E. coli aOMVs

Methods
Mice Experiments

Various doses of aOMVs ($5\times10^8$, $1\times10^9$, $5\times10^9$) or OMVs ($5\times10^9$) were intraperitoneally injected to mice (wild type C57BL/6 genetic background, 6 weeks old) once a week for three weeks. Blood samples were taken from mice 3 days after each injection and assayed for their antibodies specific for E. coli lysates or OMV proteins. The mouse serum was 1:500 diluted in 1% BSA/PBS and placed in 96-well plates coated with 200 ng of E. coli lysates or OMV proteins. After incubation for 2 h, immunological changes were measured with a peroxidase-conjugated anti-mouse antibody.

Results

Figure 25A:
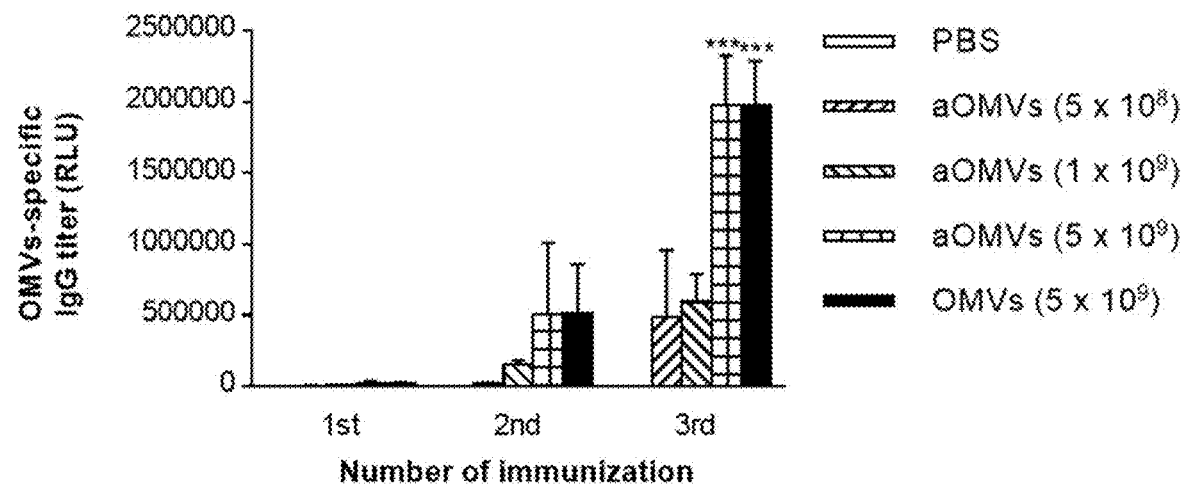
FIG. 25A is a graph showing the levels of *E. coli* OMV-specific antibodies measured in the course of three intraperitoneal injection of $5\times10^9$ of *E. coli* OMVs or various dose of aOMVs ($5\times10^8$, $1\times10^9$, $5\times10^9$) at regular intervals of one week. ***, P<0.001; versus sham group; one-way ANOVA with Tukey's multiple comparison test.
Figure 25B:
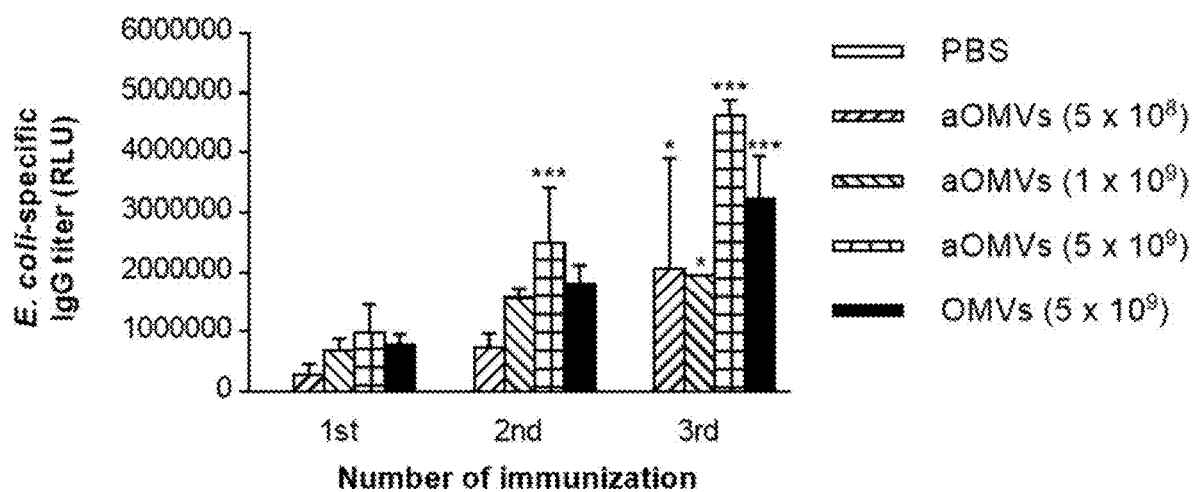
FIG. 25 B is a graph showing the levels of *E. coli* protein-specific antibodies measured in the course of three intraperitoneal injection of $5 \times 10^9$ of *E. coli* OMVs or various dose of aOMVs ($5 \times 10^8$, $1 \times 10^9$, $5 \times 10^9$) at regular intervals of one week. *, P<0.05; ***, P<0.001; versus sham group; one-way ANOVA with Tukey's multiple comparison test. Error bars indicate SEM. N=4.

Even a low dose of aOMVs ($5\times10^8$) could induce E. coli OMV or lysates protein-specific antibodies in the mouse blood with a peak at 7 days after the third injection (FIG. 25, Panels A-B).

Example 7: Isolation and Characterization of P. aeruginosa aOMVs

Methods
Preparation of aOMVs

A P. aeruginosa PAO1 strain was acquired from ATCC company. The bacterial culture was pelleted, resuspended in 20% sucrose in 20 mM Tris, pH 8.0 (4 mL per g cells) and lysozyme (600 μg per g cells) were added. The resulting spheroplasts were pelleted, and then sonicated in ice-cold 10 mM Tris, pH 8.0. The cells were pelleted at 8,000×g for 5 min, and then whole membranes were pelleted from the supernatants at 40,000×g for 60 min. The membranes were resuspended in distilled water, freeze-thawed, and incubated in 0.5% Sarkosyl (sodium N-lauroylsarcinosinate; 20 min, 25° C.). The outer membrane was pelleted (40,000×g for 90 min), and incubated with high pH solution (200 mM $Na_2CO_3$, pH 14.0) for 1 hour at 25° C. The pellets were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min, and considered aOMVs.

Quantification of aOMVs

Protein concentration of aOMVs was determined with a Bradford dye assay (Bio-Rad Laboratories). aOMV particle concentration were assessed by ZetaView analyzer (Particle Metrix GmbH). Measurements were assessed in triplicates and each individual data was obtained from two stationary layers with five times measurements in each layer. Sensitivity of camera was configured at 70 in all measurements. Data were analyzed using ZetaView analysis software version 8.2.30.1.

Generation of OMVs

P. aeruginosa cultures were pelleted at 6,000×g, 4° C. for 20 min, twice, and then the supernatant fraction was filtered through a 0.45-μm vacuum filter and was concentrated by ultrafiltration Vivaflow 200 module (Sartorius) with a 100 kDa cut-off membrane. The retentate was again filtered through a 0.22-μm vacuum filter to remove any remaining cells. The resulting filtrate was subjected to ultracentrifugation at 150.000×g. 4° C. for 3 h and resuspended with PBS.

Transmission Electron Microscopy

Formvar/carbon Cu copper grids (Electron Microscopy Sciences) were glow discharge-treated before aOMVs were loaded. Then aOMVs were washed two times in distilled water and then fixed using 2.5% glutaraldehyde dissolved PBS. After two further washes in filtered water, the samples were stained using 2% uranyl acetate for 1.5 min. Negative-stained samples were examined on a digitized LEO 912AB Omega electron microscope (Carl Zeiss SMT) at 120 kV with a Veleta CCD camera (Olympus-SiS).

RNA and DNA Analysis

RNA from aOMVs or OMVs was isolated using miR-CURY™ RNA isolation kit for biofluids (Exiqon) according to manufacturer's protocol. DNA was isolated using Qiamp DNA Blood Mini kit (Qiagen) according to manufacturer's protocol. One microliter of isolated RNA or DNA were analyzed for its quality, yield, and nucleotide length with capillary electrophoresis using Agilent RNA 6000 Nanochip and Agilent High sensitivity DNA chip, respectively, on an Agilent 2100 Bioanalyzer® (Agilent Technologies).

Figure 26:
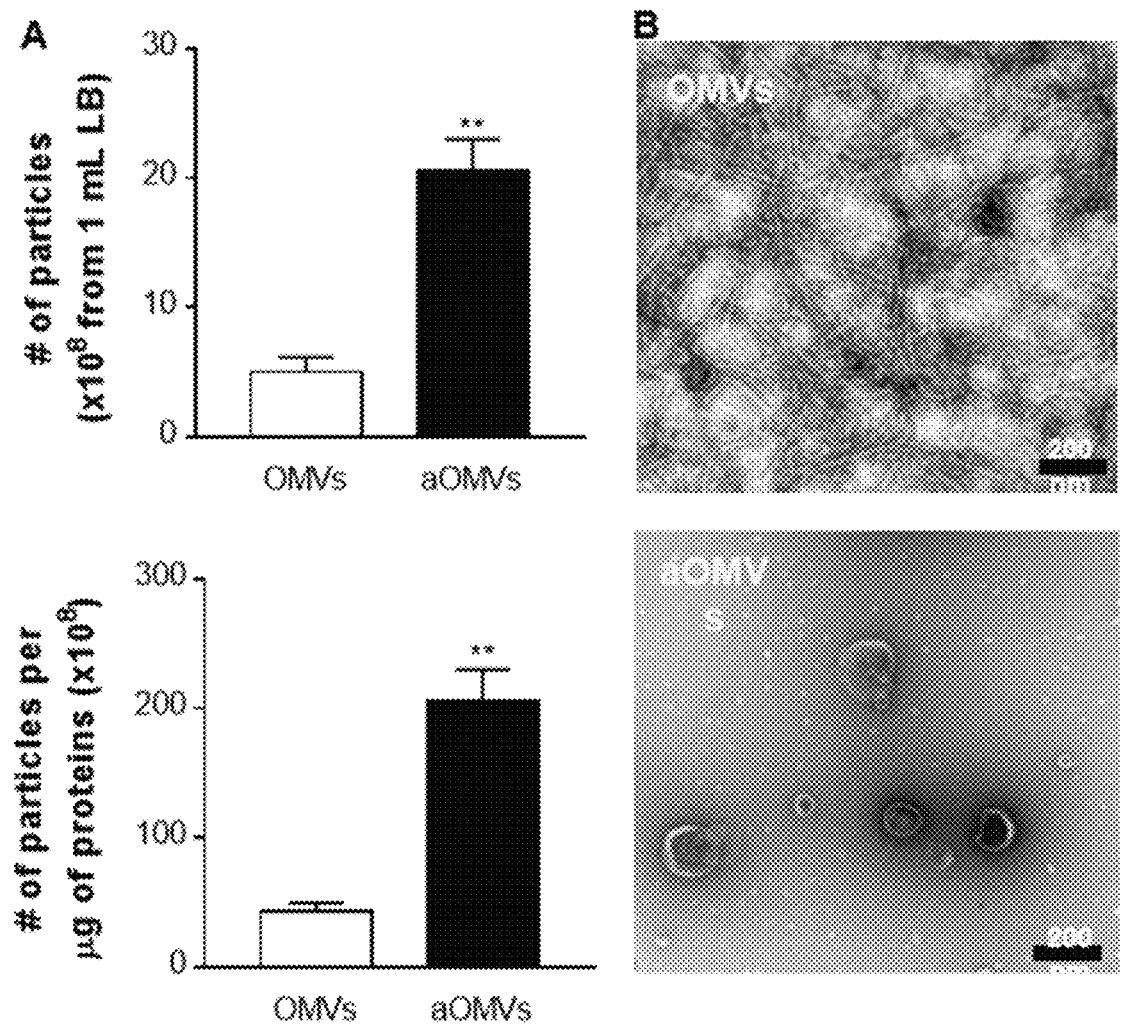
FIG. 26, Panel A depicts the particle numbers of *P. aeruginosa* naturally occurring outer membrane vesicles (OMVs) and *P. aeruginosa* artificial OMVs (aOMVs) per 1 mL LB media (upper graph) and the particle numbers of *P. aeruginosa* OMVs and *P. aeruginosa* aOMVs per one microgram of proteins (lower graph). **, P<0.01; two-tailed unpaired T test. Error bars indicate SEM. N=3.
Figure 27:
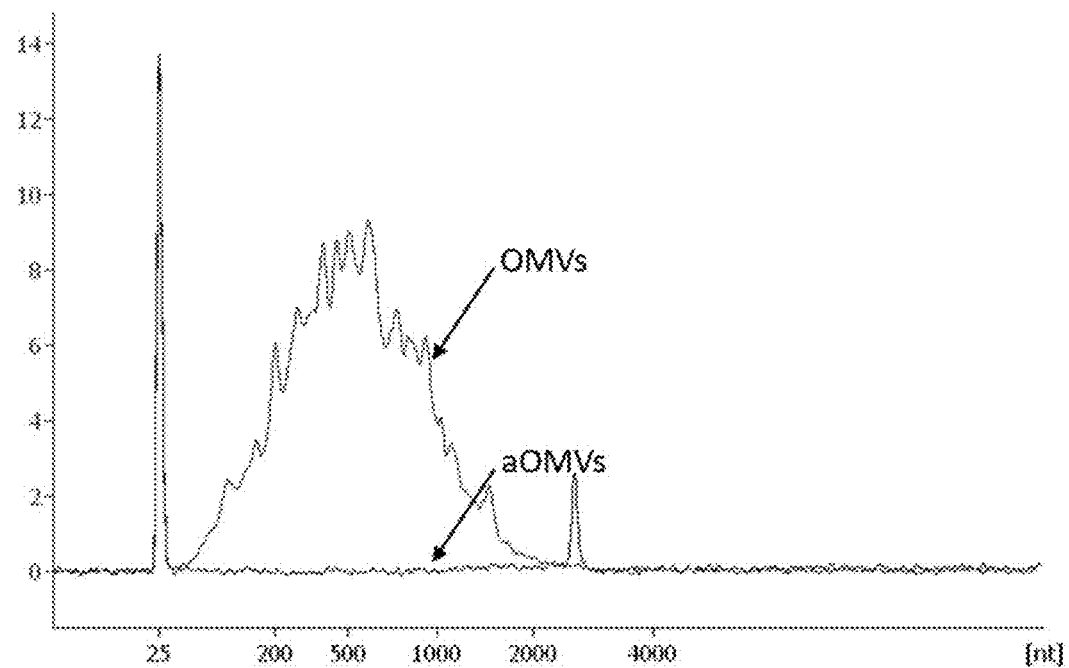
FIG. 27 depicts an electropherogram of RNA molecules isolated from *P. aeruginosa* aOMVs and RNA molecules isolated from *P. aeruginosa* OMVs.
Figure 28:
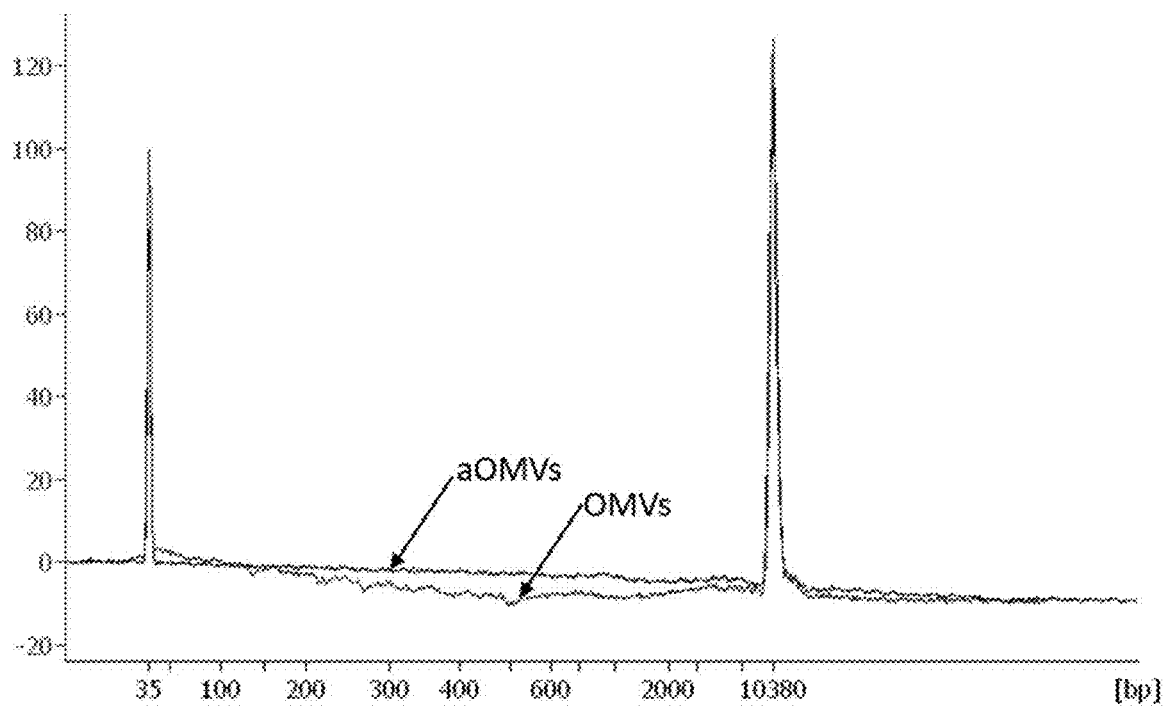
FIG. 28 depicts an electropherogram of DNA molecules isolated from *P. aeruginosa* aOMVs and DNA molecules isolated from *P. aeruginosa* OMVs.

Results aOMVs were prepared in higher yield than naturally produced OMVs (FIG. 26, Panel A). aOMVs presented similar shape and size with OMVs, but were clearer as visualized by transmission electron microscopy (FIG. 26, Panel B). RNA contents in aOMVs were almost removed in contrast to OMVs (FIG. 27). DNA peaks were not detectable in both aOMVs and OMVs (FIG. 28).

Example 8: Proteomic Analysis of P. aeruginosa aOMV Proteins

Methods
LC-Ms/Ms Analysis:

Two biological replicate aOMVs or OMVs (30 μg) were digested with trypsin using the filter-aided sample preparation (FASP) method and C18 spin columns desalting according to manufacturer's instructions. All fractions were dried on Speedvac and reconstituted in 3% acetonitrile and 0.2% formic acid and analyzed on Orbitrap Fusion Tribrid mass spectrometer interfaced with Easy-nLC 1200 (Thermo Fisher Scientific, Waltham, Mass.). Peptides were trapped on the Acclaim Pepmap 100 C18 trap column (100 μm×2 cm, particle size 5 μm; Thermo Fischer Scientific) and separated on the in-house packed C18 analytical column (75 μm×30 cm, particle size 3 μm) using the gradient from 5% to 33% B in 160 min, from 33% to 100% B in 5 min, solvent A was 0.2% formic acid and solvent B was 80% acetonitrile and 0.2% formic acid. Precursor ion mass spectra were recorded at 120 000 resolution, the most intense precursor ions were selected, fragmented using HCD at collision energy setting of 30 and the MS/MS spectra were recorded at 30 000 resolution with the maximum injection time of 125 ms and the isolation window of 1.0 Da. Charge states 2 to 7 were selected for fragmentation, dynamic exclusion was set to 45 s with 10 ppm tolerance.

Results

Figure 29:
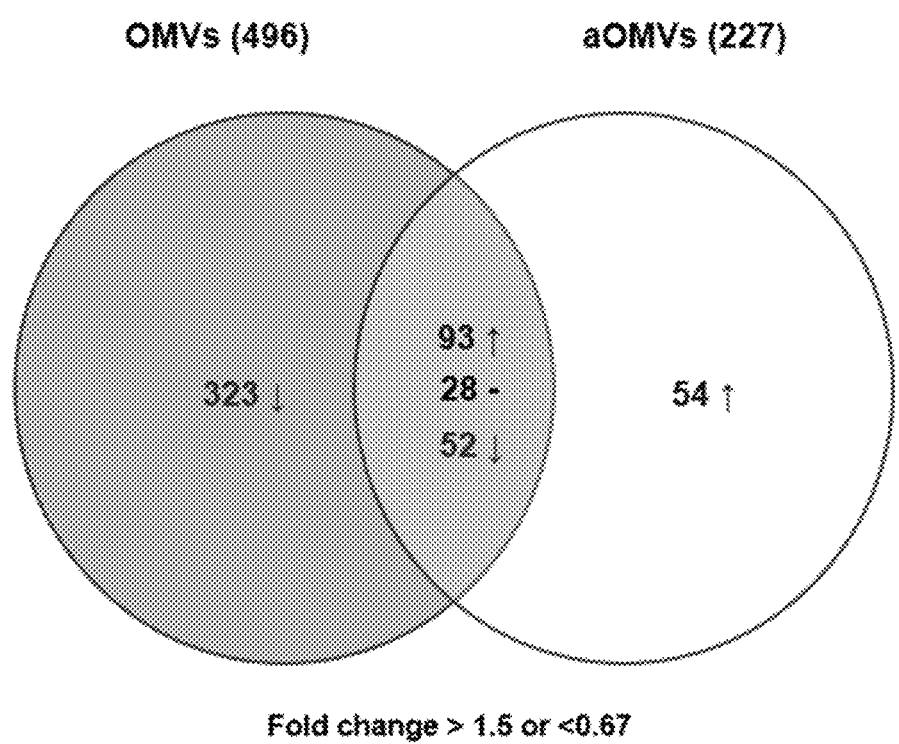
FIG. 29 depicts Venn diagram comparing proteomes of *P. aeruginosa* aOMVs to that of OMVs. T indicates the number of aOMV proteins that were present at a level more than 1.5 times the level of the same protein present in OMVs. J indicates the number of aOMV proteins that were present at a level less than 0.67 times the level of the same protein present in OMVs.

A total of 496 and 227 proteins from OMVs and aOMVs, respectively (FIG. 29) were identified. 173 proteins were identified in both vesicle preparations, whereas 323 and 54 proteins were uniquely identified in OMVs and aOMVs, respectively. Based on the relative protein abundance, 28 proteins did not change markedly in abundance among 173 proteins. However, 93 and 52 proteins were relatively increased and decreased in aOMVs, respectively, as compared to their level in naturally occurring OMVs. In the GO term subcellular localization analysis, aOMV-enriched proteome showed distinct features from OMV-enriched proteome (FIG. 30). aOMV proteome was enriched with cell outer membrane proteins, whereas OMV proteome was enriched with cytosol and inner membrane proteins. In the GO term biological process analysis, aOMV proteome was enriched with biological processes including cell motility and ion transport (FIG. 31). By contrast, OMV proteome was enriched with biological processes including translation and metabolism.

Example 9: Less Toxicity of P. aeruginosa aOMVs In Vitro

Methods

MH-S Cytokines

MH-S($1\times10^5$), a mouse lung macrophage cell line, were seeded into 24-well plates. Various dose of aOMVs and OMVs were applied to the cells to induce pro-inflammatory cytokines (TNF-α and IL-6) for 15 h. Supernatant concentrations of cytokines were measured by ELISA kit (R&D systems).

Figure 32:
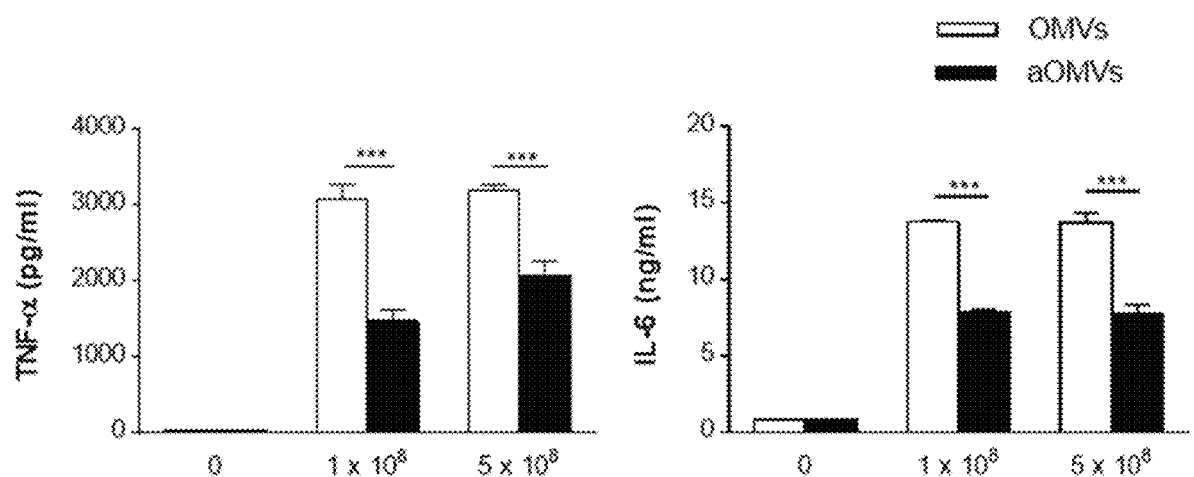
FIG. 32 depicts *P. aeruginosa* OMV- or aOMV-induced pro-inflammatory cytokines in the supernatants of MH-S cells. Various particle numbers of OMVs or aOMVs were added to the cells for 18 h, and then TNF-α (left) and IL-6 (right) were measured by ELISA. ***, P<0.001; one-way ANOVA with Tukey's multiple comparison test. Error bars indicate SEM. N=3.

Results aOMVs were observed to increase TNF-α and IL-6 from macrophages to a lesser extent than OMVs (FIG. 32), showing that aOMVs might be much safer vaccine candidate.

Example 10: Immunological Properties of P. aeruginosa aOMVs In Vitro and In Vivo Methods Antibody Titer Against P. aeruginosa Lysates $5\times10^9$ of OMVs or aOMVs were intraperitoneally injected to mice (wild-type C57BL/6 genetic background, 6 weeks old) once a week for three weeks. Blood samples were taken from mice 3 days after each injection and assayed for their antibodies specific for P. aeruginosa lysates. The mouse serum was 1:500 diluted in 1% BSA/PBS and placed in 96-well plates coated with 200 ng of E. coli lysates. After incubation for 2 h, immunological changes were measured with a peroxidase-conjugated anti-mouse antibody.

Splenocyte Cytokines

Seven days after the three injections of OMVs or aOMVs ($5\times10^9$), CD4+ T cells from spleen were isolated from the mice. The cells ($5\times10^5$) were incubated for 72 h with 1 µg/mL of P. aeruginosa proteins, followed by ELISA to quantitatively analyze TNF-α, IFN-γ, IL-4, and IL-17.

Results

Figure 33:
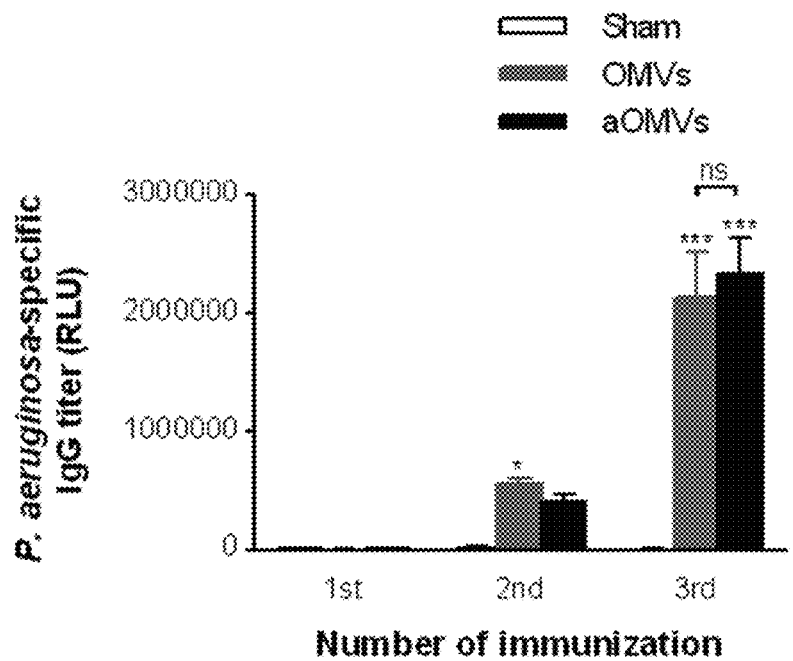
FIG. 33 is a graph showing the levels of *P. aeruginosa* protein-specific antibodies measured in the course of three intraperitoneal injection of $5 \times 10^9$ of *P. aeruginosa* OMVs or aOMVs at regular intervals of one week. *, P<0.05; ***, P<0.001; ns, not significant; versus sham group; one-way ANOVA with Tukey's multiple comparison test. Error bars indicate SEM. N=4.
Figure 34:
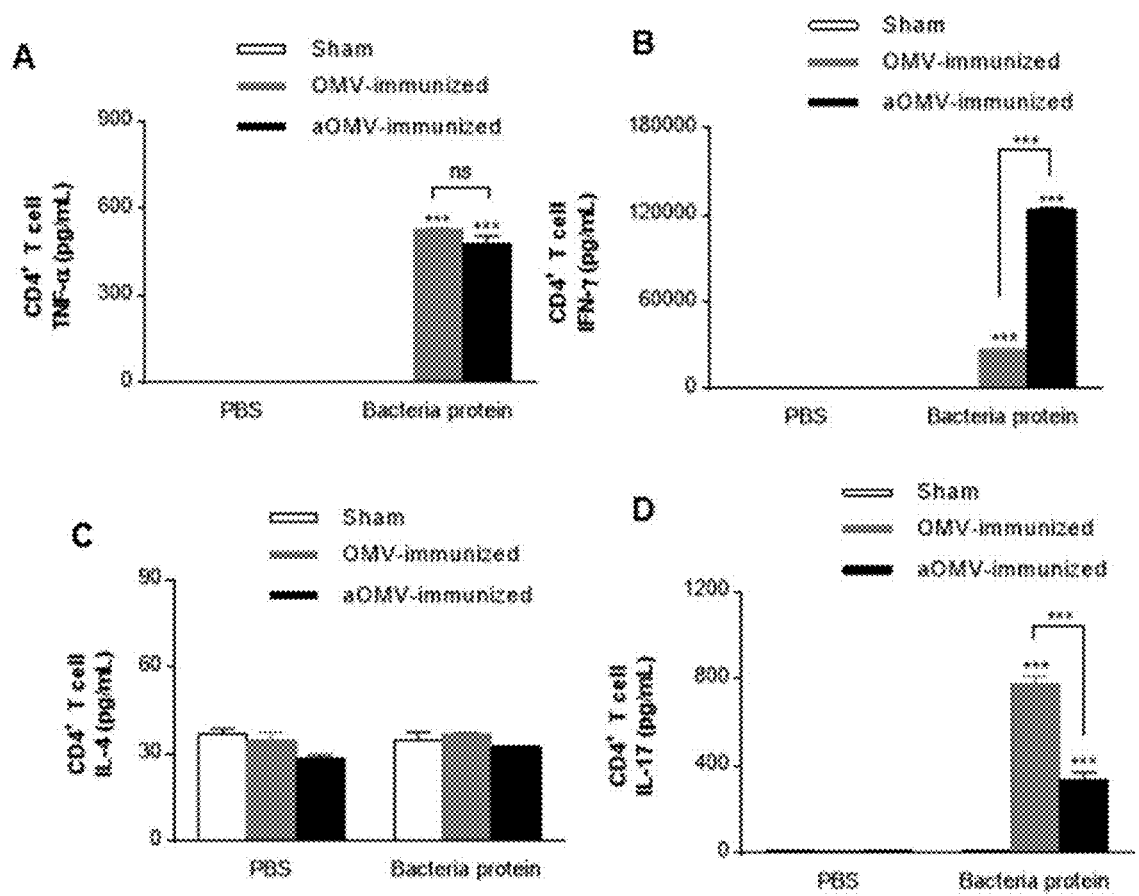
FIG. 34, Panel A depicts the level of TNF-α secreted from mouse splenic CD4+ T cells upon ex vivo treatment with *P. aeruginosa* proteins (1 μg/mL) after the mice were immunized with $5 \times 10^9$ of *P. aeruginosa* OMVs or aOMVs. ***, P<0.001; ns, not significant; versus sham group; one-way ANOVA with Tukey's multiple comparison test. Error bars indicate SEM. N=3.

The P. aeruginosa lysate-specific antibodies in the mouse blood started to from 7 days after the first injection of aOMVs, and were amplified by the second and the third injection, with a peak at 7 days after the third injection (FIG. 33). And, higher levels of TNF-α, IFN-γ, and IL-17 (Th-1 and Th-17-related) were secreted from splenic CD4+ T cells of aOMV-immunized group, compared to the sham group (FIG. 34, Panels A-D). Interestingly, IFN-γ was dramatically increased in aOMV- than OMV-immunized group. However, there was no change in the level of IL-4 in aOMV or OMV-immunized compared to sham group.

Example 11: Efficacy of P. aeruginosa aOMVs Vaccine Against P. aeruginosa-Induced Pneumonia Methods Mice Experiments $5\times10^9$ of OMVs or aOMVs were intraperitoneally injected to mice (wild-type C57BL/6 genetic background, 6 weeks old) once a week for three weeks. One week after the last immunization, sub-lethal dose ($4\times10^8$ c.f.u.) of P. aeruginosa was intranasally injected once. Mice were sacrificed at 48 h following anesthetization with i.p. injection of xylazine chloride (Bayer) and ketamine hydrochloride (Pfizer). Bronchoalveolar lavage (BAL) fluid were collected from mice, and then cytokines in the supernatant were analyzed by DuoSet ELISA Development kit (R&D Systems). For histology, lungs were excised after whole body perfusion, immediately embedded into OCT compound (Leica), sectioned (4 µm), and stained with hematoxylin and eosin.

Results

Figure 35:
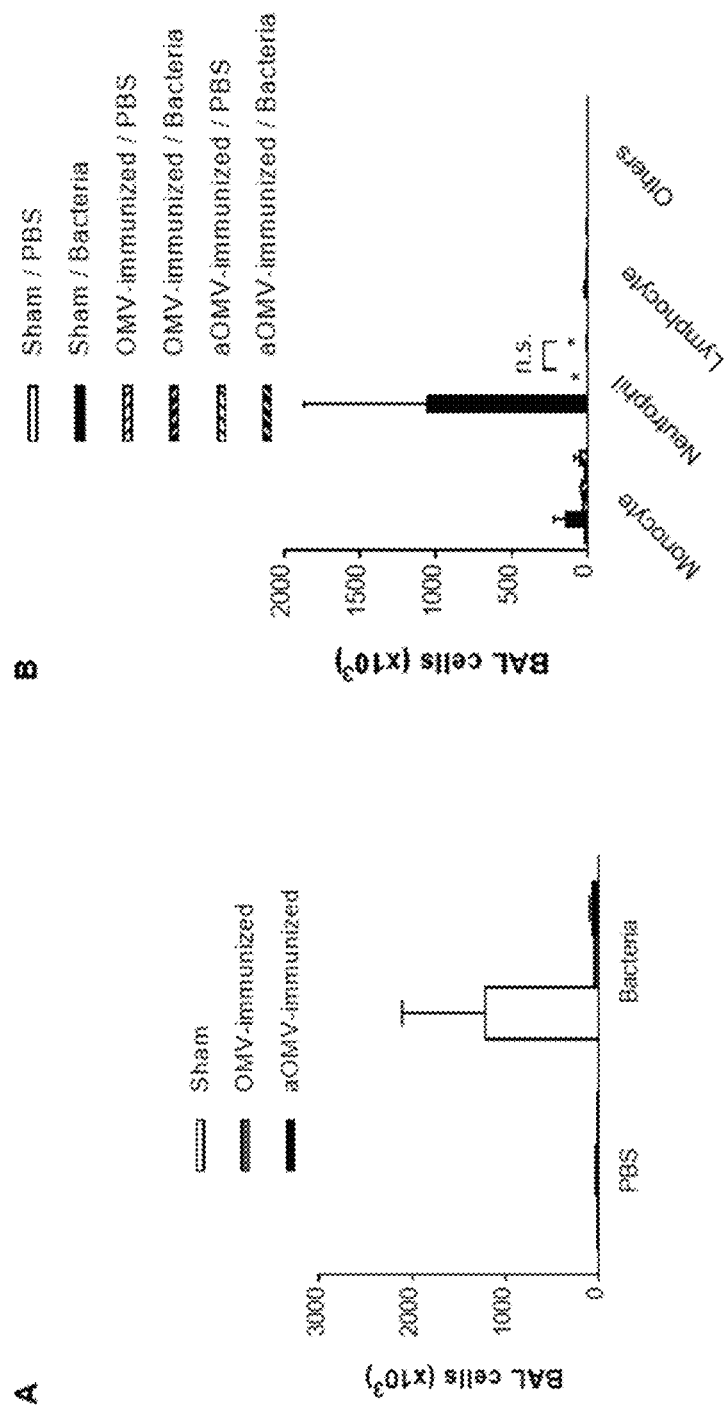
FIG. 35, Panel A depicts the number of total leukocytes in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. Versus sham group; one-way ANOVA with Tukey's multiple comparison test. Error bars indicate SEM. N=4.
Figure 36:
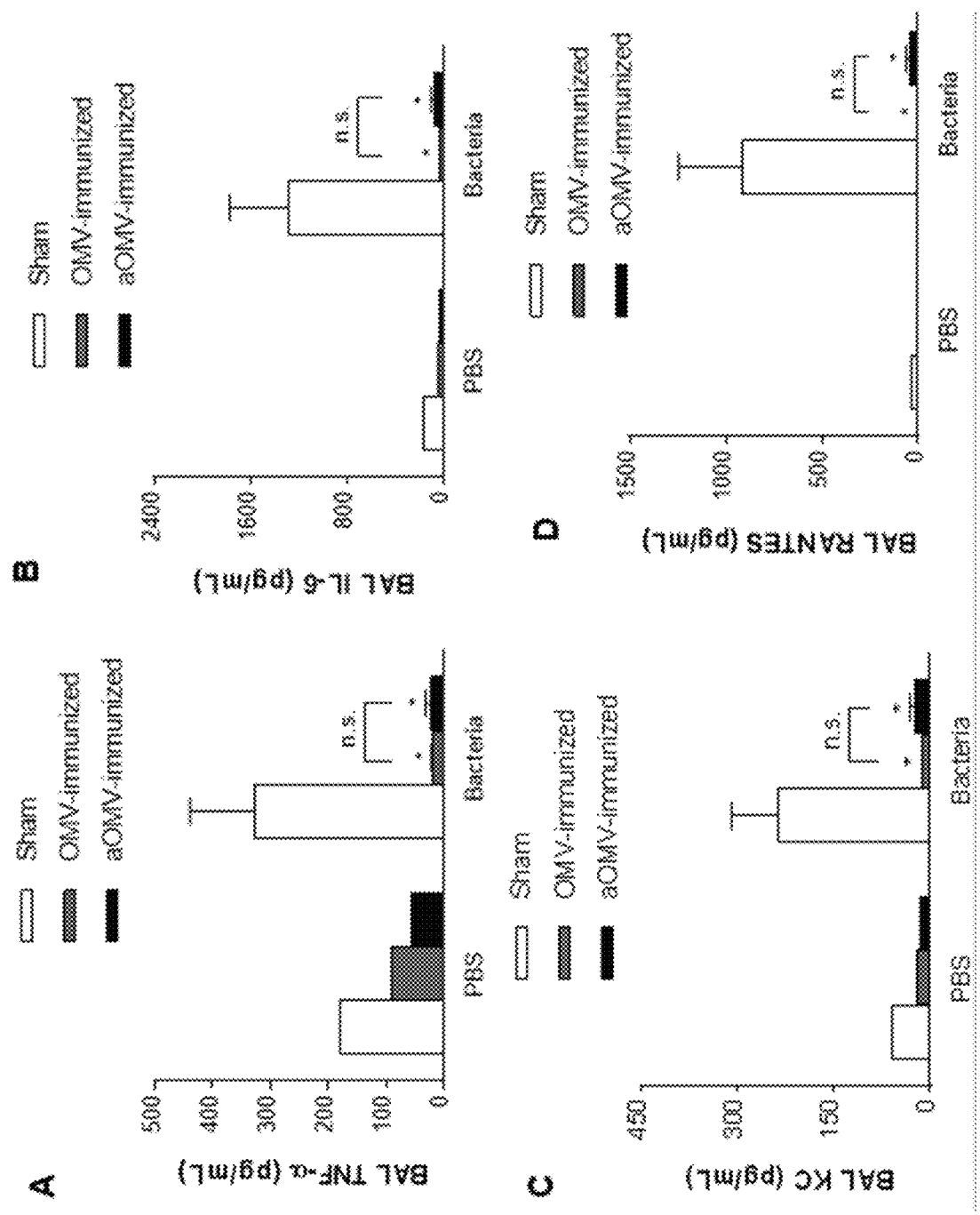
FIG. 36, Panel A depicts the levels of TNF-α in the BAL fluid at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. *, P<0.05; n.s., not significant; versus sham group; one-way ANOVA with Tukey's multiple comparison test. Error bars indicate SEM. N=4.
Figure 37:
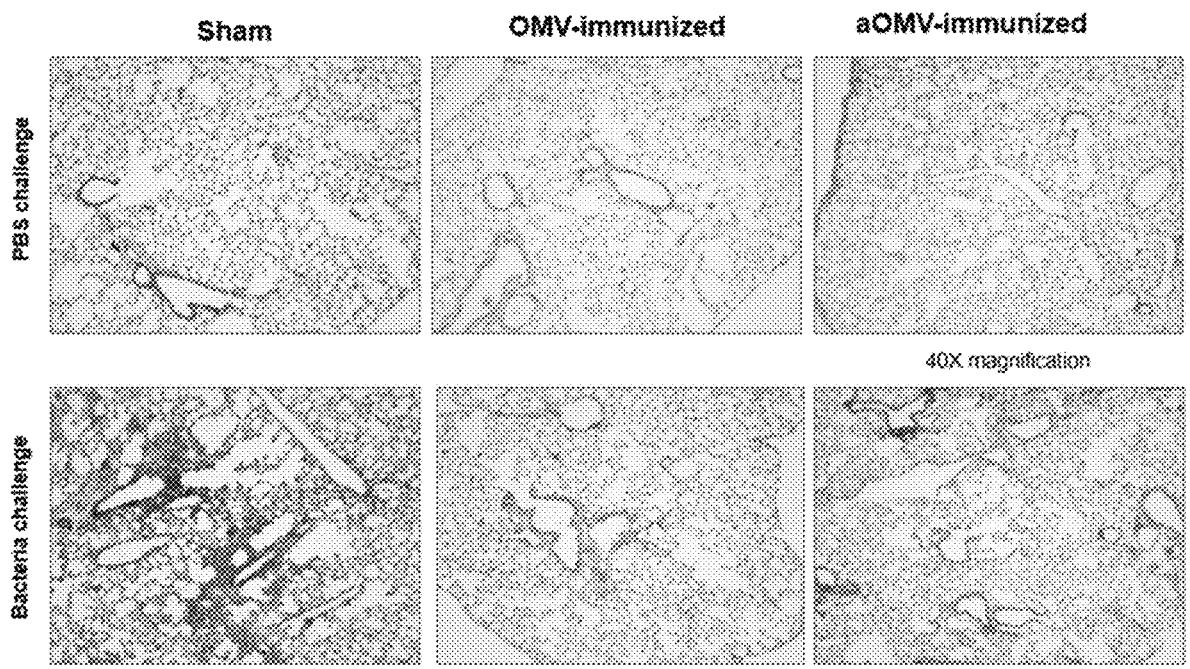
FIG. 37 depicts images of hematoxylin-eosin-stained lung sections at 48 h after intranasal challenge with nonlethal dose of *P. aeruginosa* ($4 \times 10^8$ c.f.u.) in mice immunized with $5 \times 10^9$ of *P. aeruginosa* OMVs or aOMVs at weekly intervals for three weeks. 40× magnification.

Forty eight hours after the challenge with P. aeruginosa, an increase in BAL cells was observed in sham mice, whereas the infiltration was inhibited in aOMV-immunized mice (FIG. 35, Panels A-B). Especially, the number of neutrophils was decreased if the mice had been immunized with aOMVs. Moreover, BAL fluid pro-inflammatory cytokines (TNF-α and IL-6) and chemokine levels for neutrophils and macrophages were significantly decreased in mice immunized with aOMVs, as compared to sham mice (FIG. 36, Panels A-D). Also, histology of the lung showed that the infiltration of immune cells into bronchial and alveolar regions was reduced in aOMV-immunized mice (FIG. 37). Taken together, the data obtained above indicate that P. aeruginosa aOMVs can be used as an effective vaccine comparable to OMVs for pneumonia.

Example 12: Isolation and Characterization of E. coli rePDNVs

Methods

Figure 38B:
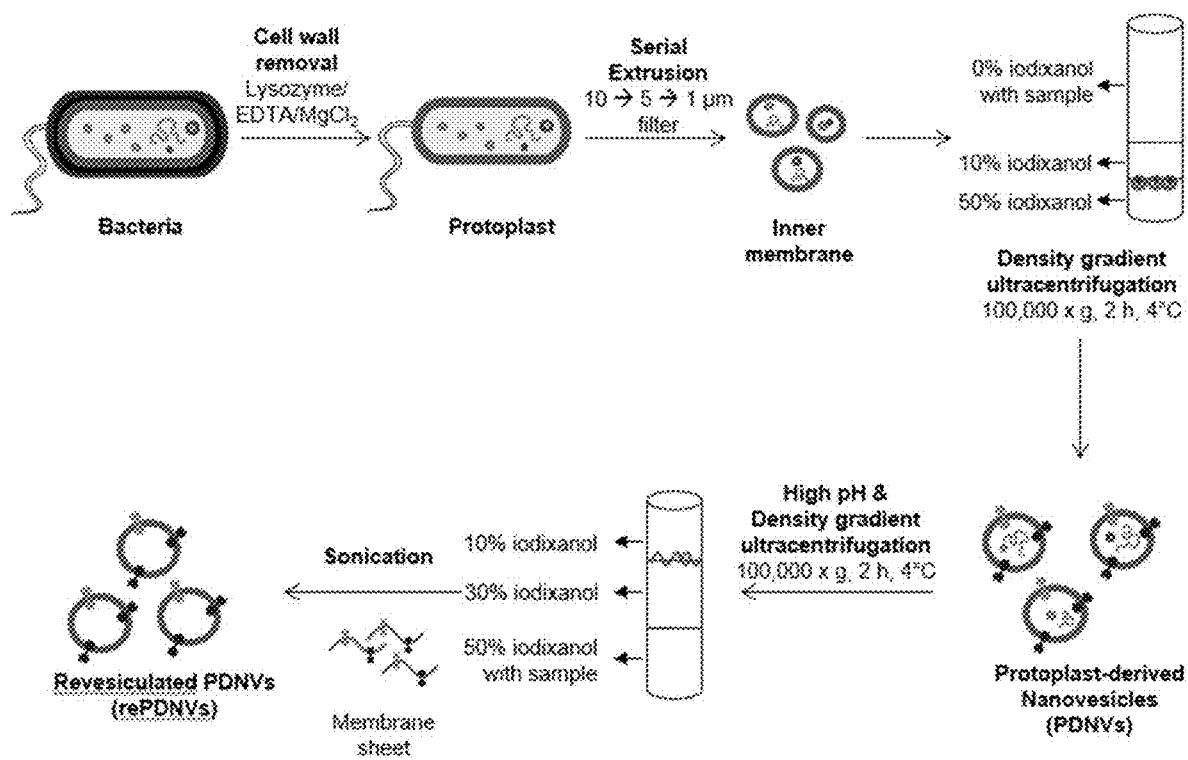
FIG. 38B depicts steps for generation of rePDNVs according to an embodiment of the present disclosure.

Preparation of rePDNVs rePDNVs were purified as described previously with some modifications (Nano Lett. 2015 Jan. 14; 15(1):266-74). A uropathogenic Escherichia coli strain was acquired to produce rePDNVs. The bacterial culture was pelleted and resuspended in 10 mM EDTA, followed by incubation for 30 min. Lysozyme (2 mg/mL) was added to the pellet and the protoplast was harvested at 4,000×g for 20 min after incubation for 1 h. The protoplast was passed five times through each of the polycarbonate membrane filters (Whatman) with a pore size of 10 µm, 5 µm, and 1 µm using a mini-extruder (Avanti Polar Lipids). The extruded samples were placed on the top of the density gradient cushion with 50% iodixanol (Axis-Shield PoC AS) overlaid with 10% iodixanol at the bottom of the ultracentrifuge tube. The layers formed between 10% and 50% iodixanol after ultracentrifugation at 100,000×g for 2 hours was collected, which is called PDNVs. The acquired PDNVs were incubated with high pH solution (200 mM Na2CO3, pH 14.0) for 1 hour at 25° C. And then, the incubated samples were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min, and considered rePDNVs (FIG. 38).

Quantification of rePDNVs

Protein concentration of rePDNVs was determined with a Bradford dye assay (Bio-Rad Laboratories). rePDNV particle concentration were assessed by ZetaView analyzer (Particle Metrix GmbH). Measurements were assessed in triplicates and each individual data was obtained from two stationary layers with five times measurements in each layer. Sensitivity of camera was configured at 70 in all measurements. Data were analyzed using ZetaView analysis software version 8.2.30.1.

Transmission Electron Microscopy

Formvar/carbon Cu copper grids (Electron Microscopy Sciences) were glow discharge-treated before rePDNVs were loaded. Then rePDNVs were washed two times in distilled water and then fixed using 2.5% glutaraldehyde dissolved PBS. After two further washes in filtered water, the samples were stained using 2% uranyl acetate for 1.5 min. Negative-stained samples were examined on a digitized LEO 912AB Omega electron microscope (Carl Zeiss SMT) at 120 kV with a Veleta CCD camera (Olympus-SiS).

SDS-PAGE

*E. coli* lysates, PDNVs, and rePDNVs were separated by 10% SDS-PAGE and whole protein bands were stained by Coomassie brilliant blue G-250 dye (Thermo Fisher Scientific). For Western blot analysis, separated gel by 10% SDS-PAGE was transferred to a polyvinylidene difluoride membrane. The blocked membrane was then incubated with anti-OmpA antibody (lab-made), anti-lipid A antibody (Abcam), or anti-FtsZ antibody (Antibodies-online, Inc.). After incubation with horseradish peroxidase-conjugated secondary antibody, the immunoreactive bands were visualized with a chemiluminescent substrate.

RNA and DNA Analysis

RNA from rePDNVs or PDNVs was isolated using miR-CURY™ RNA isolation kit for biofluids (Exiqon) according to manufacturer's protocol. DNA was isolated using Qiamp DNA Blood Mini kit (Qiagen) according to manufacturer's protocol. One microliter of isolated RNA or DNA were analyzed for its quality, yield, and nucleotide length with capillary electrophoresis using Agilent RNA 6000 Nanochip and Agilent High sensitivity DNA chip, respectively, on an Agilent 2100 Bioanalyzer® (Agilent Technologies).

Figure 39:
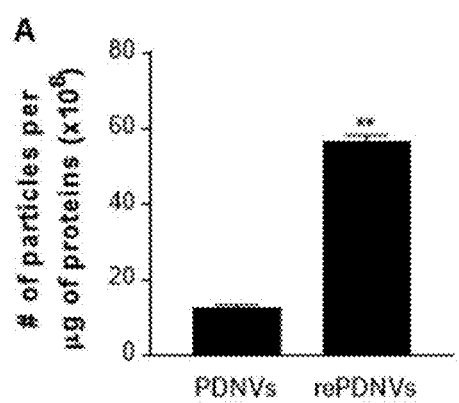
FIG. 39, Panel A depicts the particle number of *E. coli* PDNVs and rePDNVs per one microgram of proteins. **, P<0.01; two-tailed unpaired T test. Error bars indicate SEM. N=3.
Figure 39:
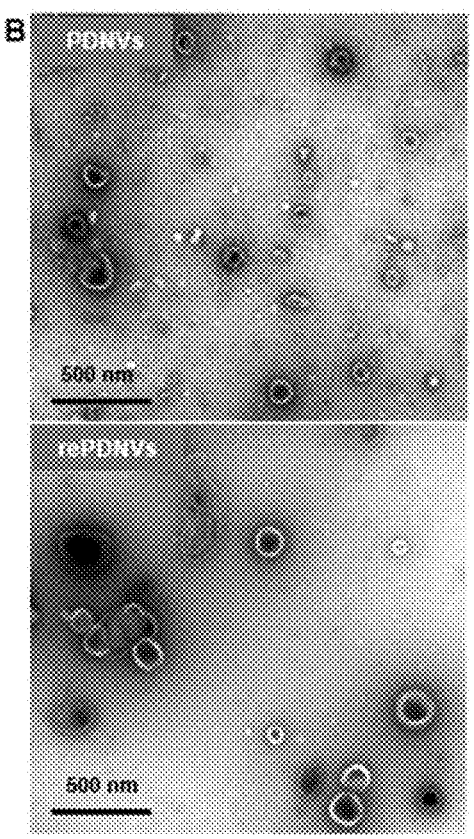
Figure 40:
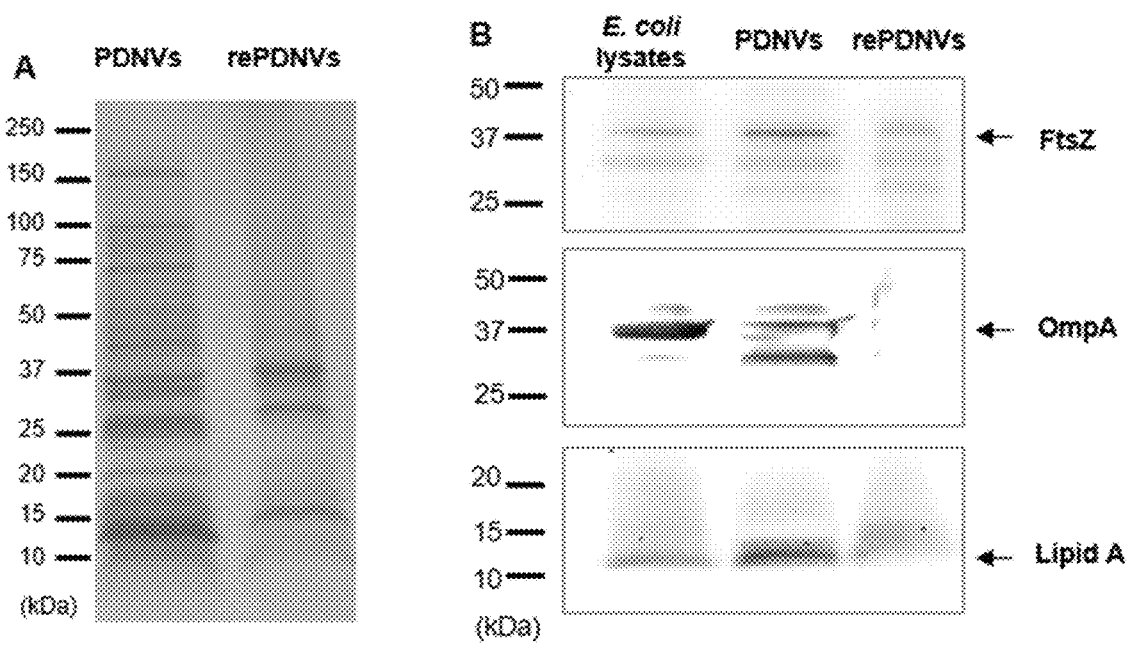
FIG. 40, Panel A depicts SDS-PAGE analysis of *E. coli* PDNVs and rePDNVs visualized by Coomassie Brilliant Blue staining.
Figure 41A:
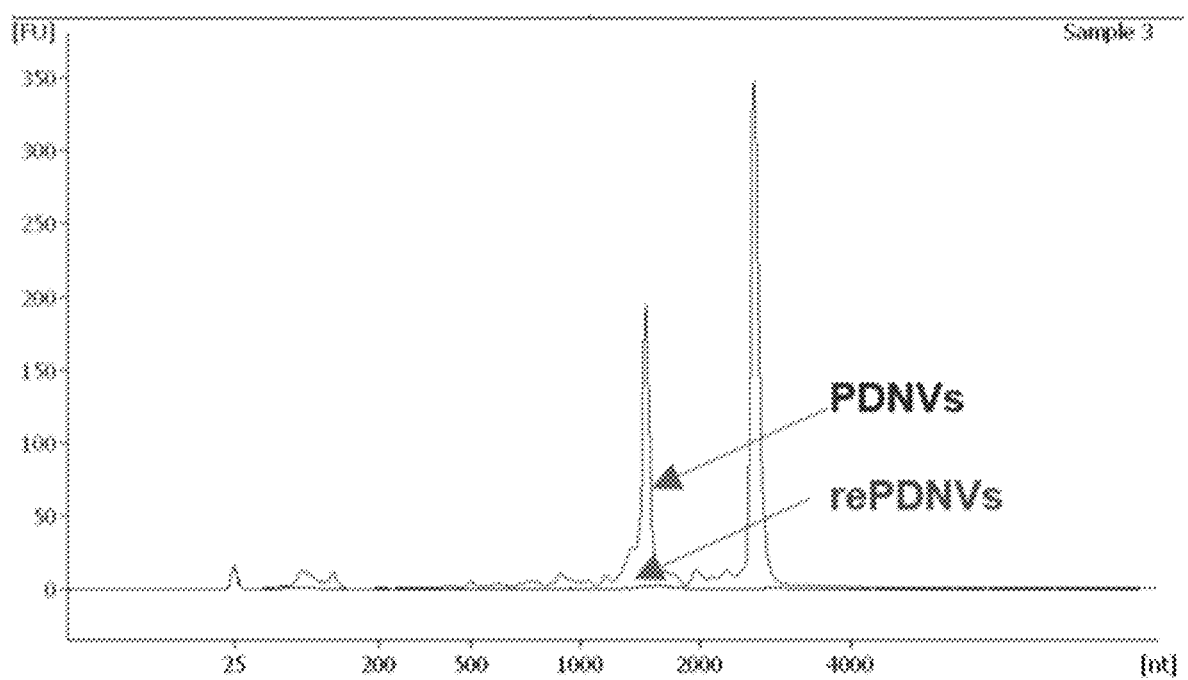
FIG. 41, Panel A depicts an electropherogram of RNA molecules isolated from *E. coli* rePDNVs and RNA molecules isolated from PDNVs.
Figure 41B:
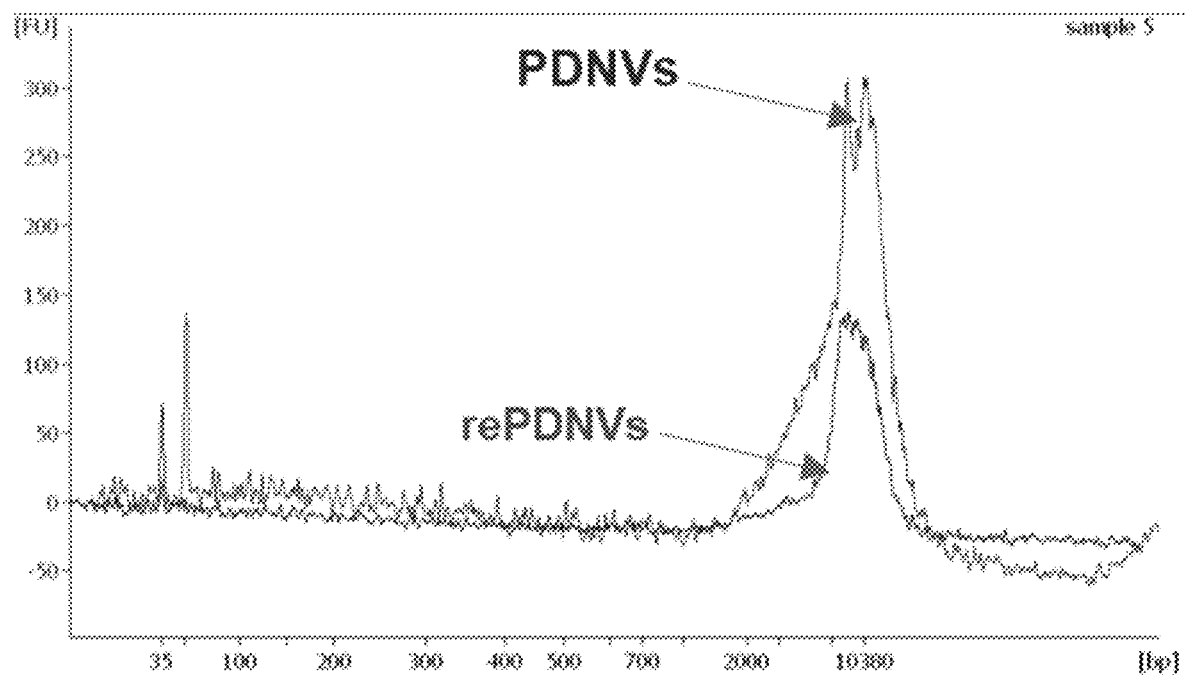

Results rePDNVs were prepared in higher purity than PDNVs (FIG. 39, Panel A). rePDNVs presented similar shape and size with PDNVs, but were clearer as visualized by transmission electron microscopy (FIG. 39, Panel B). Large molecular of proteins in rePDNVs were removed (FIG. 40, Panel A), cytosolic proteins such as FtsZ were mostly removed in rePDNVs (FIG. 40, Panel B) as compared to PDNVs. Moreover, OmpA and lipid A, which are major components on outer membrane, were decreased in rePDNVs than PDNVs indicating that the rePDNVs had lesser outer membrane contamination than PDNVs (FIG. 40, Panel B). RNA peaks were not detected in rePDNVs in contrast to PDNVs which retained some RNA (FIG. 41, Panel A). rePDNVs DNA contents was mostly removed (FIG. 41, Panel B).

Example 13: Proteomic Analysis of *E. coli* rePDNV Proteins

Methods
LC-Ms/Ms Analysis:

Two biological replicate rePDNVs or PDNVs (30 μg) were digested with trypsin using the filter-aided sample preparation (FASP) method and C18 spin columns desalting according to manufacturer's instructions. All fractions were dried on Speedvac and reconstituted in 3% acetonitrile and 0.2% formic acid and analyzed on Orbitrap Fusion Tribrid mass spectrometer interfaced with Easy-nLC 1200 (Thermo Fisher Scientific, Waltham, Mass.). Peptides were trapped on the Acclaim Pepmap 100 C18 trap column (100 μm×2 cm, particle size 5 μm; Thermo Fischer Scientific) and separated on the in-house packed C18 analytical column (75 μm×30 cm, particle size 3 μm) using the gradient from 5% to 33% B in 160 min, from 33% to 100% B in 5 min, solvent A was 0.2% formic acid and solvent B was 80% acetonitrile and 0.2% formic acid. Precursor ion mass spectra were recorded at 120 000 resolution, the most intense precursor ions were selected, fragmented using HCD at collision energy setting of 30 and the MS/MS spectra were recorded at 30 000 resolution with the maximum injection time of 125 ms and the isolation window of 1.0 Da. Charge states 2 to 7 were selected for fragmentation, dynamic exclusion was set to 45 s with 10 ppm tolerance.

Results

Figure 42:
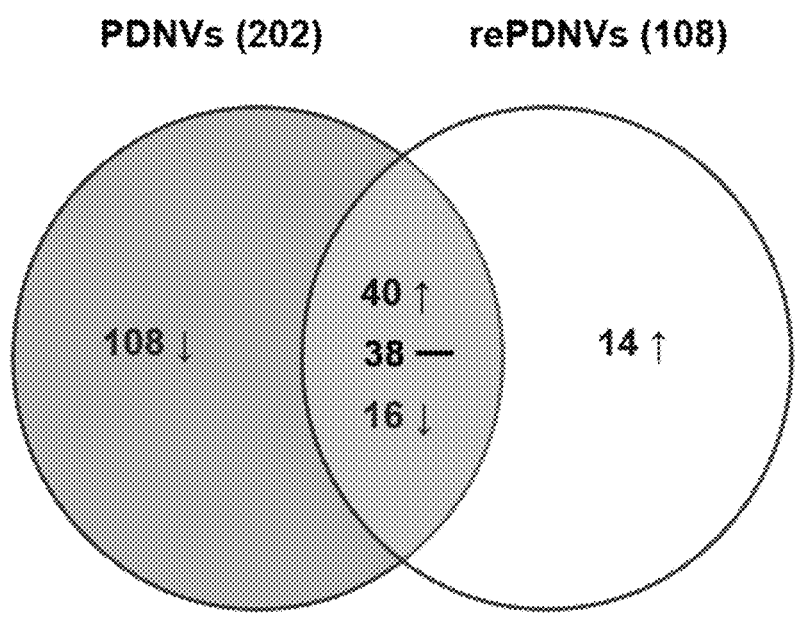
FIG. 42 depicts a Venn diagram of the proteome of *E. coli* PDNVs and rePDNVs.
Figure 43:
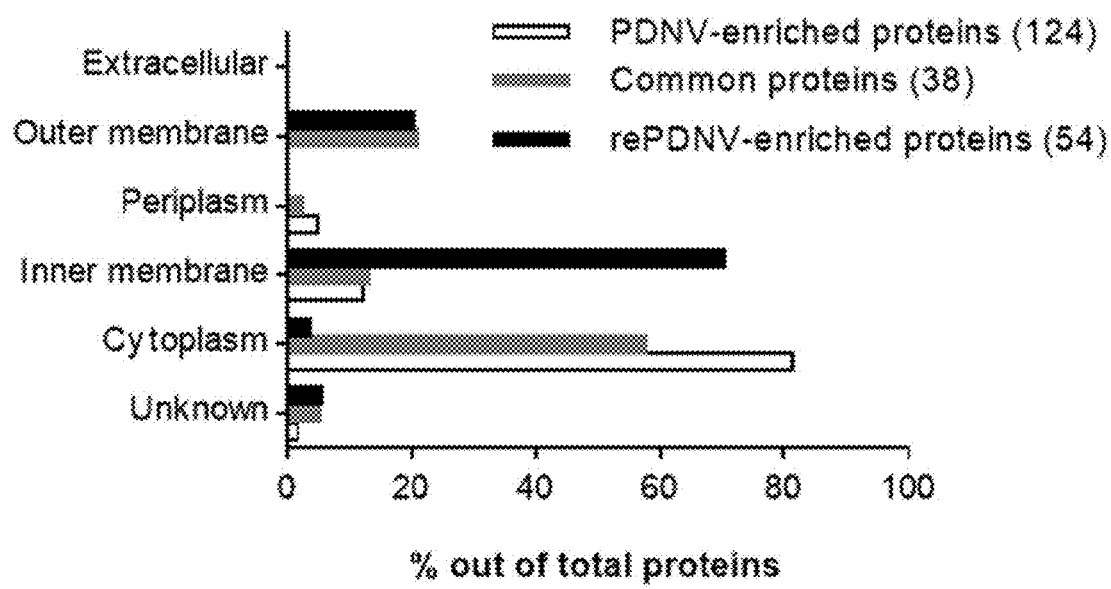
FIG. 43 depicts proteomic analysis of *E. coli* common proteins, PDNV-enriched proteins, and rePDNV-enriched proteins analyzed by GO subcellular localization annotations.

We identified total 202 and 108 proteins from PDNVs and rePDNVs, respectively (FIG. 42). 94 proteins were identified in both vesicle preparations, whereas 108 and 14 proteins were uniquely identified in PDNVs and rePDNVs, respectively. Based on the relative protein abundance, 38 proteins did not change markedly in abundance among 94 proteins. However, 40 and 16 proteins were relatively increased and decreased in rePDNVs, respectively. In the GO term subcellular localization analysis, rePDNV-enriched proteome showed distinct feature from PDNV-enriched proteome (FIG. 43). rePDNV proteome was enriched with cell inner membrane proteins, whereas PDNV proteome was enriched with cytosolic proteins.

Example 14: Less Toxicity of *E. coli* rePDNVs In Vitro

Methods
RAW 264.7 Cytokines

RAW 264.7 ($1 \times 10^5$), a mouse macrophage cell line, were seeded into 24-well plates. $1 \times 10^8$ of rePDNVs, PDNVs, or OMVs were applied to the cells to induce pro-inflammatory cytokines (TNF-α and IL-6) for 15 h. Supernatant concentrations of cytokines were measured by ELISA kit (R&D systems).

Figure 44:
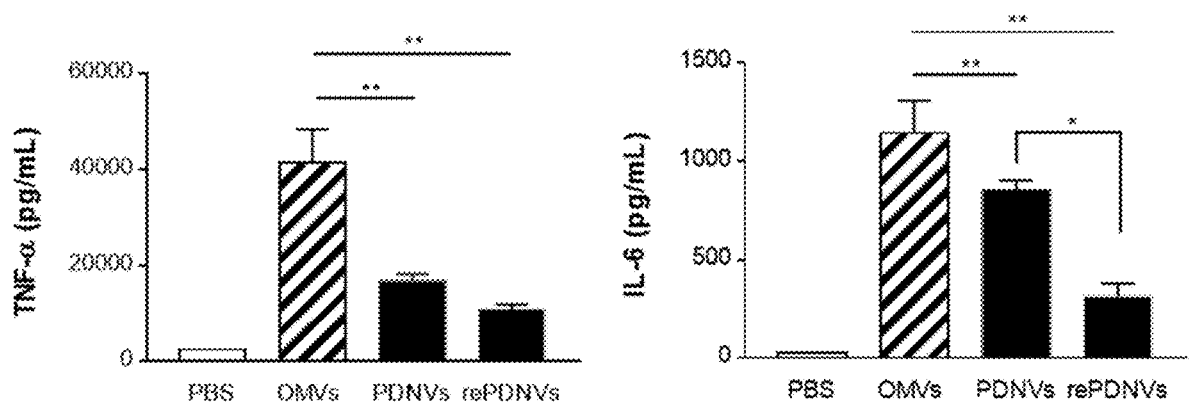
FIG. 44 depicts *E. coli* OMV-, PDNV- or rePDNV-induced pro-inflammatory cytokines in the supernatants of RAW 264.7 cells. $1 \times 10^8$ particle numbers of OMVs, PDNVs, or rePDNVs were added to the cells for 15 h, and then TNF-α (left) and IL-6 (right) were measured by ELISA. *, $P<0.05$; **, $P<0.01$; one-way ANOVA with Tukey's multiple comparison test. Error bars indicate SEM. N=3.

Results rePDNVs could not induce TNF-α and IL-6 from macrophages in contrast to OMVs (FIG. 44). Moreover, IL-6 level in rePDNV group was measured to a lesser extent than PDNVs.

Example 15: Immunological Properties of *E. coli* rePDNVs In Vitro and In Vivo

Methods
Dendritic Cell Cytokines:

Bone marrow cells were harvested from the femur and the tibia of mice (C57BL/6). The cells were differentiated into dendritic cells in 10% FBS/RPMI supplemented with nutrients and 20 ng/mL GM-CSF for one week. Differentiated dendritic cells ($1 \times 10^5$) were seeded into 24-well plates. Two doses of rePDNVs or PDNVs ($1 \times 10^9$, $2 \times 10^9$) were applied to the cells to induce TNF-α, IL-6, IL-12p70, and IL-4 for 24 h. Supernatant concentrations of cytokines were measured by ELISA kit (R&D systems).

Antibody Titer Against *E. coli* Lysates:

$5 \times 10^9$ of rePDNVs or PDNVs were intraperitoneally injected to mice (wild-type C57BL/6 genetic background, 6 weeks old) once a week for three weeks. Blood samples were taken from mice 3 days after each injection and assayed for their antibodies specific for *E. coli* lysates. The mouse serum was 1:500 diluted in 1% BSA/PBS and placed in 96-well plates coated with 200 ng of *E. coli* lysates. After incubation for 2 h, immunological changes were measured with a peroxidase-conjugated anti-mouse antibody.

Results

Figure 45:
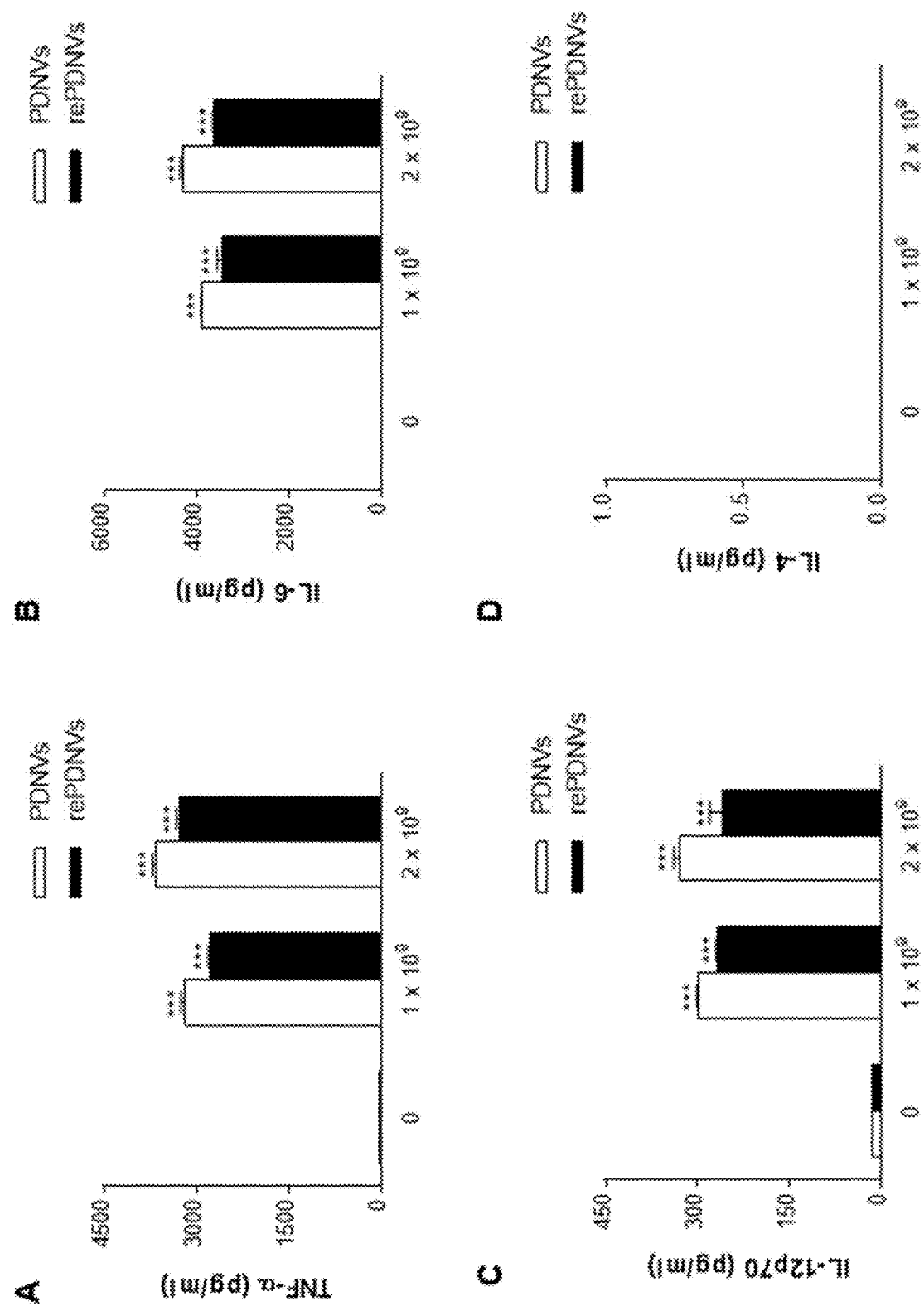
FIG. 45, Panel A is a graph showing TNF-α level in the supernatants of bone marrow-derived dendritic cells treated with *E. coli* PDNVs or rePDNVs for 24 h. *, $P<0.001$; versus control; one-way ANOVA with Tukey's multiple comparison test. Error bars indicate SEM. N=3.
Figure 46:
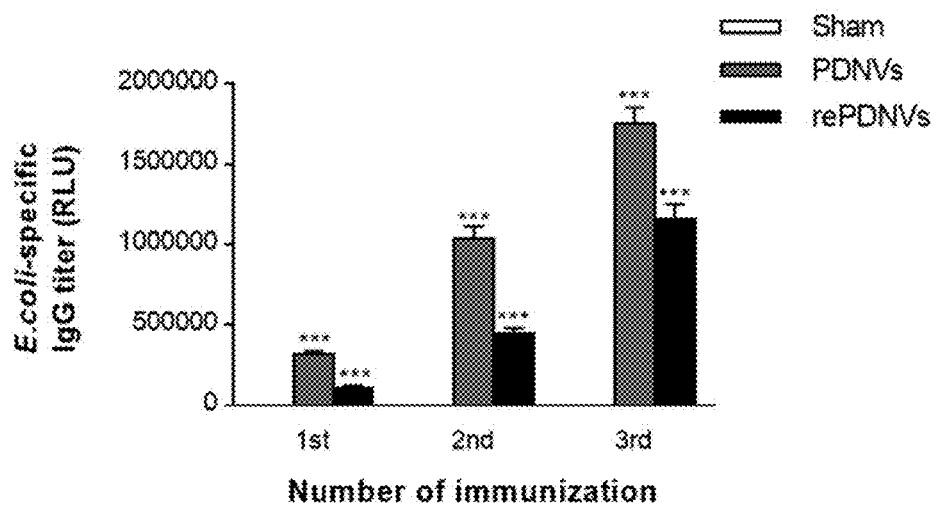
FIG. 46 is a graph showing the levels of *E. coli* protein-specific antibodies measured in the course of three intraperitoneal injection of $5 \times 10^9$ of *E. coli* PDNVs or rePDNVs at regular intervals of one week. ***, $P<0.001$; versus sham group; one-way ANOVA with Tukey's multiple comparison test. Error bars indicate SEM. N=4.

TNF-α, IL-6, and IL-12p70, cytokines inducing T helper type 1 response, increased with an increase in the dose of rePDNVs, similar to PDNVs (FIG. 45, Panels A-D). However, there was no change in the level of IL-4, a cytokine inducing T helper type 2 response. The *E. coli* lysates-specific antibodies in the mouse blood started to from 7 days after the first injection of rePDNVs, and were amplified by the second and the third injection, with a peak at 7 days after the third injection (FIG. 46).

Example 16: Isolation and Characterization of Mice Melanoma Tissue-Derived EVs

Methods
Preparation of Tumor EVs

Figure 47:
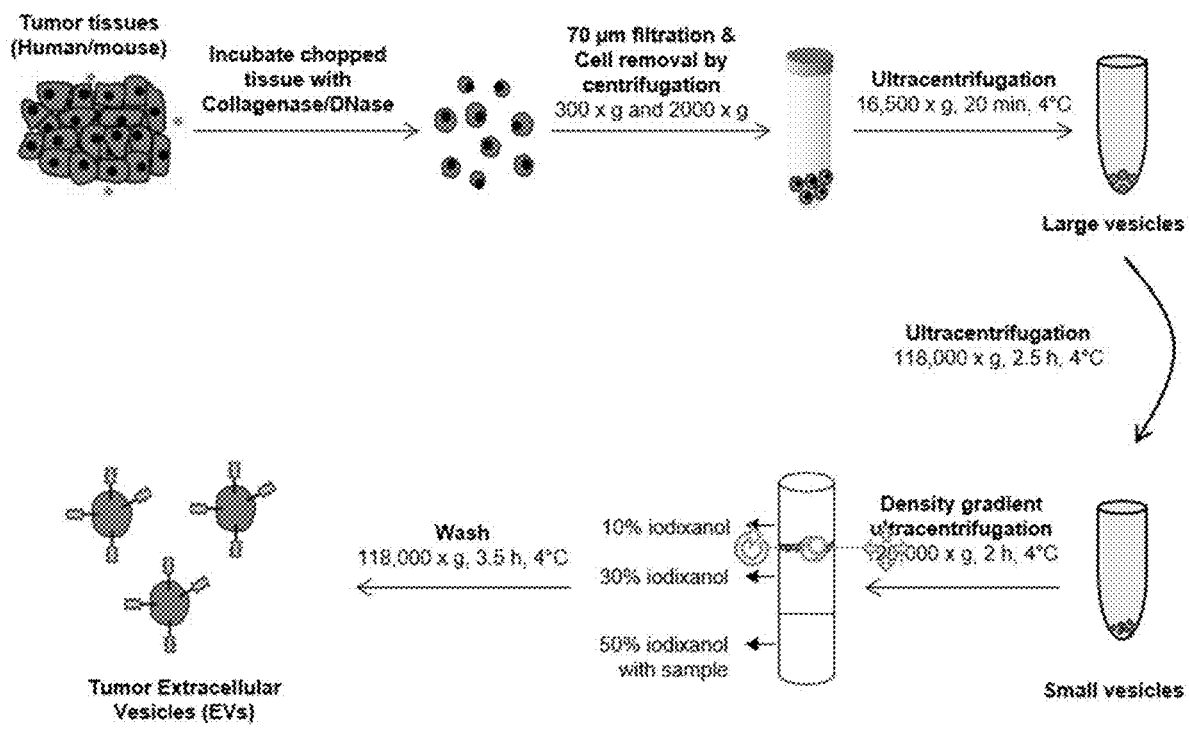
FIG. 47 depicts steps for generation of tumor extracellular vesicles (EVs) according to an embodiment of the present disclosure.

Tumor pieces from human or mice were gently sliced into small fragments (1-2 mm) and incubated with Collagenase D (Roche) (2 mg/ml) and DNase I (Roche) (40 U/ml) for 30 min at 37° C. to dissolve fibrotic structures. After a filtration step (70 μm pore size), cells and tissue debris were eliminated by centrifugation at 3,00×g for 10 min and 2,000×g for 20 min. Supernatant were centrifuged at 16,500×g for 20 min and 118,000×g for 2.5 h to collect larger vesicles and smaller vesicles, respectively (Ti45 rotor: fixed angle rotor). All centrifugations were performed at 4° C. Larger and smaller vesicles were resuspended in PBS, combined and further purified by an isopycnic centrifugation using an iodixanol gradient (Axis-Shield PoC AS). EVs (larger and smaller EVs) in PBS (1 mL) were mixed with 60% iodixanol (3 mL) and laid on the bottom of an ultracentrifuge tube followed by addition of 30% iodixanol (4 mL) and then 10% iodixanol (3 mL). Samples were ultracentrifuged at 178,000×g (SW 41 Ti, Beckman Coulter) for 2 h. EVs were collected from the interface between the 30% and 10% iodixanol layers. Collected EVs were then diluted with PBS (up to 94 ml) and ultracentrifuged at 118,000×g (Type 45 Ti) for 3.5 h. The pelleted EVs were resuspended in PBS for future applications (FIG. 47). The pelleted EVs are mostly comprised of small vesicles. These EVs are also referred to herein as "tEXO".

Transmission Electron Microscopy

One mice melanoma tissue was acquired after sacrificing the mouse, and the sample was chopped into small pieces. Samples were placed in 150 μm deep membrane carriers (Leica Microsystems) that was filled with 20% BSA in PBS and high pressure frozen using an EMPactI (Leica Microsystems). A rapid freeze substitution protocol using 2% uranyl acetate in dehydrated acetone for 1 h was then utilized. The temperature was increased by 3° C./hour to −50° C. where samples stayed for the remainder of the protocol. Samples were washed with dehydrated acetone before starting infiltration with increasing concentrations of HM20, followed with 3 changes with HM20 (2 h each and once overnight). Samples were polymerized in UV light for 48 h. Thin sections (70 nm) were cut and contrasted with 2% uranyl acetate in 25% ethanol (4 min) and Reynold's lead citrate (2 min). For analysis of EVs, formvar/carbon Cu copper grids (Electron Microscopy Sciences) were glow discharge-treated before EVs were loaded. Then EVs were washed two times in distilled water and then fixed using 2.5% glutaraldehyde dissolved PBS. After two further washes in filtered water, the samples were stained using 2% uranyl acetate for 1.5 min. Negative-stained samples were examined on a digitized LEO 912AB Omega electron microscope (Carl Zeiss SMT) at 120 kV with a Veleta CCD camera (Olympus-SiS).

Results

Figure 48:
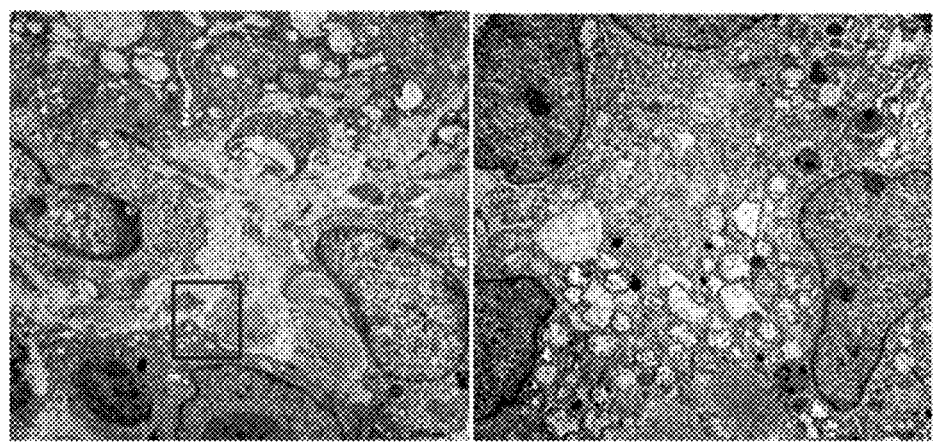
FIG. 48 depicts transmission electron microscopy images of mouse melanoma tissue. Scale bar=2000 nm.
Figure 49:
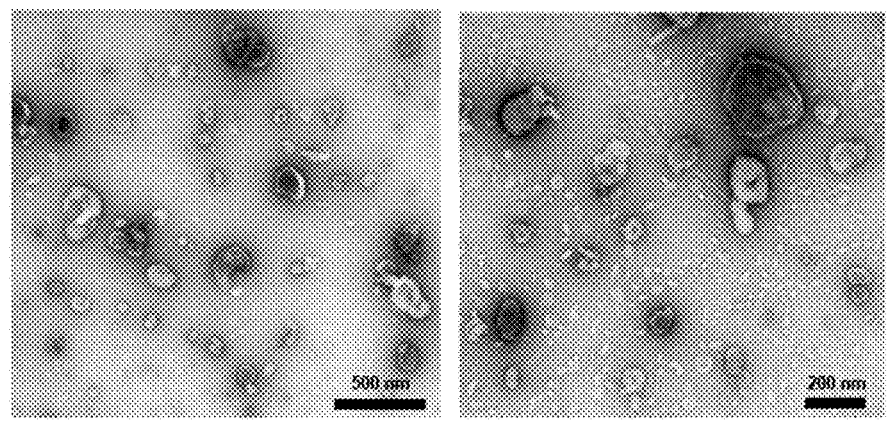
FIG. 49 depicts transmission electron microscopy images of melanoma tissue-derived EVs. Left scale bar=500 nm. Right scale bar=200 nm.

The existence of EVs in the interstitial space of a mouse melanoma tissue was confirmed by electron microscopy (FIG. 48). And, there were both large vesicles (100-200 nm in diameter) and small vesicles (40-100 nm in diameter) (FIG. 49).

Example 17: Inhibitory Activity of Mouse Melanoma Tissue-Derived EVs Against Melanoma Growth Methods
Mice Experiments Mice (wild type C57BL/6 genetic background, 6 weeks old) were subcutaneously injected with $5 \times 10^5$ melanoma cells (B16F10), and maintained for one week to form a measurable mass of tumor (2-3 mm). Then, melanoma EVs (10 μg) were intraperitoneally injected three times in combination with *E. coli* aOMVs or rePDNVs ($5 \times 10^9$) to the mice at regular intervals of one week. The tumor size was measured two times a week. The tumor volume was calculated according to the formula $v = 1 \times s^2 / 2$ [v, volume; 1, a length of the longest axis of the cancer mass; s, a length of the shortest axis].

Results

Figure 50:
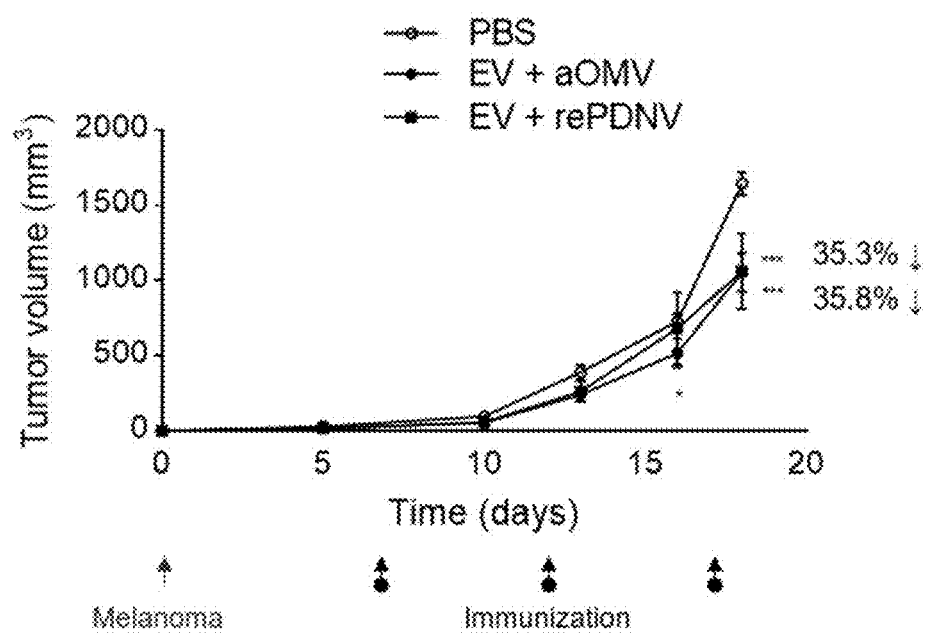
FIG. 50 depicts melanoma volume in mice injected with melanoma cells and immunized with PBS, 10 μg of mouse melanoma EVs with *E. coli* aOMVs ($5 \times 10^9$), or 10 μg of mouse melanoma EVs with *E. coli* rePDNVs ($5 \times 10^9$) at 5-day intervals three times. *, $P<0.05$; ***, $P<0.001$; versus sham group; one-way ANOVA with Tukey's multiple comparison test. Error bars indicate SEM. N=6.

A combination of tumor EVs with aOMVs or rePDNVs caused significant reduction (35%) in the tumor volume (FIG. 50).

Example 18: Increased Immunogenicity of Mouse Melanoma Tissue-Derived EVs by aOMVs or rePDNVs Methods
Antibody Titer Against Tumor Lysates or EV Proteins Melanoma EVs (10 μg) were intraperitoneally injected three times in combination with *E. coli* aOMVs or rePDNVs (5×10) to the mice at regular intervals of one week. Blood samples were taken from mice 3 days after each injection and assayed for their antibodies specific for B16F10 lysates or EV proteins. The mouse serum was 1:500 diluted in 1% BSA/PBS and placed in 96-well plates coated with 200 ng of B16F10 lysates or EV proteins. After incubation for 2 h, immunological changes were measured with a peroxidase-conjugated anti-mouse antibody.

Splenocyte Cytokines

Seven days after the three injections of melanoma EVs (10 μg) in combination with *E. coli* aOMVs or rePDNVs ($5 \times 10^9$), CD4+ T cells from spleen were isolated from the mice. The cells ($5 \times 10^5$) were incubated for 72 h with 1 μg/mL of melanoma EV proteins, followed by ELISA to quantitatively analyze TNF-α, IFN-γ, IL-4, and IL-17.

Results

Figure 51:
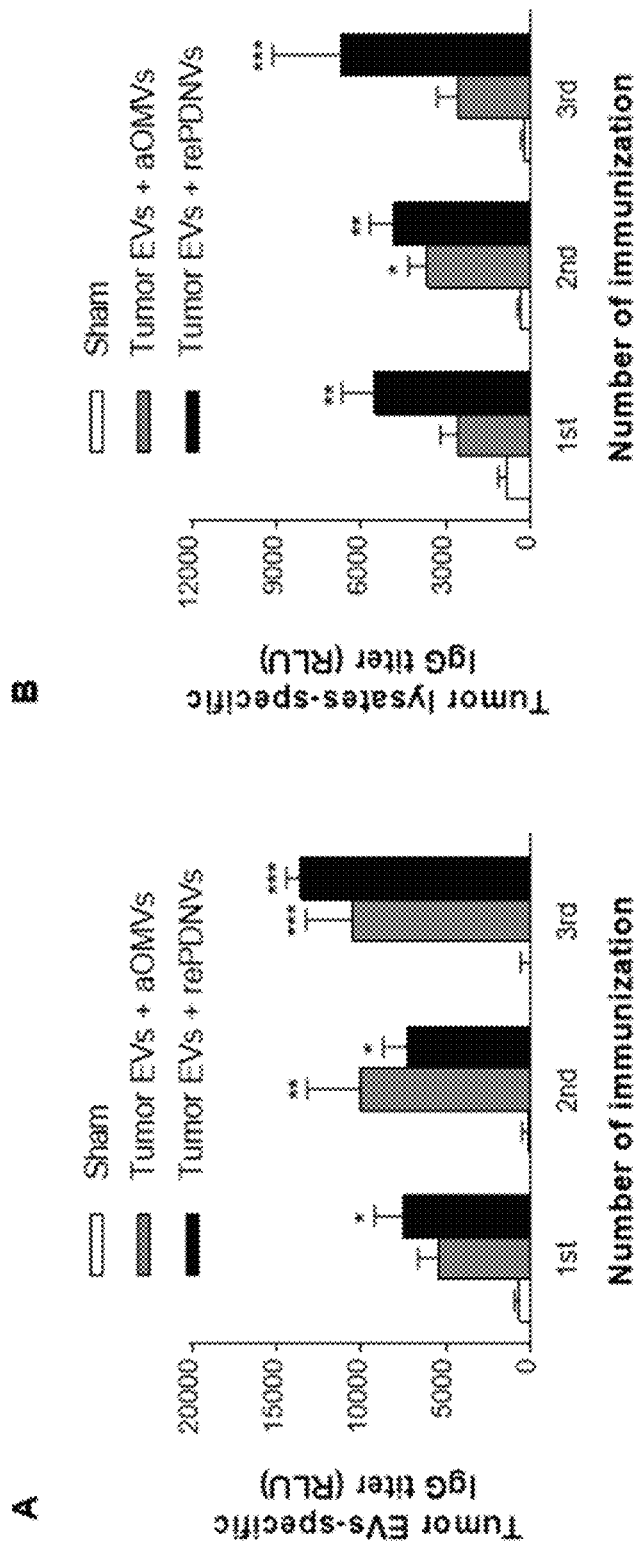
FIG. 51, Panel A is a graph showing the levels of melanoma EV-specific antibodies measured in the course of three intraperitoneal injection of mouse melanoma EVs (10 μg) with *E. coli* aOMVs or rePDNVs ($5 \times 10^9$) at regular intervals of 5 days. *, $P<0.05$; , $P<0.01$; *, $P<0.001$; versus sham group; one-way ANOVA with Tukey's multiple comparison test. Error bars indicate SEM. N=6.
Figure 52:
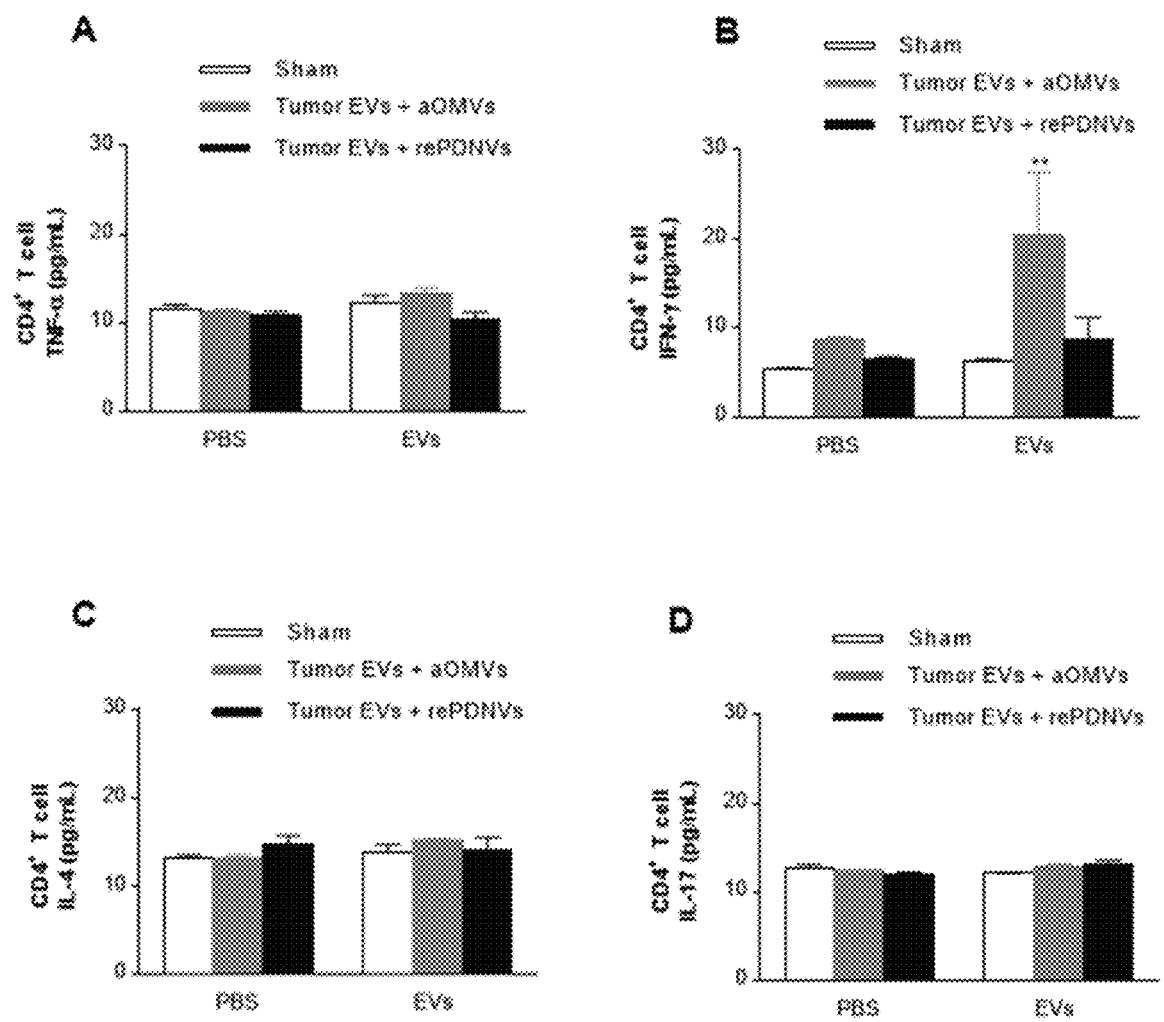
FIG. 52, Panel A depicts the level of TNF-α secreted from mouse splenic CD4+ T cells upon ex vivo treatment with melanoma EV proteins (1 μg/mL) after the mice were immunized with mouse melanoma EVs (10 μg) with *E. coli* aOMVs or rePDNVs ($5 \times 10^9$). Versus sham group; one-way ANOVA with Tukey's multiple comparison test. Error bars indicate SEM. N=3.

An increase in the B16F10 lysates or EV-specific antibodies in the mouse blood was evoked in EV-immunized mice together with aOMVs or rePDNVs (FIG. 51, Panels A-B). And, higher levels of IFN-γ were secreted from splenic CD4+ T cells of only EV-immunized group in combination with aOMVs, compared to the sham group (FIG. 52, Panels A-D).

Example 19: Inhibitory Activity of Mouse Colon Cancer Tissue-Derived EVs Against Colon Cancer Growth Methods
Mice Experiments Mice (wild type C57BL/6 genetic background, 6 weeks old) were subcutaneously injected with 5×10$^6$ colon cancer cells (CT26), and maintained for one week to form a measurable mass of tumor (2-3 mm). Then, colon cancer EVs (10 µg) were intraperitoneally injected three times in combination with *E. coli* aOMVs or rePDNVs (5×10$^9$) to the mice at regular intervals of one week. The tumor size was measured two times a week. The tumor volume was calculated according to the formula v=1×s$^2$/2 [v, volume; 1, a length of the longest axis of the cancer mass; s, a length of the shortest axis].

Results

Figure 53:
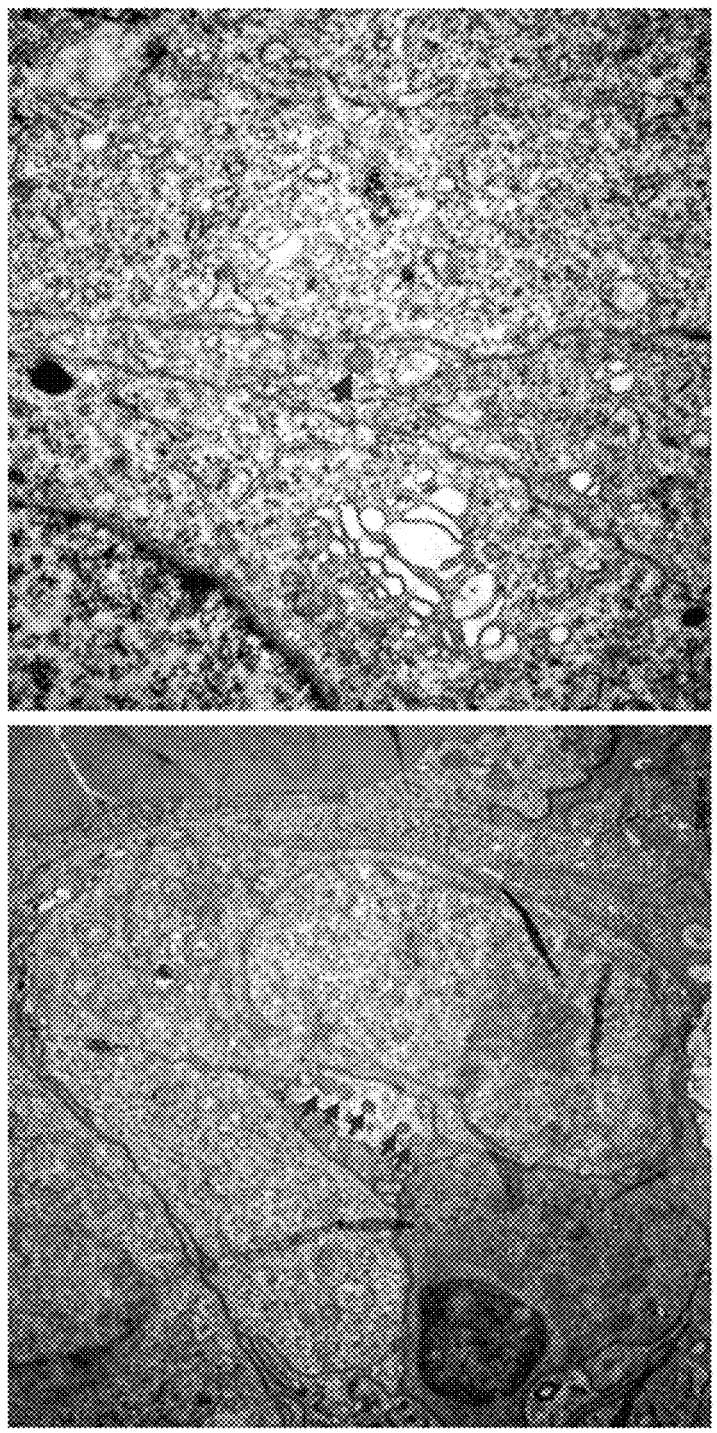
FIG. 53 depicts transmission electron microscopy images of mouse colon cancer tissue. The arrows point to EVs present in the cancer tissue. Scale bar=2000 nm (left) and 1000 nm (right).
Figure 54:
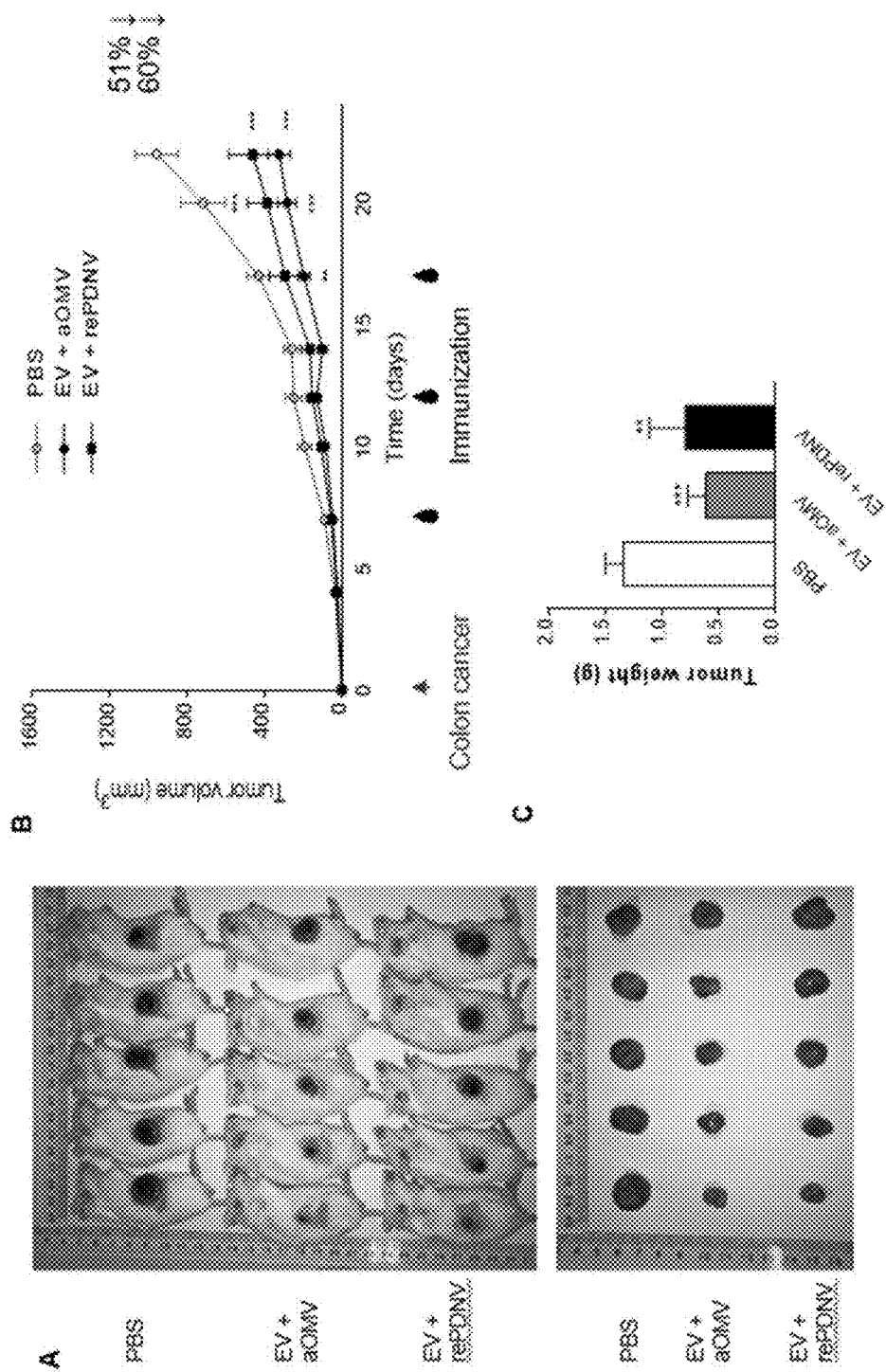
FIG. 54, Panel A depicts whole body (upper) and dissected tumor (lower) images of mice immunized with/without 10 μg of mouse colon cancer EVs with *E. coli* aOMVs or rePDNVs ($5 \times 10^9$) at 5-day intervals three times.

EVs from mouse colon cancer tissue were isolated as described in FIG. 53. The existence of EVs in the interstitial space of a mouse colon cancer tissue was confirmed by electron microscopy (FIG. 53). A combination of tumor EVs with aOMVs or rePDNVs caused significant reduction (51% or 60%, respectively) in the tumor volume (FIG. 54, Panel A-B) and the weight of tumor mass (FIG. 54, Panel C).

Example 20: Increased Immunogenicity of Mouse Colon Cancer Tissue-Derived EVs by aOMVs or rePDNVs Methods
Antibody Titer Against Tumor Lysates or EV Proteins Colon cancer tissue-derived EVs (10 µg) were intraperitoneally injected three times in combination with *E. coli* aOMVs or rePDNVs (5×10$^9$) to the mice at regular intervals of one week. Blood samples were taken from mice 3 days after each injection and assayed for their antibodies specific for CT26 lysates or EV proteins. The mouse serum was 1:500 diluted in 1% BSA/PBS and placed in 96-well plates coated with 200 ng of CT26 lysates or EV proteins. After incubation for 2 h, immunological changes were measured with a peroxidase-conjugated anti-mouse antibody.

Splenocyte Cytokines

Seven days after the three injections of colon cancer EVs (10 µg) in combination with *E. coli* aOMVs or rePDNVs (5×10$^9$), CD4+ T cells from spleen were isolated from the mice. The cells (5×10$^5$) were incubated for 72 h with 1 µg/mL of colon cancer EV proteins, followed by ELISA to quantitatively analyze TNF-α, IFN-γ, IL-4, and IL-17.

Results

Figure 55:
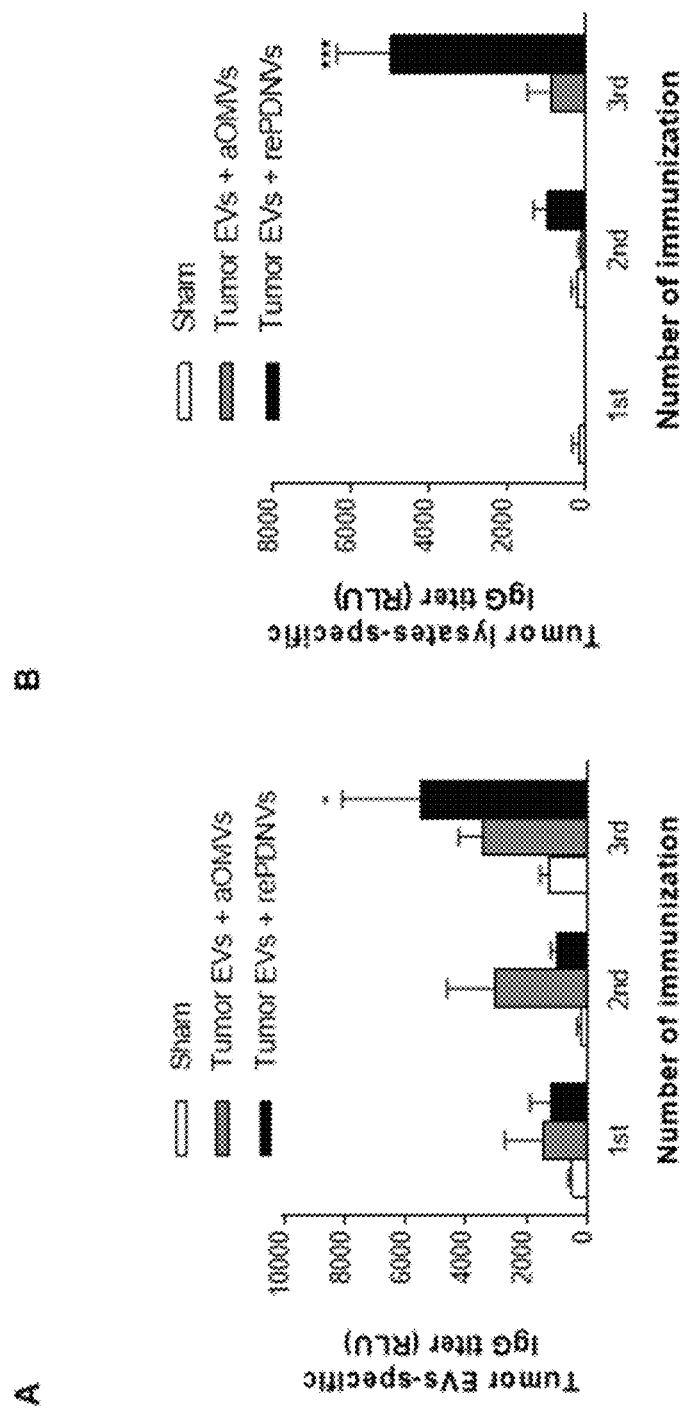
FIG. 55, Panel A is a graph showing the levels of colon cancer EV-specific antibodies measured in the course of three intraperitoneal injection of mouse colon cancer EVs (10 μg) with *E. coli* aOMVs or rePDNVs ($5 \times 10^9$) at regular intervals of 5 days. *, $P<0.05$; versus sham group; one-way ANOVA with Tukey's multiple comparison test. Error bars indicate SEM. N=5.
Figure 56:
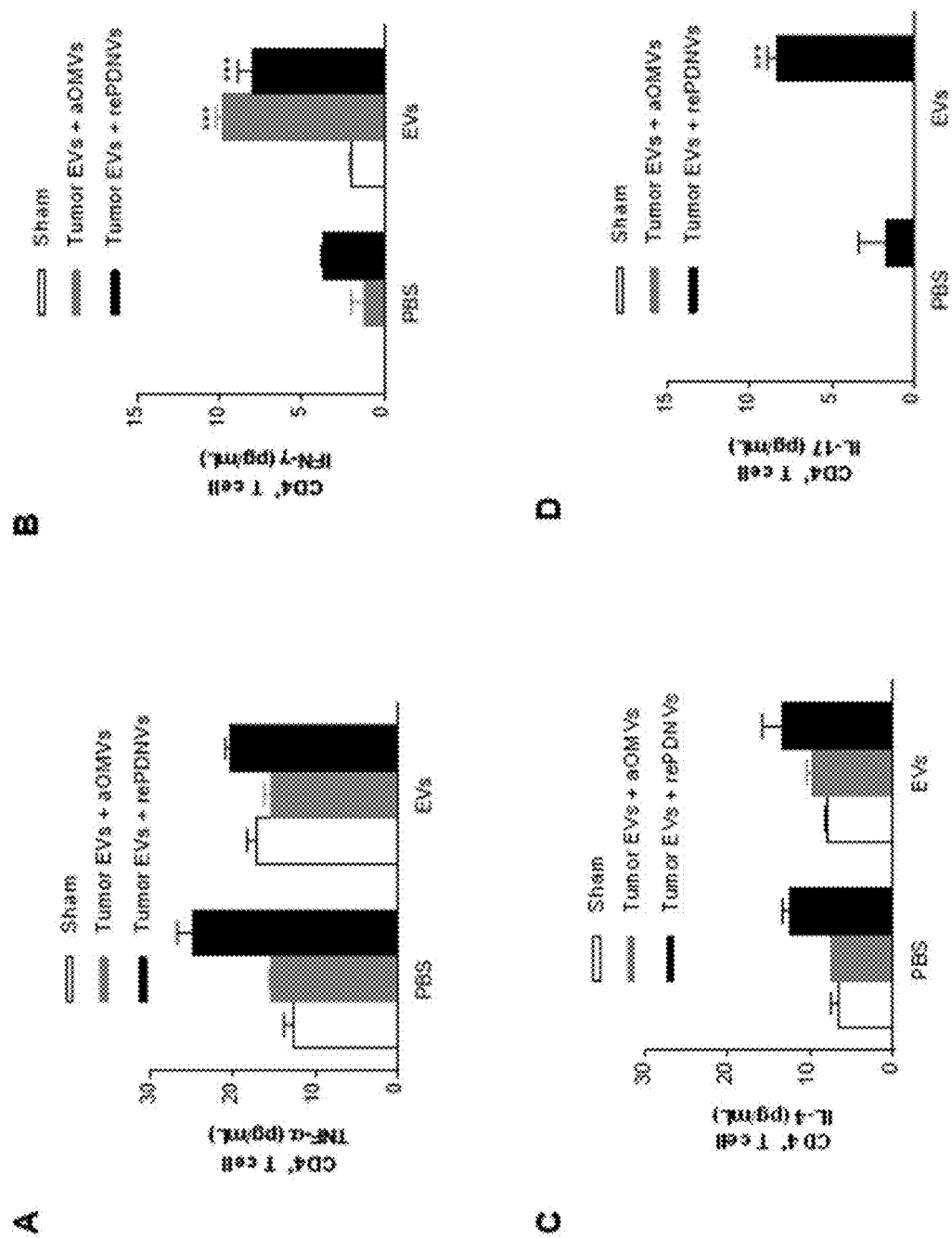
FIG. 56, Panel A depicts the level of TNF-α secreted from mouse splenic CD4+ T cells upon ex vivo treatment with colon cancer EV proteins (1 μg/mL) after the mice were immunized with mouse colon cancer EVs (10 μg) with *E. coli* aOMVs or rePDNVs ($5\times10^9$). Versus sham group; one-way ANOVA with Tukey's multiple comparison test. Error bars indicate SEM. N=3.

An increase in the CT26 lysates or EV-specific antibodies in the mouse blood was evoked in EV-immunized mice together with aOMVs or rePDNVs (FIG. 55, Panels A-B). And, higher levels of IFN-γ were secreted from splenic CD4+ T cells of EV-immunized group in combination with aOMVs or rePDNVs, compared to the sham group (FIG. 56, Panels A-D).

Example 21: Immunization with Human Melanoma Patient-Derived EVs Together with *E. coli* aOMVs Methods
Preparation of Tumor EVs Human melanoma patient-derived EVs were isolated using same protocol described in FIG. 47.

Antibody Titer Against Tumor EV Proteins

Mice (wild type C57BL/6 genetic background, 6 weeks old) were intraperitoneally injected once a week for three weeks with 10 µg of tumor EVs alone or in combination with *E. coli* aOMVs (5×10$^9$). Blood samples were taken from mice 3 days after each injection and assayed for their antibodies specific for tumor EV proteins. The mouse serum was 1:500 diluted in 1% BSA/PBS and placed in 96-well plates coated with 200 ng of tumor EV proteins. After incubation for 2 h, immunological changes were measured with a peroxidase-conjugated anti-mouse antibody.

Splenocyte Cytokines

Seven days after the three injections of tumor EVs (10 µg) alone or in combination with *E. coli* aOMVs (5×10$^9$). CD4+ T cells from spleen were isolated from the mice. The cells (5×10$^5$) were incubated for 72 h with 1 µg/mL of tumor EVs, followed by ELISA to quantitatively analyze TNF-α, IFN-γ, and IL-4.

Results

Figure 57:
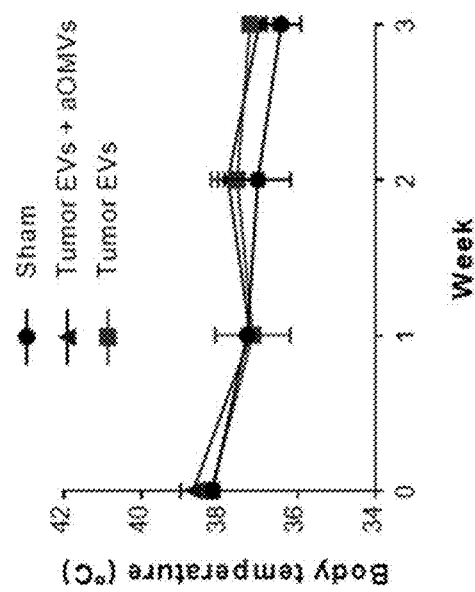
FIG. 57 depicts the body weight (left) and body temperature (right) of mice immunized intraperitoneally with 10 μg of human melanoma EVs with/without *E. coli* aOMVs ($5\times10^9$) at weekly intervals for three weeks. Error bars indicate SEM. N=4.
Figure 57:
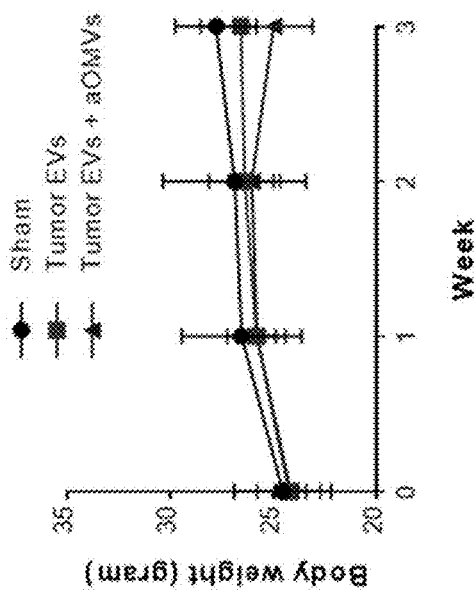
Figure 58:
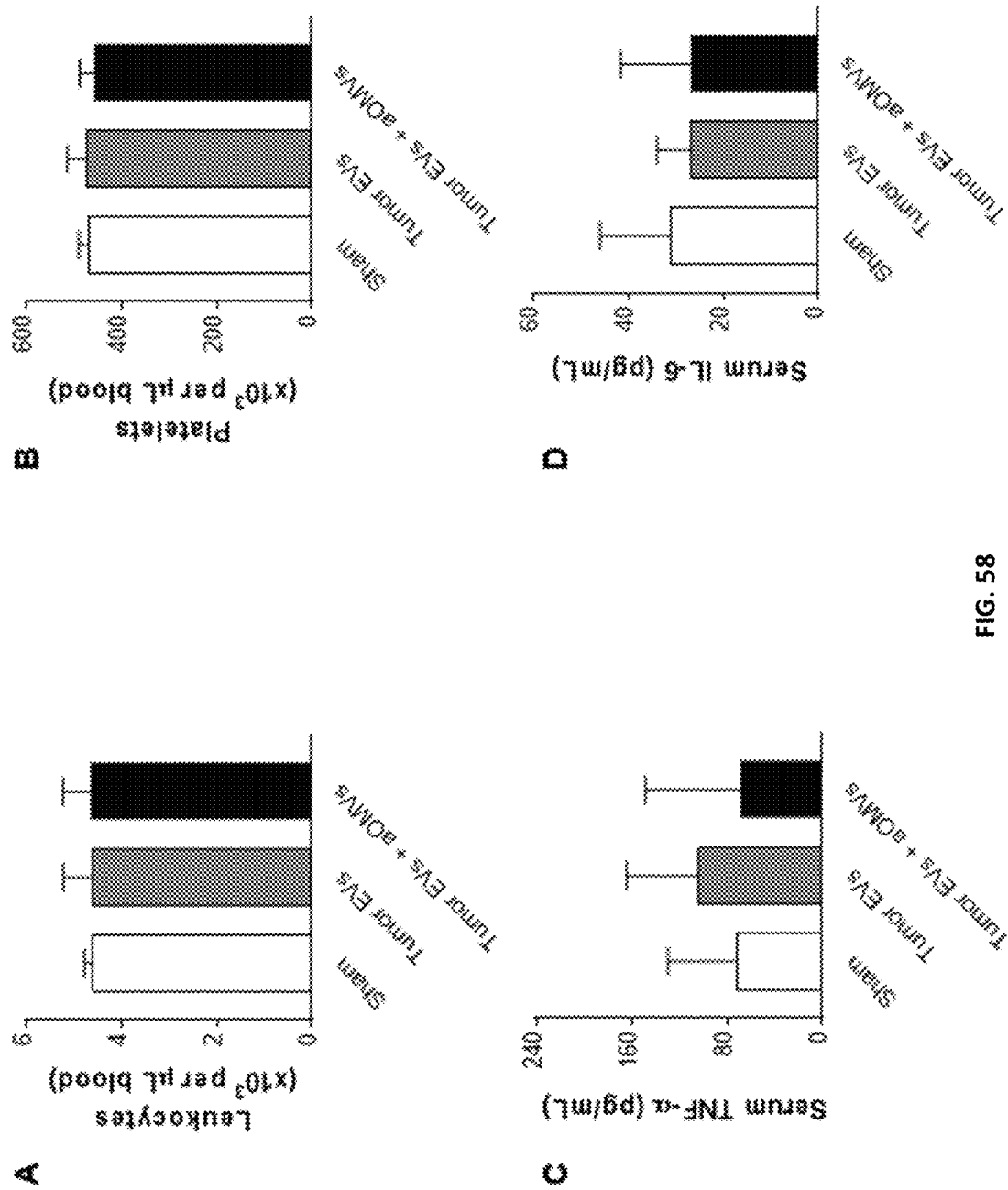
FIG. 58, Panel A depicts the number of total leukocytes in the blood of mice immunized intraperitoneally with human melanoma EVs (10 μg) with/without *E. coli* aOMVs ($5\times10^9$) 1 week after the last immunization. Versus sham group; one-way ANOVA with Tukey's multiple comparison test. Error bars indicate SEM. N=4.
Figure 59:
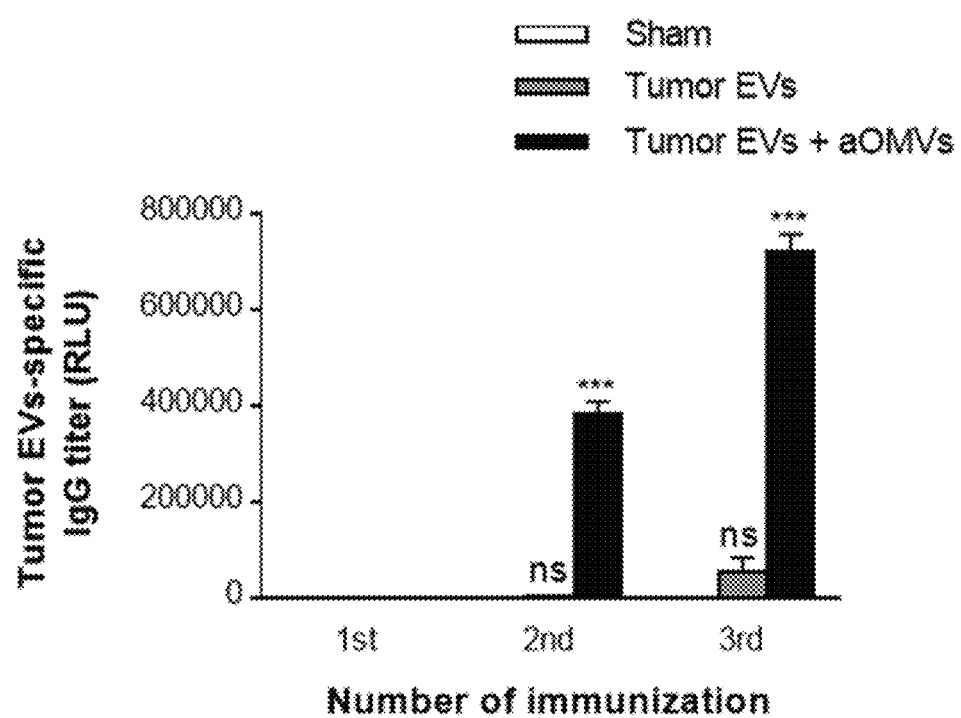
FIG. 59 is a graph showing the levels of human melanoma EV protein-specific antibodies measured in the course of three intraperitoneal injection of 10 μg of human melanoma EVs with/without *E. coli* aOMVs ($5\times10^9$) at regular intervals of one week. ***, P<0.001; ns, not significant; versus sham group; one-way ANOVA with Tukey's multiple comparison test. Error bars indicate SEM. N=4.
Figure 60:
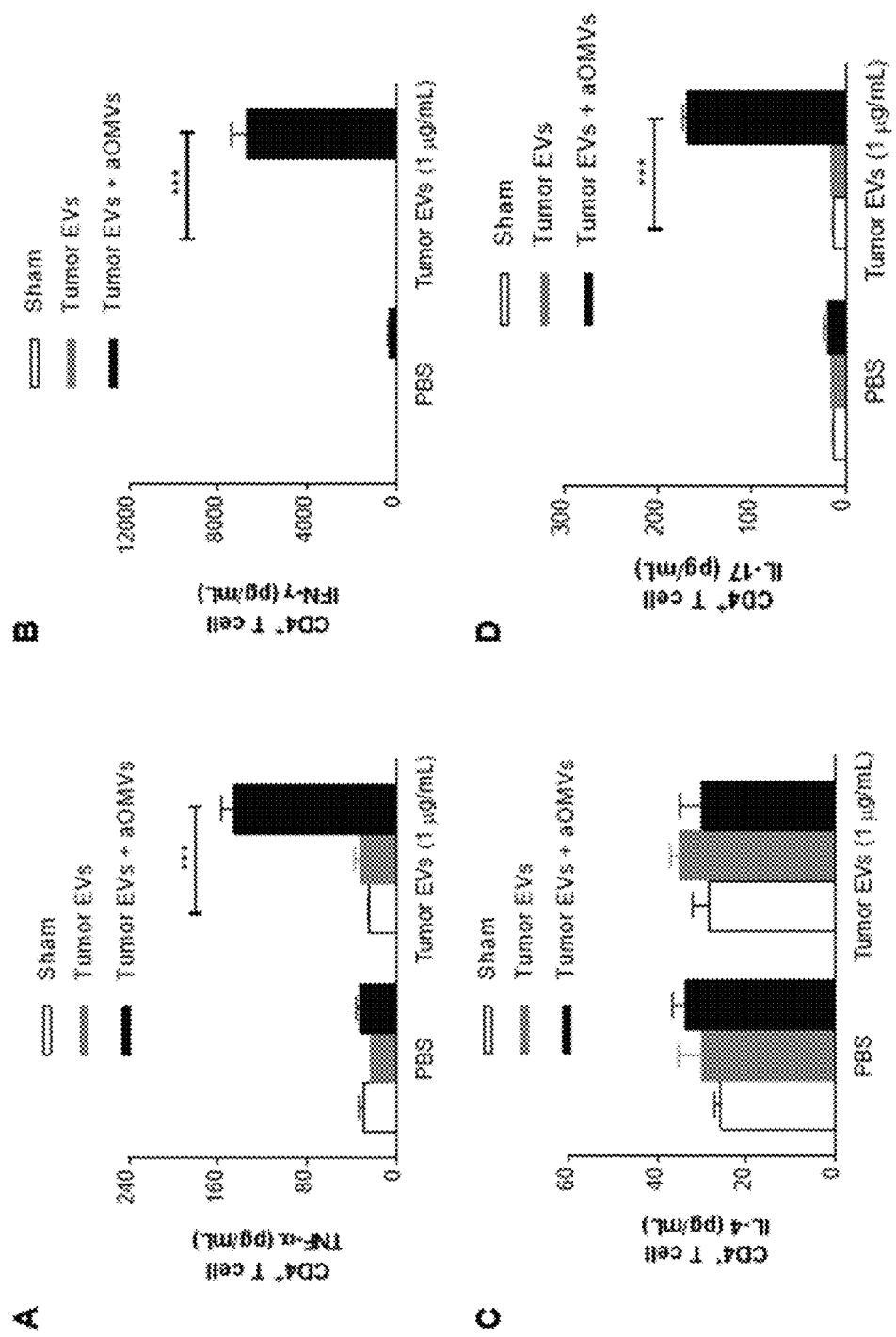
FIG. 60, Panel A depicts the level of TNF-γ secreted from mouse splenic CD4+ T cells upon ex vivo treatment with human melanoma EVs after the mice were immunized with 10 μg of human melanoma EVs with/without *E. coli* aOMVs ($5\times10^9$). ***, P<0.001; versus sham group; one-way ANOVA with Tukey's multiple comparison test. Error bars indicate SEM. N=3.

There were no changes of body weight, temperature, and systemic inflammation during immunization with tumor EVs alone or in combination with *E. coli* aOMVs (FIGS. 57 and 58, Panels A-D). The tumor EV-specific antibodies in the mouse blood started to from 7 days after the first injection of tumor EVs with aOMVs, and were amplified by the second and the third injection, with a peak at 7 days after the third injection (FIG. 59). Moreover, higher levels of TNF-α, IFN-γ, and IL-17 were secreted from splenic CD4+ T cells of tumor EV+aOMV-immunized group, compared to the sham- or only tumor EV-immunized group (FIG. 60, Panels A-D). However, there was no change in the level of IL-4 between groups.

Figure 61:
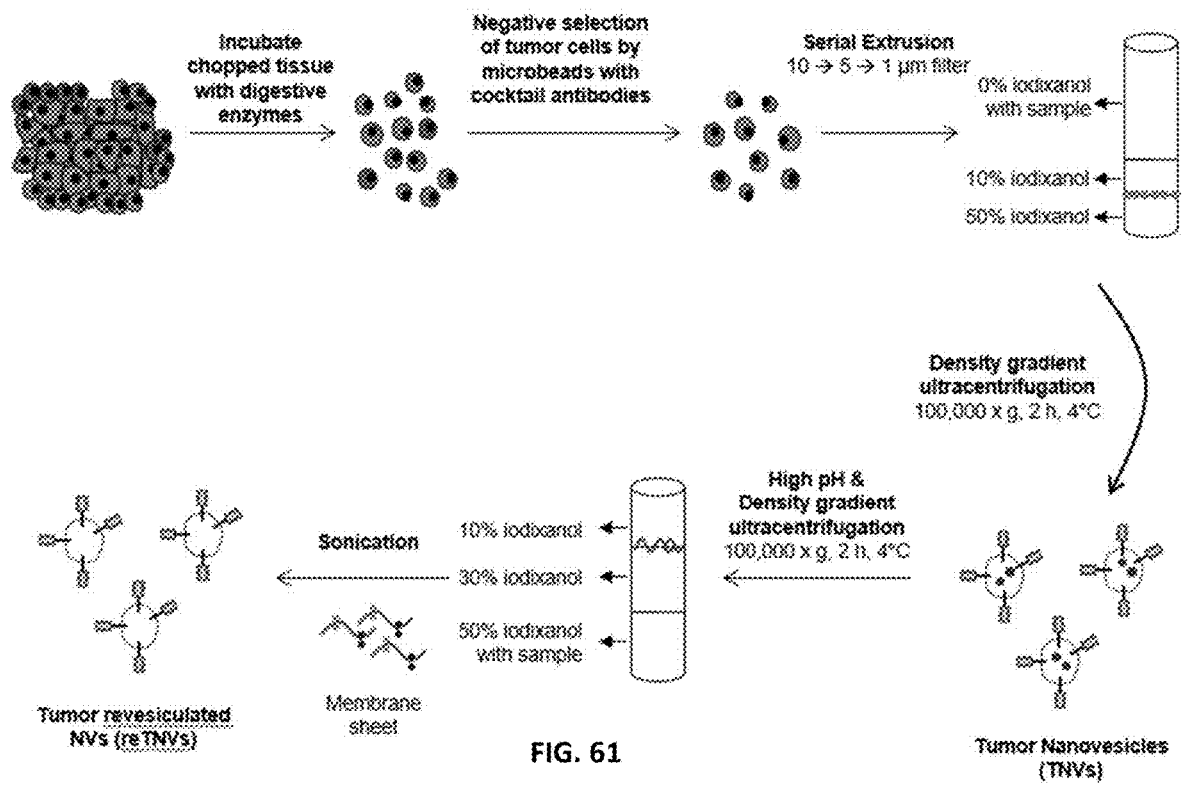
FIG. 61 depicts steps for generation of revesiculated tumor nanovesicles (reTNVs) by extrusion according to an embodiment of the present disclosure.

Example 22: Isolation of Revesiculated Tumor-Derived Nanovesicles (reTNVs) from Mice Tumor Tissues by Extrusion Methods
Preparation of Tumor MVs Melanoma or colon cancer tissues were acquired from mice, and then dissociated into single-cell suspensions by commercial kit using combination of collagenase and DNase (Miltenyl Biotec Inc.). For isolation of tumor cells, the total single-cell suspensions were loaded onto a MACS Column (Miltenyl Biotec Inc.) following incubation with microbeads coated with a cocktail of monoclonal antibodies against the non-tumor cells (Miltenyl Biotec Inc.). The harvested tumor cells were passed five times through each of the polycarbonate membrane filters (Whatman) with a pore size of 10 µm, 5 µm, and 1 µm using a mini-extruder (Avanti Polar Lipids). The extruded samples were placed on the top of the density gradient cushion with 50% iodixanol (Axis-Shield PoC AS) overlaid with 10% iodixanol at the bottom of the ultracentrifuge tube. The layers formed between 10% and 50% iodixanol after ultracentrifugation at 100,000×g for 2 hours was collected, which is called tumor-derived nanovesicles (NVs or tNVs). The acquired NVs were incubated with high pH solution (200 mM Na$_2$CO$_3$, pH 14.0) for 1 hour at 25° C. And then, the incubated samples were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min, and considered reTNVs (FIG. 61).

Results

Figure 62:
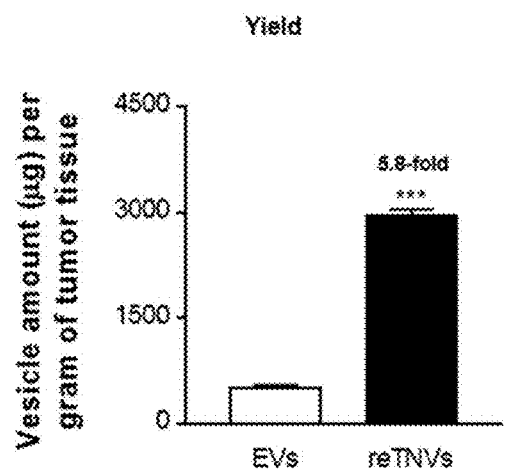
FIG. 62 depicts melanoma-derived reTNV or EV protein amount from one gram of mice melanoma tissue. ***, P<0.001; two-tailed unpaired T test. Error bars indicate SEM. N=3.
Figure 63:
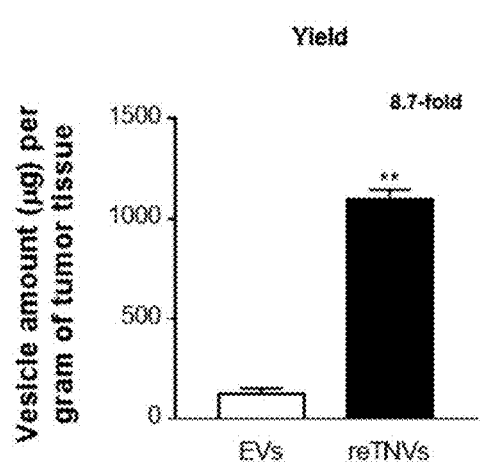
FIG. 63 depicts colon cancer cell-derived reTNV or EV protein amount from one gram of mouse colon cancer tissue. **, P<0.01; two-tailed unpaired T test. Error bars indicate SEM. N=2.

Melanoma and colon cancer cell-derived reTNVs were prepared in higher yield than tissue-derived EVs, 5.8- and 8.7-fold, respectively (FIGS. 62 and 63).

Example 23: Effect of EV, aOMV, and Combination of EV and aOMV on Tumor Load and Survival Mice were subcutaneously immunized three times at weekly intervals with melanoma EVs (5 μg), *E. coli* aOMVs ($5 \times 10^9$), or both followed by subcutaneous injection with $5 \times 10^5$ melanoma cells at 4th week. Then, melanoma EVs (5 μg), *E. coli* aOMVs ($5 \times 10^9$), or both were subcutaneously injected two times at regular intervals of one week. The tumor size was measured and tumor volume was calculated as described in Example 18.

Figure 64A:
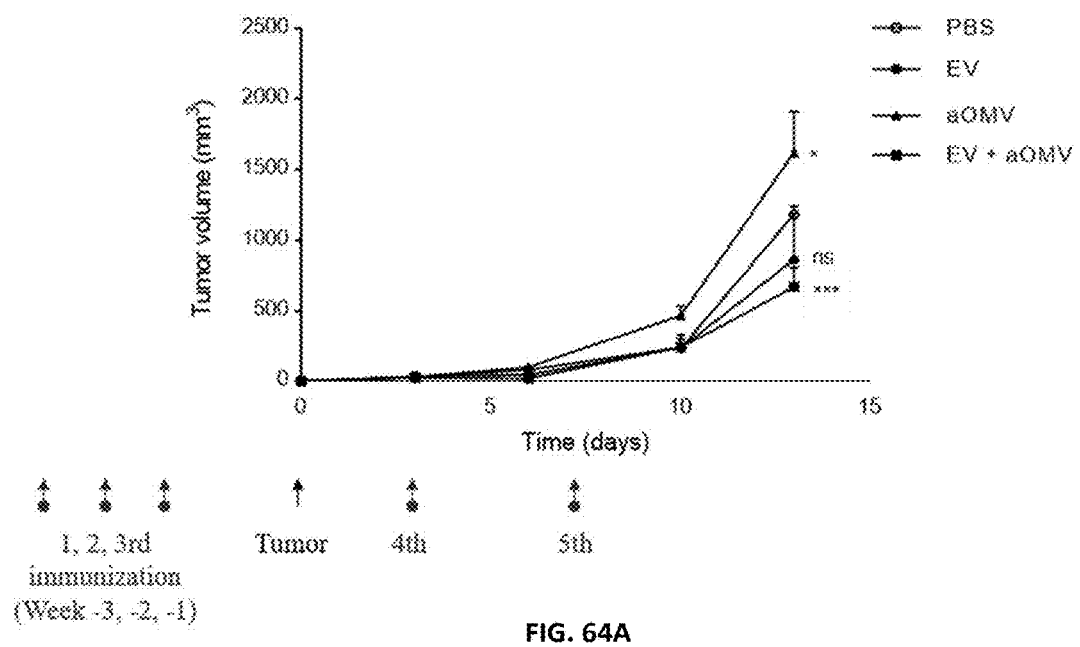
FIG. 64A depicts melanoma volume in mice injected with melanoma cells. Mice were subcutaneously immunized three times at weekly intervals with mouse melanoma EVs (5 μg), *E. coli* aOMVs ($5\times10^9$), or combination of thereof. Mice were inoculated with B16F10 cells, and then additionally immunized two times. *, P<0.05; ***, P<0.001; ns, not significant; versus PBS group; one-way ANOVA with Tukey's multiple comparison test. Error bars indicate SEM. N=5.
Figure 64B:
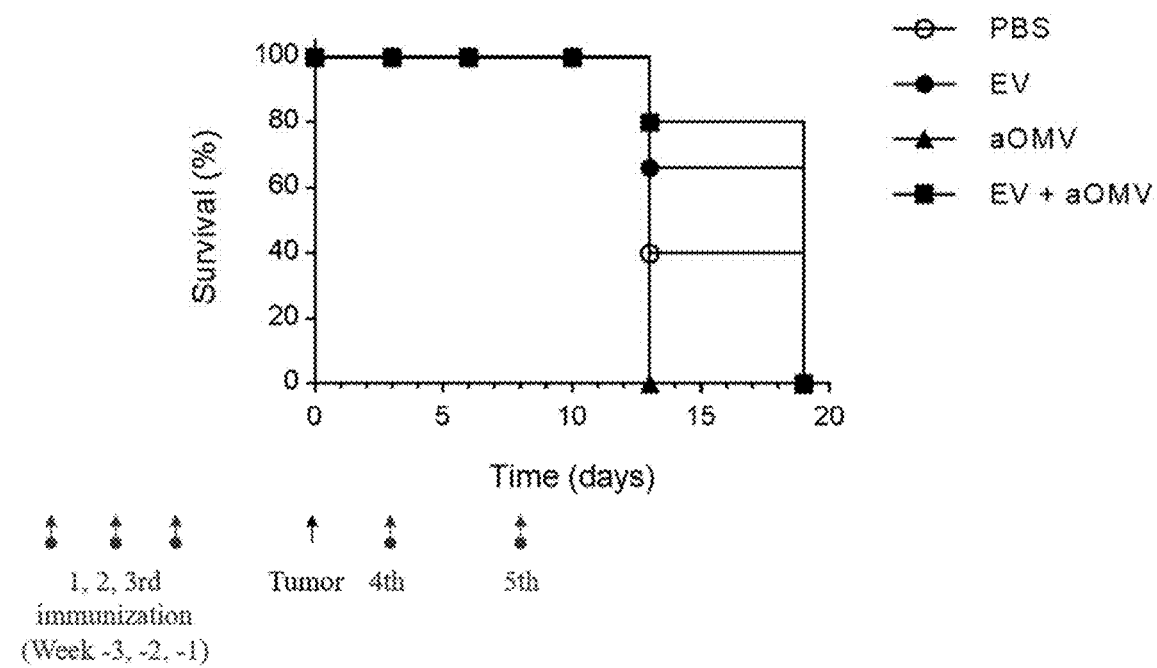
FIG. 64B depicts survival rate in mice injected with melanoma cells. Mice were subcutaneously immunized three times at weekly intervals with mouse melanoma EVs (5 μg), *E. coli* aOMVs ($5\times10^9$), or combination of them. Mice were inoculated with B16F10 cells, and then additionally immunized two times. Tumor-bearing mice were euthanized when tumors became surpassed 1000 mm³ in tumor volume. N=5.

Melanoma EVs with aOMVs resulted in slowing of tumor growth, whereas EVs or aOMVs alone did not show any tumor regression. See FIG. 64A. Tumor-bearing mice were euthanized when tumors became surpassed 1000 mm³ in tumor volume. Mice immunized with combination of melanoma EVs and aOMVs showed a higher survival rate than other groups (PBS, EV alone, and aOMV alone). See FIG. 64B.

Example 24: Activation of Bone Marrow-Derived Dendritic Cells (BMDCs) by *E. coli* aOMVs Methods Preparation of aOMVs: The *E. coli* culture was pelleted, resuspended in 20% sucrose in 20 mM Tris, pH 8.0 (4 mL per g cells), lysozyme (600 μg per g cells), and 0.1 M EDTA (0.2 mL per g cells) were added. The resulting spheroplasts were pelleted, and then sonicated in ice-cold 10 mM Tris, pH 8.0. The cells were pelleted at 8,000×g for 5 min, and then whole membranes were pelleted from the supernatants at 40,000×g for 60 min. The membranes were resuspended in distilled water, freeze-thawed, and incubated in 0.5% Sarkosyl (sodium N-lauroylsarcinosinate; 20 min, 25° C.). The outer membrane was pelleted (40,000×g for 90 min), and incubated with high pH solution (200 mM $Na_2CO_3$, pH 11) for 1 hour at 25° C. The pellets were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min to produce aOMVs.

Preparation of tEXO: Tumor pieces from human or mice were gently sliced into small fragments (1-2 mm) and incubated with Collagenase D (Roche) (2 mg/ml) and DNase I (Roche) (40 U/ml) for 30 min at 37° C. to dissolve fibrotic structures. After a filtration step (70 μm pore size), cells and tissue debris were eliminated by centrifugation at 300×g for 10 min and 2,000×g for 20 min. Supernatants were centrifuged at 16,500×g for 20 min and 118,000×g for 2.5 h to collect larger vesicles and smaller vesicles, respectively (Ti45 rotor: fixed angle rotor). All centrifugations were performed at 4° C. Only smaller vesicles were resuspended in PBS, these are referred to herein as tEXO.

BMDC uptake of *E. coli* aOMVs: Bone marrow cells were harvested from the femur and the tibia of mice (C57BL/6). The cells were differentiated into dendritic cells in 10% FBS/RPMI supplemented with nutrients and 20 ng/mL GM-CSF for one week. Separately, isolated aOMVs ($1 \times 10^9$) were labeled with DiO, followed by treated to BMDCs for 12 h, and examined for uptake using confocal microscope.

Analysis of maturation markers on BMDCs by flow cytometry: For analysis of surface activation markers, BMDCs treated with *E. coli* aOMVs ($5 \times 10^9$) for 24 h were blocked for non-specific staining with 2.4G2 (anti-Fc-receptor) for 30 min at 4° C. in PBS/0.1% BSA, washed and stained for 30 min, at 4° C. in PBS/0.1% BSA with the following antibodies; rat anti-mouse MHCII-AF700 (M5/114.15.2) obtained from eBioscience, rat anti-mouse CD44-BV786 (IM7), rat anti-mouse CD83-PE (Michel-19) and rat anti-mouse CD40-PECF594 (3/23) obtained from BD Biosciences, rat anti-mouse CD86-BV605 (GL-1) and hamster anti-mouse CD80-AF647 (16-10A1) obtained from BioLegend. To exclude dead cells, 7-Aminoactinomycin D (Sigma Aldrich) stained positive cells were excluded from the analysis. Events were collected and analysed by using a Fortessa-X20 Flow cytometer (BD Biosciences) and FlowJo software (Tree Star).

Results

Figure 65:
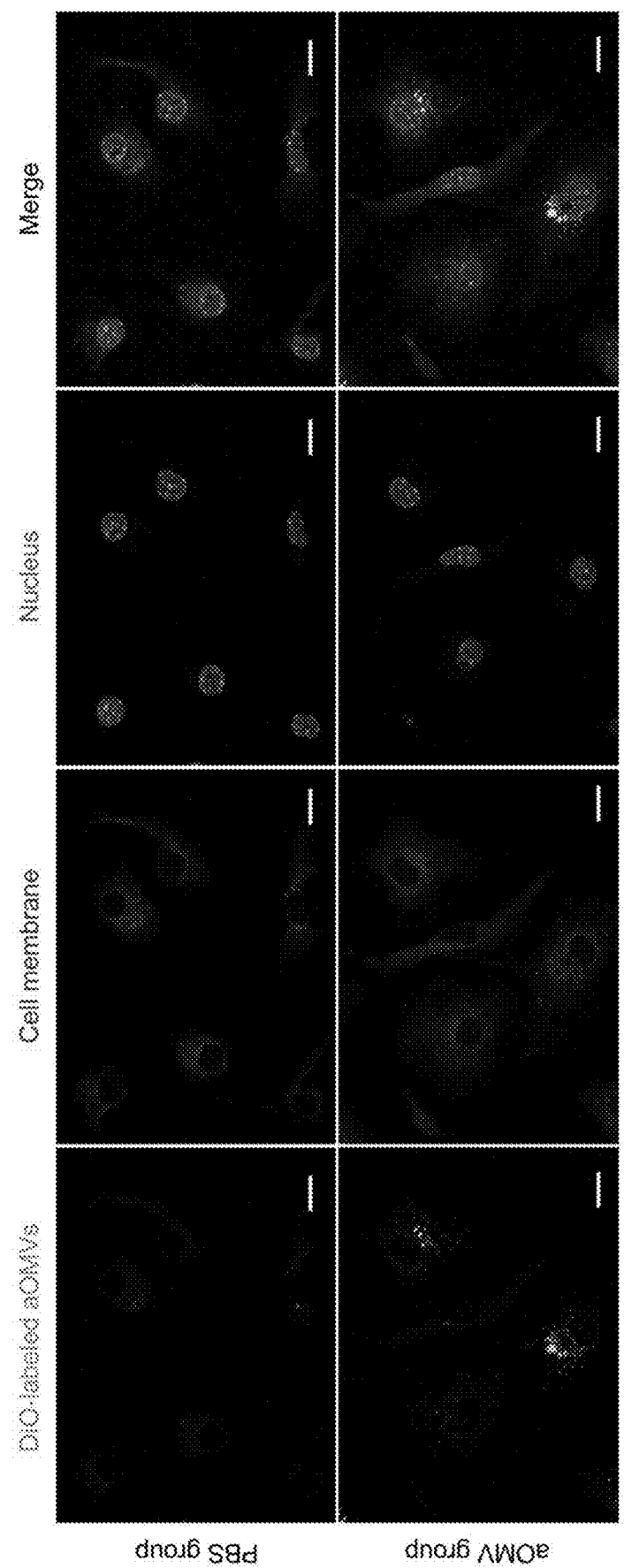
FIG. 65 is a graph showing aOMV uptake by mouse bone marrow-derived dendritic cells (BMDCs). aOMVs ($1\times10^9$) were incubated with BMDCs for 12 h, and then aOMVs, cell membrane, and nuclei were stained by DiO, Cellmask Deep Red, and DAPI, respectively. Scale bars, 20 μm.
Figure 66A:
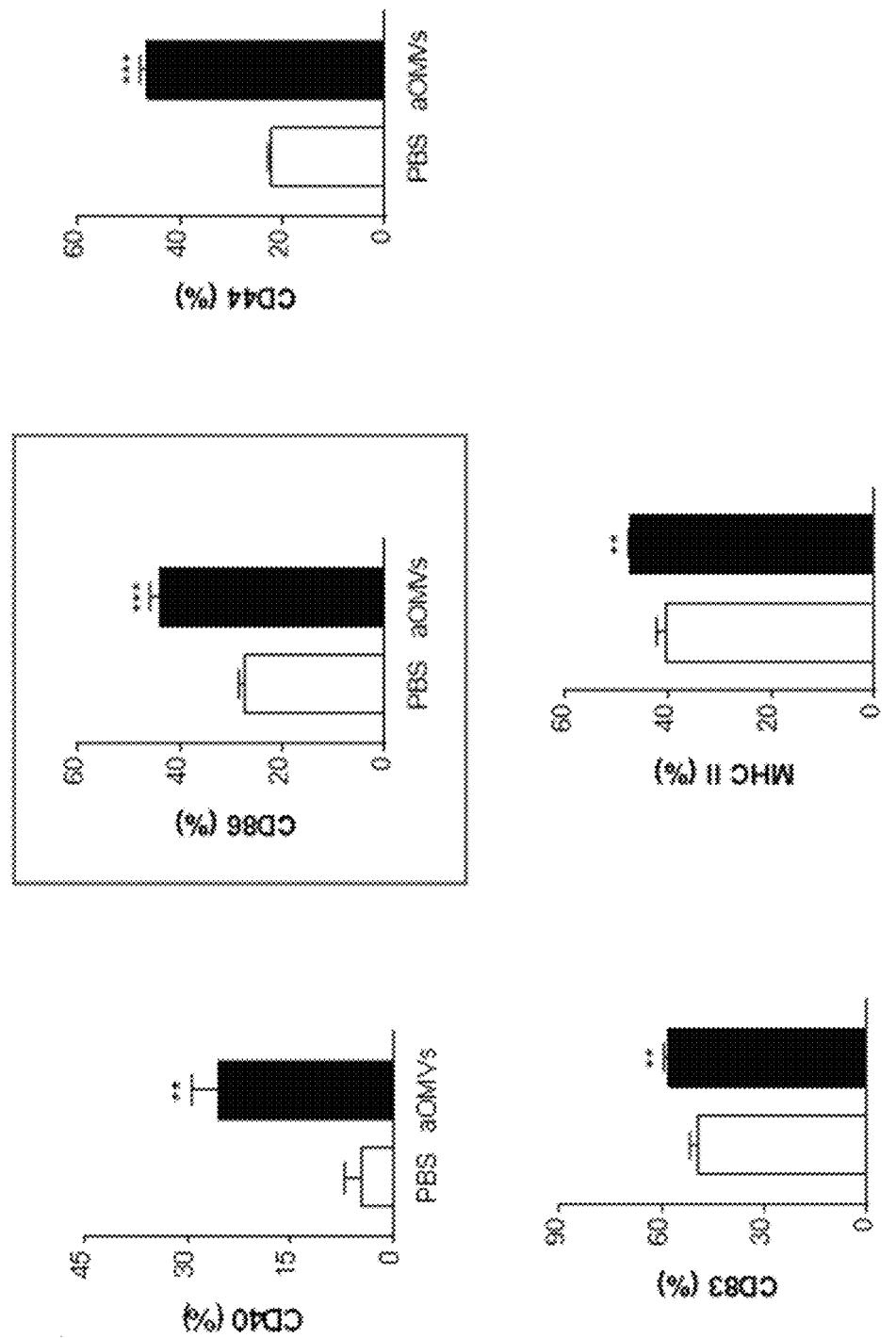
FIG. 66A shows the expression levels of dendritic cell maturation markers, including CD40, CD80, CD44, CD80, and MHC II. aOMVs ($5\times10^9$) were incubated with BMDCs for 24 h and analyzed by flow cytometry which is shown as the percentage of total cells. , P<0.01; *, P<0.001; two-tailed unpaired T test. Error bars indicate SEM. N=3.
Figure 66B:
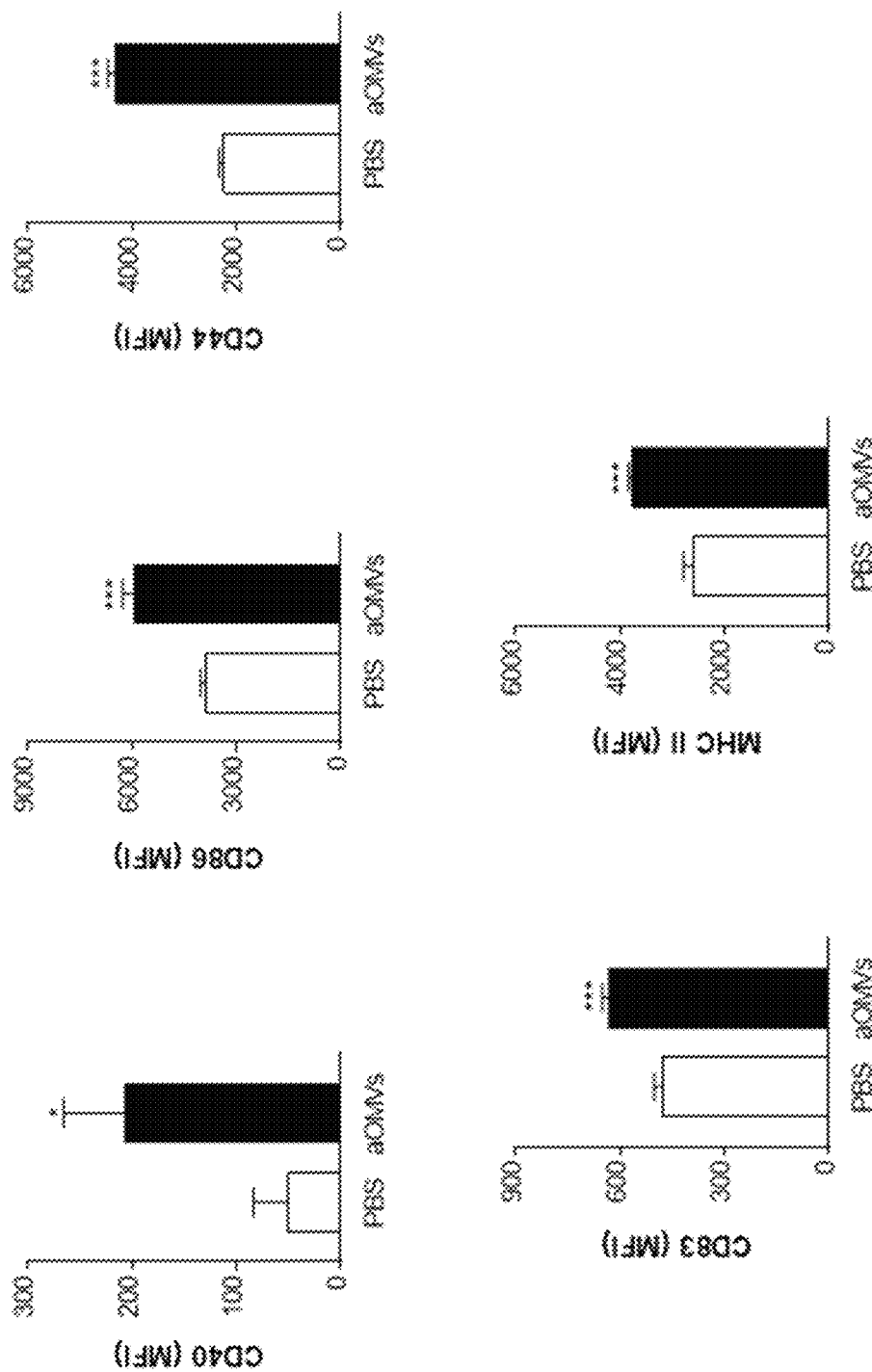
FIG. 66B shows the expression levels of dendritic cell maturation markers, including CD40, CD80, CD44, CD80, and MHC II. aOMVs ($5\times10^9$) were incubated with BMDCs for 24 h and analyzed by flow cytometry which is shown as the mean fluorescence intensity (MFI). *, P<0.05; ***, P<0.001; two-tailed unpaired T test. Error bars indicate SEM. N=3.

DiO-labeled aOMVs were internalized by BMDCs, so could be detected inside of cells (FIG. 65). FACS analysis revealed that incubation with aOMVs increases the levels of dendritic cell maturation/activation markers (FIG. 66).

Example 25: Anti-Tumor Effect of Mouse Melanoma-Derived Exosomes (tEXO) and *E. coli* aOMVs, and Elucidating the Underlying Mechanism Methods Mice experiments: Mice (wild-type C57BL/6 genetic background, 6 weeks old) were subcutaneously injected with melanoma cells (B16F10; $5 \times 10^5$), and maintained for three days to form a measurable mass of tumor (2-3 mm). Then, tEXO ($5 \times 10^9$) were subcutaneously injected in combination with *E. coli* aOMVs ($5 \times 10^9$) to the mice five times at 3-day intervals. For anti-PD-1 immunotherapy, anti-mouse PD-1 antibody (100 μg; BioXcell) was intraperitoneally injected into mice 1 day prior to immunization with tEXO and *E. coli* aOMVs. The tumor size was measured at 1- to 2-day intervals. The tumor volume was calculated according to the formula $v = l \times s2/2$ [v, volume; 1, a length of the longest axis of the tumor mass; s, a length of the shortest axis]. For metastasis assay, mice were intravenously injected with B16F10 ($1 \times 10^5$), and then subcutaneously immunized with tEXO ($5 \times 10^9$) and/or *E. coli* aOMVs ($5 \times 10^9$) five times at 3-day intervals. At day 17, mice were killed and the number of colonies metastasized in the lungs were counted.

Tissue histological analysis: Tumor, lung, liver, heart, and kidney were excised and fixed in 4% formaldehyde overnight at room temperature. The tissues were embedded in paraffin, sectioned (4 μm), and stained with hematoxylin and eosin.

Flow cytometry analysis of immune cells from mice: Mice were immunized with tEXO ($5 \times 10^9$) and/or *E. coli* aOMVs ($5 \times 10^9$) five times at 3-day intervals. At day 17, tumors and inguinal lymph nodes were removed upon sacrifice and single cell suspensions were made. Cells were counted for absolute numbers using Muse cell counter (Millipore) and stained for surface expression for 30 min at 4° C. in PBS/0.1% BSA with the following antibodies: rat anti-mouse F4/80-eF660 (BM8) and rat anti-mouse MHCII-AF700 (M5/114.15.2) obtained from eBioscience; hamster anti-mouse CD11c-PeCy7 (HL3), rat anti-mouse CD11b-BV510 (M1/70), rat anti-mouse Ly6g-BV650 (1A8), rat anti-mouse CD19-PECF594 (1D3), hamster anti-mouse CD3e-BUV737 (500A2), rat anti-mouse NKG2A/C/E-BV421 (20d5), rat anti-mouse CD45-APC-Cy7 (30-F11) and rat anti-mouse CD8a-FITC (53-6.7) obtained from BD Biosciences; rat anti-mouse CD4-BV785 (RM4-5) and rat anti-mouse Ly6c-BV605 (HK1.4) obtained from BioLegend. To exclude dead cells, 7-Aminoactinomycin D (Sigma Aldrich) was used for the analysis. Events were collected and analyzed by using a Fortessa-X20 Flow cytometer (BD Biosciences) and FlowJo software (Tree Star).

Splenocyte cytokines: Mice were immunized with tEXO ($5\times10^9$) and/or *E. coli* aOMVs ($5\times10^9$) five times at 3-day intervals. At day 17, CD8+ T cells were purified from mice spleen using CD8+ T cell isolation kit (Miltenyi Biotec) according to manufacturer's instructions. The cells ($5\times10^5$) were incubated for 72 h with 1 µg/mL of tEXO, followed by ELISA to quantitatively analyze IFN-γ.

Cytotoxic T lymphocyte (CTL) killing assay: Reactive CTLs were produced from spleens of mice immunized with tEXO ($5\times10^9$) and/or *E. coli* aOMVs ($5\times10^9$) five times at 3-day intervals. At day 17, splenic lymphocytes were isolated from immunized mice using Pan T cell isolation kit II (Miltenyi Biotec) according to manufacturer's instructions. To acquire effector CTLs, purified splenic T cells ($2\times10^6$) were cultured with tEXO (5 µg/mL) in the presence of IL-2 (20 U/mL). After 6 days, T cells were harvested and used as effector cells. B16F10 ($1\times10^4$) as target cells were mixed with different ratios (12.5, 25, and 50) of effector cells for 24 h at 37° C. The killing rate of effector cells was calculated as: [1−(OD of effector and target cells−OD of effector cells)/OD of target cells]×100%.

Results

Figure 67A:
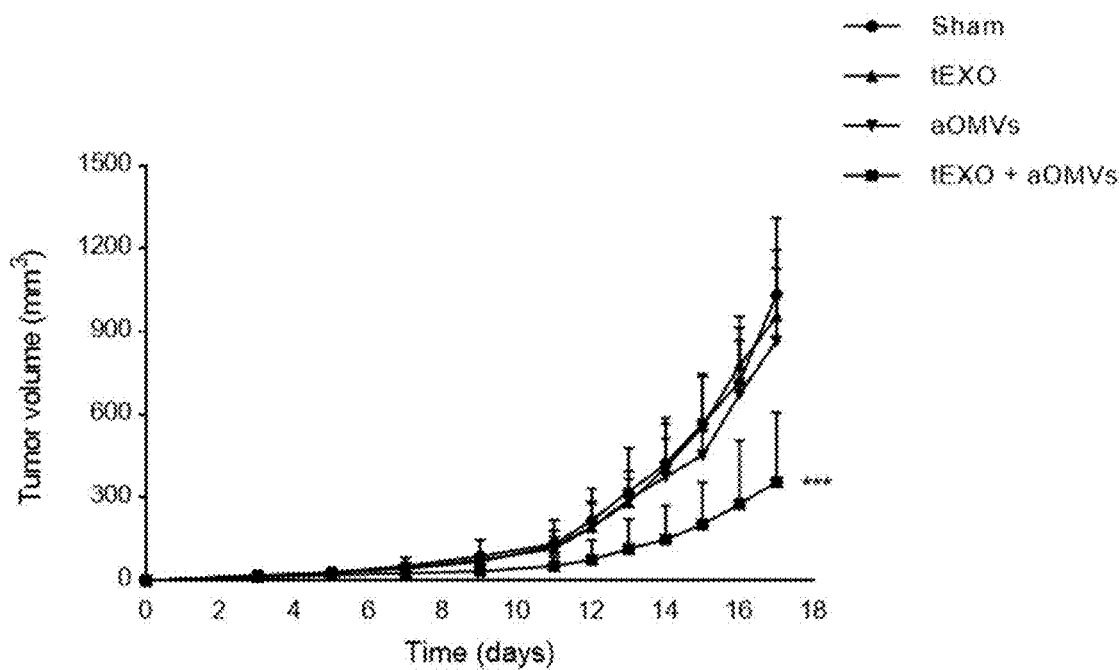
FIG. 67A shows melanoma volume in mice immunized with mouse melanoma exosomes (tEXO; $5\times10^9$) and/or E. coli aOMVs ($5\times10^9$) five times at 3-day intervals. ***, P<0.001; versus sham group; one way ANOVA with Tukey's multiple comparison test. Error bars indicate SEM. N=14.
Figure 67B:
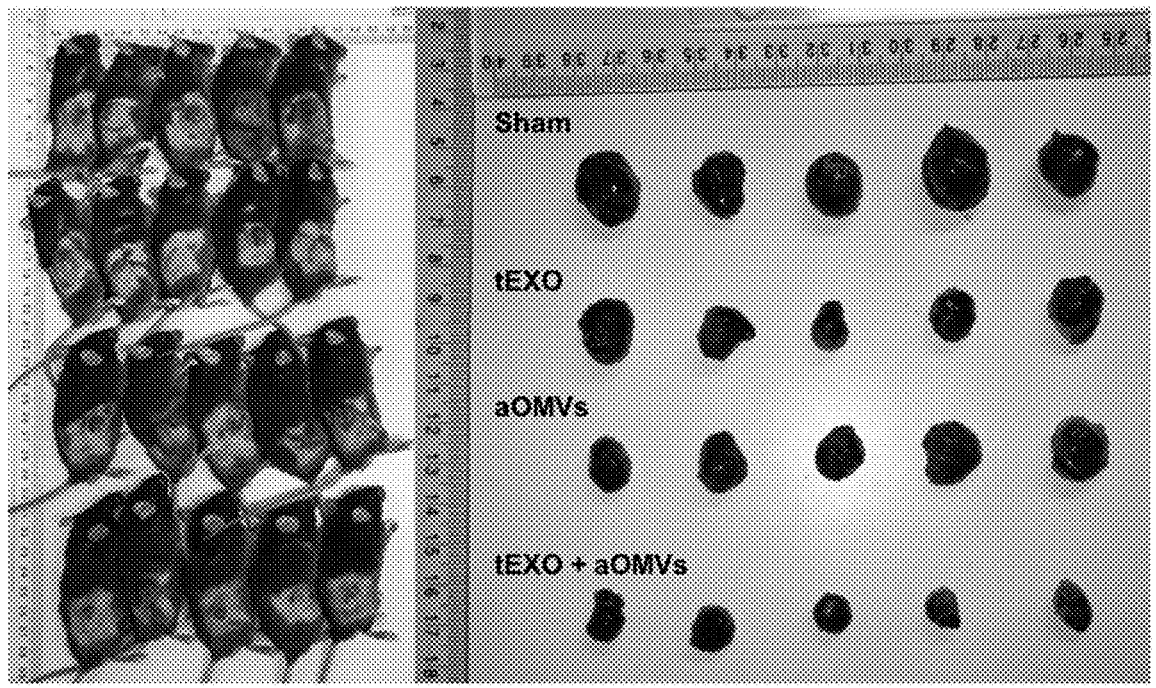
FIG. 67B shows whole body and dissected tumor images (Day 17) of mice immunized with tEXO ($5\times10^9$) and/or E. coli aOMVs ($5\times10^9$) five times at 3-day intervals. N=5.
Figure 68:
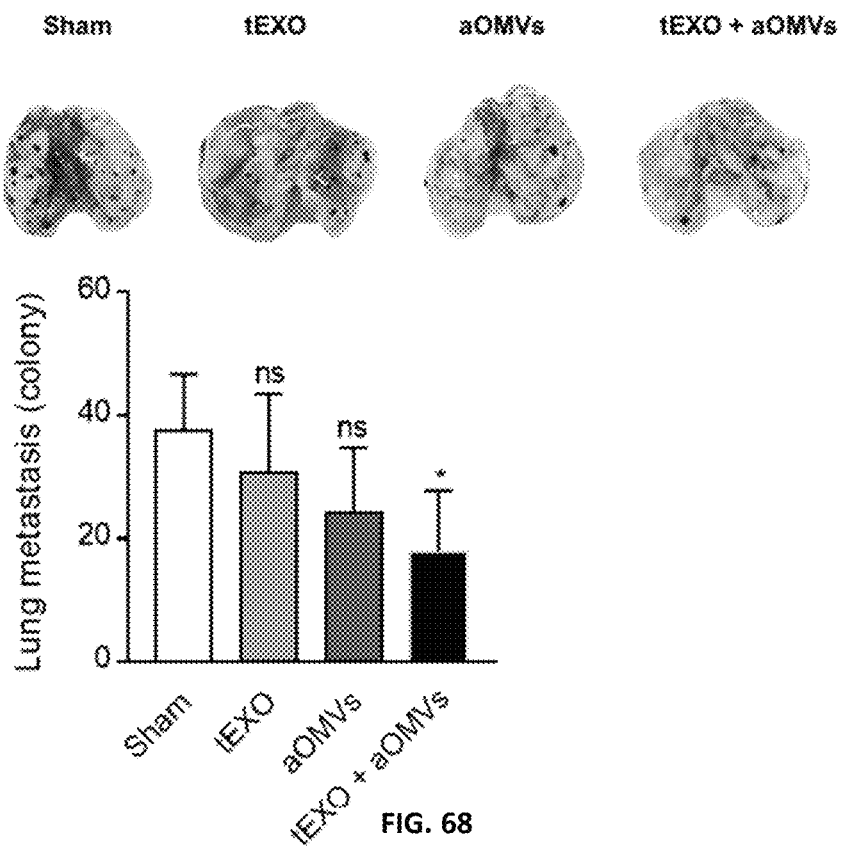
FIG. 68 is a graph of the number of metastasized melanoma colonies (Day 17) in mice lungs immunized with tEXO ($5\times10^9$) and/or E. coli aOMVs ($5\times10^9$) five times at 3-day intervals. ***, P<0.001; ns, not significant; versus sham group; one way ANOVA with Tukey's multiple comparison test. Error bars indicate SEM. N=5.
Figure 69:
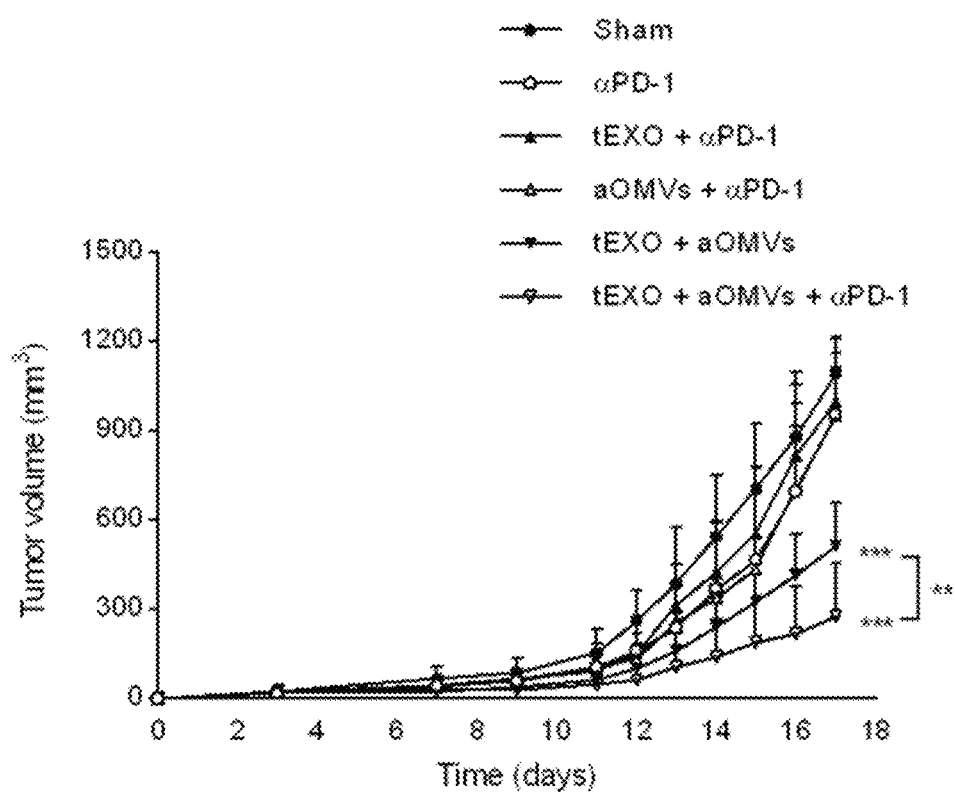
FIG. 69 shows therapeutic vaccination plus anti-PD-1 immunotherapy in mice with melanoma. Mice were immunized with tEXO ($5\times10^9$) and/or E. coli aOMVs ($5\times10^9$) five times at 3-day intervals, and treated with anti-PD-1 therapy (100 µg) 1 day prior to immunization. , P<0.01; *, P<0.001; versus sham group; one way ANOVA with Tukey's multiple comparison test. Error bars indicate SEM. N=7.
Figure 70A:
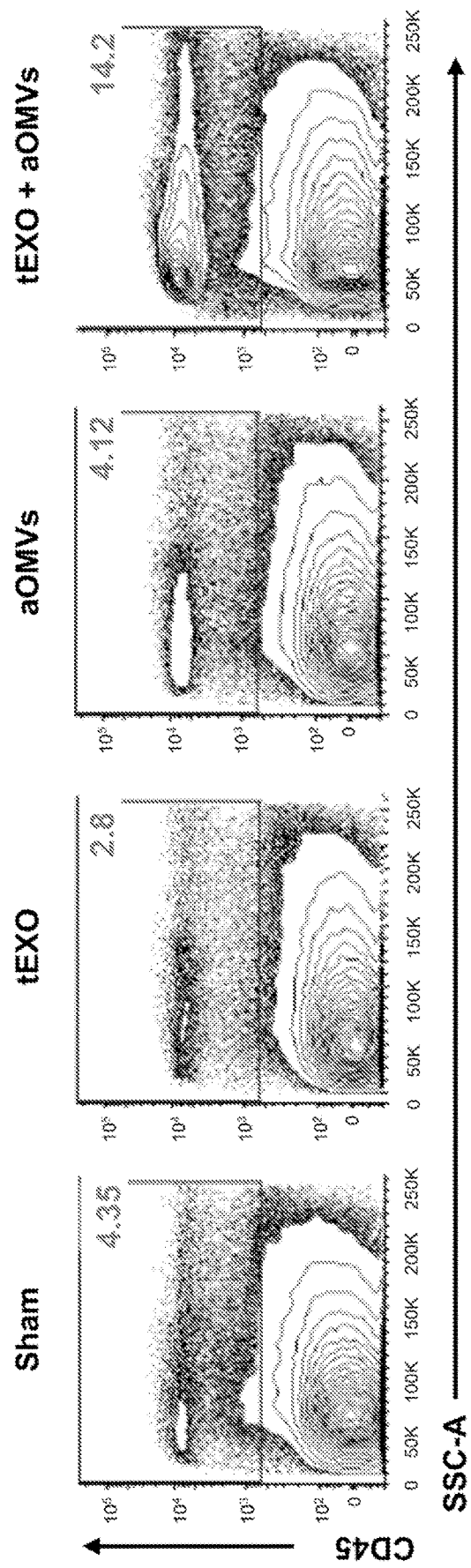
FIG. 70A shows representative fluorescence-activated cell sorting plots for measuring the population of tumor infiltrating lymphocytes in the tumor tissue (Day 17), after mice were immunized with tEXO ($5\times10^9$) and/or E. coli aOMVs ($5\times10^9$) five times at 3-day intervals.
Figure 70B:
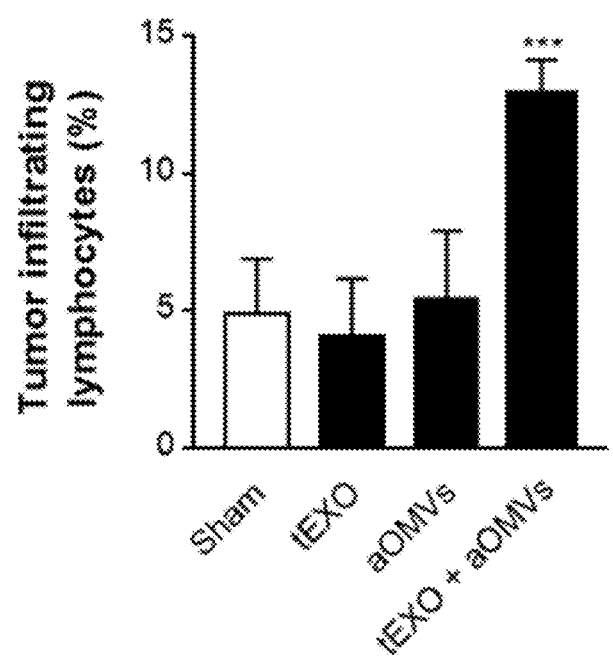
FIG. 70B shows the percentage of infiltrating lymphocytes in tumor tissues (Day 17), after mice were immunized with tEXO ($5\times10^9$) and/or E. coli aOMVs ($5\times10^9$) five times at 3-day intervals. ***, P<0.001; versus sham group; one way ANOVA with Tukey's multiple comparison test. Error bars indicate SEM. N=4.
Figure 70C:
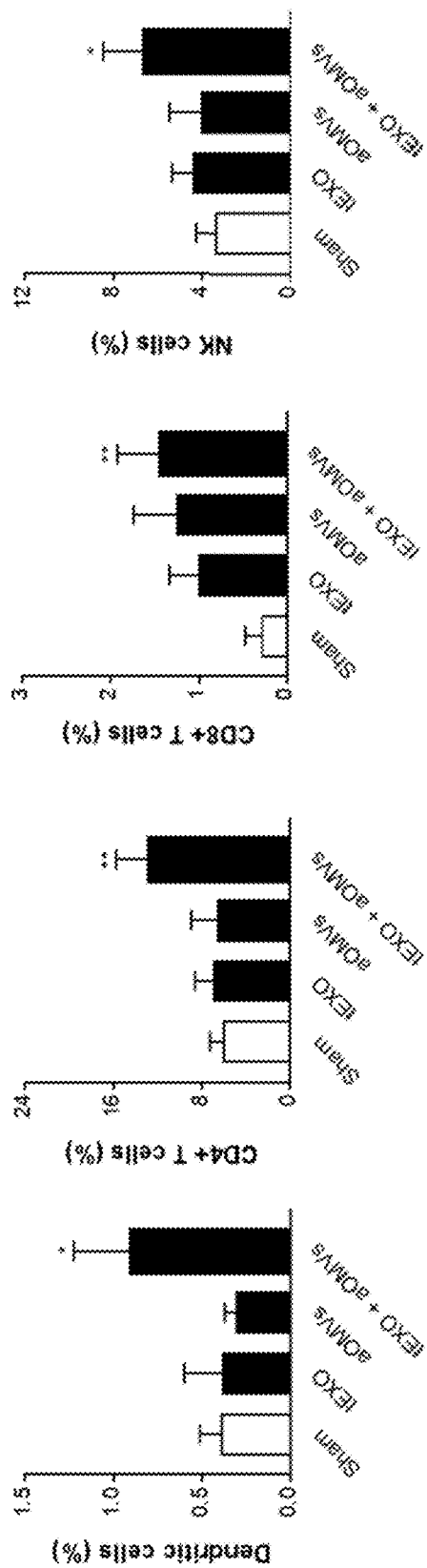
FIG. 70C shows the percentage of various infiltrating cell types in tumor tissues (Day 17), after mice were immunized with tEXO ($5\times10^9$) and/or E. coli aOMVs ($5\times10^9$) five times at 3-day intervals. *, P<0.05; **, P<0.01; versus sham group; one way ANOVA with Tukey's multiple comparison test. Error bars indicate SEM. N=4.
Figure 71:
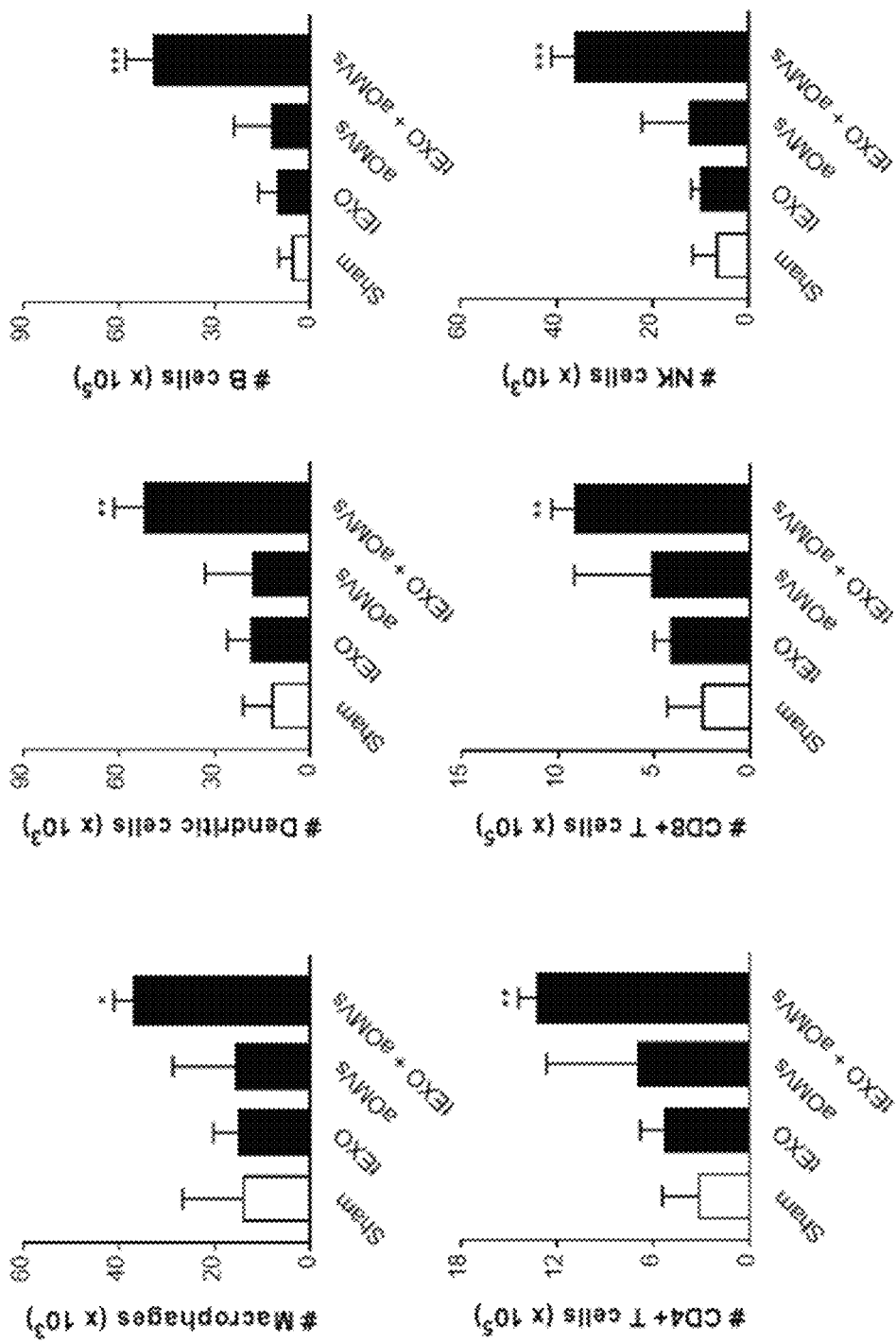
FIG. 71 shows the percentage of various infiltrating cell types in lymph nodes (Day 17), after mice were immunized with tEXO ($5\times10^9$) and/or E. coli aOMVs ($5\times10^9$) five times at 3-day intervals. *, P<0.05; , P<0.01; *, P<0.001; versus sham group; one way ANOVA with Tukey's multiple comparison test. Error bars indicate SEM. N=4.
Figure 72A:
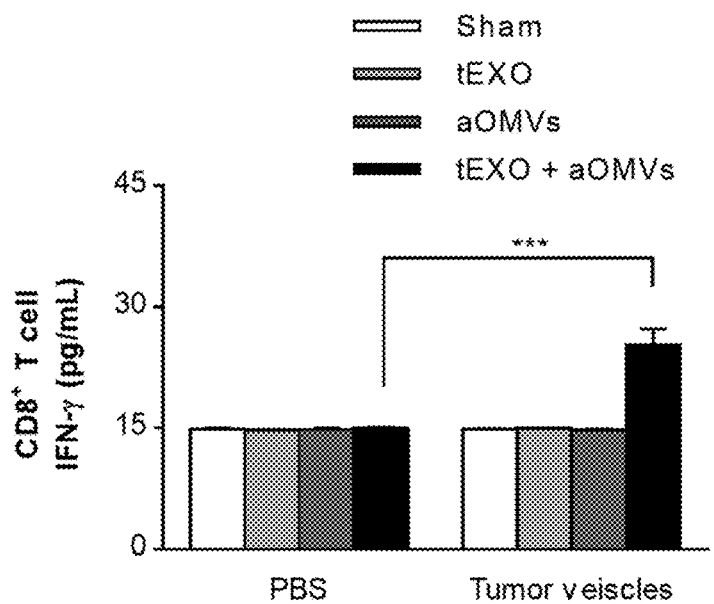
FIG. 72A shows the level of IFN-gamma secreted from mouse splenic CD8+ T cells upon ex vivo treatment with tEXO (1 µg/mL). Spleens were dissected from mice immunized with tEXO ($5\times10^9$) and/or E. coli aOMVs ($5\times10^9$) five times at 3-day intervals. ***, P<0.001; one way ANOVA with Tukey's multiple comparison test. Error bars indicate SEM. N=3.
Figure 72B:
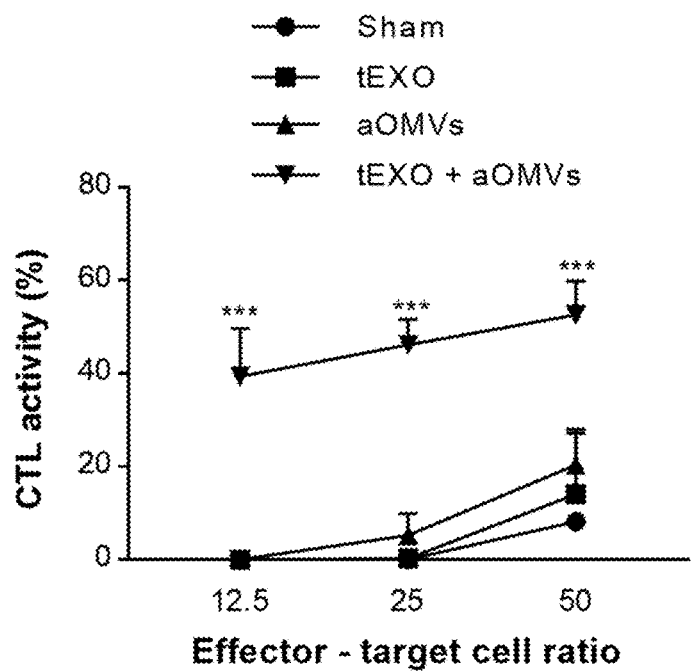
FIG. 72B is a graph of induction of potent melanoma-specific cytotoxic T lymphocytes (CTL) by immunization with tEXO ($5\times10^9$) and aOMVs ($5\times10^9$). Lysis of B16F10 (target cell) was evaluated by MTT assay after incubation with restimulated splenic T cell (effector cell). ***, P<0.001; versus sham group; one way ANOVA with Tukey's multiple comparison test. Error bars indicate SEM. N=3.

A combination of tEXO with *E. coli* aOMVs caused significant reduction (65%) in the tumor volume (FIGS. 67A and B) with grossly visible tumor necrosis (data not shown). Under our immunization approach, no systemic toxicity was observed in the heart, liver, lung, and kidney (data not shown). Also, we investigated the therapeutic effect of tEXO and aOMVs on the growth of metastasized melanoma. As a result, the mice immunized with tEXO plus aOMVs showed significantly reduced numbers of metastasized lung colonies (FIG. 68). Moreover, the combination of tEXO+aOMVs and αPD-1 IgG therapy dramatically decreased tumor growth, compared with αPD-1 monotherapy or tEXO+aOMV immunization (FIG. 69). Next, we performed immunization study to examine the presence of tumor infiltrating lymphocyte (TIL) in tumor tissues. Flow cytometry analysis showed that the levels of CD45+ cells in the mice immunized with tEXO and aOMVs was significantly elevated (FIGS. 70A and B). Especially, dendritic cells, CD4+ T cells, CD8+ T cells, and NK cells were mostly observed in tumor tissues treated with tEXO and aOMVs (FIG. 70C). Furthermore, a significant increase in various adaptive immune cells in draining lymph nodes was detected in tEXO/aOMV-immunized mice (FIG. 71). To further evaluate the role of CD8+ T cells in immunotherapeutic effect mediated by tEXO and aOMVs, splenic CD8+ T cells were isolate from immunized mice for immunoassay. Higher levels of IFN-γ were secreted from splenic CD8+ T cells of tEXO-immunized group in combination with aOMVs, compared to the sham group (FIG. 72A). Also, tEXO-specific CTLs could be stimulated from splenocytes immunized with tEXO and aOMVs, and these CTLs showed a higher level of lysis activity against B16F10 cells than those from mice immunized with sham, tEXO, or aOMVs (FIG. 72B).

Example 26: Intratumoral Immunization with *E. coli* aOMVs

Methods

Mice experiments: Melanoma cells (B16F10; $5\times10^5$) were subcutaneously implanted in both flanks of mice (wild type C57BL/6 genetic background, 6 weeks old). At day 3, two doses ($10^9$ or $10^{10}$) of *E. coli* aOMVs were immunized intratumorally in right flank of mice seven times at 3-day intervals. Also, anti-mouse PD-1 antibody (100 µg; BioXcell) was intraperitoneally injected into mice 1 day prior to immunization with *E. coli* aOMVs. The size of tumors located on both flanks was measured at 2- to 3-day intervals. The tumor volume was calculated according to the formula v=l×s2/2 [v, volume; 1, a length of the longest axis of the tumor mass; s, a length of the shortest axis].

Results

Figure 73:
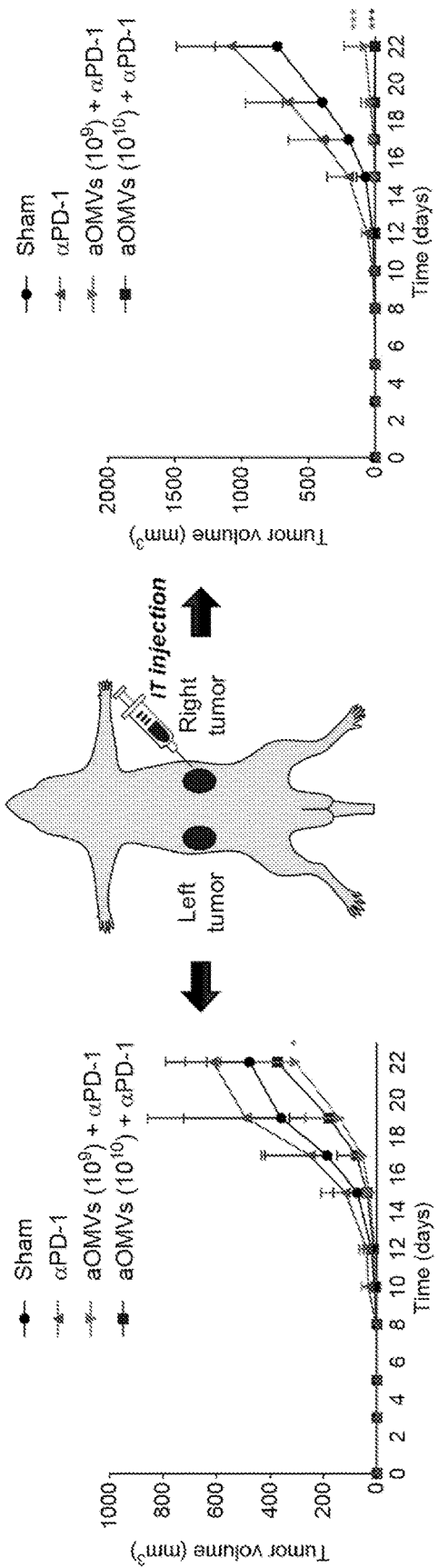
FIG. 73 shows melanoma volume in mice immunized intratumorally with E. coli aOMVs ($10^9$ or $10^{10}$) seven times at 3-day intervals in combination with anti-PD-1 therapy (100 µg). *, P<0.05; ***, P<0.001; versus sham group; one way ANOVA with Tukey's multiple comparison test. Error bars indicate SEM. N=9.

Intratumoral immunization with low dose of aOMVs ($10^9$) resulted in significant tumor shrinkage, and moreover, high dose of aOMVs ($10^{10}$) showed undetectable tumor volume (FIG. 73). Also, aOMV immunization had an impact on regression of tumor implanted into the other flank, revealing systemic anti-tumor effect of intratumoral injection of aOMVs.

Example 27: Comparison of Adjuvant Activity of *E. coli* aOMVs with Other Types of Adjuvants Methods Antibody titer against tumor vesicular proteins: Mice (wild type C57BL/6 genetic background, 6 weeks old) were intraperitoneally injected once a week for three weeks with human melanoma tEXO ($5\times10^9$) with/without various adjuvants. Alum (100 µg), Incomplete freund's adjuvant (IFA; 50 µL), CpG DNA (10 µg), and *E. coli* aOMVs ($5\times10^9$) were used as adjuvants. Blood samples were taken from mice 3 days after each injection and assayed for their antibodies specific for melanoma vesicular proteins. The mouse serum was 1:500 diluted in 1% BSA/PBS and placed in 96-well plates coated with 200 ng of human melanoma tEXO. After incubation for 2 h, immunological changes were measured with a peroxidase-conjugated anti-mouse antibody.

Results

Figure 74:
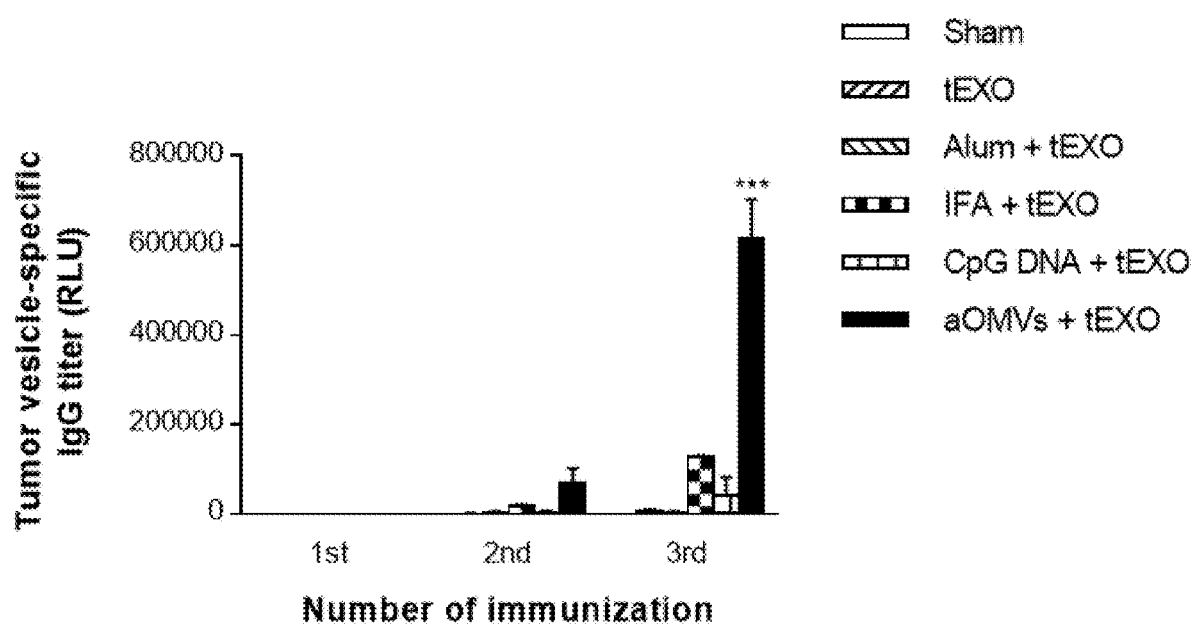
FIG. 74 is a graph showing the levels of human melanoma tEXO-specific antibodies measured in the course of three intraperitoneal injection of human tEXO ($5\times10^9$) with/without various adjuvants at weekly intervals. Alum (100 µg), Incomplete freund's adjuvant (IFA; 50 µL), CpG DNA (10 µg), and E. coli aOMVs ($5\times10^9$) were used as adjuvants. ***, P<0.001; versus sham group; one way ANOVA with Tukey's multiple comparison test. Error bars indicate SEM. N=5.

To compare the immune adjuvant activity of aOMVs with those of other traditional adjuvants such as alum, IFA, or CpG DNA, tumor vesicle-specific antibodies were evaluated in the serum of mice immunized with human melanoma tEXO and each adjuvant. The strongest antibody response against tumor vesicles was obtained by a combination of tEXO and aOMVs (FIG. 74) as compared to traditional adjuvants such as alum, IFA, or CpG DNA. Thus, aOMVs are significantly better adjuvants as compared to traditional adjuvants such as alum, IFA, or CpG DNA.

Example 28: Optimization of the Safety and Efficacy of *E. coli* aOMVs in Cancer Immunotherapy Methods Preparation of aOMVs under different pH condition: The outer membrane was isolated from *E. coli* culture using same method described in Example 24. The membrane was incubated with various high pH solution (200 mM $Na_2CO_3$, pH 9, 10, 11, and 12) for 1 hour at 25° C. The pellets were applied to 4 mL of 50% iodixanol (Axis-Shield PoC AS), followed by addition of 4 mL of 30% iodixanol and 2 mL of 10% iodixanol to ultracentrifuge tube. The layers formed between 10% and 30% iodixanol after ultracentrifugation at 100,000×g for 2 hours was collected. Finally, the samples were sonicated for 30 min to produce aOMVs.

Transmission electron microscopy (TEM): Formvar/carbon Cu copper grids (Electron Microscopy Sciences) were glow discharge-treated before aOMVs were loaded. Then aOMVs were washed two times in distilled water and then fixed using 2.5% glutaraldehyde dissolved PBS. After two further washes in filtered water, the samples were stained using 2% uranyl acetate for 1.5 min. Negative-stained samples were examined on a digitized LEO 912AB Omega electron microscope (Carl Zeiss SMT) at 120 kV with a Veleta CCD camera (Olympus-SiS).

DNA analysis: RNA from aOMVs or OMVs was isolated using miRCURY' RNA isolation kit for biofluids (Exiqon) according to manufacturer's protocol. DNA was isolated using Qiamp DNA Blood Mini kit (Qiagen) according to manufacturer's protocol. One microliter of isolated RNA or DNA were analyzed for its quality, yield, and nucleotide length with capillary electrophoresis using Agilent RNA 6000 Nanochip and Agilent High sensitivity DNA chip, respectively, on an Agilent 2100 Bioanalyzer® (Agilent Technologies).

RAW 264.7 cytokines: RAW 264.7 ($1 \times 10^5$), a mouse macrophage cell line, were seeded into 24-well plates. OMVs and aOMVs isolated under different pH condition were applied to the cells to induce pro-inflammatory cytokines (TNF-α and IL-6) for 15 h. Supernatant concentrations of cytokines were measured by ELISA kit (R&D systems).

Antibody titer against tumor vesicular proteins: Mice (wild type C57BL/6 genetic background, 6 weeks old) were intraperitoneally injected once a week for three weeks with human melanoma tEXO ($5 \times 10^9$) with/without E. coli aOMVs ($5 \times 10^9$) isolated under different pH condition. Blood samples were taken from mice 3 days after each injection and assayed for their antibodies specific for melanoma vesicular proteins. The mouse serum was 1:500 diluted in 1% BSA/PBS and placed in 96-well plates coated with 200 ng of human melanoma tEXO. After incubation for 2 h, immunological changes were measured with a peroxidase-conjugated anti-mouse antibody. For experiment to investigate the optimal mixture ratio of tEXO and aOMVs, aOMVs ($5 \times 10^9$) were mixed with different ratios (0.01, 0.1, 1, 10, and 100) of tEXO for immunization. Mice were intraperitoneally injected one a week for three weeks with various ratio of tEXO and aOMVs, and then blood samples were taken from mice 3 days after each injection. Antibody titer specific for human melanoma tEXO was examined using same method as mentioned in above.

Results

Figure 75A:
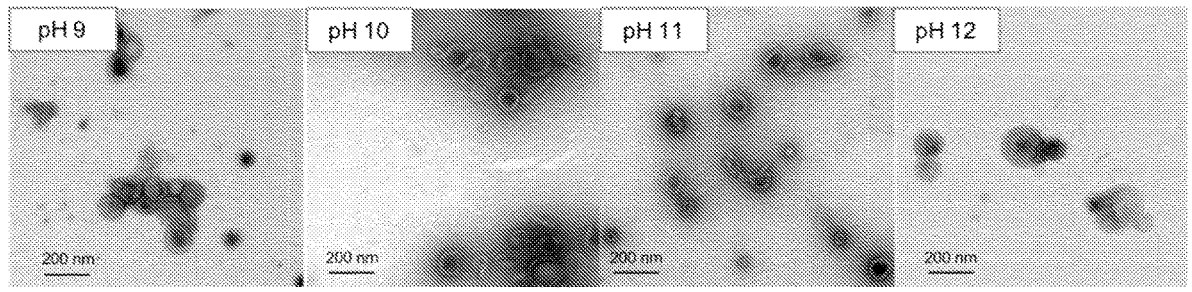
FIG. 75A shows the morphological characters of E. coli aOMVs isolated by various high pH conditions.
Figure 75B:
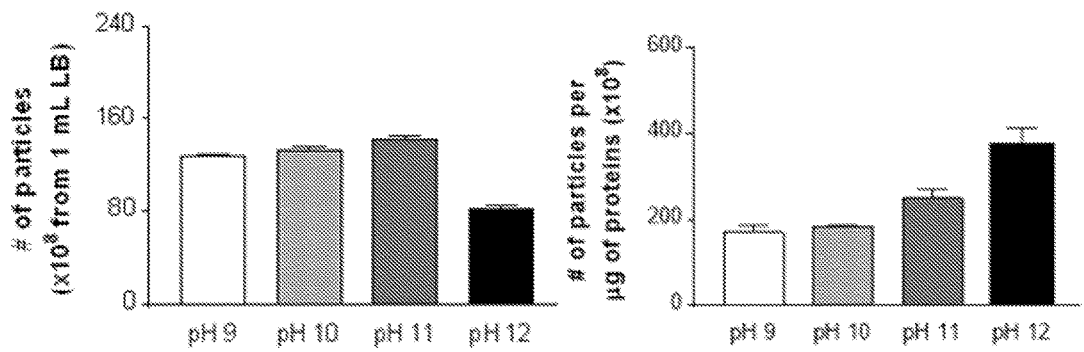
FIG. 75B shows the number of total particles derived from 1 mL LB media (left) and the number of particles per one microgram of proteins (right) from E. coli aOMVs isolated by various high pH conditions. Error bars indicate SEM. N=3.
Figure 75C:
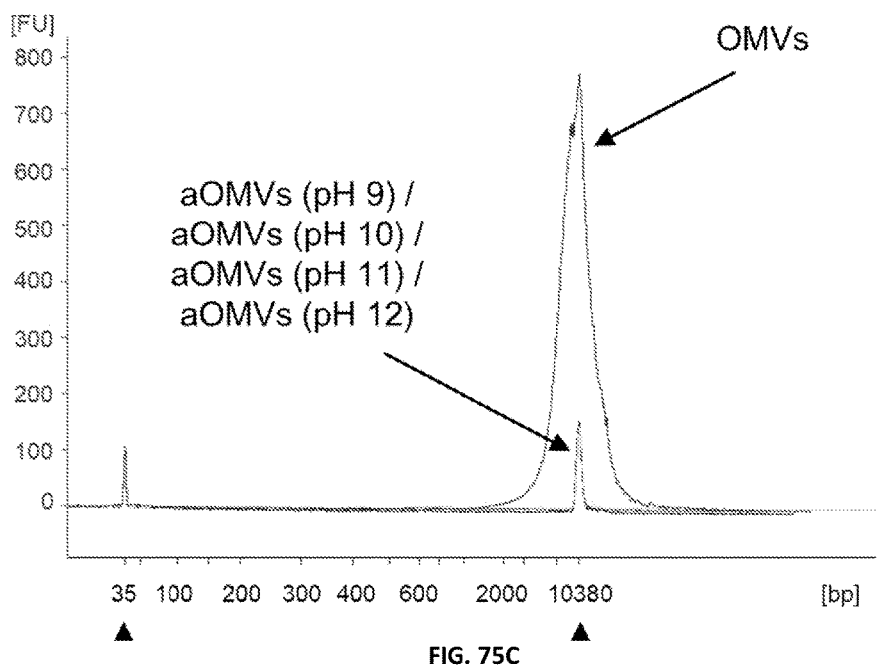
FIG. 75C shows an electropherogram of DNA molecules isolated from E. coli aOMVs according to various high pH conditions.
Figure 76:
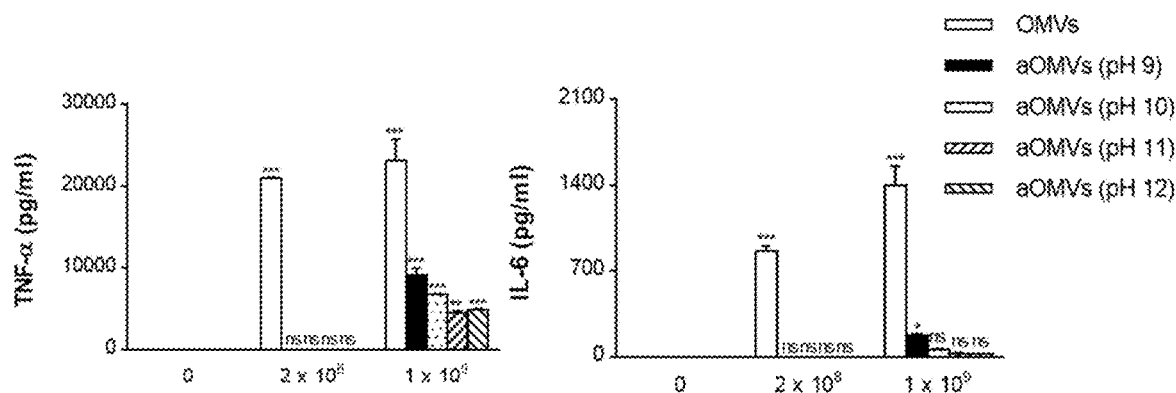
FIG. 76 shows E. coli aOMV-induced pro-inflammatory cytokines in the supernatants of RAW 264.7 cells. OMVs or aOMVs isolated by various high pH conditions were added to the cells for 15 h, and then TNF-alpha (left) and IL-6 (right) were measured by ELISA. *, P<0.05; , P<0.01; *, P<0.001; ns, not significant; versus 0 group; one way ANOVA with Tukey's multiple comparison test. Error bars indicate SEM. N=3.
Figure 77:
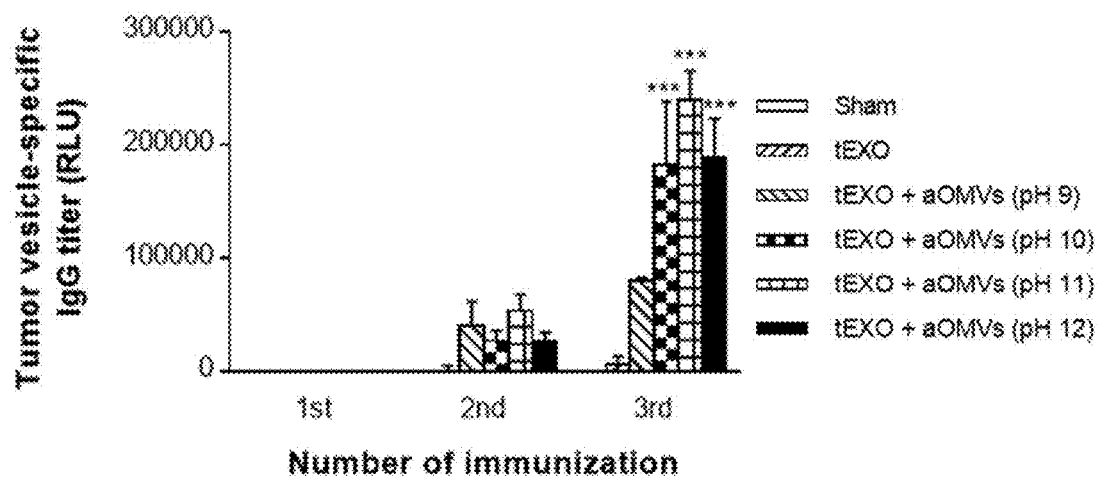
FIG. 77 is a graph showing the levels of human melanoma tEXO-specific antibodies measured in the course of three intraperitoneal injection of human tEXO ($5\times10^9$) with/without aOMVs ($5\times10^9$) isolated by various high pH conditions at weekly intervals. ***, P<0.001; versus sham group; one way ANOVA with Tukey's multiple comparison test. Error bars indicate SEM. N=5.
Figure 78:
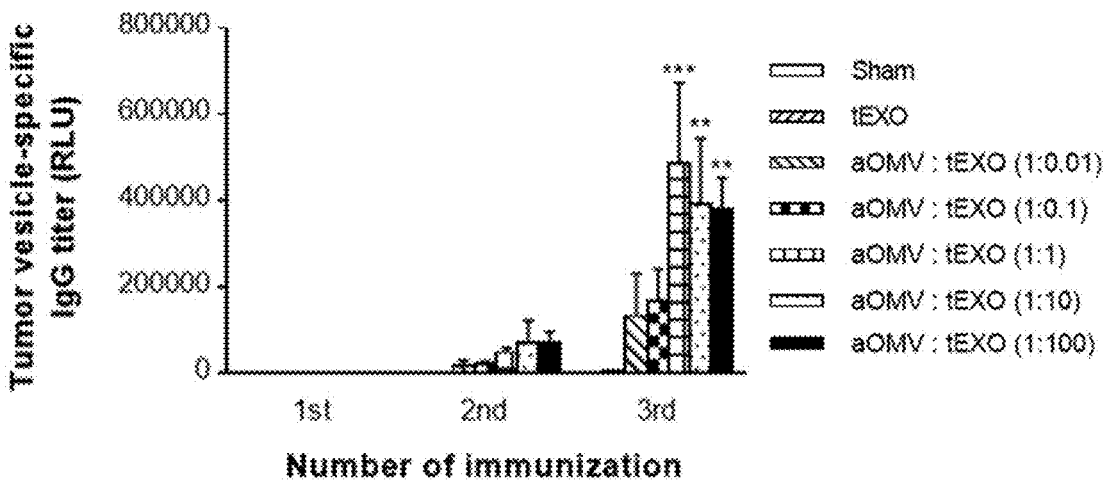
FIG. 78 is a graph showing the levels of human melanoma tEXO-specific antibodies measured in the course of three intraperitoneal injection of various particle ratio of tEXO and aOMVs at weekly intervals. , P<0.05; *, P<0.001; versus sham group; one way ANOVA with Tukey's multiple comparison test. Error bars indicate SEM. N=5.

To develop safer and more effective aOMVs, we first investigated the effect of different pH conditions on the aOMV isolation and characterization. E. coli aOMVs were generated under each pH 9, pH 10, pH 11, or pH 12 condition, and then visualized by TEM showing nanosized spherical structure without contaminants in all conditions (FIG. 75A). Especially, pH 11 and pH 12 showed the highest level of yield and purity, respectively (FIG. 75B), and all pH conditions presented devoid of DNA contaminants (FIG. 75C). Safety study with RAW 264.7 cells revealed that pH 11 and pH 12 are the best optimal condition to have less toxicity (FIG. 76), and especially pH 11 showed more effective immunogenicity against tumor vesicles (FIG. 77). With regards to determination of the optimal mixture ratio of tEXO and aOMVs, immunization with the ratio 1:1 induced the highest levels of antibody against tumor vesicles (FIG. 78).

Example 29: Anti-Tumor Effect of aOMVs from Other Bacterial Strains

Methods

Mice experiments: aOMVs were generated from Pseudomonas aeruginosa, E. coli BW25113, and E. coli ΔmsbB mutant using isolation method described in Example 24. Mice (wild-type C57BL/6 genetic background, 6 weeks old) were subcutaneously injected with melanoma cells (B16F10; $5 \times 10^5$), and maintained for three days to form a measurable mass of tumor (2-3 mm). Then, tEXO ($5 \times 10^9$) were subcutaneously injected in combination with various kinds of aOMVs ($5 \times 10^9$) to the mice five times at 3-day intervals. For anti-PD-1 immunotherapy, anti-mouse PD-1 antibody (100 μg; BioXcell) was intraperitoneally injected into mice 1 day prior to immunization with tEXO and aOMVs. The tumor size was measured at 1- to 2-day intervals. The tumor volume was calculated according to the formula $v = l \times s^2 / 2$ [v, volume; l, a length of the longest axis of the tumor mass; s, a length of the shortest axis].

Antibody titer against tumor vesicular proteins: Mice (wild type C57BL/6 genetic background, 6 weeks old) were intraperitoneally injected once a week for three weeks with human melanoma tEXO ($5 \times 10^9$) with/without two kinds of aOMVs (E. coli BW25113 and E. coli ΔmsbB mutant; $5 \times 10^9$) isolated under different pH condition. Blood samples were taken from mice 3 days after each injection and assayed for their antibodies specific for melanoma vesicular proteins. The mouse serum was 1:500 diluted in 1% BSA/PBS and placed in 96-well plates coated with 200 ng of human melanoma tEXO. After incubation for 2 h, immunological changes were measured with a peroxidase-conjugated anti-mouse antibody.

Results

Figure 79:
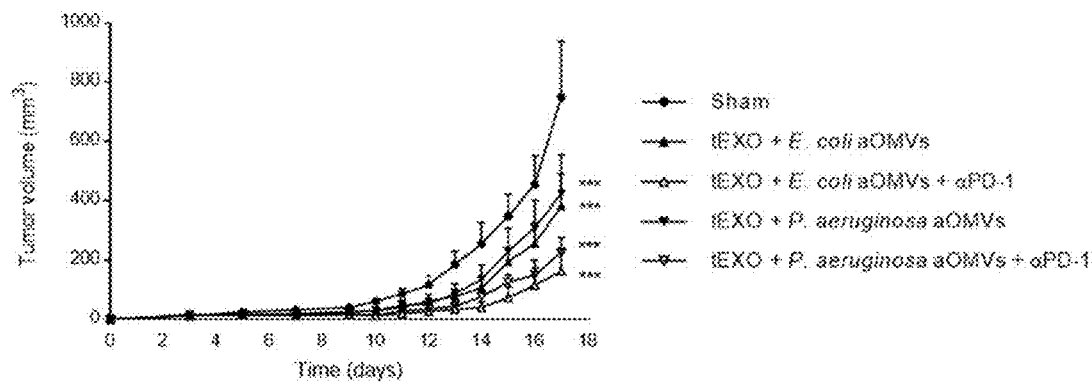
FIG. 79 shows melanoma volume in mice immunized with tEXO ($5\times10^9$) and/or P. aeruginosa aOMVs ($5\times10^9$) five times at 3-day intervals, and treated with anti-PD-1 therapy (100 µg) 1 day prior to immunization. Also, immunization with tEXO and/or E. coli aOMVs were performed for comparison. ***, P<0.001; versus sham group; one way ANOVA with Tukey's multiple comparison test. Error bars indicate SEM. N=4.
Figure 80:
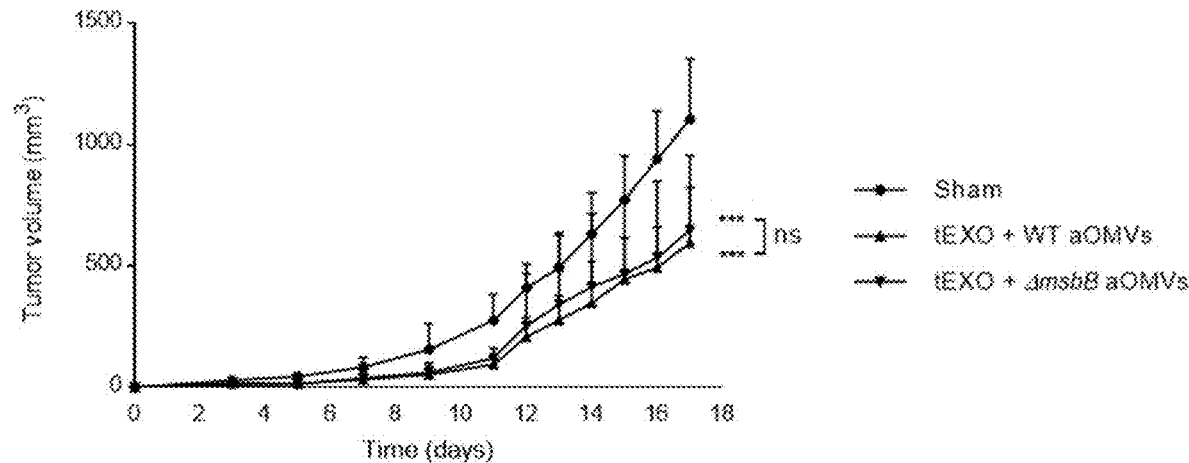
FIG. 80 shows melanoma volume in mice immunized with tEXO ($5\times10^9$) and E. coli BW25113 aOMVs ($5\times10^9$) or ΔmsbB mutant aOMVs ($5\times10^9$) five times at 3-day intervals. ***, P<0.001; ns, not significant; versus sham group; one way ANOVA with Tukey's multiple comparison test. Error bars indicate SEM. N=4.
Figure 81:
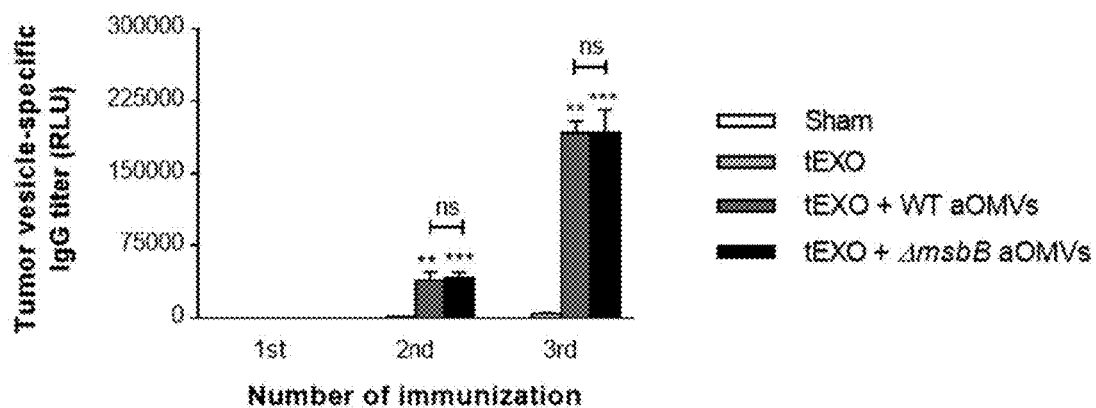
FIG. 81 is a graph showing the levels of human melanoma tEXO-specific antibodies measured in the course of three intraperitoneal injection of tEXO ($5\times10^9$) with/without E. coli BW25113 aOMVs ($5\times10^9$) or ΔmsbB mutant aOMVs ($5\times10^9$) at weekly intervals. , P<0.01; *, P<0.001; ns, not significant; versus sham group; one way ANOVA with Tukey's multiple comparison test. Error bars indicate SEM. N=5.
Figure 82:
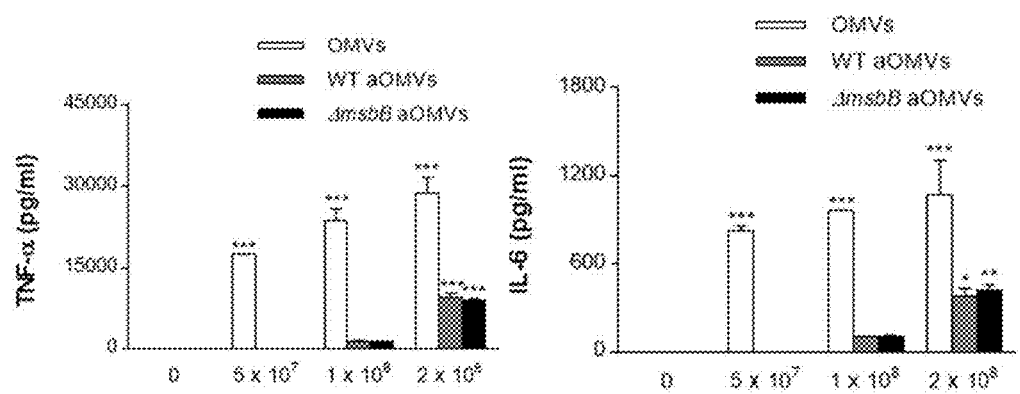
FIG. 82 shows pro-inflammatory cytokines from RAW 264.7 cells treated with E. coli BW25113 aOMVs or ΔmsbB mutant aOMVs. E. coli natural OMVs or aOMVs were added to the cells for 15 h, and then TNF-alpha (left) and IL-6 (right) were measured by ELISA. *, P<0.05; , P<0.01; *, P<0.001; ns, not significant; versus 0 group; one way ANOVA with Tukey's multiple comparison test. Error bars indicate SEM. N=3.

We wondered whether aOMVs generated from different strain of bacteria have immunotherapeutic effect against melanoma. aOMVs were isolated from P. aeruginosa, and they induced significant regression of tumor in similar to E. coli aOMVs (FIG. 79). Also, there was also combination effect with PD-1 IgG therapy revealing dramatically reduced tumor growth. We next investigated the relative role of LPS on aOMVs in anti-tumor effect. We used aOMVs from genetically mutated E. coli, whose gene encoding lipid A acyltransferase (msbB) involved in the synthesis of the lipid components of LPS. Both E. coli BW25113 wild-type and ΔmsbB mutant bacteria-derived aOMVs caused significant reduction in the tumor volume (FIG. 80), suggesting that LPS would not be key factor in the immunotherapeutic mechanism mediated by aOMVs. Also, an increase in tumor vescle-specific antibodies in the mouse blood was evoked in ΔmsbB mutant bacterial aOMV-immunized mice, comparable to wild-type bacterial aOMVs (FIG. 81). With regard to side effect, both E. coli BW25113 wild-type and ΔmsbB mutant bacteria-derived aOMVs induced less pro-inflammatory cytokines from RAW 264.7 than natural OMVs (FIG. 82).

Example 30: Isolation of Polyethylene Glycol (PEG) Precipitation-Based Tumor Vesicles (tPEG) from Mice Melanoma Methods Preparation of tPEG: Melanoma tissues from mice were gently sliced into small fragments (1-2 mm) and incubated with Collagenase D (Roche) (2 mg/ml) and DNase I (Roche) (40 U/ml) for 30 min at 37° C. to dissolve fibrotic structures. After a filtration step (70 μm pore size), cells, tissue debris, and large vesicles were eliminated by centrifugation at 300×g for 10 min, 2,000×g for 20 min, and 16,500×g for 20 min. The resulting supernatants were mixed with 50% PEG (Sigma Aldrich) to make a final PEG concentration of 10%.

After incubation for 2 h at 4° C., the samples were centrifuged at 3,000×g for 10 min for pelleting. PEG of 50% was added once again to the vesicle pellets, followed by incubation for 2 h at 4° C. and centrifugation at 3,000×g for 10 min. The supernatants were discarded and the resulting pellets were considered as tPEG.

Preparation of tNV: Melanoma tissues were acquired from mice, and then dissociated into single-cell suspensions by commercial kit using combination of collagenase and DNase (Miltenyl Biotec). For isolation of tumor cells, the total single-cell suspensions were loaded onto a MACS Column (Miltenyl Biotec) following incubation with microbeads coated with a cocktail of monoclonal antibodies against the non-tumor cells (Miltenyl Biotec Inc). The harvested tumor cells were passed five times through each of the polycarbonate membrane filters (Whatman) with a pore size of 10 µm, 5 µm, and 1 µm using a mini-extruder (Avanti Polar Lipids). The extruded samples were placed on the top of the density gradient cushion with 50% iodixanol (Axis-Shield PoC AS) overlaid with 10% iodixanol at the bottom of the ultracentrifuge tube. The layers formed between 10% and 50% iodixanol after ultracentrifugation at 100,000×g for 2 hours was collected, which is called tumor-derived nanovesicles (tNV).

Mice experiments: Mice (wild-type C57BL/6 genetic background, 6 weeks old) were subcutaneously injected with melanoma cells (B16F10; $5×10^5$), and maintained for three days to form a measurable mass of tumor (2-3 mm). Then, aOMVs ($5×10^9$) were subcutaneously injected in combination with various kinds of tumor vesicles (tEXO, tNV, and tPEG; $5×10^9$) to the mice five times at 3-day intervals. For anti-PD-1 immunotherapy, anti-mouse PD-1 antibody (100 µg; BioXcell) was intraperitoneally injected into mice 1 day prior to immunization. The tumor size was measured at 1- to 2-day intervals. The tumor volume was calculated according to the formula v=1×s2/2 [v, volume; 1, a length of the longest axis of the tumor mass; s, a length of the shortest axis].

Results

Figure 83:
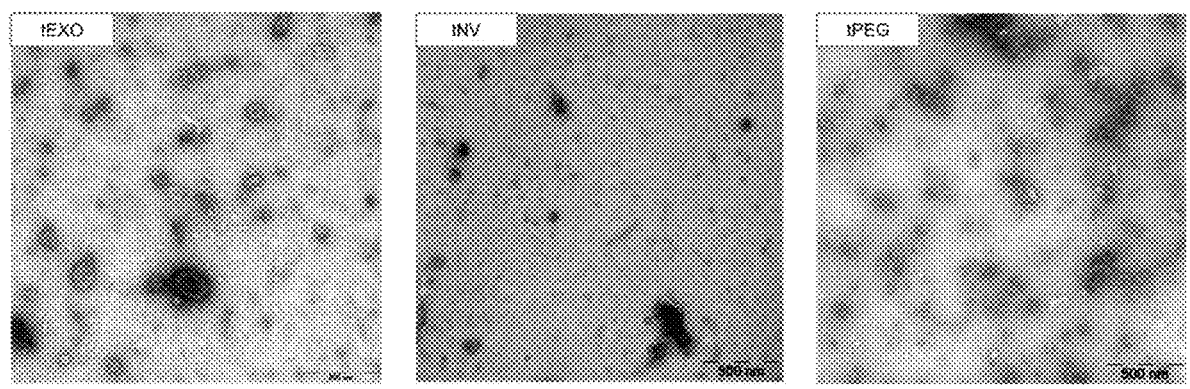
FIG. 83 shows the morphological characters of mice melanoma vesicles (tPEG) isolated by polyethylene glycol (PEG). For comparison, another type of vesicles (tNV) isolated by extrusion with micrometer-sized membrane filters were studied.
Figure 84:
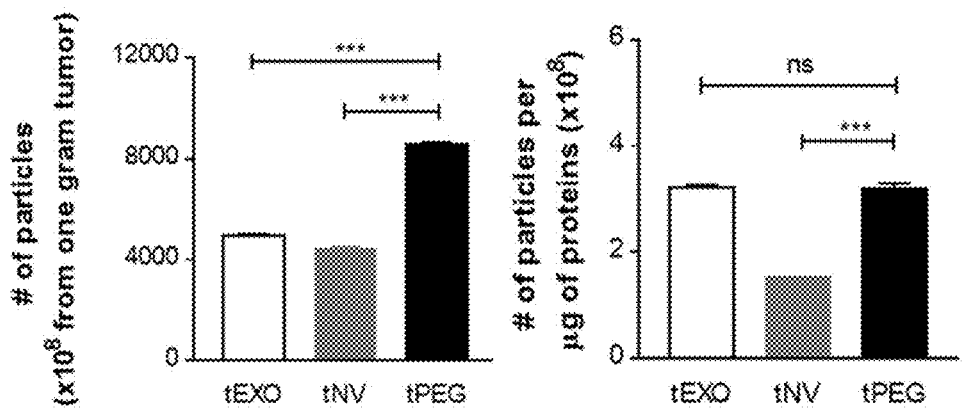
FIG. 84 shows the number of particles isolated from one gram of mice melanoma (left) and the number of particles per one microgram of vesicular proteins from tumor vesicles (right). ***, P<0.001; ns, not significant; one way ANOVA with Tukey's multiple comparison test. Error bars indicate SEM. N=3.
Figure 85:
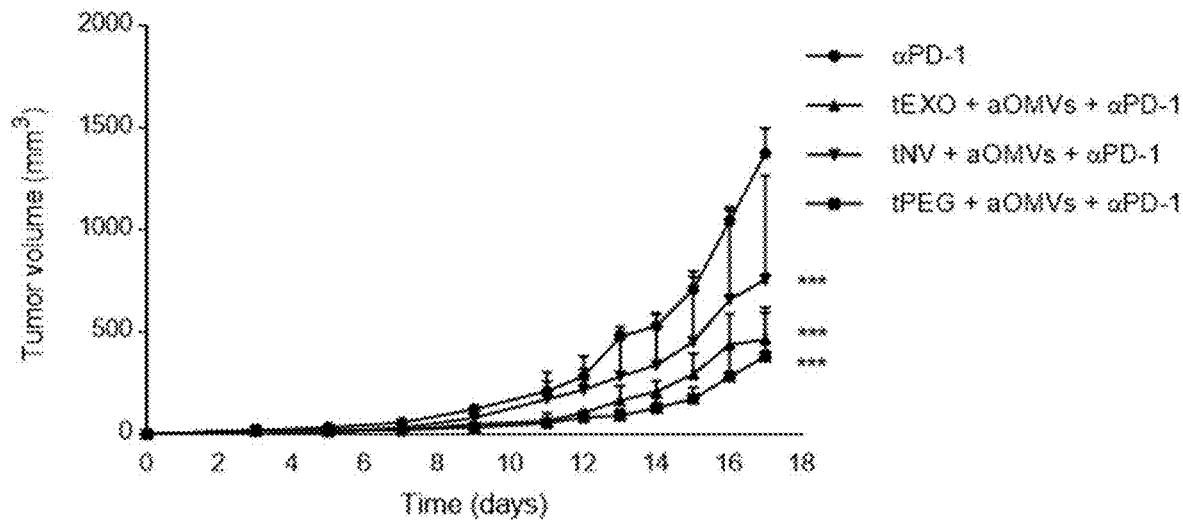
FIG. 85 shows melanoma volume in mice immunized with various types of tumor vesicles (tEXO, tNV and tPEG; $5 \times 10^9$) and $E.\ coli$ aOMVs ($5 \times 10^9$) five times at 3-day intervals, and treated with anti-PD-1 therapy (100 µg) 1 day prior to immunization. ***, P<0.001; versus αPD-1 group; one way ANOVA with Tukey's multiple comparison test. Error bars indicate SEM. N=4.

The existence of vesicles in tPEG was confirmed by electron microscopy (FIG. 83), and tPEG showed higher yield and purity than other types of tumor vesicles (FIG. 84). Also, tPEG together with aOMVs induced significant antitumor response, which is slightly better effect than tEXO or tNVs (FIG. 85).

Example 31: Immunotherapeutic Effect of STING Agonist-Loaded aOMVs

Methods

Figure 86:
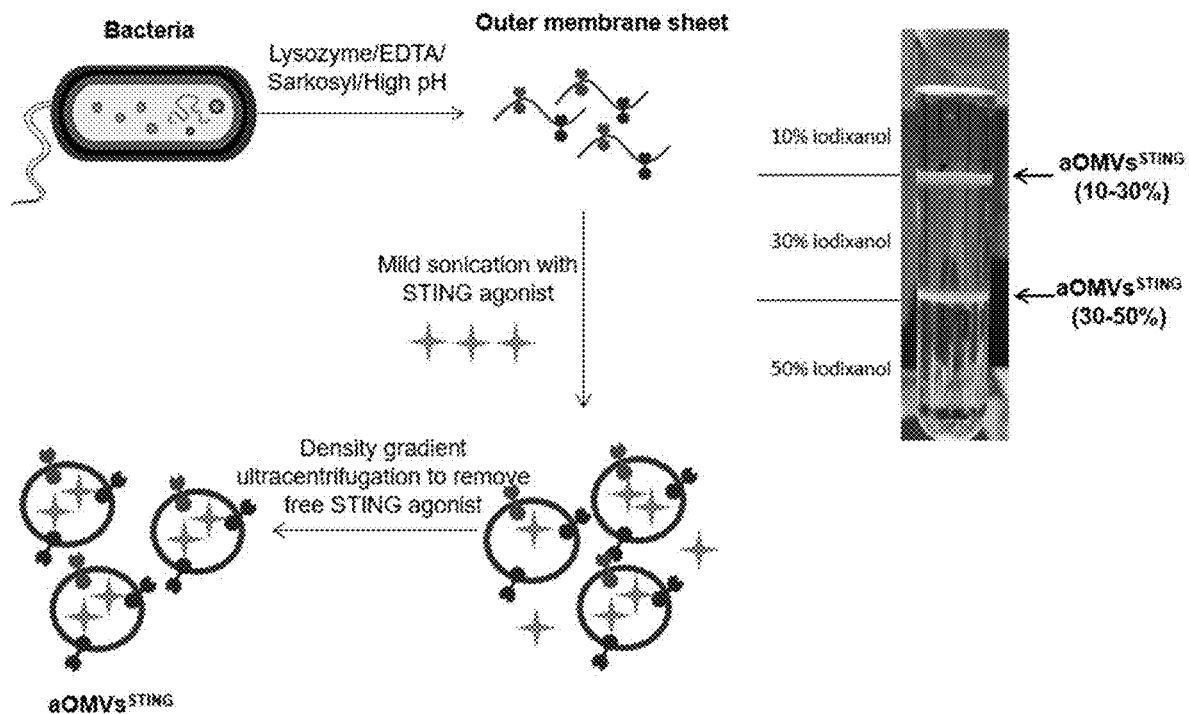
FIG. 86 shows schematic diagram of a method of preparing aOMVs loaded with a STING agonist and a photograph of aOMVs loaded with STING agonist following iodixanol gradient ultracentrifugation. Upper and lower arrow indicate aOMVs with STING agonist on 10-30% and 30-50% iodixanol gradient layers, respectively.

Incorporation of STING agonist into *E. coli* aOMVs: The outer membrane was isolated from *E. coli* culture using same method described in Example 24. High pH solution (200 mM $Na_2CO_3$)-treated outer membrane was mixed with DMXAA (Tocris Bioscience) used as STING agonist, followed by mild sonication at 25° C. for 1 hour. The mixture was then applied to 4 mL of 50% iodixanol (Axis-Shield PoC AS), followed by addition of 4 mL of 30% iodixanol and 2 mL of 10% iodixanol to ultracentrifuge tube. To remove free STING agonist, ultracentrifugation was done at 100,000×g for 2 hours, and then the layer formed between 30% and 50% iodixanol was collected. The vesicles were called aOMVs$^{STING}$ (30-50%) and stored at −80° C. until use (FIGS. 86A and 86B). Also, STING agonist-loaded aOMVs on 10-30% iodixanol gradient layers were isolated (aOMVs$^{STING}$ (10-30%); FIG. 86B).

Quantification of STING agonist into aOMVs: An equal volume of acetonitrile was added to aOMVs$^{STING}$ and the mixture was sonicated and centrifuged at 13,000 rpm for 10 min. The supernatant was collected and injected into HPLC system (UltiMate 3000 HPLC; ThermoFisher Scientific) equipped with a C18 column (100×2.1 mm, 2.6 µm; Phenomenex). For STING agonist detection, absorbance was measured at 254 nm.

BMDC cytokines: Differentiated BMDCs ($4×10^6$) were seeded into 6-well plates. The cells were treated with free STING agonist (20 µg), aOMVs, aOMVs$^{STING}$ (10-30%; $5×10^9$), or various concentrations of aOMVs$^{STING}$ (30-50%; $5×10^8$, $1×10^9$, $2×10^9$, $5×10^9$) for 24 h to induce INF-beta. Supernatant concentrations of cytokines were measured by ELISA kit (R&D systems).

Mice experiments: Mice (wild-type C57BL/6 genetic background, 6 weeks old) were subcutaneously injected with melanoma cells (B16F10; $5×10^5$), and maintained for three days to form a measurable mass of tumor (2-3 mm). Then, tEXO ($5×10^9$) were subcutaneously injected in combination with aOMVs ($5×10^9$) or aOMVs$^{STING}$ (30-50%; $5×10^9$) to the mice five times at 3-day intervals. The tumor size was measured at 2-day intervals. The tumor volume was calculated according to the formula v=1×s2/2 [v, volume; 1, a length of the longest axis of the tumor mass; s, a length of the shortest axis].

Results

Figure 87A:
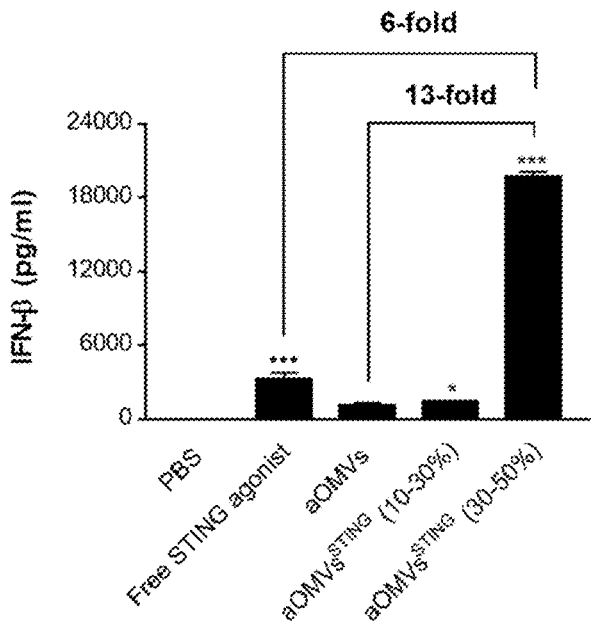
FIG. 87A is a graph of IFN-beta in the supernatants of mouse BMDCs treated with STING agonist (20 µg), aOMVs, aOMVs$^{STING}$ (10-30%), or aOMVs$^{STING}$ (30-50%) for 24 h. The same number of particles ($5 \times 10^9$) was used in aOMVs and aOMVs$^{STING}$ group. *, P<0.05; ***, P<0.001; versus PBS; one way ANOVA with Tukey's multiple comparison test. Error bars indicate SEM. N=2.
Figure 87B:
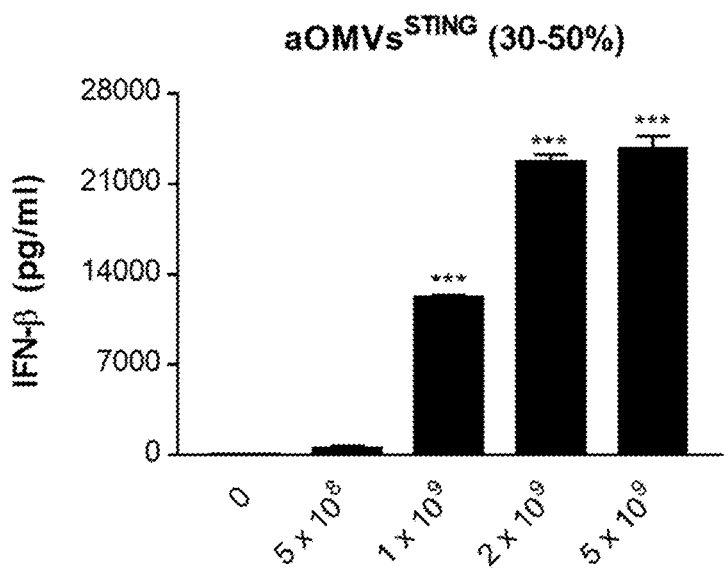
FIG. 87B is a graph of IFN-beta in the supernatants of mouse BMDCs treated with various concentrations of aOMVs$^{STING}$ (30-50%) for 24 h. ***, P<0.001; versus PBS; one way ANOVA with Tukey's multiple comparison test. Error bars indicate SEM. N=2.
Figure 88:
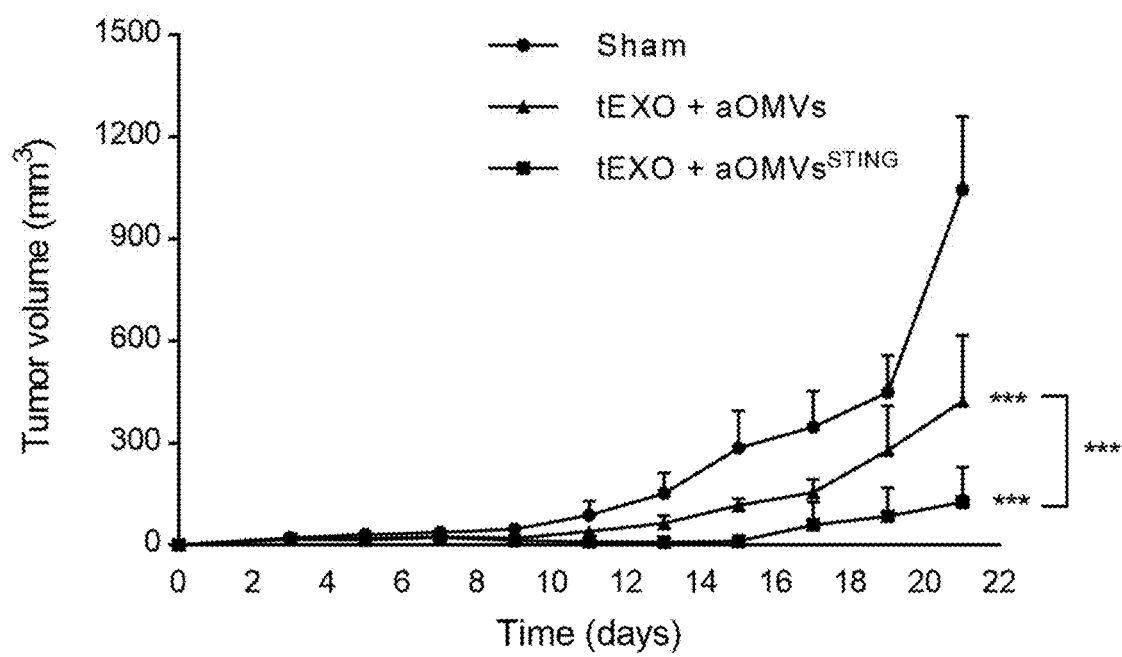
FIG. 88 shows melanoma volume in mice immunized with tEXO ($5 \times 10^9$) and $E.\ coli$ aOMVs$^{STING}$ (30-50%; $5 \times 10^9$) five times at 3-day intervals. Also, the immunization with tEXO and $E.\ coli$ aOMVs ($5 \times 10^9$) was performed for comparison. ***, P<0.001; versus sham group; one way ANOVA with Tukey's multiple comparison test. Error bars indicate SEM. N=4.

We first isolated aOMVs$^{STING}$ (10-30%) and aOMVs$^{STING}$ (30-50%) on 10-30% and 30-50% iodixanol gradient layers, respectively, as indicated in FIGS. 86A and 86B. aOMVs$^{STING}$ (10-30%) induced a little IFN-beta when they were treated to mouse BMDCs, whereas aOMVs$^{STING}$ (30-50%) showed much higher activity on IFN-beta secretion than aOMVs alone (13-fold; FIG. 87A). Based on that $5×10^9$ of aOMVs$^{STING}$ (30-50%) harbor 20 µg of STING agonist, we compared the immunogenic activity of aOMVs$^{STING}$ (30-50%) with free STING agonist. As a result, aOMVs$^{STING}$ (30-50%) were more potent than free STING agonist to induce IFN-beta production (6-fold; FIG. 87A). Moreover, aOMVs$^{STING}$ (30-50%) induced the release of IFN-beta in a dose-dependent manner (FIG. 87B). With regards to antitumor growth experiment in vivo, aOMVs$^{STING}$ (30-50%) dramatically decreased melanoma growth, compared with aOMV immunization (FIG. 88).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A composition comprising non-naturally occurring artificial outer membrane vesicles (aOMVs) generated from a gram-negative bacterium,
    wherein the aOMVs are deficient in the following components present in the gram-negative bacterium: periplasmic proteins, inner membrane proteins, nucleic acids, cytoplasmic proteins, and ribosomes; and
    wherein the aOMVs are enriched in outer membrane proteins,
    wherein the gram-negative bacterium is not genetically modified to reduce production of lipopolysaccharides (LPS), and wherein when administered to a subject, the aOMVs produce a reduced inflammatory response comprising production of a lower level of tumor necrosis factor alpha (TNF-α) and/or interleukin-6 (IL-6), as compared to that produced by administering naturally occurring outer membrane vesicles (OMVs) released by the gram-negative bacterium.

2. The composition of claim 1, further comprising tumor vesicles (TVs), wherein the TVs comprise at least one tumor antigen.

3. The composition of claim 1, wherein the aOMVs are loaded with a therapeutic agent.

4. The composition of claim 1, wherein the aOMVs are loaded with a STING agonist, wherein the aOMVs loaded with the STING agonist form a layer between 30% and 50% iodixanol when ultracentrifuged on a density gradient formed by 10%, 30%, and 50% iodixanol.

5. The composition of claim 4, wherein the STING agonist is a cyclic dinucleotide (CDN) or 5,6-dimethylxanthenone-4-acetic acid (DMXAA).

6. A method for producing an immune response to a gram-negative bacterium in a mammalian subject, the method comprising administering the composition of claim 1 to the subject in an amount effective to induce an immune response to the gram-negative bacterium in the mammalian subject.

7. The method of claim 6, wherein the administering produces reduced inflammatory response comprising production of a lower level of tumor necrosis factor alpha (TNF-α) and/or interleukin-6 (IL-6), as compared to that produced by administering naturally occurring OMVs released by the gram-negative bacterium.

8. A method for treating cancer in a subject, the method comprising administering to the subject the composition of claim 2.

9. The method of claim 8, wherein the administering results in induction of antibodies against the tumor vesicles at a titer more than twice the titer of antibodies against the tumor vesicles induced using an adjuvant instead of the aOMVs.

10. The method of claim 8, further comprising administering an immune checkpoint inhibitor to the subject.

11. The method of claim 10, wherein the immune checkpoint inhibitor comprises an anti-PD-1 antibody or an anti-PDL1 antibody.

12. The method of claim 11, wherein the administration of aOMVs, TVs, and the anti-PD-1 antibody results in reduction of tumor volume in the subject which reduction is at least two times higher than achieved by administration of aOMVs and the anti-PD-1 antibody or TVs and the anti-PD-1 antibody.

13. The method of claim 8, wherein the aOMVs are prepared by revesiculation of vesicles composed of outer membrane.

14. The method of claim 13, wherein revesiculation comprises exposing the vesicles to an alkaline pH.

15. The method of claim 8, wherein the administering comprises intratumoral injection.

16. A method for generating non-naturally occurring artificial outer membrane vesicles (aOMVs) from a gram-negative bacterium, the method comprising:
    a) disrupting a spheroplast generated from the gram-negative bacterium to generate vesicles comprising outer membrane and vesicles comprising inner membrane, optionally wherein disrupting comprises applying shear force to the spheroplast or acoustic energy to the spheroplast;
    b) exposing the vesicles to an ionic surfactant to disrupt vesicles comprising inner membrane and to an alkaline pH to open the vesicles comprising outer membrane thereby generating outer membrane sheets;
    c) purifying the outer membrane sheets; and
    d) applying energy to the purified outer membrane sheets sufficient to convert the outer membrane sheets into aOMVs, thereby generating the-non-naturally occurring aOMVs.

17. The method of claim 16, comprising generating the spheroplast from the gram-negative bacterium by incubating the gram-negative bacterium with lysozyme under conditions sufficient for the removal of the peptidoglycan layer in cell wall of the gram-negative bacterium, thereby converting the gram-negative bacterium into the spheroplast.

18. The method of claim 16, wherein step b) comprises exposing the vesicles to the ionic surfactant to disrupt vesicles comprising inner membrane, isolating the vesicles comprising the outer membrane, and exposing the vesicles comprising the outer membrane to the alkaline pH.

19. The method of claim 18, wherein the alkaline pH comprises a pH of 11-14.

20. A method for generating non-naturally occurring artificial outer membrane vesicles (aOMVs) from a gram-negative bacterium, the method comprising:
    a) disrupting a spheroplast generated from the gram-negative bacterium to generate vesicles comprising outer membrane and vesicles comprising inner membrane, optionally wherein disrupting comprises applying shear force to the spheroplast or acoustic energy to the spheroplast;
    b) exposing the vesicles to an ionic surfactant to disrupt vesicles comprising inner membrane and to an alkaline pH to open the vesicles comprising outer membrane thereby generating outer membrane sheets;
    c) purifying the outer membrane sheets; and
    d) in the presence of a STING agonist, applying energy to the purified outer membrane sheets sufficient to convert the outer membrane sheets into aOMVs, thereby generating the non-naturally occurring aOMVs comprising the STING agonist.

* * * * *